(12) United States Patent
Eissenstat et al.

(10) Patent No.: US 8,765,667 B2
(45) Date of Patent: Jul. 1, 2014

(54) HCV PROTEASE INHIBITORS

(76) Inventors: Michael Eissenstat, Frederick, MD (US); Rongjian Lu, Gaithersburg, MD (US); Sang Uk Kang, Gaithersburg, MD (US)

( * ) Notice: Subject to any disclaimer, the term of this patent is extended or adjusted under 35 U.S.C. 154(b) by 334 days.

(21) Appl. No.: 13/060,243

(22) PCT Filed: Aug. 20, 2009

(86) PCT No.: PCT/US2009/004743
§ 371 (c)(1),
(2), (4) Date: Apr. 15, 2011

(87) PCT Pub. No.: WO2010/021717
PCT Pub. Date: Feb. 25, 2010

(65) Prior Publication Data
US 2011/0182854 A1    Jul. 28, 2011

Related U.S. Application Data

(60) Provisional application No. 61/090,493, filed on Aug. 20, 2008.

(51) Int. Cl.
*A61K 38/00*    (2006.01)

(52) U.S. Cl.
USPC ............................................................ 514/4.3

(58) Field of Classification Search
None
See application file for complete search history.

(56) References Cited

FOREIGN PATENT DOCUMENTS

| WO | WO 03/062228 | 7/2003 |
|---|---|---|
| WO | WO 03/097646 | 11/2003 |
| WO | WO 2004/039833 | 5/2004 |
| WO | WO 2007/044893 | 4/2007 |
| WO | WO 2008/019289 | 2/2008 |

OTHER PUBLICATIONS

International Search Report dated Mar. 3, 2010, issued in International Application PCT/2009/004743.

*Primary Examiner* — Thomas Heard
(74) *Attorney, Agent, or Firm* — Perkins Coie LLP

(57) ABSTRACT

Novel compounds that are potent inhibitors of hepatitis C virus protease are provided. Pharmaceutical compositions containing one or more of these inhibitors, methods of preparing the inhibitors and methods of using the inhibitors to treat hepatitis C and related disorders also are provided.

26 Claims, 86 Drawing Sheets

| Compound | Formula | Molecular Weight |
|---|---|---|
|  101 | C42H49N5O8 | 751.881 |
|  102 | C39H50N6O8 | 730.863 |
|  103 | C36H45N5O8 | 675.783 |

| Compound | Formula | Molecular Weight |
|---|---|---|
|  104 | C33H44N4O8 | 624.735 |
|  105 | C34H45N5O7 | 635.762 |
|  106 | C34H45N5O7 | 635.762 |
|  107 | C35H47N5O7 | 649.789 |

Figure 1 (continued)

| Compound | Formula | Molecular Weight |
|---|---|---|
| 108 | C38H46N4O8 | 686.806 |
| 109 | C35H45N5O6 | 631.774 |
| 110 | C33H42N6O7 | 634.734 |

| Compound | Formula | Molecular Weight |
|---|---|---|
|  111 | C35H43N5O7 | 645.757 |
|  112 | C33H42N4O9S | 670.782 |
|  113 | C40H51N5O7 | 713.876 |

| Compound | Formula | Molecular Weight |
|---|---|---|
|  114 | C34H44FN5O7 | 653.752 |
|  115 | C34H46N6O6 | 634.778 |
|  116 | C42H51N5O7 | 737.898 |

| Compound | Formula | Molecular Weight |
|---|---|---|
|  117 | C36H47N5O7 | 661.8 |
|  118 | C36H45N5O8 | 675.783 |
|  119 | C36H44N4O7 | 644.769 |

Figure 1 (continued)

| Compound | Formula | Molecular Weight |
|---|---|---|
| 120 | C35H43N5O7 | 645.757 |
| 121 | C35H44N6O7 | 660.772 |
| 122 | C36H46N4O6 | 630.786 |

| Compound | Formula | Molecular Weight |
|---|---|---|
|  123 | C36H46ClN5O7 | 696.245 |
|  124 | C40H48N6O7 | 724.859 |
|  125 | C35H45N5O6 | 631.774 |

| Compound | Formula | Molecular Weight |
|---|---|---|
|  126 | C35H45N5O6 | 631.774 |
|  127 | C38H51N5O6 | 673.855 |
|  128 | C36H46N4O6 | 630.786 |

| Compound | Formula | Molecular Weight |
|---|---|---|
|  129 | C43H51N5O9 | 781.907 |
|  130 | C37H45N7O7S | 731.873 |
|  131 | C43H51N5O9 | 781.907 |

Figure 1 (continued)

| Compound | Formula | Molecular Weight |
|---|---|---|
| 132 | C36H47N5O7 | 661.8 |
| 133 | C37H45N5O8 | 687.794 |
| 134 | C37H47N5O8 | 689.81 |

| Compound | Formula | Molecular Weight |
|---|---|---|
| 135  | C37H49N5O7 | 675.827 |
| 136  | C35H45N5O7 | 647.773 |
| 137  | C39H47N7O8 | 741.846 |

| Compound | Formula | Molecular Weight |
|---|---|---|
|  138 | C37H47N5O7 | 673.811 |
|  139 | C41H50N6O8 | 754.885 |
|  140 | C39H49N7O7 | 727.863 |

| Compound | Formula | Molecular Weight |
|---|---|---|
|  141 | C37H49N5O8 | 691.826 |
|  142 | C37H47N5O9 | 705.809 |
|  143 | C43H53N5O8 | 767.924 |

| Compound | Formula | Molecular Weight |
|---|---|---|
|  144 | C36H48N6O8 | 692.814 |
|  145 | C34H44FN5O7 | 653.752 |
|  146 | C35H46N4O7 | 634.774 |
|  147 | C33H44N4O8 | 624.735 |

| Compound | Formula | Molecular Weight |
|---|---|---|
|  148 | C36H49N5O7 | 663.816 |
|  149 | C38H47N5O9 | 717.82 |
|  150 | C36H49N5O7 | 663.816 |

| Compound | Formula | Molecular Weight |
|---|---|---|
|  151 | C35H47N5O8 | 665.788 |
|  152 | C35H44N4O8S | 680.821 |
|  153 | C33H44N4O7 | 608.736 |

| Compound | Formula | Molecular Weight |
|---|---|---|
|  154 | C35H44N4O8S | 680.821 |
|  155 | C42H51N5O7 | 737.898 |
|  156 | C33H46N4O6 | 594.753 |

Figure 1 (continued)

| Compound | Formula | Molecular Weight |
|---|---|---|
| 157 | C38H46N4O7 | 670.807 |
| 158 | C39H46N4O8 | 698.817 |
| 159 | C34H43N5O7 | 633.746 |

| Compound | Formula | Molecular Weight |
|---|---|---|
|  160 | C38H46N4O7 | 670.807 |
|  161 | C34H44N6O7 | 648.761 |
|  162 | C35H45N5O7 | 647.773 |

Figure 1 (continued)

| Compound | Formula | Molecular Weight |
|---|---|---|
| 163 | C38H48N4O6 | 656.824 |
| 164 | C41H49N5O6 | 707.872 |
| 165 | C40H46FN5O7 | 727.834 |

| Compound | Formula | Molecular Weight |
|---|---|---|
|  166 | C34H43N5O7 | 633.746 |
|  167 | C38H48N4O6 | 656.824 |
|  168 | C37H46N4O8S | 706.859 |

| Compound | Formula | Molecular Weight |
|---|---|---|
|  169 | C38H45FN4O7 | 688.797 |
|  170 | C35H44N6O7 | 660.772 |
|  171 | C39H48N4O8 | 700.833 |
|  172 | C36H46N6O7 | 674.799 |

| Compound | Formula | Molecular Weight |
|---|---|---|
|  173 | C36H45N5O7S | 691.848 |
|  174 | C41H48N6O7 | 736.87 |
|  175 | C41H49N5O7 | 723.871 |

| Compound | Formula | Molecular Weight |
|---|---|---|
|  176 | C39H48N4O8 | 700.833 |
|  177 | C37H45N5O7 | 671.795 |
|  178 | C36H46N6O7 | 674.799 |

| Compound | Formula | Molecular Weight |
|---|---|---|
|  179 | C38H46N4O8 | 686.806 |
|  180 | C38H45ClN4O7 | 705.252 |
|  181 | C35H43N5O7S | 677.821 |

| Compound | Formula | Molecular Weight |
|---|---|---|
|  182 | C37H45N5O7 | 671.795 |
|  183 | C36H44N4O7S | 676.833 |
|  184 | C39H48N4O8 | 700.833 |

| Compound | Formula | Molecular Weight |
|---|---|---|
|  185 | C39H48N4O8 | 700.833 |
|  186 | C37H45N5O7 | 671.795 |
|  187 | C36H44N4O7S | 676.833 |

| Compound | Formula | Molecular Weight |
|---|---|---|
|  188 | C39H48N4O7 | 684.834 |
|  189 | C35H43N5O7S | 677.821 |
|  190 | C38H44F2N4O7 | 706.787 |

| Compound | Formula | Molecular Weight |
|---|---|---|
|  191 | C39H48N4O7 | 684.834 |
|  192 | C38H45FN4O7 | 688.797 |
|  193 | C38H45FN4O7 | 688.797 |

| Compound | Formula | Molecular Weight |
|---|---|---|
|  194 | C35H43N5O8 | 661.756 |
|  195 | C38H45FN4O7 | 688.797 |
|  196 | C39H48N4O7 | 684.834 |

| Compound | Formula | Molecular Weight |
|---|---|---|
|  197 | C38H44F2N4O7 | 706.787 |
|  198 | C38H45FN4O7 | 688.797 |
|  199 | C39H48N4O7 | 684.834 |

| Compound | Formula | Molecular Weight |
|---|---|---|
|  200 | C36H45N5O8S | 707.847 |
|  201 | C37H45N5O7 | 671.795 |
|  202 | C38H45ClN4O7 | 705.252 |

| Compound | Formula | Molecular Weight |
|---|---|---|
|  203 | C36H46N6O7 | 674.799 |
|  204 | C39H46N4O9 | 714.816 |
|  205 | C38H46N4O8 | 686.806 |

| Compound | Formula | Molecular Weight |
|---|---|---|
|  206 | C35H43N5O7S | 677.821 |
|  207 | C38H47N5O8 | 701.821 |
|  208 | C37H44FN5O7 | 689.785 |

| Compound | Formula | Molecular Weight |
|---|---|---|
|  209 | C38H45ClN4O7 | 705.252 |
|  210 | C38H47N5O7 | 685.822 |
|  211 | C36H45N5O8S | 707.847 |

| Compound | Formula | Molecular Weight |
|---|---|---|
|  212 | C35H42FN5O7S | 695.81 |
|  213 | C35H42ClN5O7S | 712.27 |
|  214 | C38H47N5O7 | 685.82 |

| Compound | Formula | Molecular Weight |
|---|---|---|
|  215 | C38H47N5O8 | 701.82 |
|  216 | C37H44ClN5O7 | 706.24 |
|  217 | C38H45N5O7 | 683.81 |

| Compound | Formula | Molecular Weight |
|---|---|---|
|  301 | C35H49N5O7S | 683.869 |
|  302 | C45H56N6O8S | 841.041 |
|  303 | C39H50N6O9S | 778.926 |
|  304 | C43H53N7O8S | 828.002 |

Figure 2 (continued)

| Compound | Formula | Molecular Weight |
|---|---|---|
| 305 | C39H52N6O8S | 764.943 |
| 306 | C46H56N6O10S | 885.05 |
| 307 | C40H50N6O9S | 790.937 |
| 308 | C37H50N6O8S | 738.905 |

| Compound | Formula | Molecular Weight |
|---|---|---|
|  309 | C40H50N8O8S2 | 835.016 |
|  310 | C32H42N6O6S | 638.788 |
|  311 | C35H42N8O6S2 | 734.899 |

| Compound | Formula | Molecular Weight |
|---|---|---|
|  312 | C39H51N5O7S | 733.929 |
|  313 | C45H54N6O9S | 855.024 |
|  314 | C35H47N5O8S | 697.852 |
|  315 | C35H46FN5O8S | 715.842 |

| Compound | Formula | Molecular Weight |
|---|---|---|
| <br>316 | C37H51N5O10S | 757.904 |
| <br>317 | C40H54N6O8S | 778.97 |
| <br>318 | C40H52N6O9S | 792.953 |
| <br>319 | C38H50N6O8S | 750.916 |

| Compound | Formula | Molecular Weight |
|---|---|---|
|  320 | C39H49N5O8S | 747.912 |
|  321 | C40H52N6O8S | 776.954 |
|  322 | C44H55N7O9S | 858.028 |
|  323 | C42H54N8O8S | 831.006 |

| Compound | Formula | Molecular Weight |
|---|---|---|
|  324 | C38H50N6O7S | 734.917 |
|  325 | C40H54N6O9S | 794.969 |
|  326 | C46H58N6O9S | 871.067 |
|  327 | C36H47N5O10S2 | 773.925 |

| Compound | Formula | Molecular Weight |
|---|---|---|
|  328 | C38H49N5O9S2 | 783.964 |
|  329 | C38H49N5O9S2 | 783.964 |
|  330 | C37H52N6O8S | 740.921 |

| Compound | Formula | Molecular Weight |
|---|---|---|
|  331 | C36H49N5O8S | 711.879 |
|  332 | C41H52N6O10S | 820.963 |
|  333 | C41H51N5O8S | 773.95 |
|  334 | C41H51N5O8S | 773.95 |

| Compound | Formula | Molecular Weight |
|---|---|---|
|  335 | C44H54N6O7S | 811.015 |
|  336 | C41H50FN5O8S | 791.94 |
|  337 | C42H53N5O9S | 803.976 |
|  338 | C42H53N5O9S | 803.976 |

| Compound | Formula | Molecular Weight |
|---|---|---|
|  339 | C39H49N5O8S2 | 779.976 |
|  340 | C39H49N5O8S2 | 779.976 |
|  341 | C39H50N6O8S2 | 794.991 |
|  342 | C40H50N6O8S | 774.938 |

| Compound | Formula | Molecular Weight |
|---|---|---|
|  343 | C38H48N6O8S2 | 780.964 |
|  344 | C41H50ClN5O8S | 808.395 |
|  345 | C39H50N6O9S2 | 810.99 |

| Compound | Formula | Molecular Weight |
|---|---|---|
|  346 | C41H50ClN5O8S | 808.395 |
|  347 | C40H50N6O8S | 774.938 |
|  348 | C40H50N6O8S | 774.938 |
|  | C42H51N5O10S | 817.959 |

Figure 2 (continued)

| Compound | Formula | Molecular Weight |
|---|---|---|
| 349 | | |
| 350 | C42H53N5O8S | 787.977 |
| 351 | C41H50FN5O8S | 791.94 |
| 352 | C41H52N6O9S | 804.964 |

| Compound | Formula | Molecular Weight |
|---|---|---|
|  353 | C40H49FN6O8S | 792.928 |
|  354 | C41H50ClN5O8S | 808.39 |
|  355 | C41H52N6O8S | 788.96 |
|  356 | C39H50N6O9S2 | 810.99 |

Figure 2 (continued)

| Compound | Formula | Molecular Weight |
|---|---|---|
| 357 | C41H50FN5O8S | 791.94 |
| 358 | C42H53N5O8S | 787.98 |
| 359 | C41H51N5O9S | 789.95 |
| 360 | C38H47FN6O8S2 | 798.95 |

| Compound | Formula | Molecular Weight |
|---|---|---|
|  361 | C38H47ClN6O8S2 | 815.41 |
|  362 | C41H52N6O8S | 788.96 |
|  363 | C41H52N6O9S | 804.96 |
|  364 | C40H49ClN6O8S | 809.38 |

Figure 2 (continued)

| Compound | Formula | Molecular Weight |
|---|---|---|
| 365 | C39H51N7O8S | 777.94 |
| 366 | C38H48N6O8S2 | 780.96 |
| 367 | C38H48N6O8S2 | 780.96 |
| 368 | C38H48N6O8S2 | 780.96 |

Figure 2 (continued)

| Compound | Formula | Molecular Weight |
|---|---|---|
| 369 | C41H50N6O8S | 786.95 |
| 370 | C38H48N6O9S | 764.90 |
| 371 | C41H53N5O7S | 759.97 |
| 372 | C41H53N5O7S | 759.97 |

| Compound | Formula | Molecular Weight |
|---|---|---|
|  373 | C40H49FN6O8S | 792.93 |
|  374 | C39H50N6O9S2 | 810.99 |
|  375 | C39H50N6O8S2 | 794.99 |

| Compound | Formula | Molecular Weight |
|---|---|---|
|  376 | C41H54N6O7S | 774.98 |
|  377 | C41H51N5O9S | 789.95 |
|  378 | C38H48N6O8S2 | 780.96 |

| Compound | Formula | Molecular Weight |
|---|---|---|
| 379  | C38H48N6O8S2 | 780.96 |
| 380  | C37H48N6O7S | 720.89 |
| 381  | C40H50N6O8S | 774.94 |
| 382  | C40H50N6O8S | 774.94 |

| Compound | Formula | Molecular Weight |
|---|---|---|
| 383  | C37H48N6O7S | 720.89 |
| 384  | C39H50N6O7S | 746.93 |
| 385  | C38H49N7O8S2 | 795.98 |
| 386  | C42H52N6O8S | 800.98 |

| Compound | Formula | Molecular Weight |
|---|---|---|
| 387  | C41H50N6O8S | 786.95 |
| 388  | C40H50N6O8S | 774.94 |
| 389  | C39H48N6O8S2 | 792.97 |
| 390  | C36H46N6O8S3 | 786.99 |

| Compound | Formula | Molecular Weight |
|---|---|---|
|  391 | C40H50N6O9S2 | 823.00 |
|  392 | C41H50N6O8S | 786.95 |
|  393 | C39H50N6O9S2 | 810.99 |
|  394 | C40H53N7O8S2 | 824.03 |

| Compound | Formula | Molecular Weight |
|---|---|---|
| 395  | C40H50N6O9S2 | 823.00 |
| 396  | C43H53N5O9S | 815.99 |
| 397  | C39H52N8O8S2 | 825.02 |
| 398  | C41H50N6O10S | 818.95 |

| Compound | Formula | Molecular Weight |
|---|---|---|
|  399 | C40H50N6O9S | 790.94 |
|  400 | C40H50N6O9S | 790.94 |
|  401 | C39H48N6O10S2 | 824.97 |
|  402 | C41H55N7O8S2 | 838.06 |

| Compound | Formula | Molecular Weight |
|---|---|---|
| 403  | C39H48N6O8S2 | 792.97 |
| 404  | C41H53N7O8S2 | 836.04 |
| 405  | C42H48N6O8S2 | 829.01 |
| 406  | C41H46N6O8S2 | 814.98 |

| Compound | Formula | Molecular Weight |
|---|---|---|
|  407 | C41H50N6O11S2 | 867.01 |
|  408 | C40H52N6O9S2 | 825.02 |
|  409 | C39H47F3N6O9S2 | 864.96 |
|  410 | C40H52N6O11S2 | 857.01 |

| Compound | Formula | Molecular Weight |
|---|---|---|
|  411 | C39H48N6O10S2 | 824.97 |
|  412 | C39H48N6O10S2 | 824.97 |
|  413 | C41H52N6O9S2 | 837.03 |
|  414 | C41H48N6O9S3 | 865.06 |

| Compound | Formula | Molecular Weight |
|---|---|---|
|  415 | C37H46N6O9S3 | 815.00 |
|  416 | C39H51N7O8S2 | 810.01 |
|  417 | C40H52N6O8S2 | 809.02 |
|  418 | C39H50N6O8S2 | 794.99 |

Figure 2 (continued)

| Compound | Formula | Molecular Weight |
|---|---|---|
| 419 | C38H48N6O9S2 | 796.96 |
| 420 | C41H54N6O9S2 | 839.04 |
| 421 | C42H54N6O9S | 818.99 |
| 422 | C39H49N7O8S2 | 807.99 |

| Compound | Formula | Molecular Weight |
|---|---|---|
|  423 | C38H48N6O9S2 | 796.96 |
|  424 | C43H55N5O9S | 818.00 |
|  425 | C42H54N6O8S | 802.99 |
|  426 | C40H52N6O9S2 | 825.02 |

| Compound | Formula | Molecular Weight |
|---|---|---|
|  427 | C41H52N6O8S | 788.96 |
|  428 | C41H52N6O9S | 804.96 |
|  429 | C39H50N6O8S2 | 794.99 |
|  430 | C38H49N7O8S | 763.91 |

| Compound | Formula | Molecular Weight |
|---|---|---|
|  431 | C41H51FN6O9S | 822.95 |
|  432 | C41H49F2N5O8S | 809.93 |
|  433 | C40H49FN6O9S | 808.93 |
|  434 | C39H49FN6O9S2 | 828.98 |

Figure 2 (continued)

| Compound | Formula | Molecular Weight |
|---|---|---|
| 435 | C39H49FN6O9S2 | 828.98 |
| 436 | C39H47F3N6O9S2 | 864.96 |
| 437 | C42H51F3N6O9S | 872.96 |
| 438 | C42H53FN6O9S | 836.98 |

| Compound | Formula | Molecular Weight |
|---|---|---|
|  439 | C38H47FN6O9S2 | 814.95 |
|  440 | C40H52N6O8S2 | 809.02 |
|  441 | C40H51FN6O9S2 | 843.01 |
|  442 | C41H52FN6O10S | 839.96 |

Figure 2 (continued)

| Compound | Formula | Molecular Weight |
|---|---|---|
| 443 | C41H51FN6O9S | 822.95 |
| 444 | C39H49ClN6O9S2 | 845.43 |
| 445 | C38H47FN6O9S2 | 814.95 |
| 446 | C38H47ClN6O9S2 | 831.41 |

| Compound | Formula | Molecular Weight |
|---|---|---|
| 447  | C41H54N6O9S2 | 839.04 |
| 448  | C41H52N6O9S2 | 837.03 |
| 449  | C41H51FN6O9S | 822.95 |
| 450  | C40H53N7O8S2 | 824.03 |

| Compound | Formula | Molecular Weight |
|---|---|---|
|  451 | C46H63N7O9S2 | 922.18 |
|  452 | C41H49F3N6O9S | 858.93 |
|  453 | C40H51FN6O9S2 | 843.01 |
|  454 | C41H50FN5O9S | 807.94 |

Figure 2 (continued)

| Compound | Formula | Molecular Weight |
|---|---|---|
| 455 | C42H52FN5O9S | 821.97 |
| 456 | C39H49FN6O9S2 | 828.98 |
| 457 | C45H59ClN6O11S2 | 959.58 |
| 458 | C39H49ClN6O9S2 | 845.43 |

| Compound | Formula | Molecular Weight |
|---|---|---|
|  459 | C41H51FN6O10S2 | 871.02 |
|  460 | C41H55N7O8S2 | 838.06 |
|  461 | C46H61N7O11S2 | 952.16 |
|  462 | C45H58FN7O11S2 | 956.12 |

| Compound | Formula | Molecular Weight |
|---|---|---|
| 463  | C41H53N7O9S2 | 852.04 |
| 464  | C40H50FN7O9S2 | 856.01 |
| 465  | C39H49FN6O9S2 | 828.98 |
| 466  | C39H49FN6O9S2 | 828.98 |

| Compound | Formula | Molecular Weight |
|---|---|---|
|  467 | C44H54FN7O11S2 | 940.08 |
|  468 | C42H52FN7O10S2 | 898.04 |
|  469 | C40H49ClN6O9S | 825.38 |
|  470 | C38H50N6O8S3 | 815.04 |

| Compound | Formula | Molecular Weight |
|---|---|---|
|  471 | C40H51ClN6O9S2 | 859.46 |
|  472 | C37H48N6O8S3 | 801.02 |
|  473 | C39H49FN6O9S2 | 828.98 |
|  474 | C38H47FN6O9S2 | 814.95 |

| Compound | Formula | Molecular Weight |
|---|---|---|
|  475 | C38H47ClN6O9S2 | 831.41 |
|  476 | C39H51FN6O9S2 | 831.00 |
|  477 | C39H49ClN6O9S2 | 845.43 |
|  478 | C40H48Cl2N6O9S | 859.83 |

| Compound | Formula | Molecular Weight |
|---|---|---|
|  479 | C39H49FN6O9S2 | 828.98 |
|  480 | C40H51ClN6O9S2 | 859.46 |
|  481 | C40H51FN6O9S2 | 843.01 |

| Compound | Formula | Molecular Weight |
|---|---|---|
| 482  | C40H51FN6O9S | 810.94 |
| 483  | C38H50N6O8S3 | 815.04 |
| 484  | C39H52N6O8S3 | 829.07 |
| 485  | C39H49ClN6O9S2 | 845.43 |

HCV PROTEASE INHIBITORS

This application is a 371 application of PCT/US2009/004743, filed Aug. 20, 2009, which claims priority to U.S. Provisional Application No. 61/090,493, filed Aug. 20, 2008, the contents of each of which are hereby incorporated by reference in their entireties.

FIELD OF THE INVENTION

Novel compounds that are potent inhibitors of hepatitis C virus protease are provided. Pharmaceutical compositions containing one or more of these inhibitors, methods of preparing the inhibitors and methods of using the inhibitors to treat hepatitis C and related disorders also are provided.

BACKGROUND

Hepatitis C virus (HCV) is a (+)-sense single-stranded RNA virus that causes non-A, non-B hepatitis (NANBH). The virus is a small enveloped, single-stranded, positive sense RNA virus. It is the only known member of the hepacivirus genus in the family Flaviviridae. There are six major genotypes of the hepatitis C virus, which are indicated numerically as genotype 1, genotype 2, etc.

The natural course of chronic hepatitis C infection varies in different patients. Almost all patients show liver inflammation, but the rate of progression of liver scarring (fibrosis) varies significantly. It is estimated that about one third of untreated patients progress to liver cirrhosis in less than 20 years, and another third progress to cirrhosis within 30 years. The other third of patients progress very slowly and are unlikely to develop cirrhosis within their lifetimes.

The viral NS3 serine protease (NS3P) is responsible for proteolytic processing of the entire downstream region of the viral HC polyprotein, catalyzing cleavage at the NS3/NS4a, NS4a/NS4b, NS4b/NS5a, and NS5a/NS5b sites to release the mature NS3, NS4a, NS4b, NS5a, and NS5b proteins. The protease is therefore critical for viral replication and has been a target for drugs that inhibit protease function.

SUMMARY OF THE INVENTION

The invention provides novel compounds that are potent inhibitors of hepatitis C virus protease. The invention further provides pharmaceutical compositions containing one or more of these inhibitors, methods of preparing the inhibitors and methods of using the inhibitors to treat hepatitis C and related disorders.

In one aspect, the invention features a compound represented by the formula:

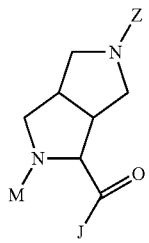

where,

Z is hydrogen, a protecting group that can be selectively removed under the conditions of organic synthesis, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted heterocycloalkyl, optionally substituted $C_3$-$C_8$ cycloalkyl, optionally substituted $C_4$-$C_8$ cycloalkenyl, optionally substituted heterocyclo, optionally substituted heteroaryl, CONRR, COOR, COR3, $SO_2$R3, SOR3, $SO_2$NRR, —PO(NRR)R3, or PO(OR)R3.

M is H, a protecting group that can be selectively removed under the conditions of organic synthesis, or a moiety selected from the group consisting of:

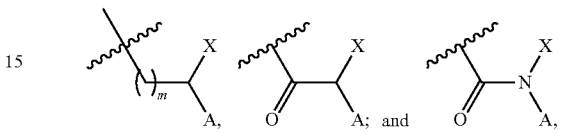

where m=1-3.

X is —NRR2, —OR, —NRP$^1$ where P$^1$ is a protecting group that can be selectively removed under the conditions of organic synthesis, optionally substituted $C_1$-$C_{12}$ alkyl, optionally substituted $C_3$-$C_7$ cycloalkyl, optionally substituted $C_2$-$C_{12}$ alkenyl, optionally substituted $C_4$-$C_7$ cycloalkenyl or X is a moiety selected from the group consisting of

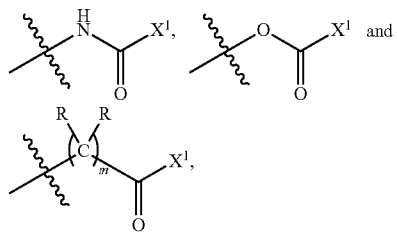

where X$^1$ is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, OR, or —NRR.

A is -D-R1, where D is a bond or optionally substituted $C_1$-$C_{12}$ alkylene, where up to three alkylene units of D are optionally and independently replaced by alkyl, alkenyl, alkynyl, aryl, $C_3$-$C_7$ cycloalkyl, $C_4$-$C_7$ cycloalkenyl, heterocyclo, heteroaryl, —CO—, —C(S)—, —CONR—, —COO—, —COOR—, —NRCO—, —O—, —NRCONR—, —S—, —SO—, —$SO_2$—, —NR—, —$SO_2$NR—, or —$NRSO_2$NR—, where up to 3 carbon atoms of D are optionally and independently substituted by R1.

J is a OH, OP$^2$, where P$^2$ is a protecting group that can be selectively removed under the conditions of organic synthesis, —NR—, or

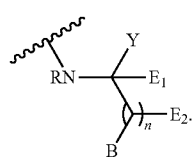

where when J is —NR— or

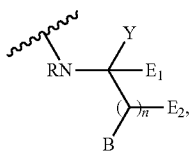

and D is optionally substituted $C_1$-$C_{12}$ alkylene, then one carbon atom of D is optionally covalently linked to —NR— or B to form a macrocyclic ring.

n=0 or 1, where when n=0 then $E_2$ is absent and B is linked directly to the carbon atom bearing Y and $E_1$.

B is —CH=CH2, R, or B is a bond to D when B and D form a macrocyclic ring, $E_1$ and $E_2$ are H, R, or $E_1$ and $E_2$ together form a 3 to 6-membered optionally substituted saturated or unsaturated carbocylic ring.

Y is COOH, COOR, CONHR, —COCONHR, $CONHSO_2R$, $CONH(SO_2)NRR$, $CONHP(O)(OR)_2$, or CONHP(O)(OR)(NRR).

each R independently is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, or optionally substituted heteroaryl, or R and R together form a 5-7-membered carbocyclic ring, fused to an aryl or heteroaryl ring, where the aryl or heteroaryl ring optionally is substituted by up to 3 R3 moieties, R1 is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, amido, carboxyl, sulfonamido, halo, —OR, —CN, —$NO_2$, —NRR, or —$OCF_3$, R2 is H, —COOR, CONRR, COR, $SO_2R$, SOR, or $SO_2NRR$. and R3 independently is selected from the group consisting of $C_1$-$C_{12}$ alkyl, $C_2$-$C_{12}$ alkenyl, $C_2$-$C_{12}$ alkynyl, $C_3$-$C_8$ cycloalkyl, $C_4$-$C_8$ cycloalkenyl, aryl, heteroaryl, and heterocyclo, each optionally substituted by up to three substituents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —$NO_2$, —NRR, —$OCF_3$, —COOR, CONRR, COR, $SO_2R$, and SOR.

In another aspect, the invention features a method of inhibiting hepatitis C virus including administering to a patient the compound as described above.

In yet another aspect, the invention features a pharmaceutical composition including a therapeutically effective amount of the compound as described above and a pharmaceutically acceptable diluent, adjuvant or excipient.

In another aspect, the invention features a method of treating hepatitis C infection in a subject including administering to a patient the composition as described above.

Each of the above aspects can have one or more of the following embodiments. Z can be a protecting group, M can be a protecting group, and J can be $OP^2$.

J can be

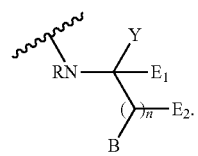

M can be

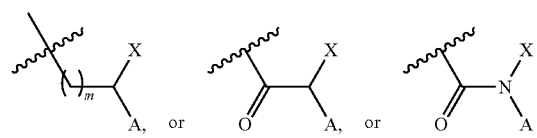

and J can be

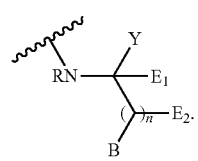

X can be —NRR2, Y can be $CO_2R$ or $CONHSO_2R$, and $E_1$ and $E_2$ together form a 3 to 6 membered optionally substituted saturated carbocylic ring.

The compound can be represented by the formula:

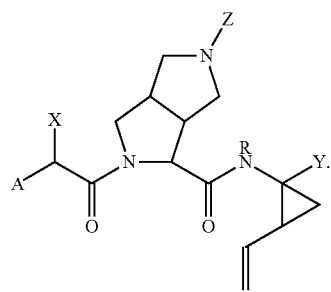

The compound can be represented by the formula:

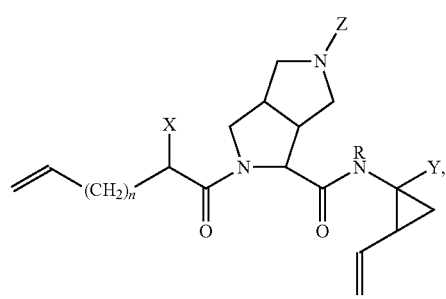

where n can be 0-10.

The compound can be represented by the formula:

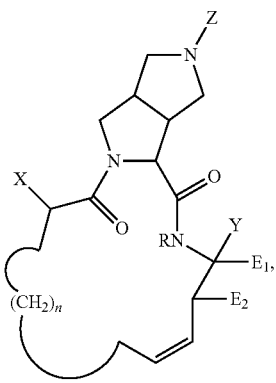

where n can be 0-8.

The compound can be represented by the formula:

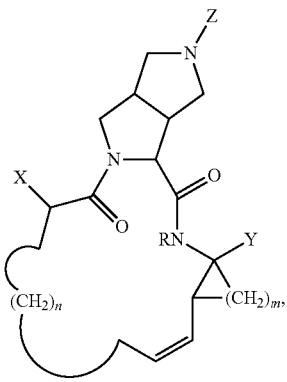

where m can be 0-3.

The compound can be represented by the formula:

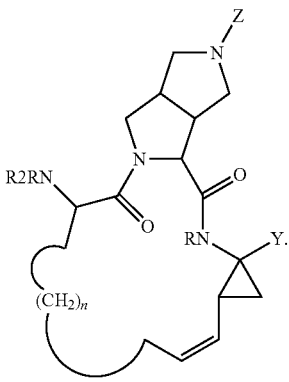

n can be 3.
R2 can be COOR.
Y can be $CO_2H$ or $CONHSO_2R$.
Z can be COR3.

R3 can be aryl or heteroaryl, where R3 can be optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —$NO_2$, —NRR, —$OCF_3$, —COOR, CONRR, COR, $SO_2R$, and SOR.

R3 can be aryl substituted with at least one aryl or heteroaryl group, and where the at least one aryl or heteroaryl group optionally can be substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, halo, —OR, —CN, —$NO_2$, —NRR, —$OCF_3$, —COOR, CONRR, COR, $SO_2R$, and SOR.

R3 can be heteroaryl substituted with at least one aryl or heteroaryl group, and where the at least one aryl or heteroaryl group optionally can be substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, halo, —OR, —CN, —$NO_2$, —NRR, —$OCF_3$, —COOR, CONRR, COR, $SO_2R$, and SOR.

R3 can be selected from the group consisting of

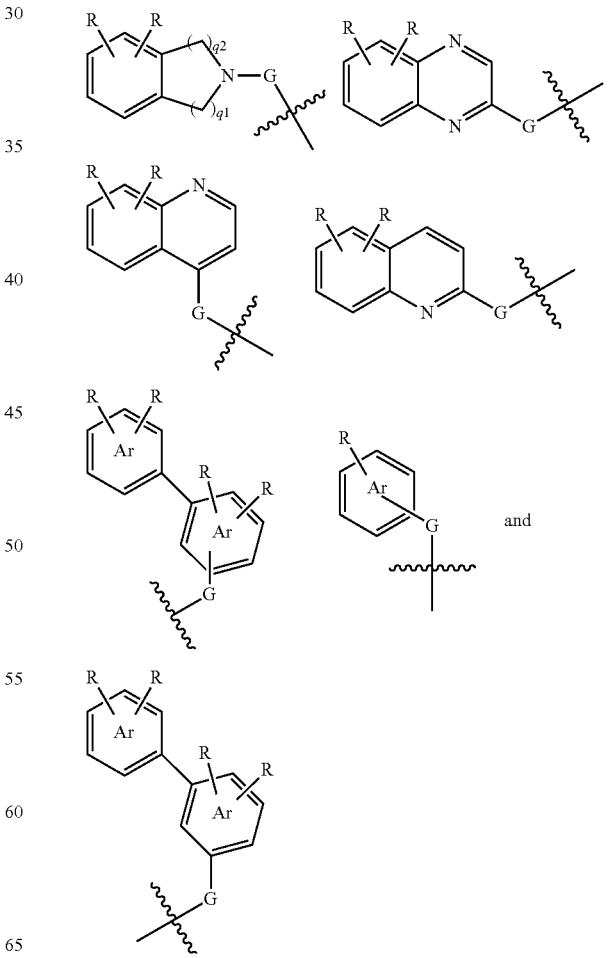

where G can be selected from the group consisting of $CH_2$—, CHR—, CO—, $SO_2$, —PO(OR)—, PO(NRR)— and NRCO—, where

can be aryl or heteroaryl, and where q1 and q2 are independently 1 or 2.

R3 can be selected from the group consisting of 4-aryl-2-thiazolyl, 6-aryl-2-pyridyl, 3-aryl-phenyl, 5-aryl-3-pyridyl, 4-aryl-2-pyridyl, 3-thiazolyl-aryl, 4-aryl-3-thienyl, 3-thienylaryl, 2-aryl-4-quinolinyl, 2-aryl-4-thiazolyl, 3-pyridylphenyl, 2-phenyl-3-indolyl, 3-pyrazolylphenyl, and 3-phenyl-2-indolyl.

The compound can be selected from the group consisting of any one of the preceding groups and be selected from: the compounds of FIGS. 1 and 2.

The method can further include administering to the subject an additional anti-hepatitis C agent.

In the method, the additional agent can be selected from the group consisting of interferon, interferon, ribivarin, adamantine.

In the method, the additional agent can be an inhibitor of hepatitis C virus helicase, polymerase, metalloprotease, or IRES.

DETAILED DESCRIPTION

Figure 1:
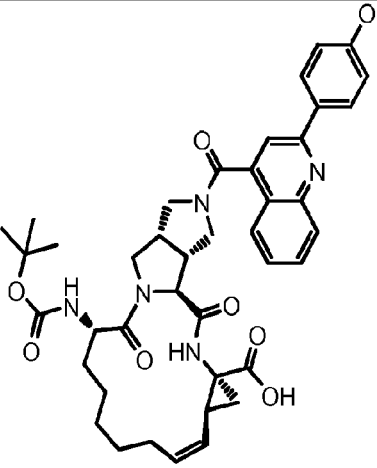
FIGS. 1 and 2 show representative HCV protease inhibitors. Each of the compounds has an $IC_{50}$ of less than or equal to 10 uM.
Figure 1:
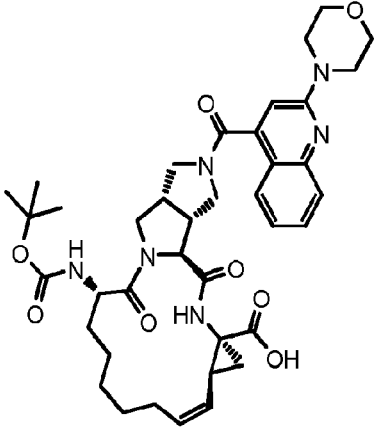
Figure 1:
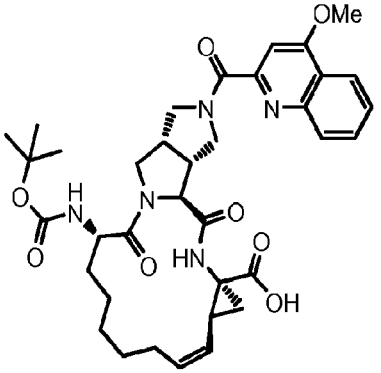
Figure 1:
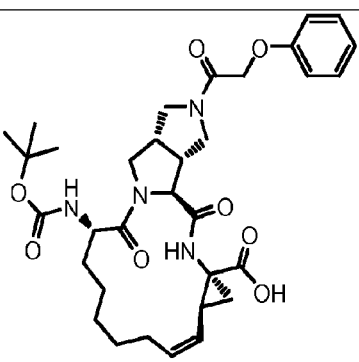
Figure 1:
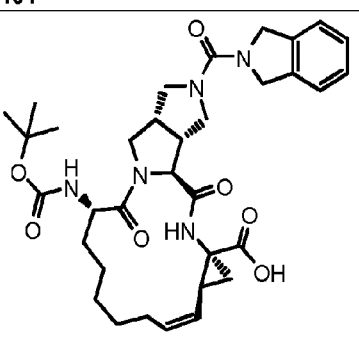
Figure 1:
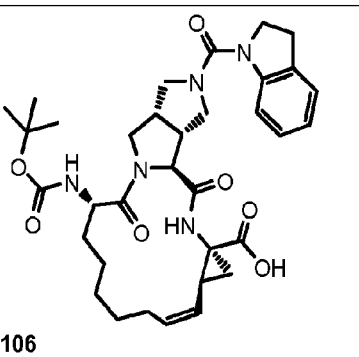
Figure 1:
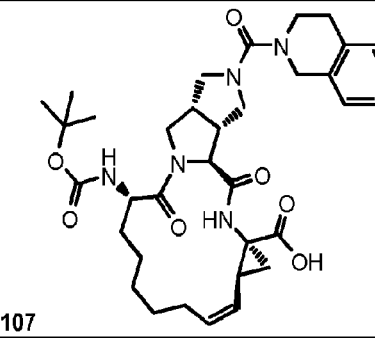
Figure 1:
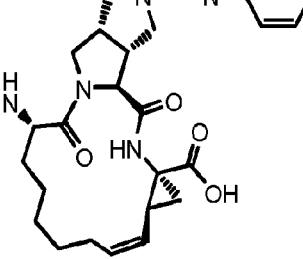
Figure 1:
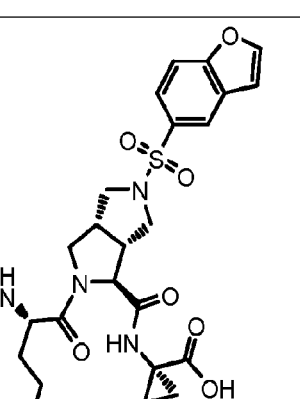
Figure 1:
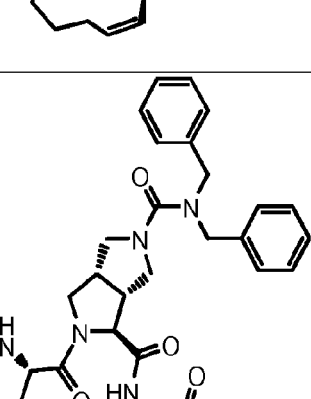
Figure 1:
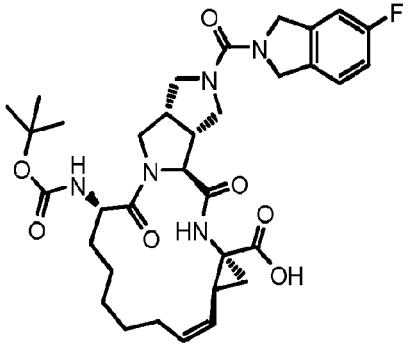
Figure 1:
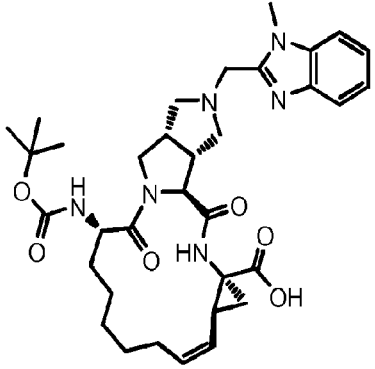
Figure 1:
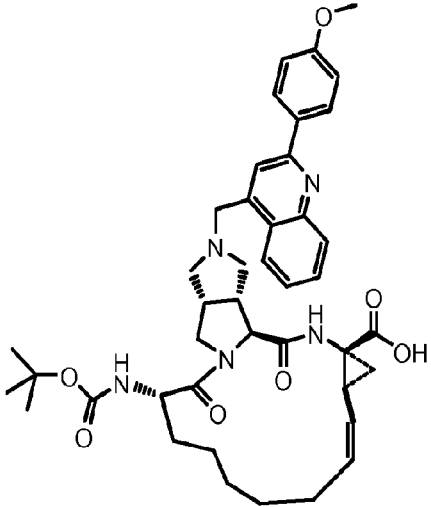
Figure 1:
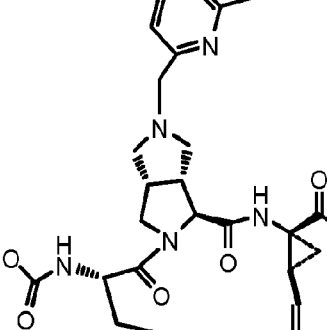
Figure 1:
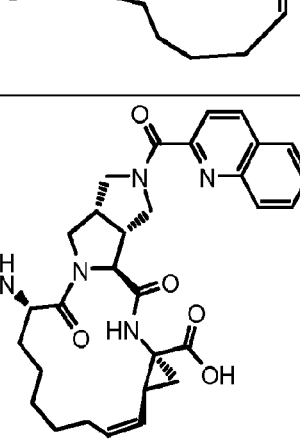
Figure 1:
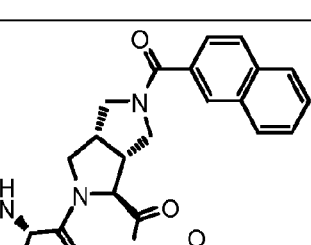
Figure 1:
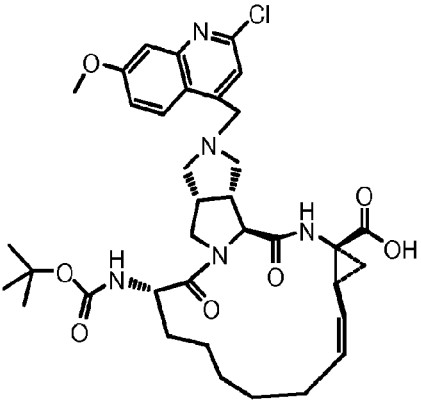
Figure 1:
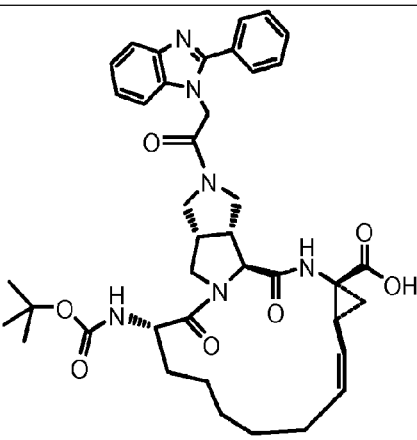
Figure 1:
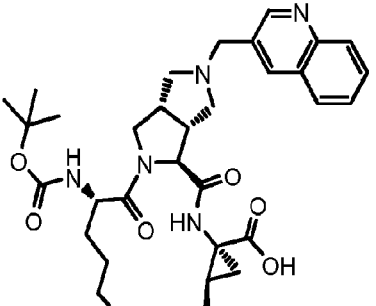
Figure 1:
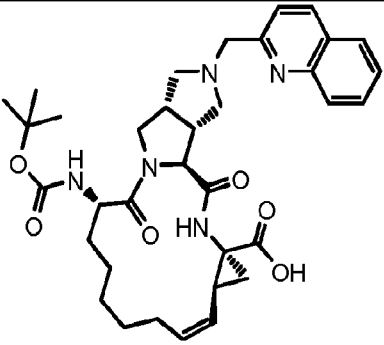
Figure 1:
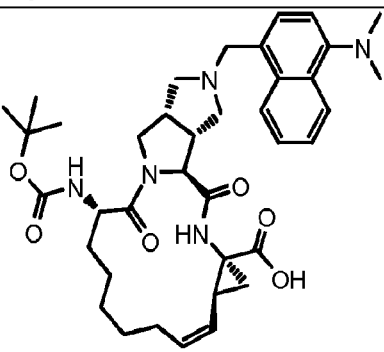
Figure 1:
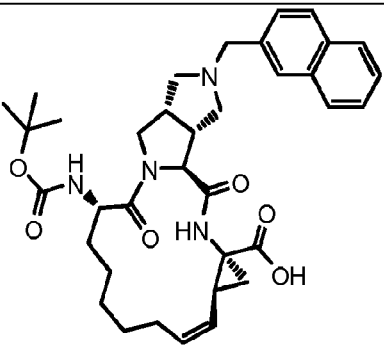
Figure 1:
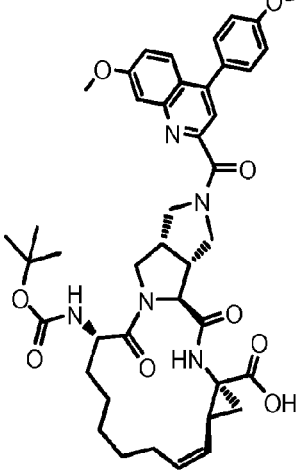
Figure 1:
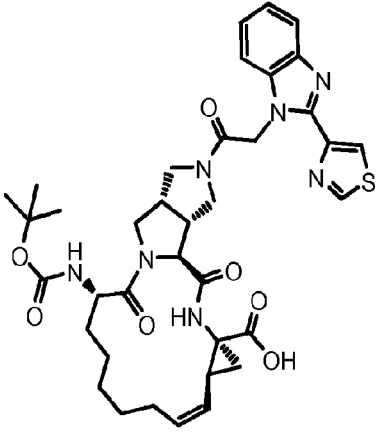
Figure 1:
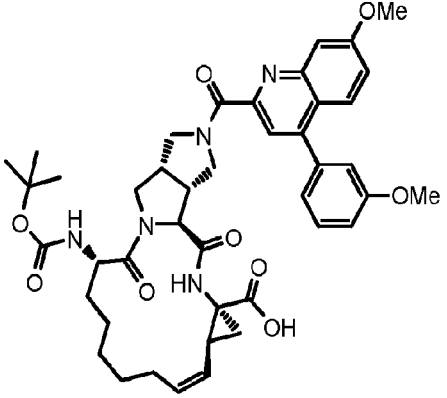
Figure 1:
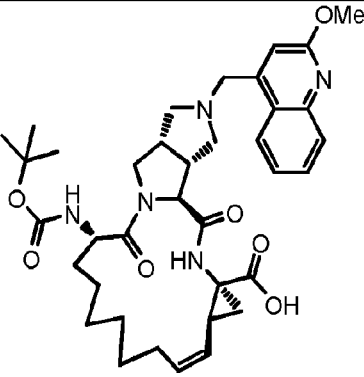
Figure 1:
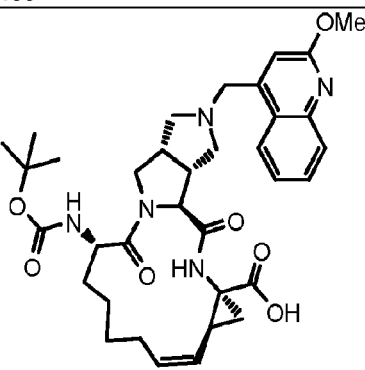
Figure 1:
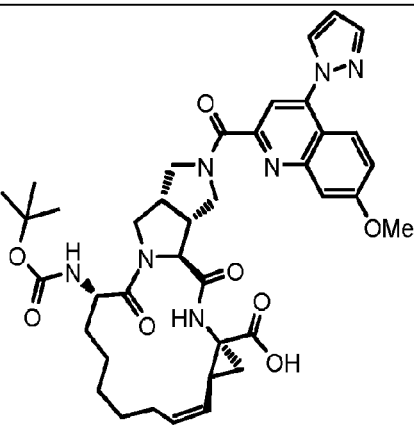
Figure 1:
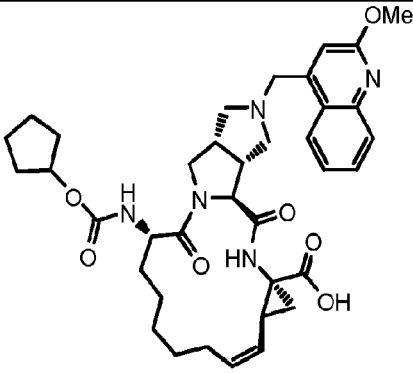
Figure 1:
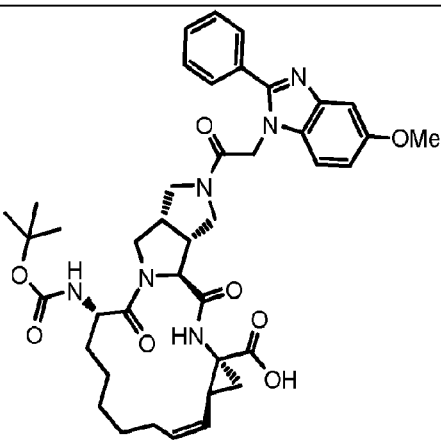
Figure 1:
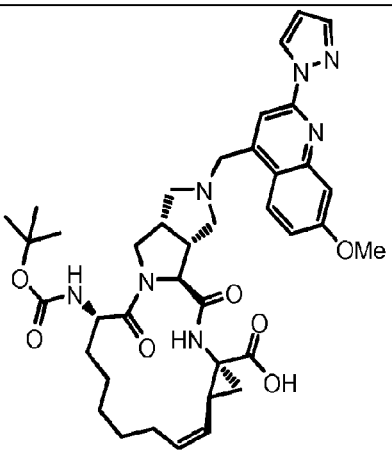
Figure 1:
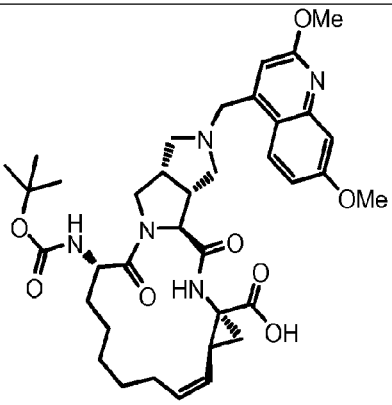
Figure 1:
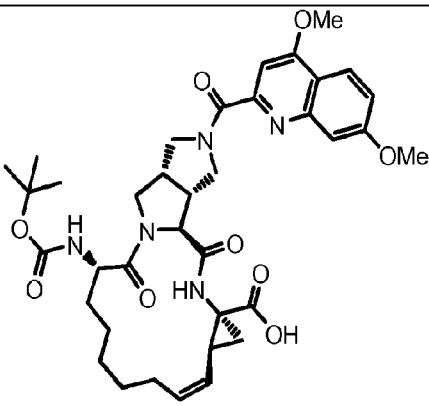
Figure 1:
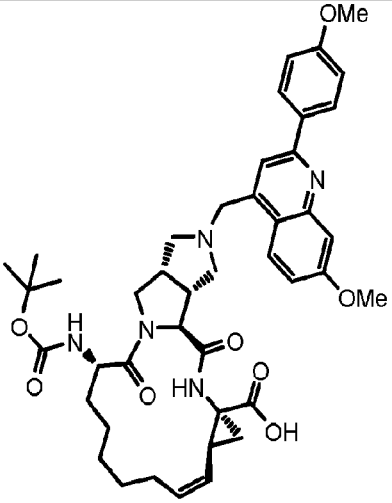
Figure 1:
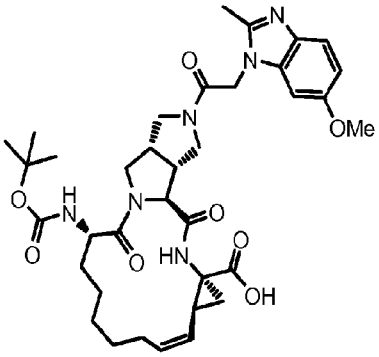
Figure 1:
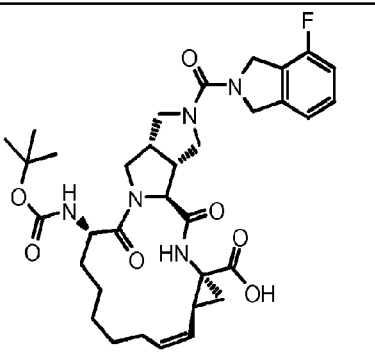
Figure 1:
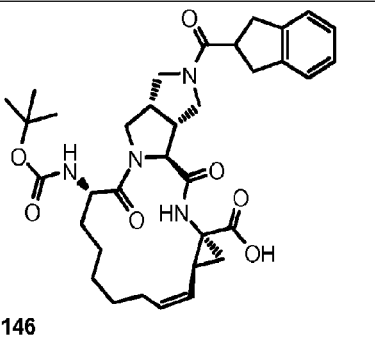
Figure 1:
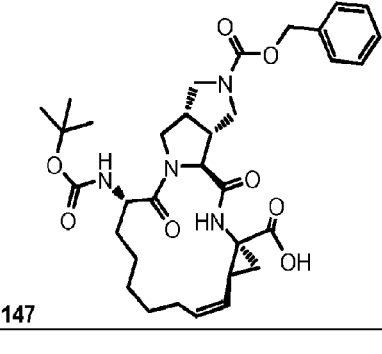
Figure 1:
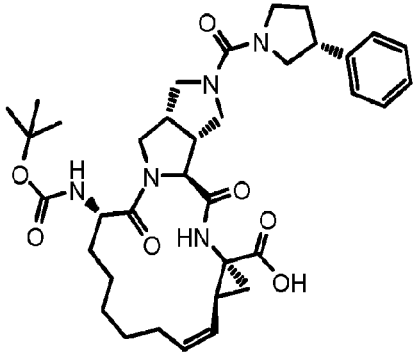
Figure 1:
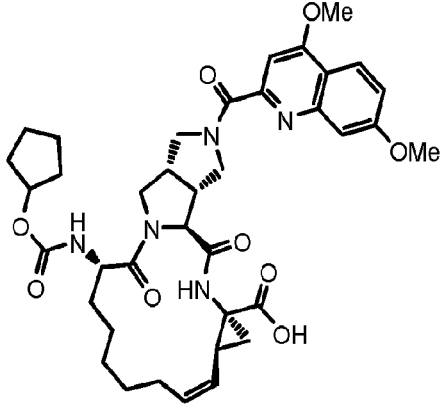
Figure 1:
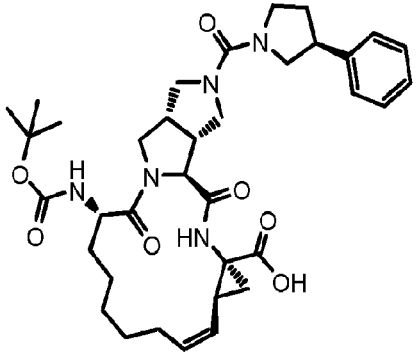
Figure 1:
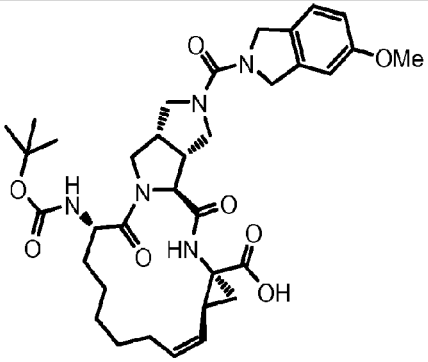
Figure 1:
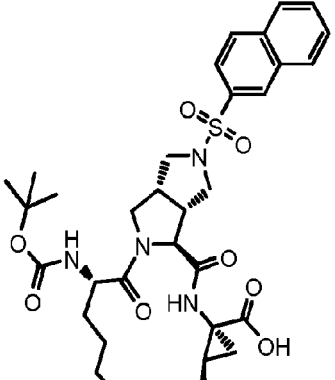
Figure 1:
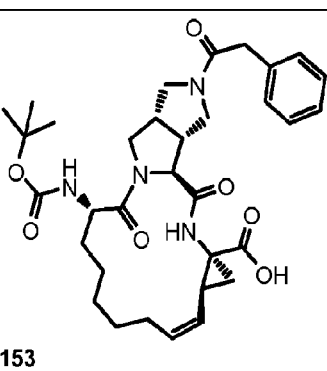
Figure 1:
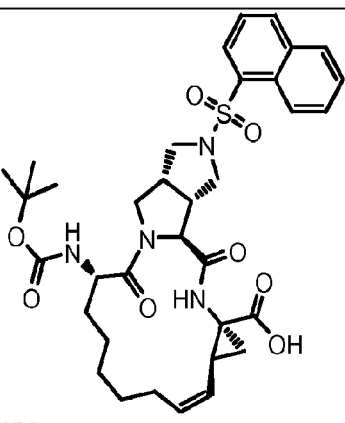
Figure 1:
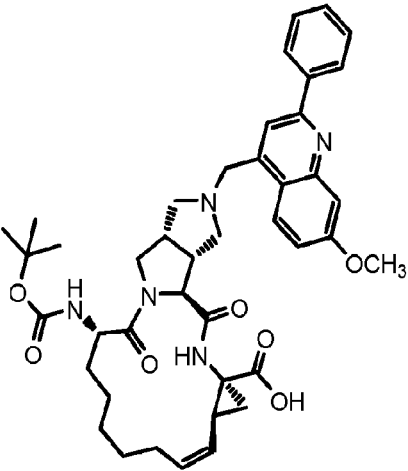
Figure 1:
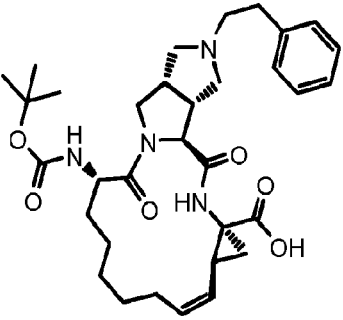
Figure 1:
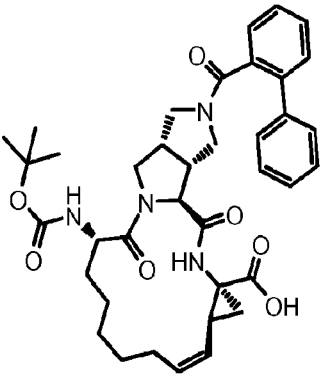
Figure 1:
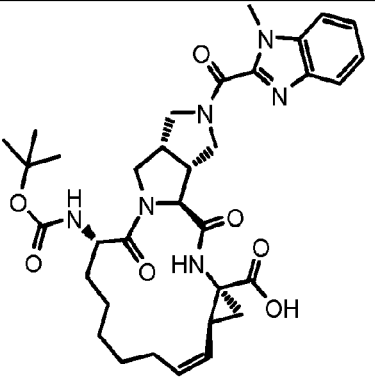
Figure 1:
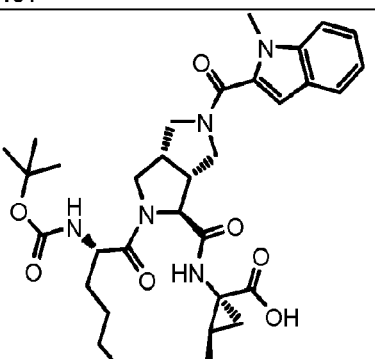
Figure 1:
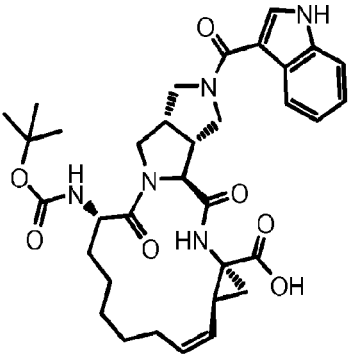
Figure 1:
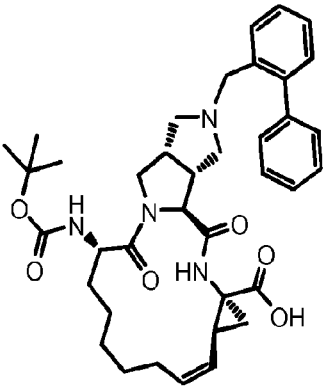
Figure 1:
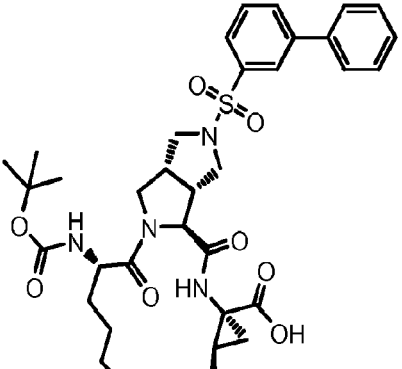
Figure 1:
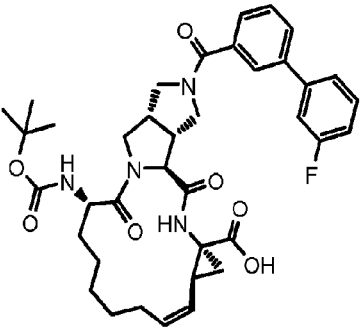
Figure 1:
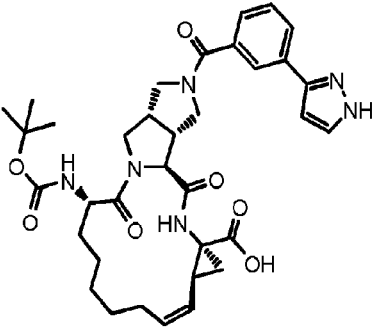
Figure 1:
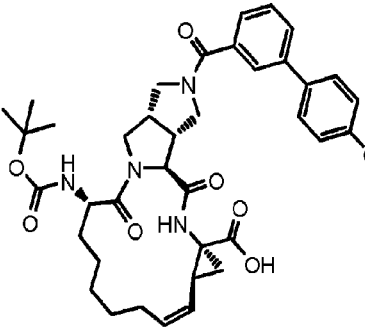
Figure 1:
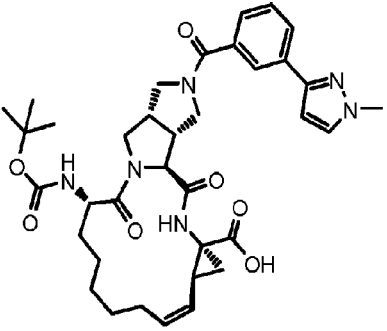
Figure 1:
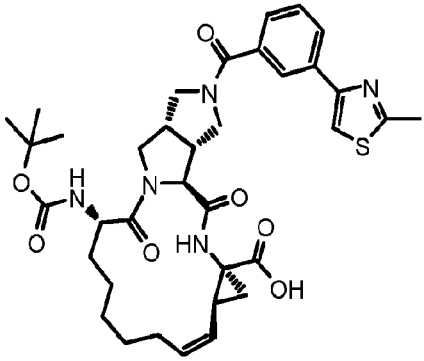
Figure 1:
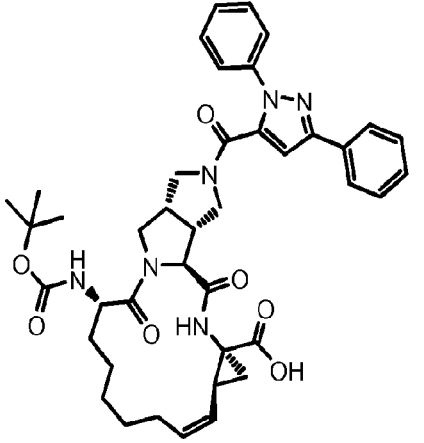
Figure 1:
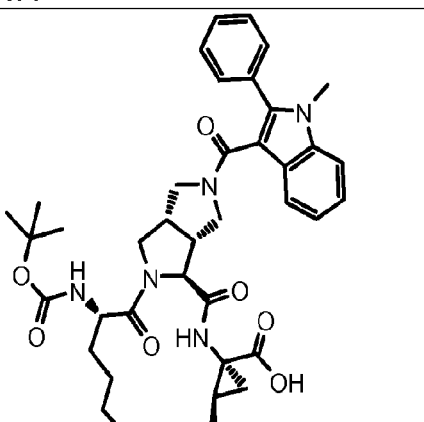
Figure 1:
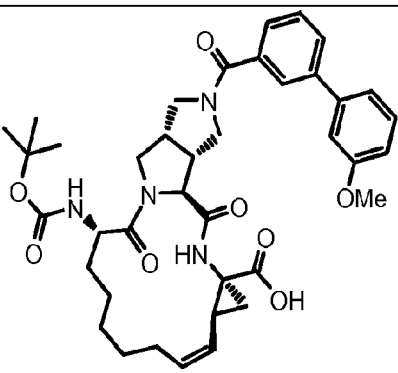
Figure 1:
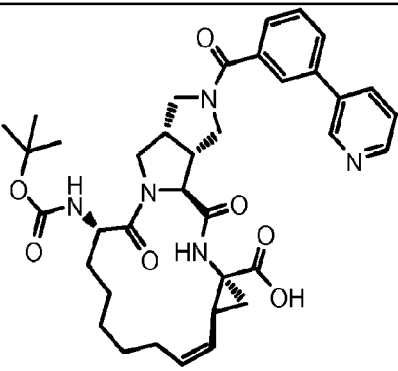
Figure 1:
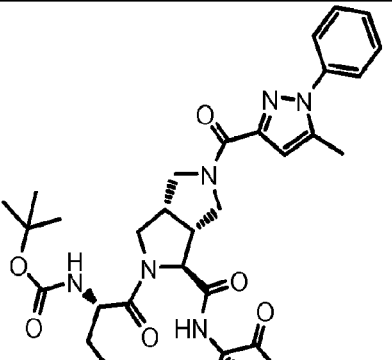
Figure 1:
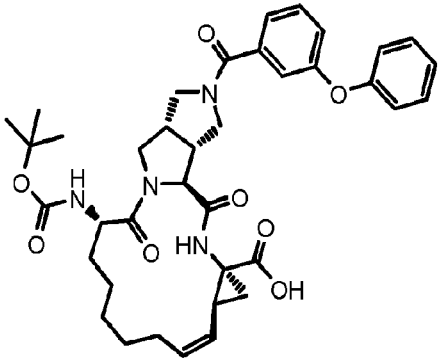
Figure 1:
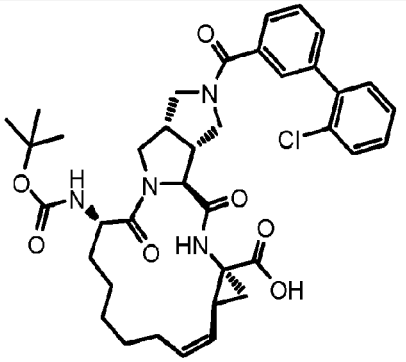
Figure 1:
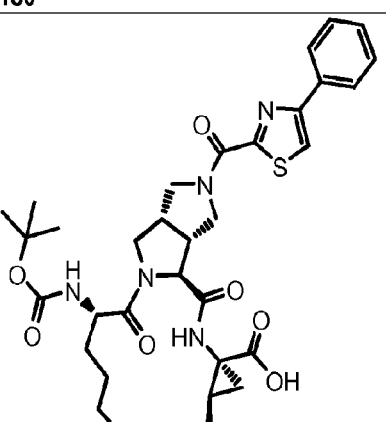
Figure 1:
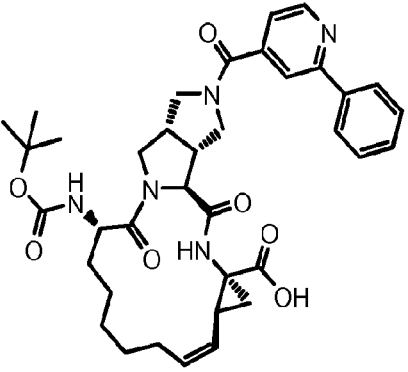
Figure 1:
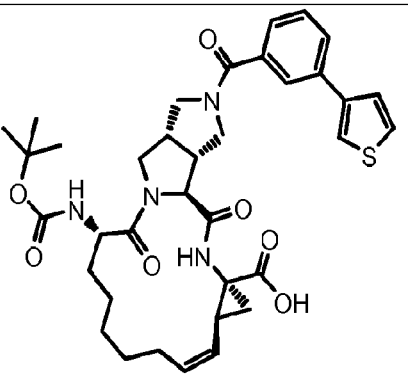
Figure 1:
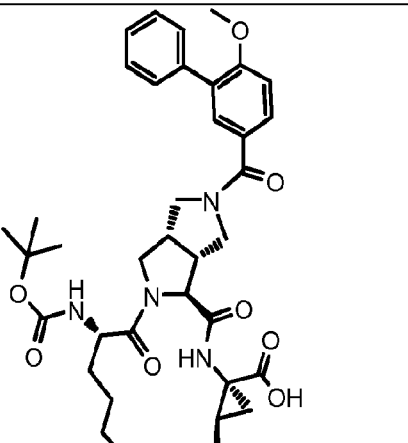
Figure 1:
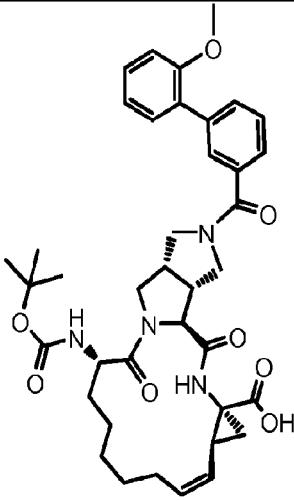
Figure 1:
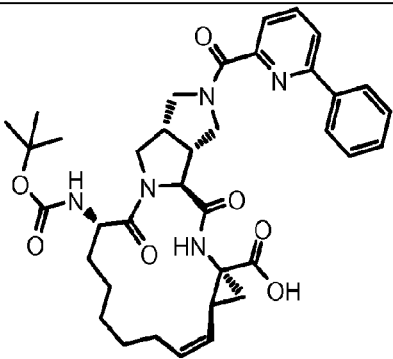
Figure 1:
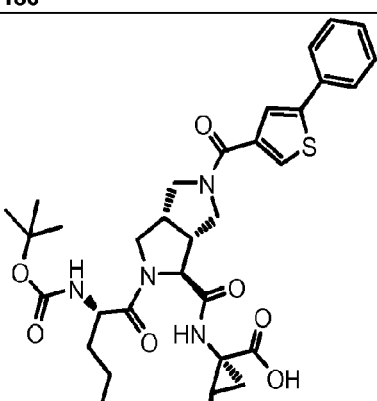
Figure 1:
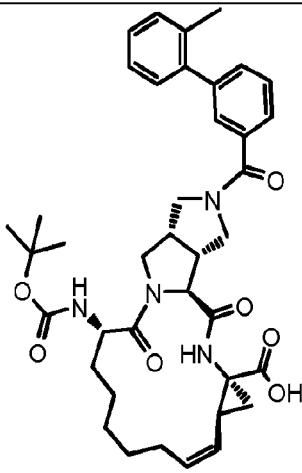
Figure 1:
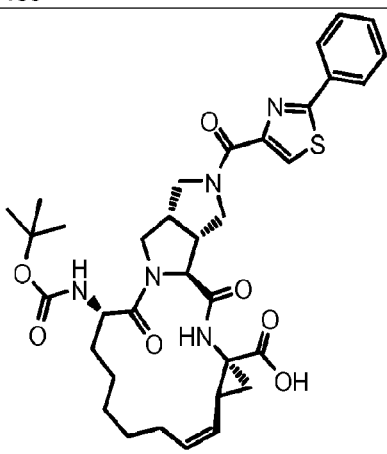
Figure 1:
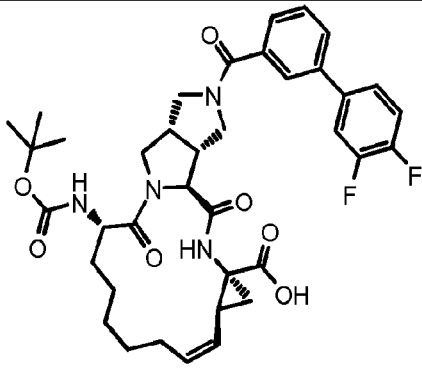
Figure 1:
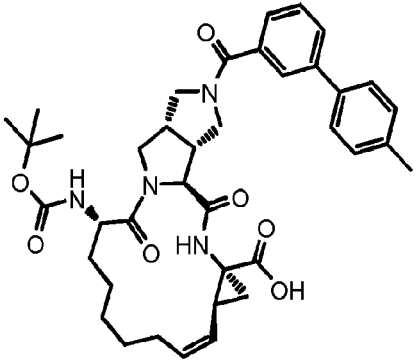
Figure 1:
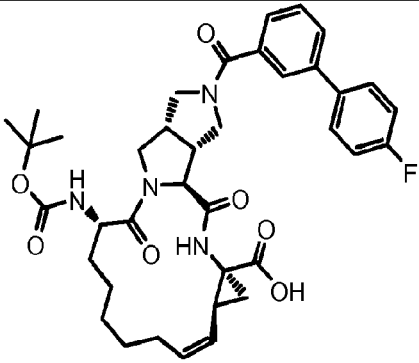
Figure 1:
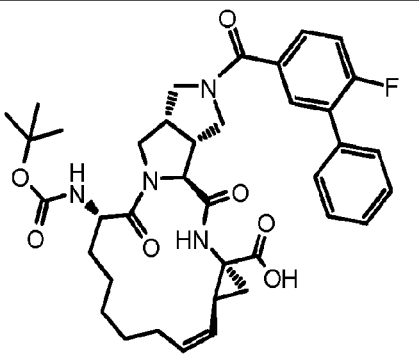
Figure 1:
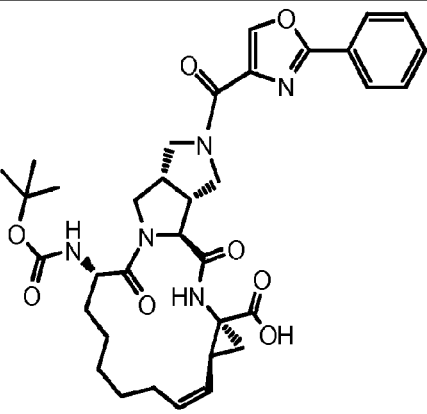
Figure 1:
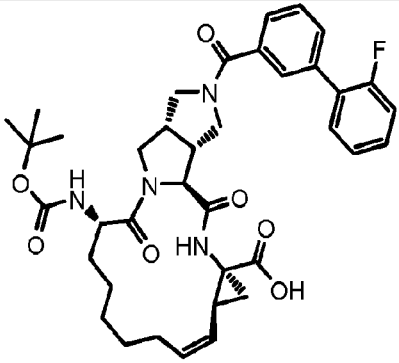
Figure 1:
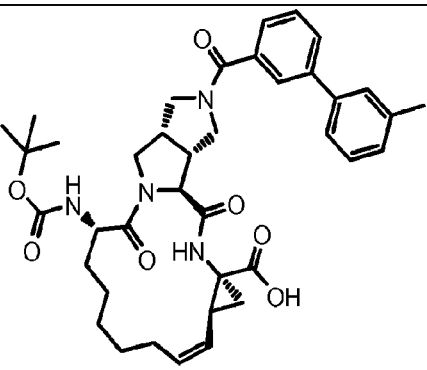
Figure 1:
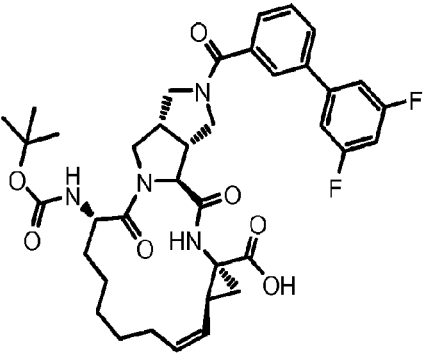
Figure 1:
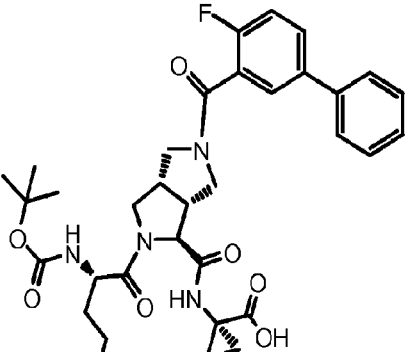
Figure 1:
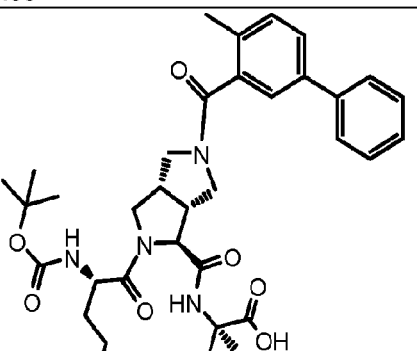
Figure 1:
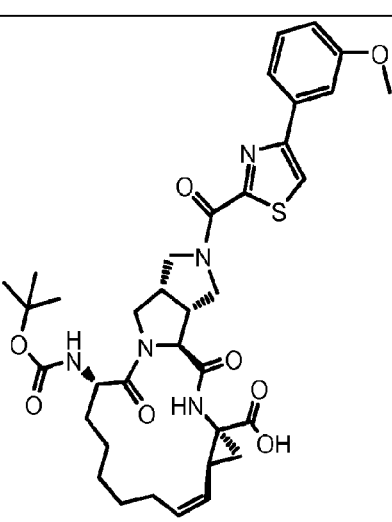
Figure 1:
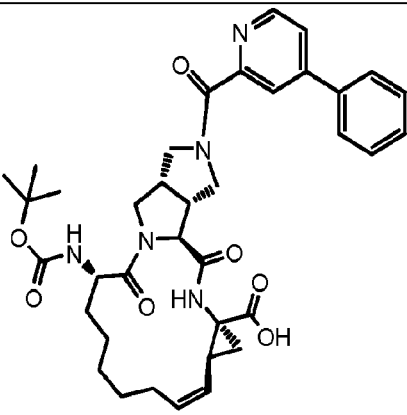
Figure 1:
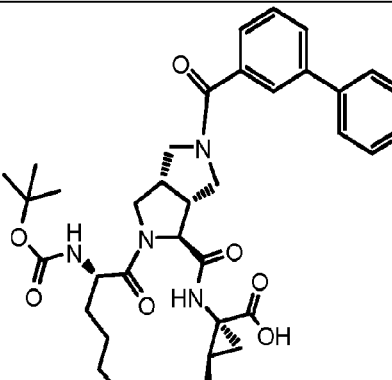
Figure 1:
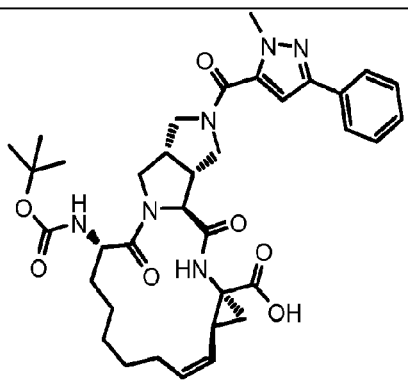
Figure 1:
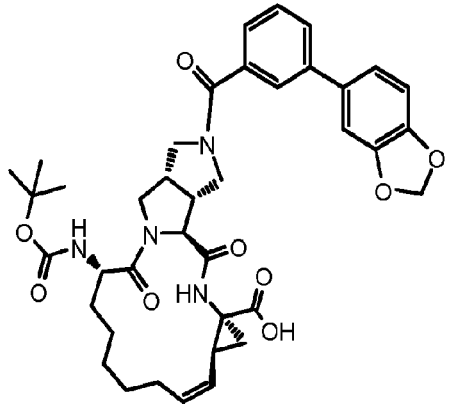
Figure 1:
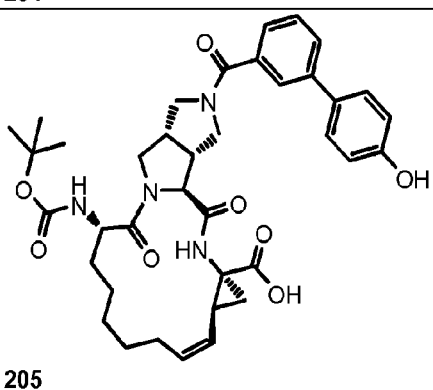
Figure 1:
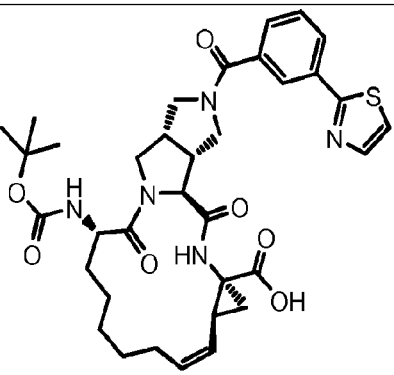
Figure 1:
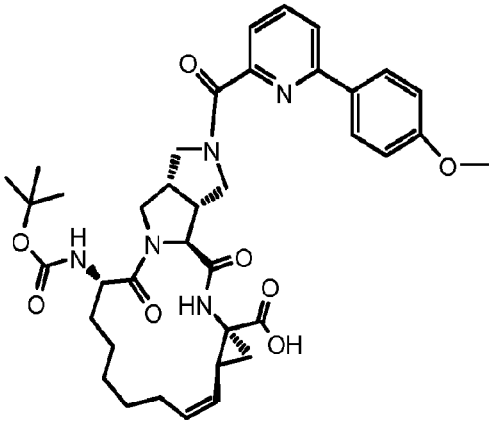
Figure 1:
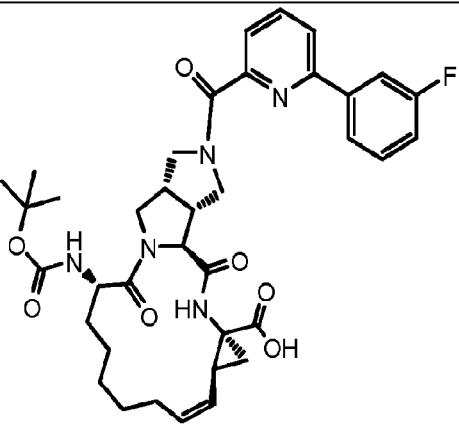
Figure 1:
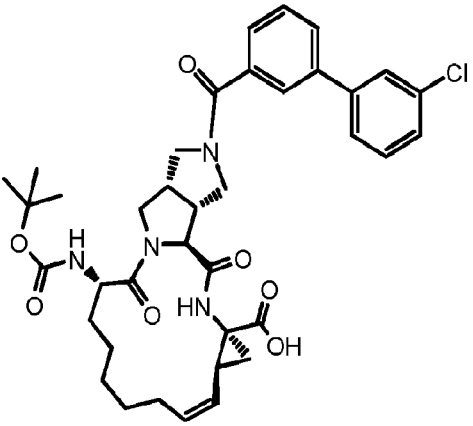
Figure 1:
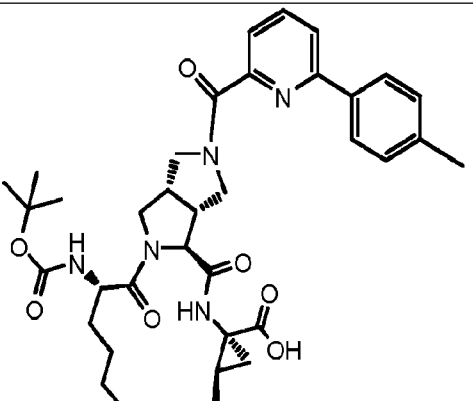
Figure 1:
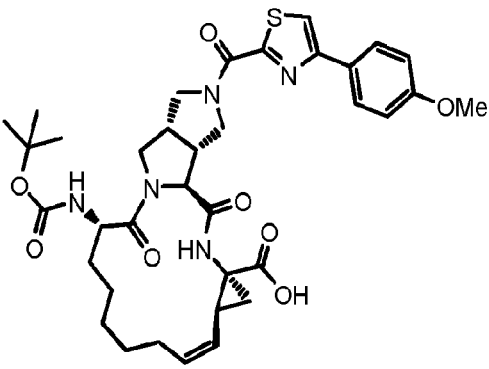
Figure 1:
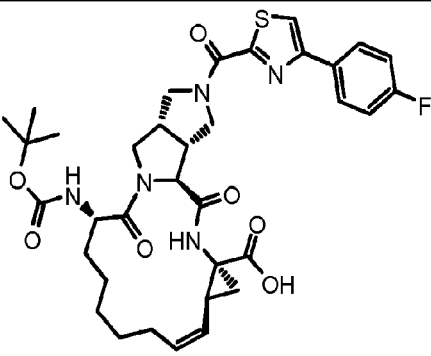
Figure 1:
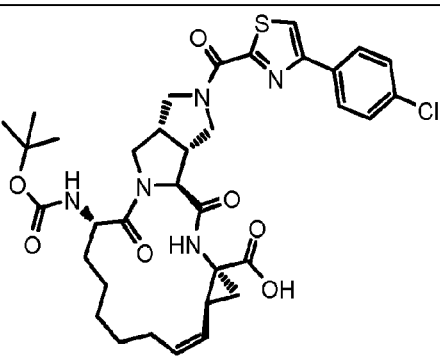
Figure 1:
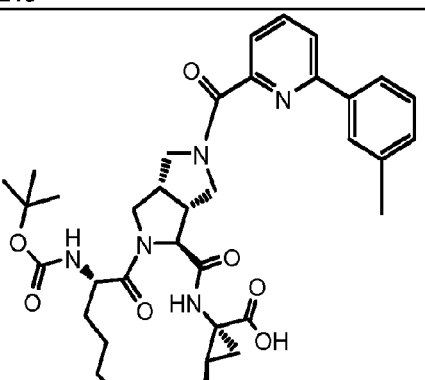
Figure 1:
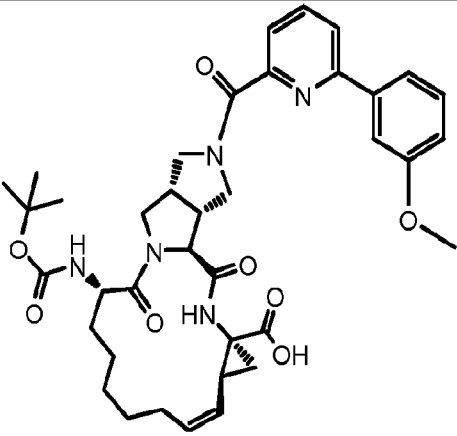
Figure 1:
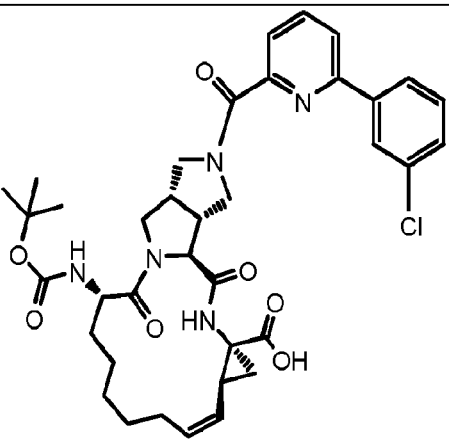
Figure 1:
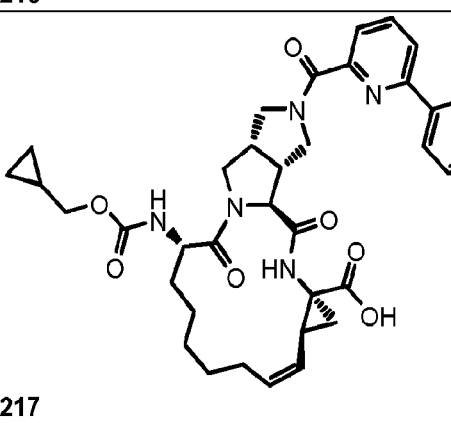

The invention provides compounds that act as novel HCV protease inhibitors and pharmaceutical compositions containing the inhibitors. The invention also provides novel chemical intermediates that are useful for preparing the HCV protease inhibitors. The inhibitors may be used for treating hepatitis C either alone, or in combination with other anti-HCV medicaments. Advantageously, patients treated with the inhibitors may also receive therapeutic doses of other anti-HCV medicaments such as viral polymerase inhibitors, HCV entry inhibitors, HCV replicase inhibitors, HCV helicase inhibitors, HCV NS51 inhibitors, RNAi molecules targeting viral gene expression, ribavarin, pegylated interferon and the like.

The applicants have found that compounds having the general formula I are potent inhibitors of the HCV protease and are effective at inhibiting replication of the hepatitis C virus:

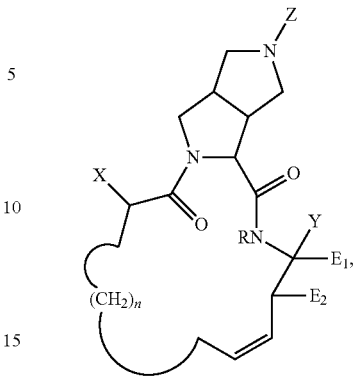

In this structure, Z may be hydrogen, a protecting group that can be selectively removed under the conditions of organic synthesis, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted heterocycloalkyl, optionally substituted $C_3$-$C_8$ cycloalkyl, optionally substituted $C_4$-$C_8$ cycloalkenyl, optionally substituted heterocyclo, optionally substituted heteroaryl, CONRR, COOR, COR3, $SO_2R3$, SOR3, $SO_2NRR$, —PO(NRR)R3, or PO(OR)R3

X may be —NRR2, —OR, —$NRP^1$ wherein $P^1$ is a protecting group that can be selectively removed under the conditions of organic synthesis, optionally substituted $C_1$-$C_{12}$ alkyl, optionally substituted $C_3$-$C_7$ cycloalkyl, optionally substituted $C_2$-$C_{12}$ alkenyl, optionally substituted $C_4$-$C_7$ cycloalkenyl, or X is a moiety selected from the group consisting of

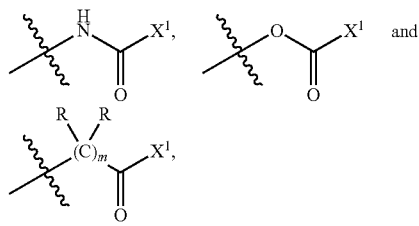

where $X^1$ is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, OR, or —NRR.

$E_1$ and $E_2$ are H, or $E_1$ and $E_2$ together form a 3 to 6-membered optionally substituted saturated or unsaturated carbocylic ring.

Y is COOH, COOR, CONHR, —COCONHR, $CONHSO_2R$, $CONH(SO_2)NRR$, $CONHP(O)(OR)_2$, or CONHP(O)(OR)(NRR);

each R independently is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, or optionally substituted heteroaryl, or R and R together form a 5-7-membered carbocyclic ring, fused to an aryl or heteroaryl ring, where the said aryl or heteroaryl ring optionally is substituted by up to 3 R3 moieties, RR2 is H, —COOR, CONRR, COR, SO₂R, SOR, or SO₂NRR and R3 independently is selected from the group consisting of C₁-C₁₂ alkyl, C₂-C₁₂ alkenyl, C₂-C₁₂ alkynyl, C₃-C₈ cycloalkyl, C₄-C₈ cycloalkenyl, aryl, heteroaryl, and heterocyclo, each optionally substituted by up to three substitutents independently selected from the group consisting of optionally substituted C₁-C₁₂ alkyl, optionally substituted C₂-C₁₂ alkenyl, optionally substituted C₂-C₁₂ alkynyl, optionally substituted C₃-C₈ cycloalkyl, optionally substituted C₄-C₈ cycloalkenyl, optionally substituted aryl, optionally substituted heteroaryl, optionally substituted heterocyclo, halo, —OR, —CN, —NO₂, —NRR, —OCF₃, —COOR, CONRR, COR, SO₂R, and SOR.

Advantageously, E₁ and E₂ together form a 3-6 membered carbocylic ring and the compound has the formula:

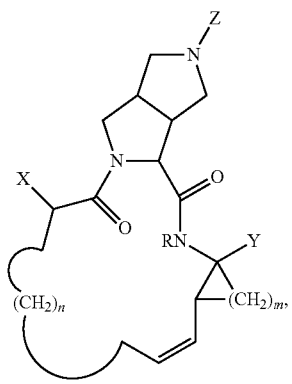

where m is 1-4.

In other embodiments, m is 1 and n is 3, and the compound has the formula

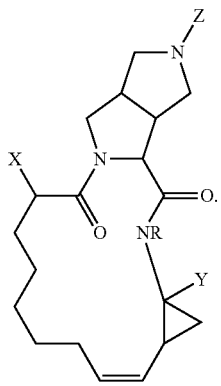

In other embodiments, X is NRCOOR, and in still other embodiments, Y is CO₂H or CONHSO₂R.

Advantageously, Z is COR3, where R3 is as defined above. In specific embodiments, R3 is aryl or heteroaryl, wherein R3 is optionally substituted by up to three substitutents independently selected from the group consisting of optionally substituted C₁-C₁₂ alkyl, optionally substituted C₂-C₁₂ alkenyl, optionally substituted C₂-C₁₂ alkynyl, optionally substituted C₃-C₈ cycloalkyl, optionally substituted C₄-C₈ cycloalkenyl, optionally substituted aryl, optionally substituted heteroaryl, optionally substituted heterocyclo, halo, —OR, —CN, —NO₂, —NRR, —OCF₃, —COOR, CONRR, COR, SO₂R, and SOR.

In other embodiments, R3 may be aryl or heteroaryl, optionally substituted with at least one aryl or heteroaryl group, and wherein said at least one aryl or heteroaryl group optionally is substituted by up to three substitutents independently selected from the group consisting of optionally substituted C₁-C₁₂ alkyl, optionally substituted C₂-C₁₂ alkenyl, optionally substituted C₂-C₁₂ alkynyl, optionally substituted C₃-C₈ cycloalkyl, optionally substituted C₄-C₈ cycloalkenyl, halo, —OR, —CN, —NO₂, —NRR, —OCF₃, —COOR, CONRR, COR, SO₂R, and SOR.

In still other embodiments, R3 is selected from the group consisting of

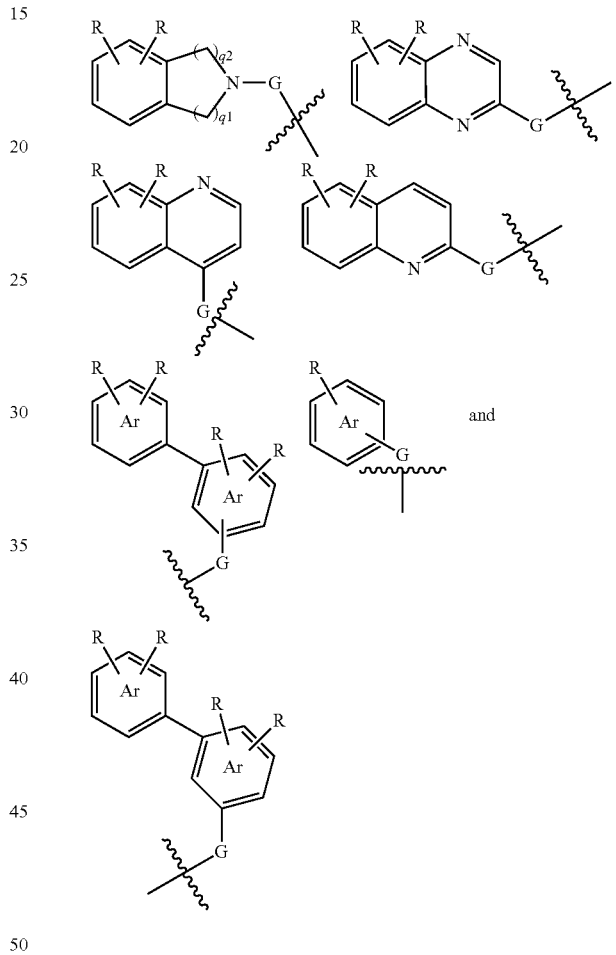

where G is selected from the group consisting of a bond, CH₂—, CHR—, CHRCHR—, CO—, COCHR—, SO₂, —PO(OR)—, PO(NRR)—, NRCO—, and —(CHR)₁₋₃—C(O)N—;

where

is aryl or heteroaryl, and where q1 and q2 are independently 1 or 2.

In other embodiments, R3 may be, for example, selected from the group consisting of:

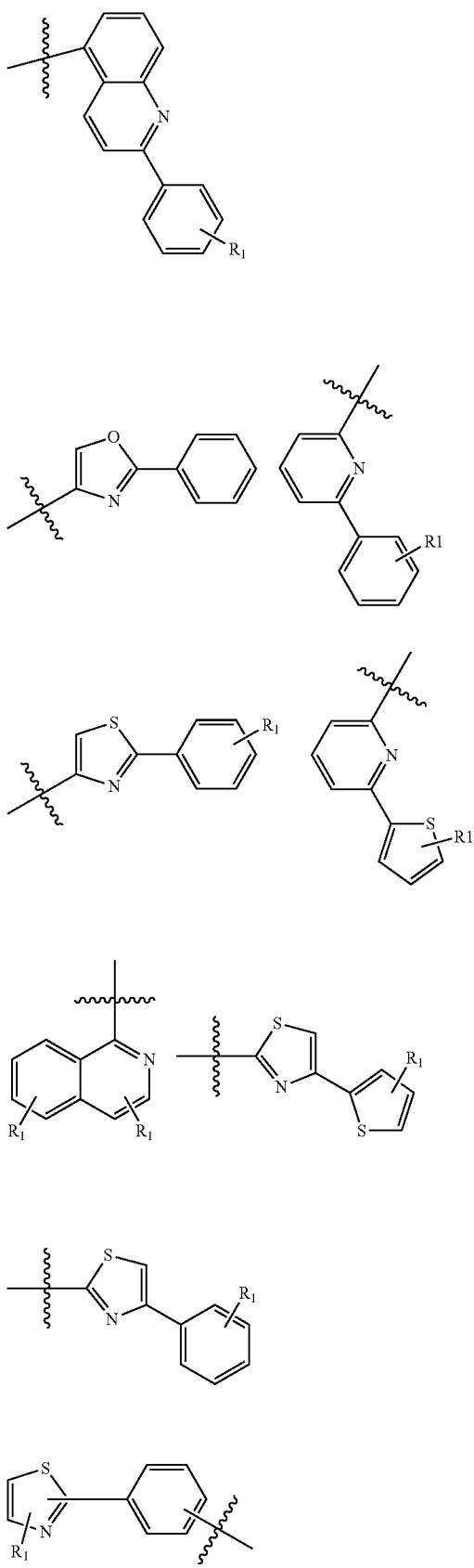
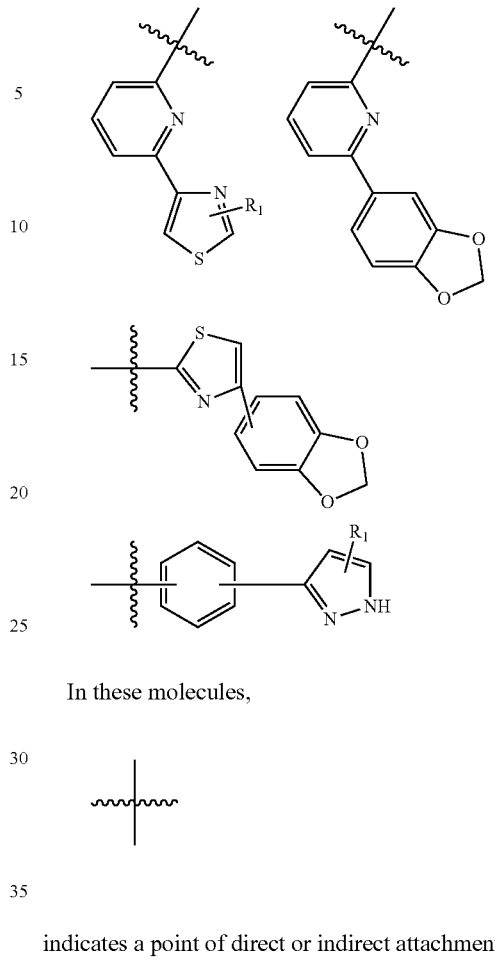

In these molecules, indicates a point of direct or indirect attachment to the fused hexahydro-pyrrolo-pyrrole moiety. Indirect attachment may be via G, as defined above. It will be appreciated that each of these structures are merely exemplary, and that R3 may include, for example, other regioisomers of these structures, and that the ring moieties may be substituted in the manner described above that is permitted by the valencies of the atoms. In addition, it will further be appreciated that the specific points of attachment where the R3 moiety is linked to the fused hexahydro-pyrrolo-pyrrole moiety may be via any atom of R3 that is permitted by normal rules of valency. Further specific examples of R3 moieties are shown in the compounds of FIGS. 1 and 2.

In other specific embodiments, R3 is 4-aryl-2-thiazolyl, 6-aryl-2-pyridyl, 3-aryl-phenyl, 5-aryl-3-pyridyl, 4-aryl-2-pyridyl, 3-thiazolyl-aryl, 4-aryl-3-thienyl, 3-thienylaryl, 2-aryl-4-quinolinyl, 2-aryl-4-thiazolyl, 3-pyridylphenyl, 2-phenyl-3-indolyl, 3-pyrazolylphenyl, or 3-phenyl-2-indolyl.

Figure 2:
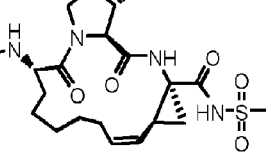
Figure 2:
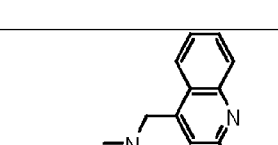
Figure 2:
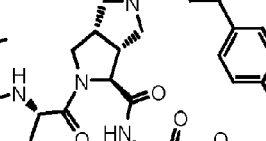
Figure 2:
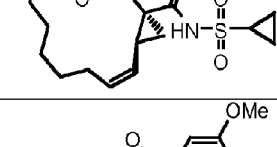
Figure 2:
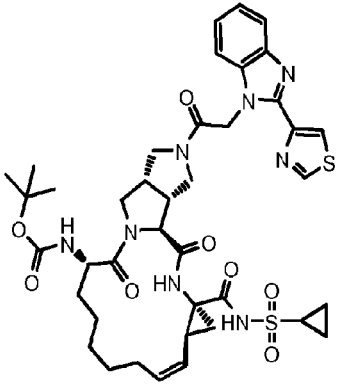
Figure 2:
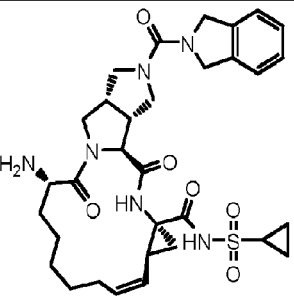
Figure 2:
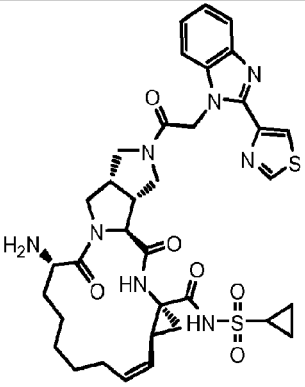
Figure 2:
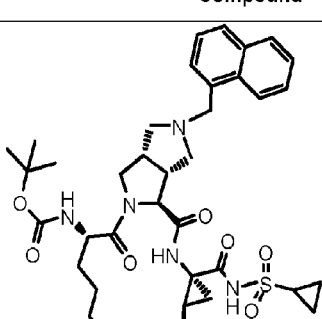
Figure 2:
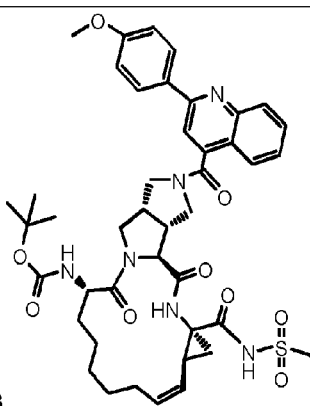
Figure 2:
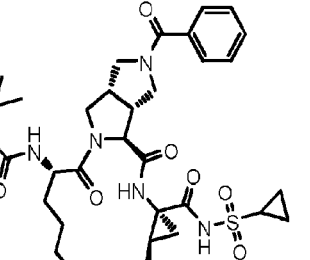
Figure 2:
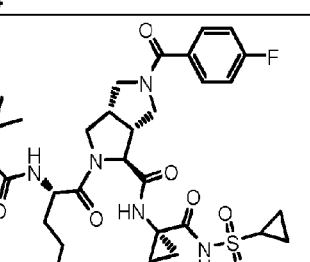
Figure 2:
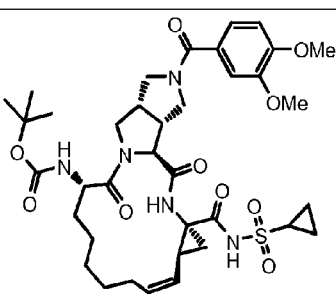
Figure 2:
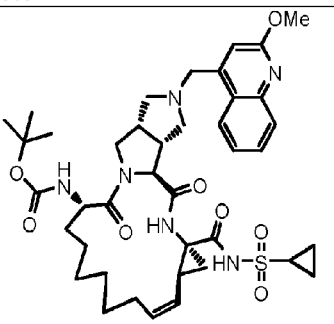
Figure 2:
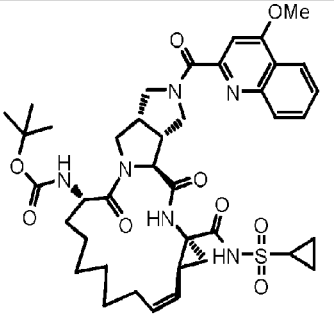
Figure 2:
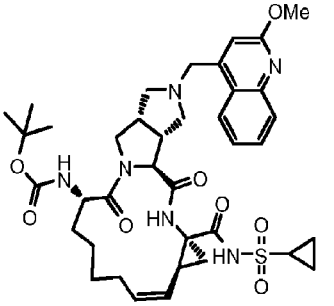
Figure 2:
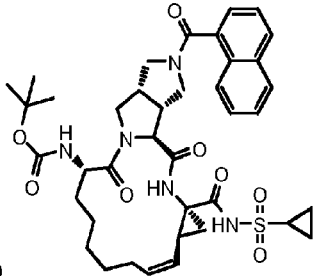
Figure 2:
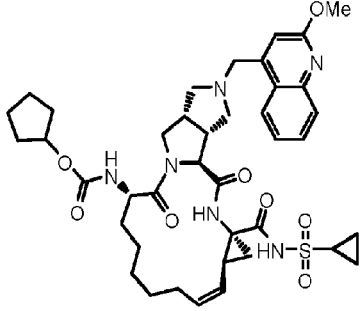
Figure 2:
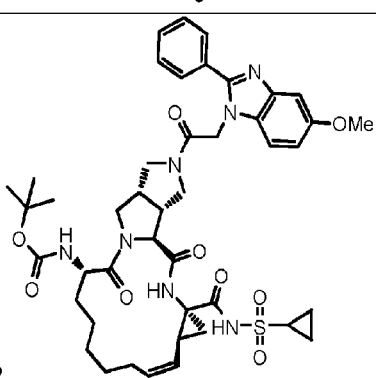
Figure 2:
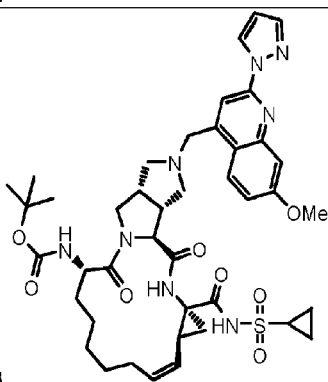
Figure 2:
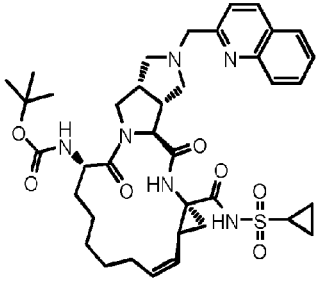
Figure 2:
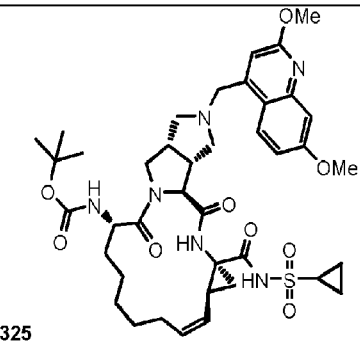
Figure 2:
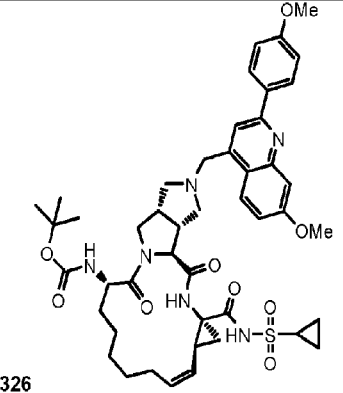
Figure 2:
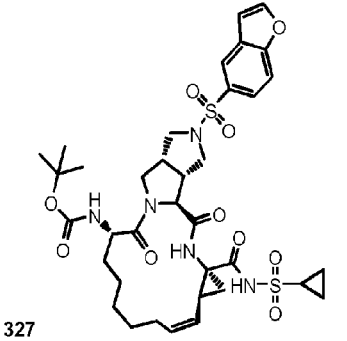
Figure 2:
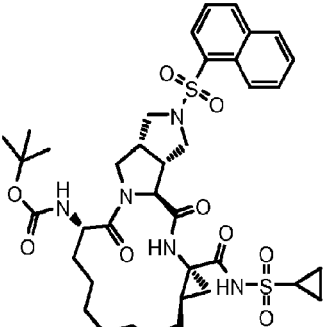
Figure 2:
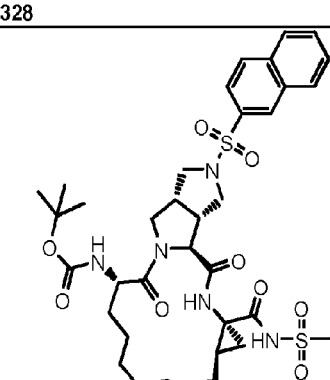
Figure 2:
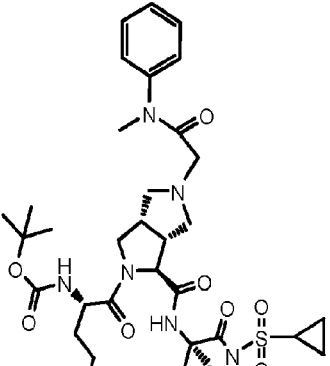
Figure 2:
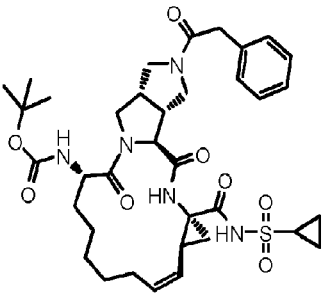
Figure 2:
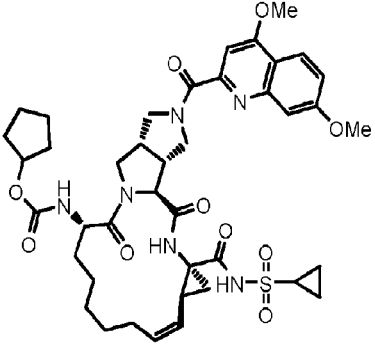
Figure 2:
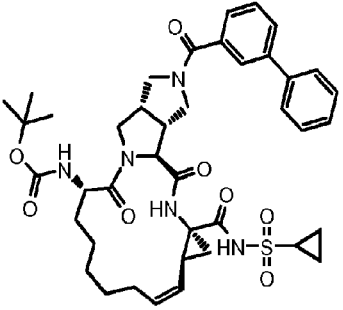
Figure 2:
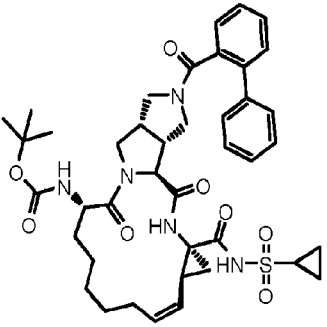
Figure 2:
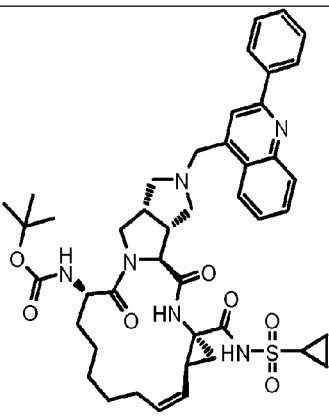
Figure 2:
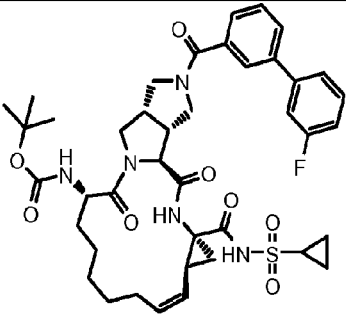
Figure 2:
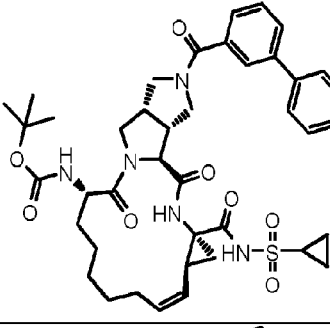
Figure 2:
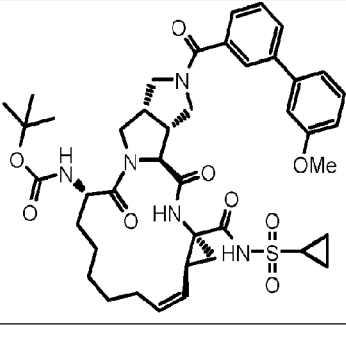
Figure 2:
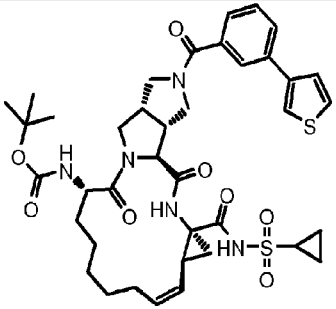
Figure 2:
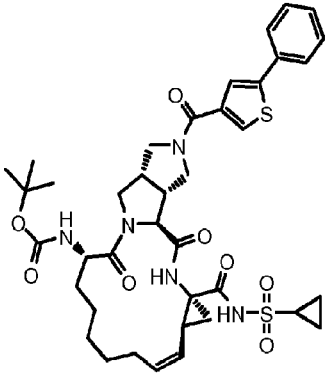
Figure 2:
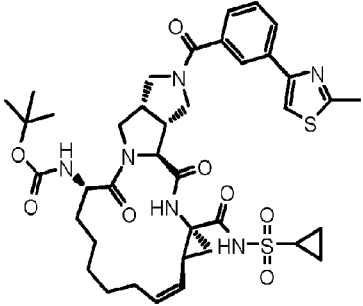
Figure 2:
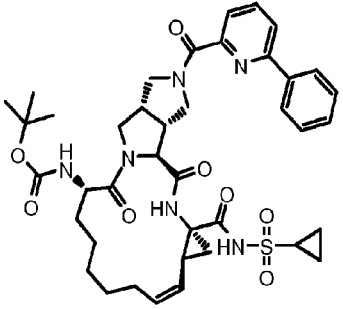
Figure 2:
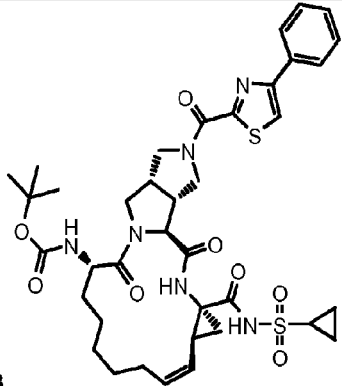
Figure 2:
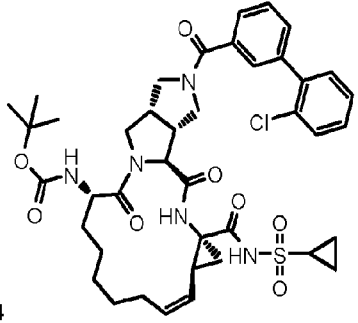
Figure 2:
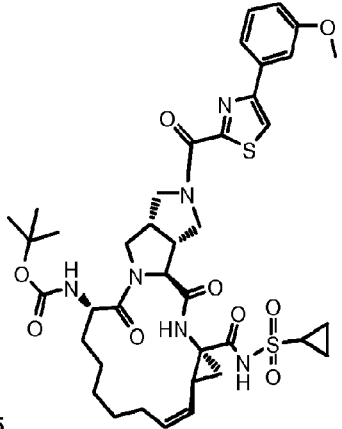
Figure 2:
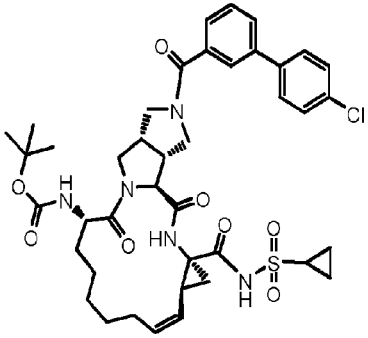
Figure 2:
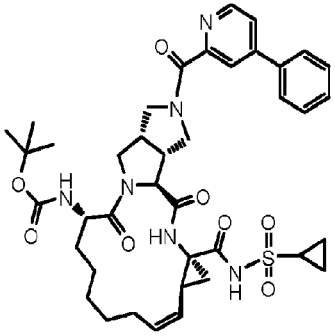
Figure 2:
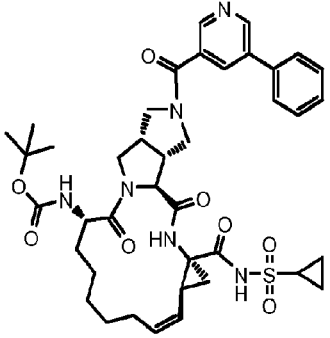
Figure 2:
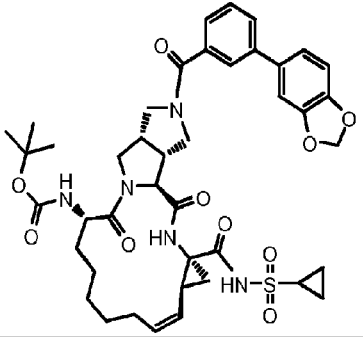
Figure 2:
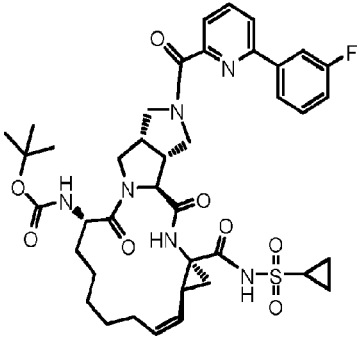
Figure 2:
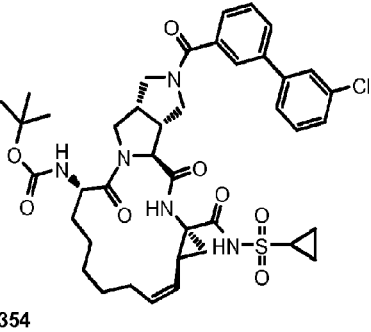
Figure 2:
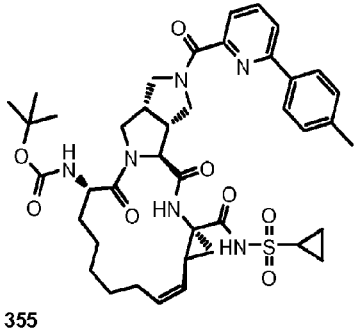
Figure 2:
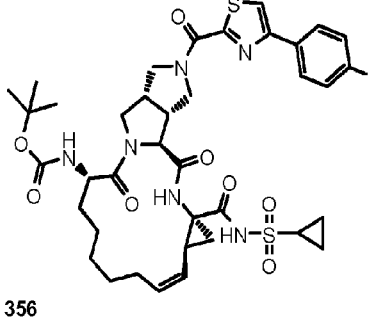
Figure 2:
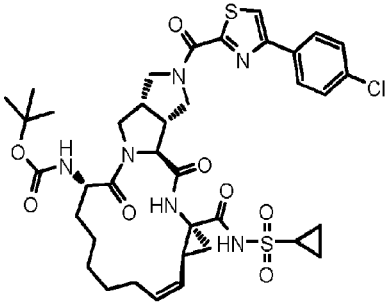
Figure 2:
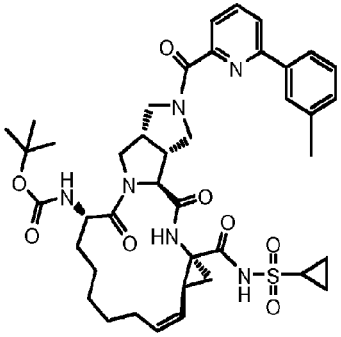
Figure 2:
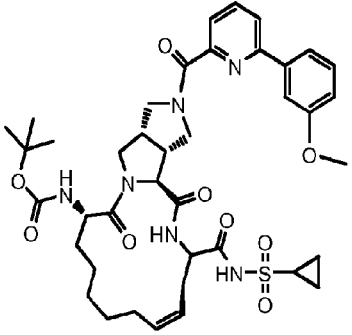
Figure 2:
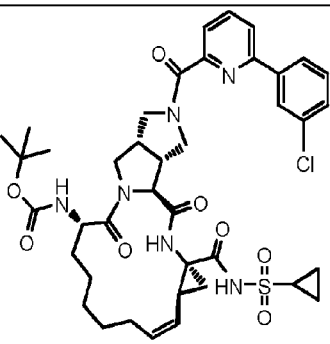
Figure 2:
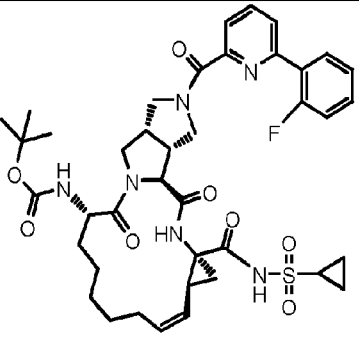
Figure 2:
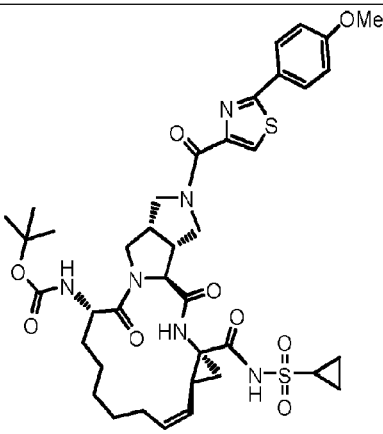
Figure 2:
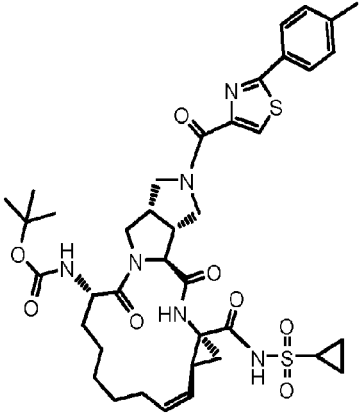
Figure 2:
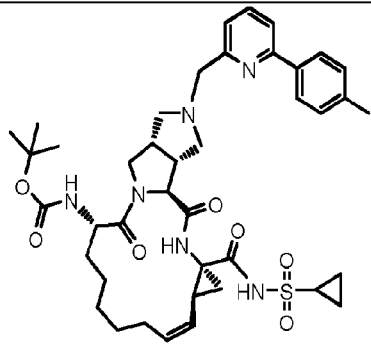
Figure 2:
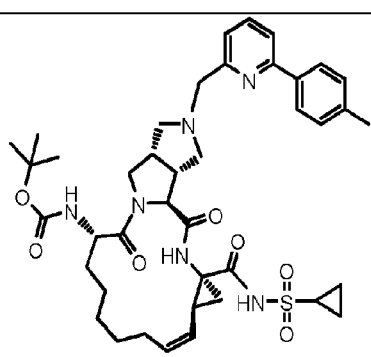
Figure 2:
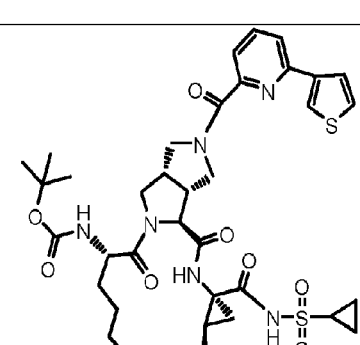
Figure 2:
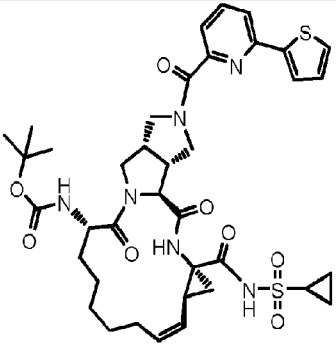
Figure 2:
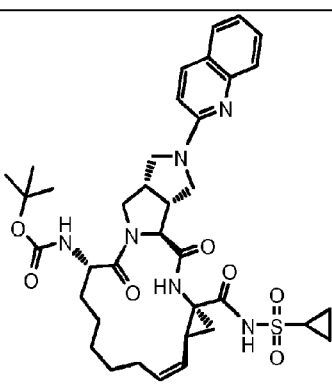
Figure 2:
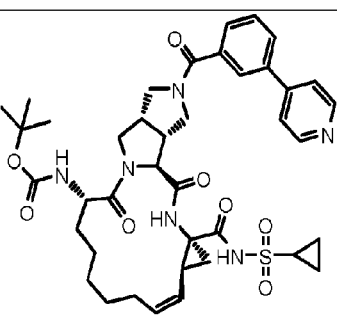
Figure 2:
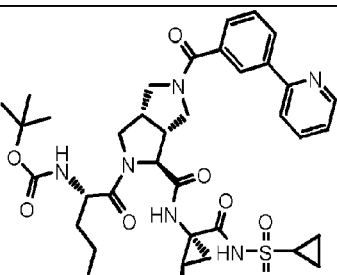
Figure 2:
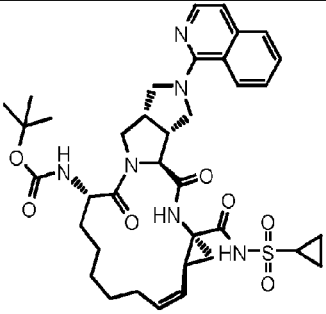
Figure 2:
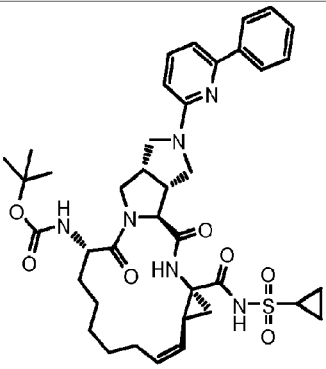
Figure 2:
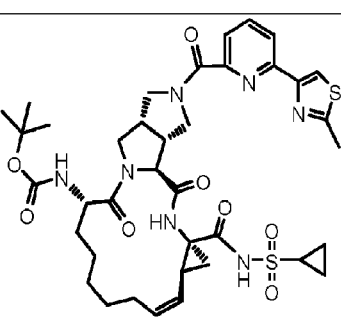
Figure 2:
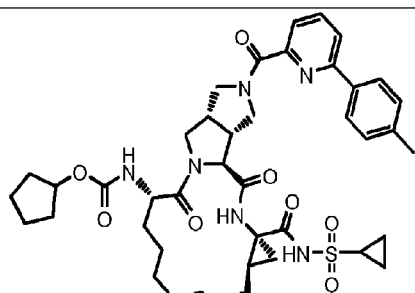
Figure 2:
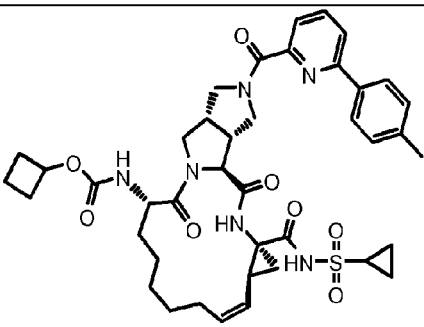
Figure 2:
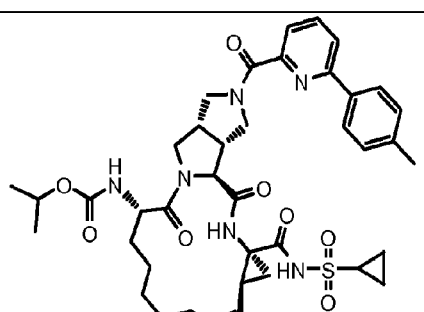
Figure 2:
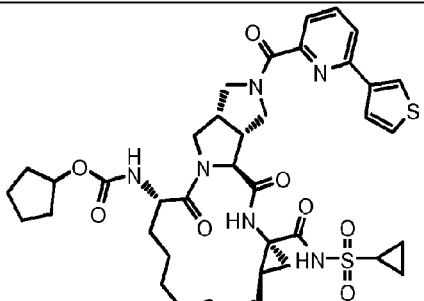
Figure 2:
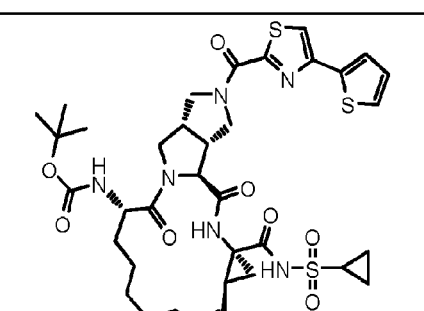
Figure 2:
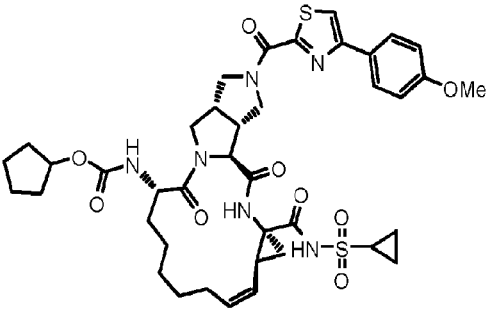
Figure 2:
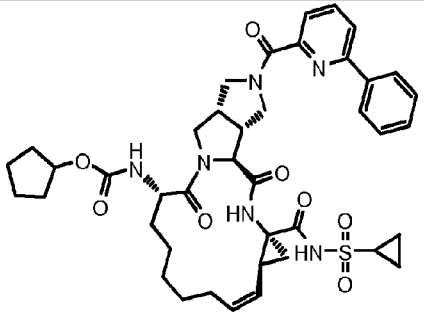
Figure 2:
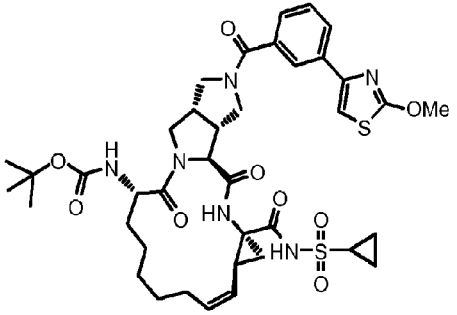
Figure 2:
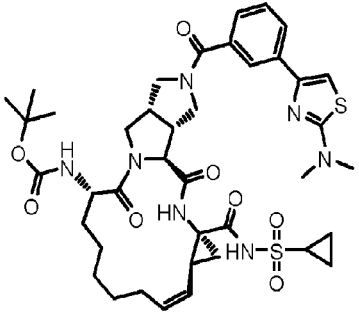
Figure 2:
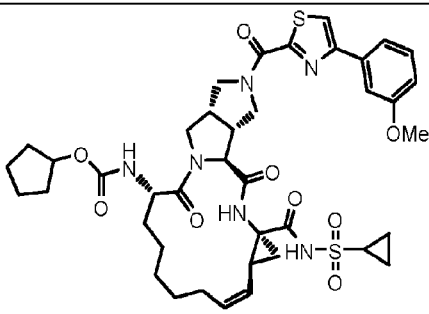
Figure 2:
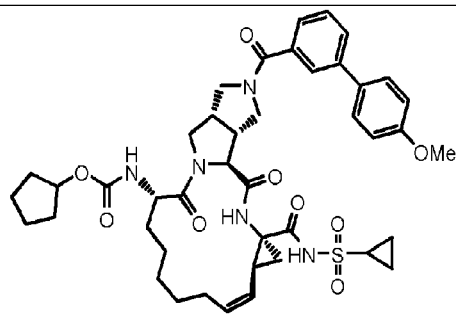
Figure 2:
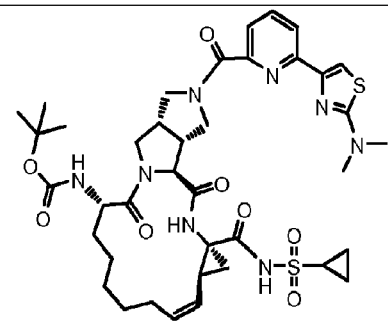
Figure 2:
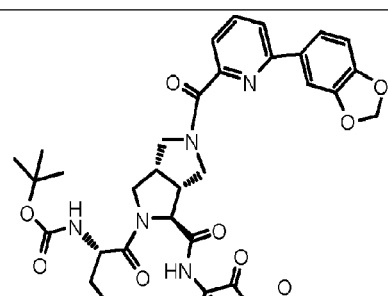
Figure 2:
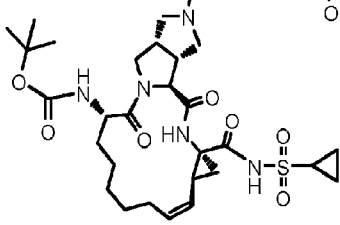
Figure 2:
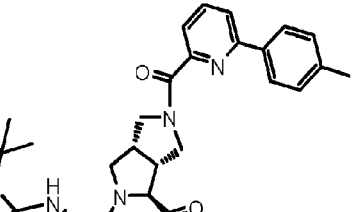
Figure 2:
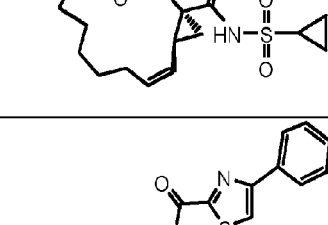
Figure 2:
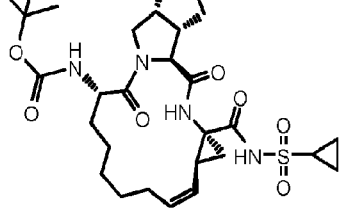
Figure 2:
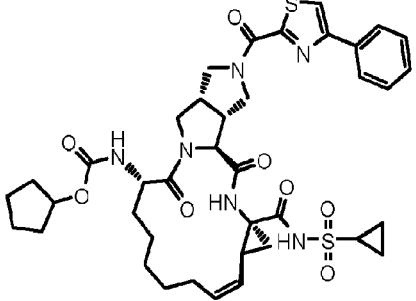
Figure 2:
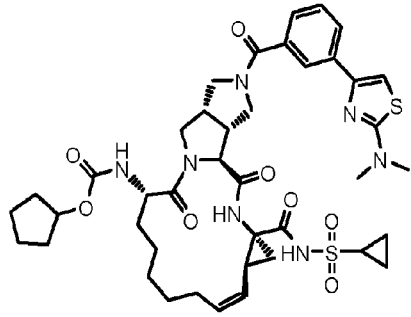
Figure 2:
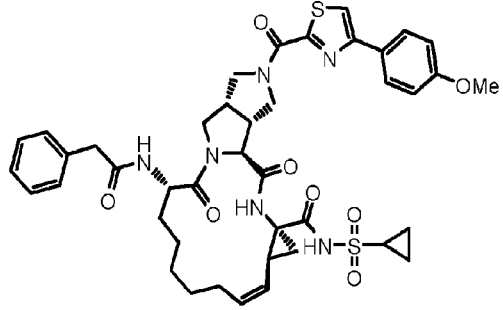
Figure 2:
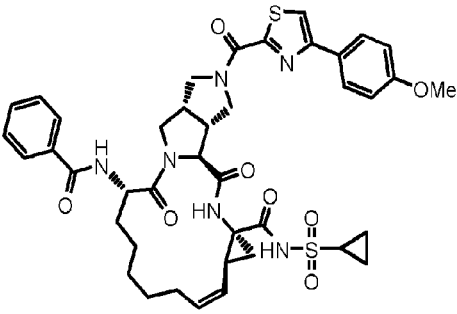
Figure 2:
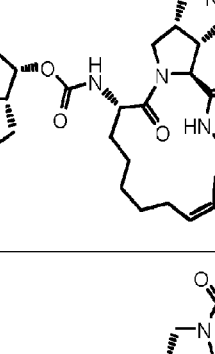
Figure 2:
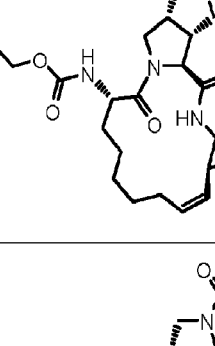
Figure 2:
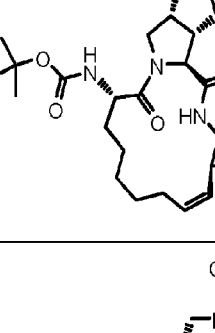
Figure 2:
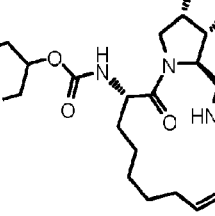
Figure 2:
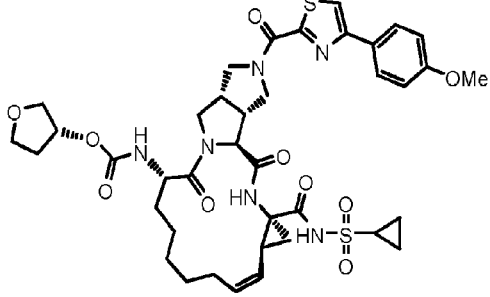
Figure 2:
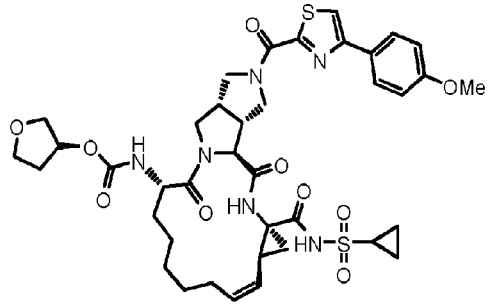
Figure 2:
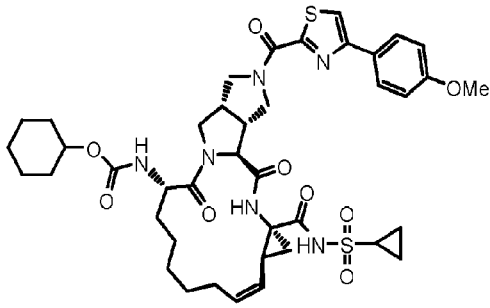
Figure 2:
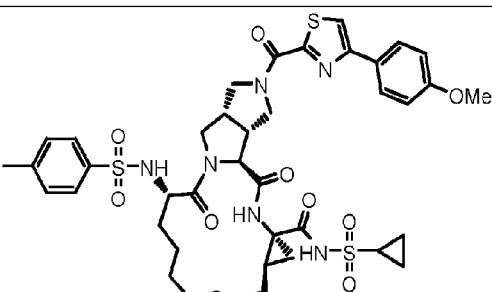
Figure 2:
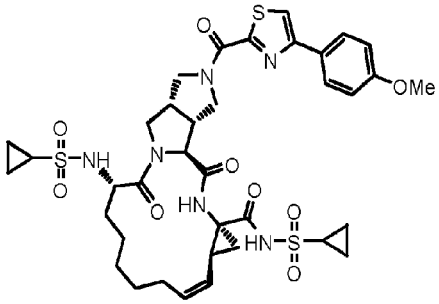
Figure 2:
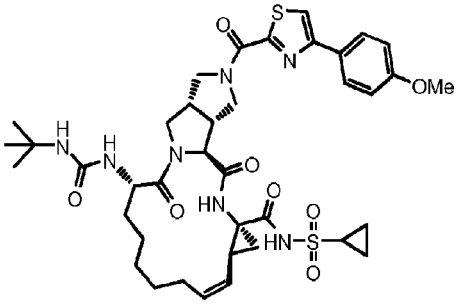
Figure 2:
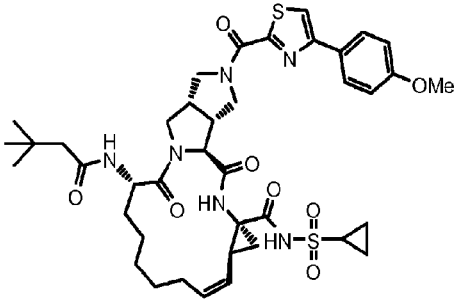
Figure 2:
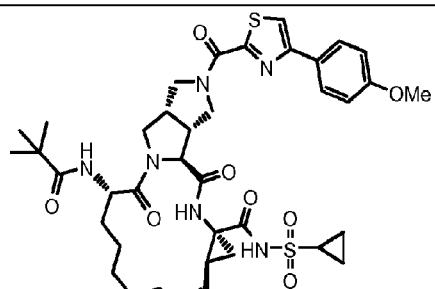
Figure 2:
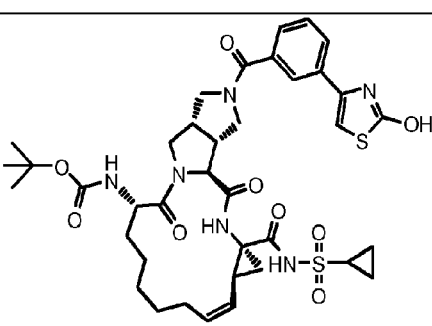
Figure 2:
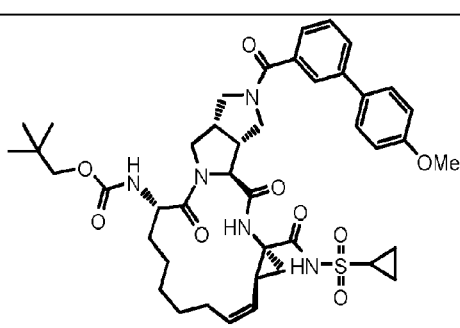
Figure 2:
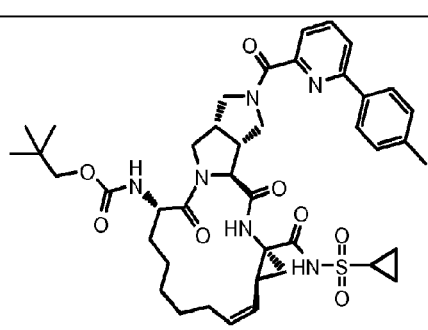
Figure 2:
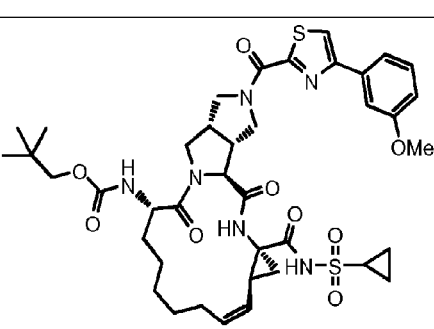
Figure 2:
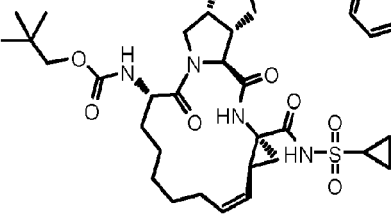
Figure 2:
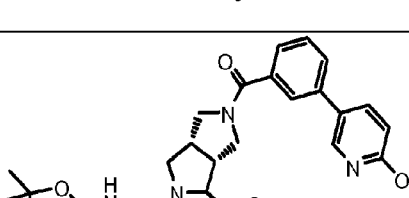
Figure 2:
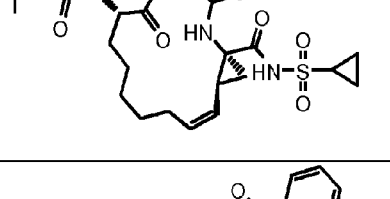
Figure 2:
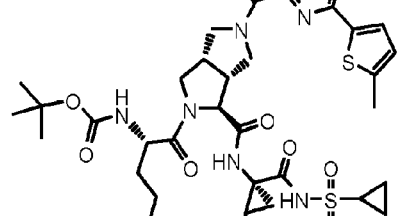
Figure 2:
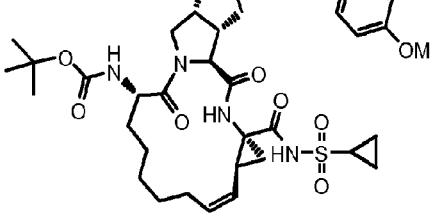
Figure 2:
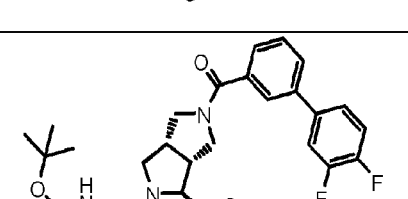
Figure 2:
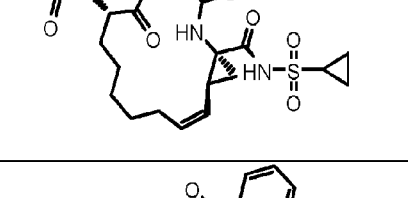
Figure 2:
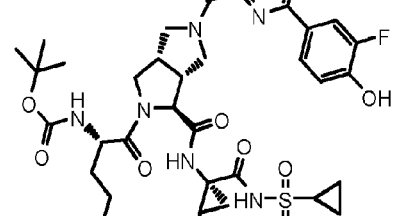
Figure 2:
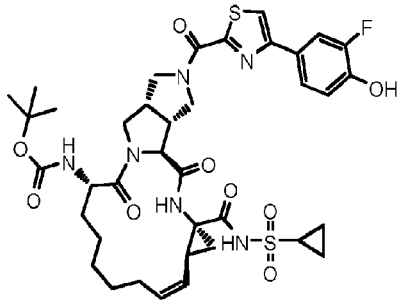
Figure 2:
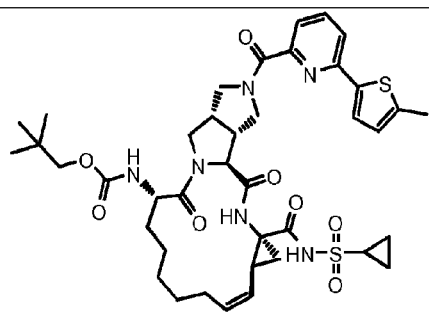
Figure 2:
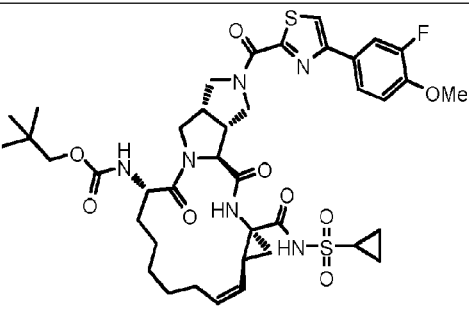
Figure 2:
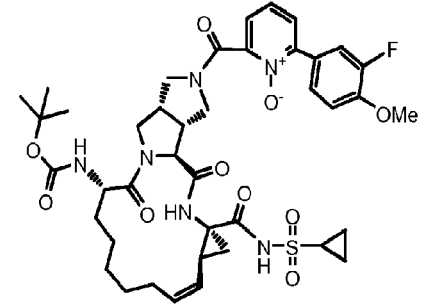
Figure 2:
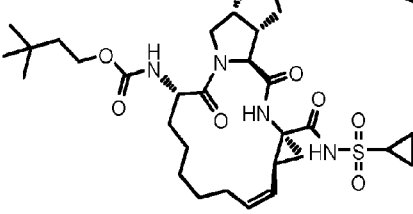
Figure 2:
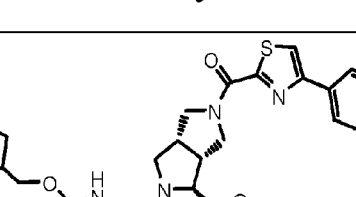
Figure 2:
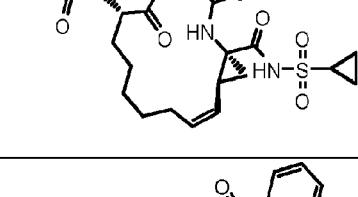
Figure 2:
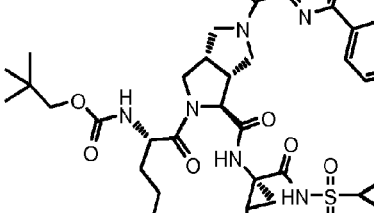
Figure 2:
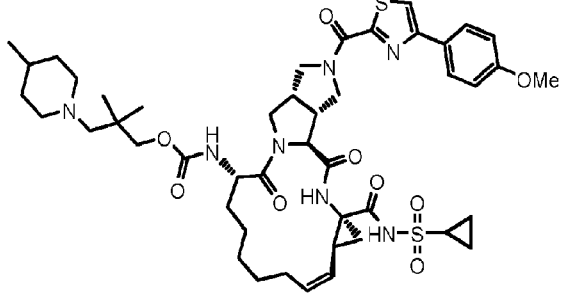
Figure 2:
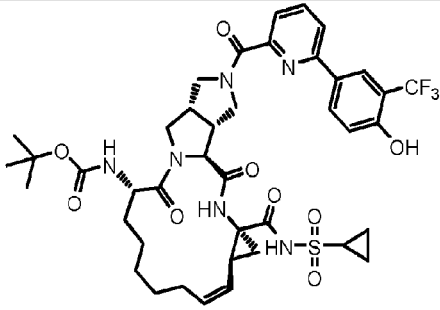
Figure 2:
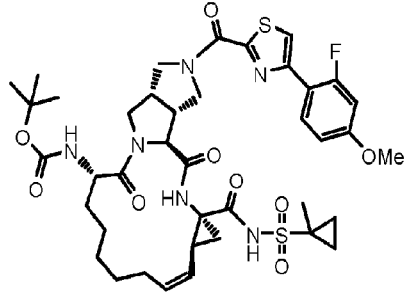
Figure 2:
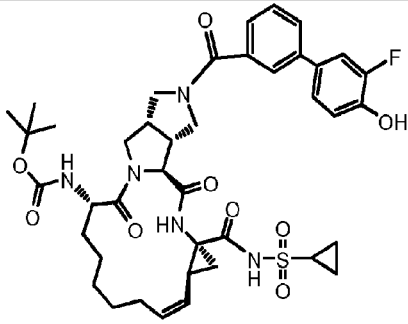
Figure 2:
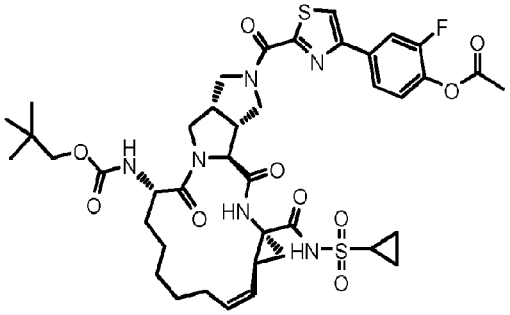
Figure 2:
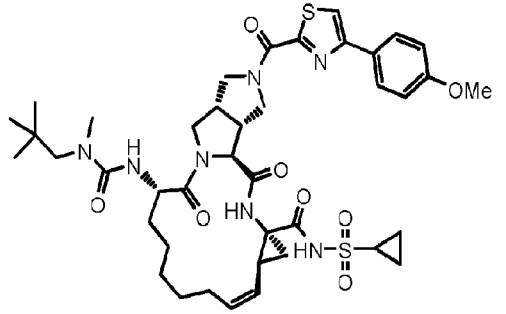
Figure 2:
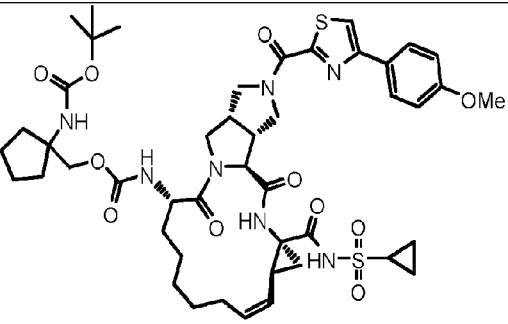
Figure 2:
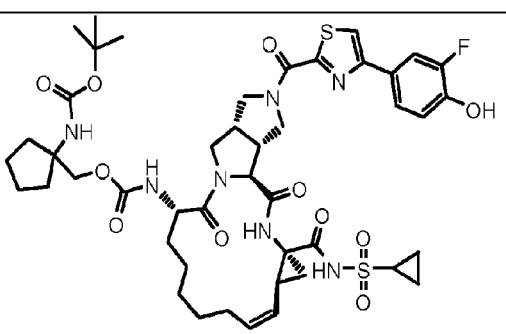
Figure 2:
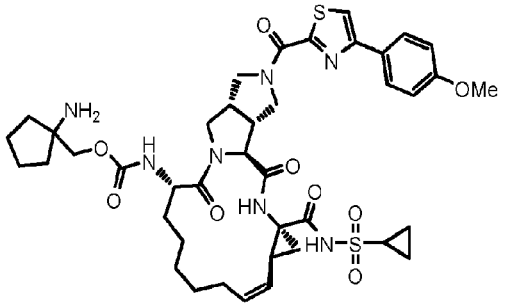
Figure 2:
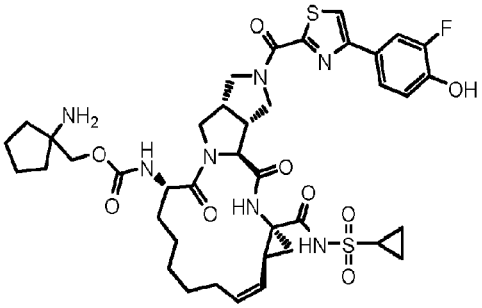
Figure 2:
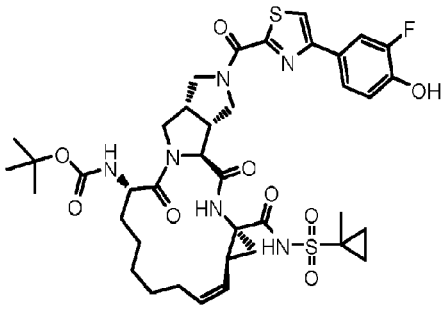
Figure 2:
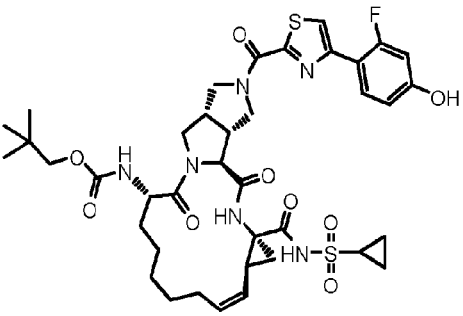
Figure 2:
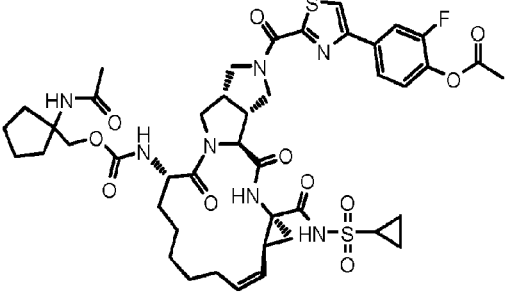
Figure 2:
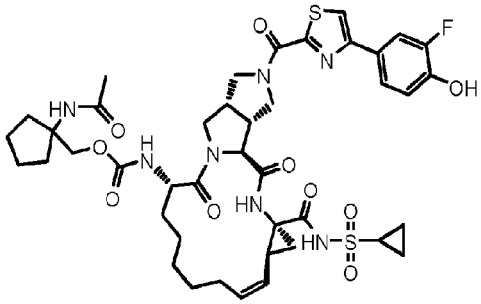
Figure 2:
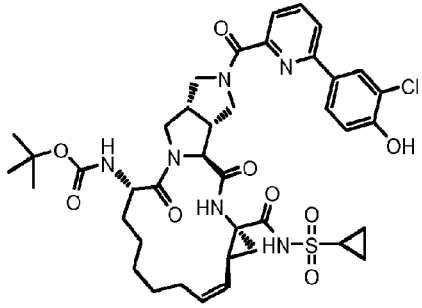
Figure 2:
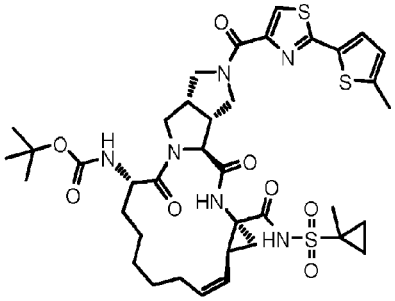
Figure 2:
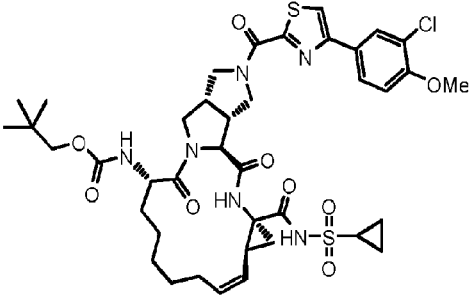
Figure 2:
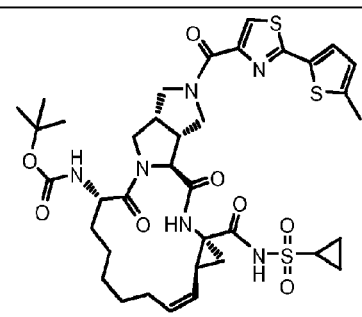
Figure 2:
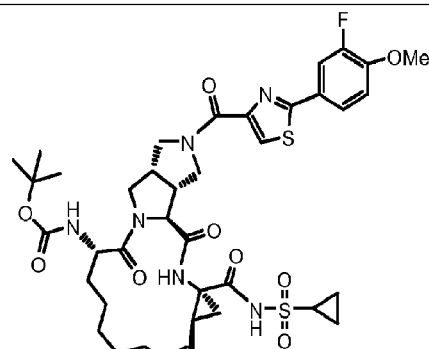
Figure 2:
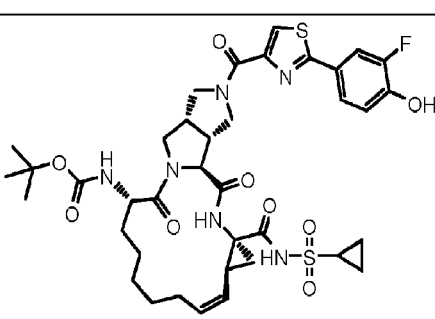
Figure 2:
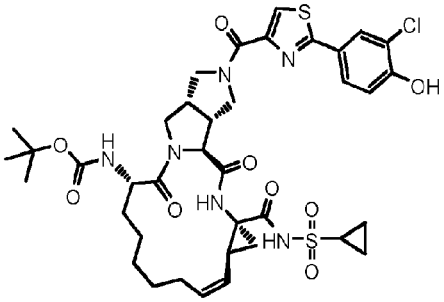
Figure 2:
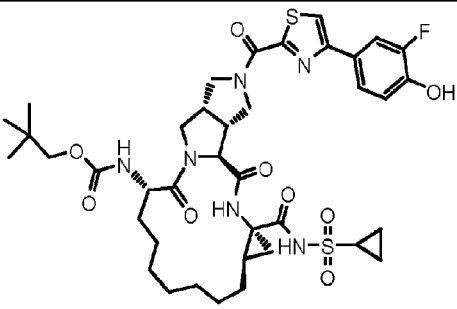
Figure 2:
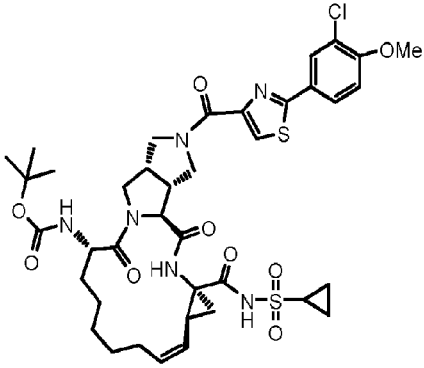
Figure 2:
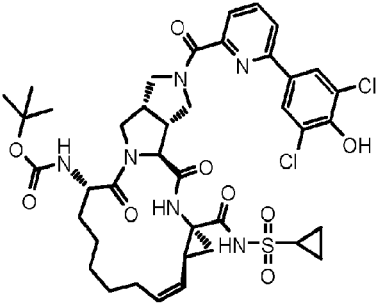
Figure 2:
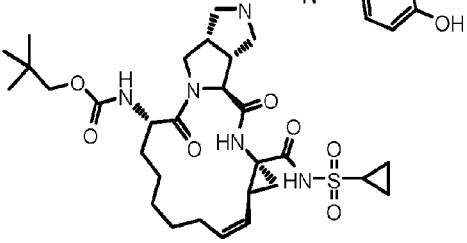
Figure 2:
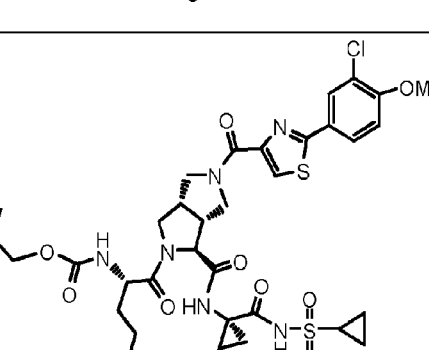
Figure 2:
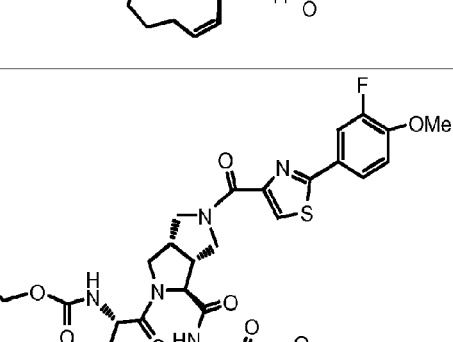
Figure 2:
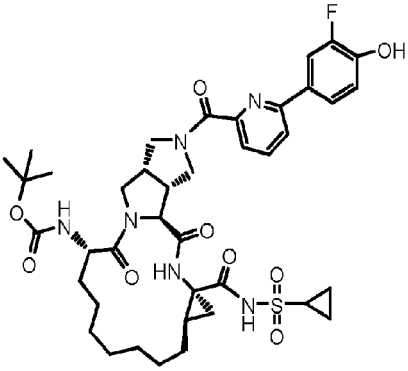
Figure 2:
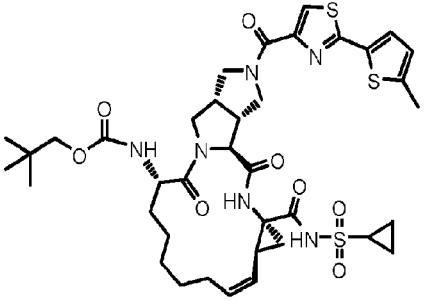
Figure 2:
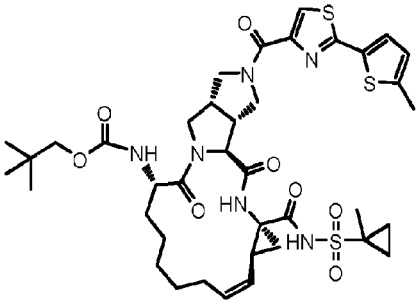
Figure 2:
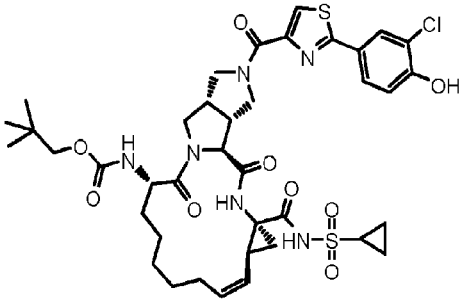

Specific examples of HCV protease inhibitors of the invention are described in FIGS. 1 and 2. It will further be appreciated that the compounds shown in FIGS. 1 and 2 provide a wide variety of exemplary substituents corresponding to the X, Y, and Z moieties described above. The compounds described herein include those compounds where, for example, any X moiety shown in FIG. 1 or 2 may be present together with any Y or Z moiety shown in FIGS. 1 and 2, as if these possible combinations were laid out in a table. In particular, when Y

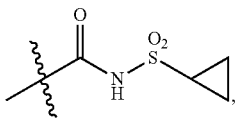 [SMILES: *C(=O)NS(=O)(=O)C1CC1]

is any X moiety shown in FIG. 1 or 2 may be present together with any Y or Z moiety shown in FIGS. 1 and 2.

The invention further provides novel compounds that are useful, for example, as intermediates for making the HCV protease inhibitors described above. These novel compounds may be represented by the formula II below. The skilled artisan will recognize that formula II also encompasses HCV protease inhibitors of the invention.

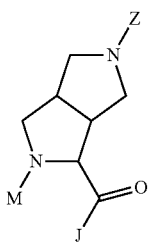

II

In compounds of Formula II, Z may be is hydrogen, a protecting group that can be selectively removed under the conditions of organic synthesis, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted heterocycloalkyl, optionally substituted $C_3$-$C_8$ cycloalkyl, optionally substituted $C_4$-$C_8$ cycloalkenyl, optionally substituted heterocyclo, optionally substituted heteroaryl, CONRR, COOR, COR3, $SO_2R3$, SOR3, $SO_2NRR$, —PO(NRR)R3, or PO(OR)R3.

M is H, a protecting group that can be selectively removed under the conditions of organic synthesis, or a moiety selected from the group consisting of:

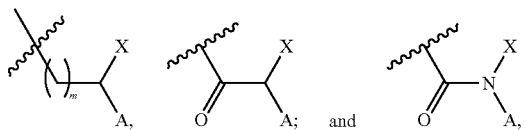

where m=1-3.

X is —$NRR2$, —OR, —$NRP^1$ where $P^1$ is a protecting group that can be selectively removed under the conditions of organic synthesis, optionally substituted $C_1$-$C_{12}$ alkyl, optionally substituted $C_3$-$C_7$ cycloalkyl, optionally substituted $C_2$-$C_{12}$ alkenyl, optionally substituted $C_4$-$C_7$ cycloalkenyl, or X is a moiety selected from the group consisting of

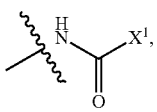 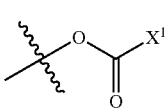 and

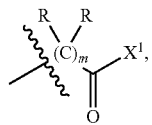

where $X^1$ is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, OR, or —NRR.

A is -D-R1, where D is a bond or optionally substituted $C_1$-$C_{12}$ alkylene, wherein up to three alkylene units of D are optionally and independently replaced by alkyl, alkenyl, alkynyl, aryl, $C_3$-$C_7$ cycloalkyl, $C_4$-$C_7$ cycloalkenyl, heterocyclo, heteroaryl, —CO—, —C(S)—, —CONR—, —COO—, —COOR—, —NRCO—, —O—, —NRCONR—, —S—, —SO—, —$SO_2$—, —NR—, —$SO_2$NR—, or —$NRSO_2$NR—, where up to 3 carbon atoms of D are optionally and independently substituted by R1;

J is a OH, $OP^2$, where $P^2$ is a protecting group that can be selectively removed under the conditions of organic synthesis, —NR—, or

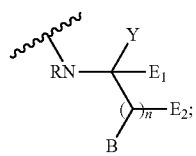

where when J is —NR— or

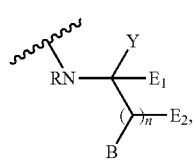

and D is optionally substituted $C_1$-$C_{12}$ alkylene, then one carbon atom of D is optionally covalently linked to —NR— or B to form a macrocyclic ring.

n is 0 or 1, where when n=0 then $E_2$ is absent and B is linked directly to the carbon atom bearing Y and $E_1$.

B can be —CH=CH2, R, or B is a bond to D when B and D form a macrocyclic ring, $E_1$ and $E_2$ are H, R, or $E_1$ and $E_2$ together form a 3 to 6-membered optionally substituted saturated or unsaturated carbocyclic ring;

Y is COOH, COOR, CONHR, —COCONHR, $CONHSO_2R$, $CONH(SO_2)NRR$, $CONHP(O)(OR)_2$, or CONHP(O)(OR)(NRR);

each R independently is hydrogen, optionally substituted $C_1$-$C_{12}$ alkyl, optionally substituted $C_2$-$C_{12}$alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, or optionally substituted heteroaryl, or R and R together form a 5-7-membered carbocyclic ring, fused to an aryl or heteroaryl ring, where the aryl or heteroaryl ring optionally is substituted by up to 3 R3 moieties, R1 is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, amido, carboxyl, sulfonamido, halo, —OR, —CN, —$NO_2$, —NRR, or —$OCF_3$, R2 is H, —COOR, CONRR, COR, $SO_2R$, SOR, or $SO_2NRR$. and R3 independently is selected from the group consisting of $C_1$-$C_{12}$ alkyl, $C_2$-$C_{12}$ alkenyl, $C_2$-$C_{12}$ alkynyl, $C_3$-$C_8$ cycloalkyl, $C_4$-$C_8$ cycloalkenyl, aryl, heteroaryl, and heterocyclo, each optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —$NO_2$, —NRR, —$OCF_3$, —COOR, CONRR, COR, $SO_2R$, and SOR.

In one embodiment, Z is a protecting group, M is a protecting group, and J is $OP^2$. In other specific embodiments, J is

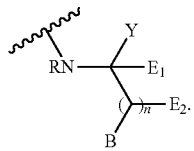

and/or M is

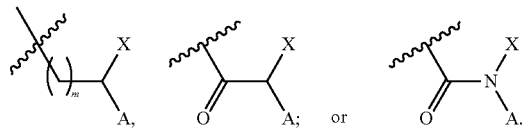

In other specific embodiments, X is —NRR2, Y is $CO_2R$ or $CONHSO_2R$, and $E_1$ and $E_2$ together form a 3 to 6 membered optionally substituted saturated carbocyclic ring.

In further embodiments, the compound has the formula III

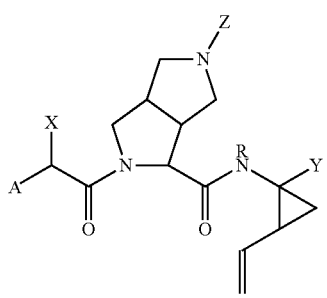

where X, A, Z, R and Y are as defined above. In specific embodiments of compounds of Formula III, the compounds may be represented by the Formula IV

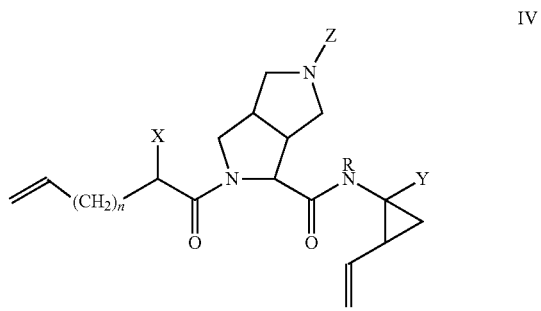

where n is 0-10.

The compounds of the present invention may be used in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Pharmaceutically acceptable salts include a salt with an inorganic base, organic base, inorganic acid, organic acid, or basic or acidic amino acid. Inorganic bases which form the instant pharmaceutically acceptable salts include alkali metals such as sodium or potassium, alkali earth metals such as calcium and magnesium or aluminum, and ammonia. Organic bases which form the instant pharmaceutically acceptable salts include trimethylamine, triethylamine, pyridine, picoline, ethanolamine, diethanolamine, triethanolamine, dicyclohexylamine. Inorganic acids which form the instant pharmaceutically acceptable salts include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

Methods of Synthesizing the Compounds of the Invention:

The compounds as described above may be prepared by standard methods of synthetic organic chemistry that are well known in the art. Schemes 1-4 below show specific routes to the compounds but the skilled artisan will recognize that other routes for the synthesis of the compound are possible.

Scheme 1 shows a general method of preparing the fused hexahydro-pyrrolo-pyrrole compounds.

Scheme 1

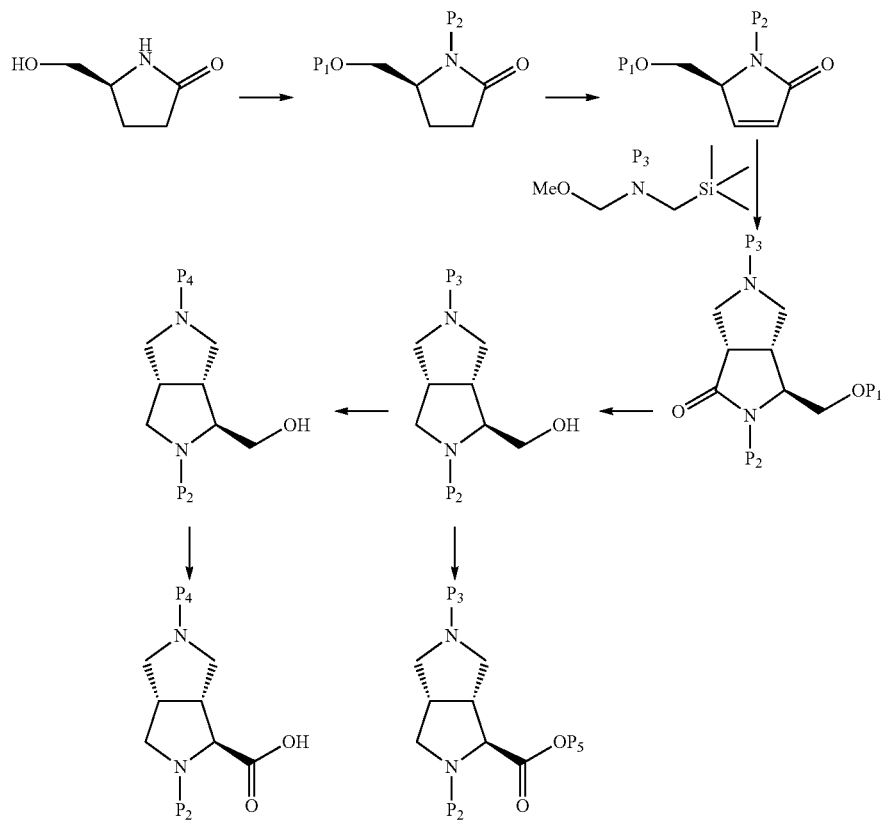

The free hydroxyl and amino groups of (S)-(+)-5-(hydroxymethyl)-pyrrolidin-2-one can be appropriately protected by groups P1 and P2 respectively. Similarly P3, P4 P5 and P6 in this scheme and/or the schemes below also represent protecting groups on the respective functional groups that can be selectively removed to allow regioselective elaboration of the desired group. The extended unsaturation can be introduced using methods commonly used in the art. The fused heterocyclic ring can be formed, for example, using the silyl amino reagent as shown in the scheme above. Reaction conditions such as solvent, temperature, etc. can be modified depending on the desired product. For example, the reaction can be carried in a solvent such as dichloromethane and an acid such as trifluoroacetic acid can be introduced at room temperature. Subsequent quenching with a base such as triethylamine followed by isolation and/or purification can provide the desired fused hexahydro-pyrrolo-pyrrole ring compound. Selective deprotection and oxidation converts the hydroxyl group to a carboxylic acid or the corresponding ester as desired.

Scheme 2 shows a general method of forming the macrocyclic ring intermediates starting from the fused hexahydro-pyrrolo-pyrrole compounds.

Scheme 2

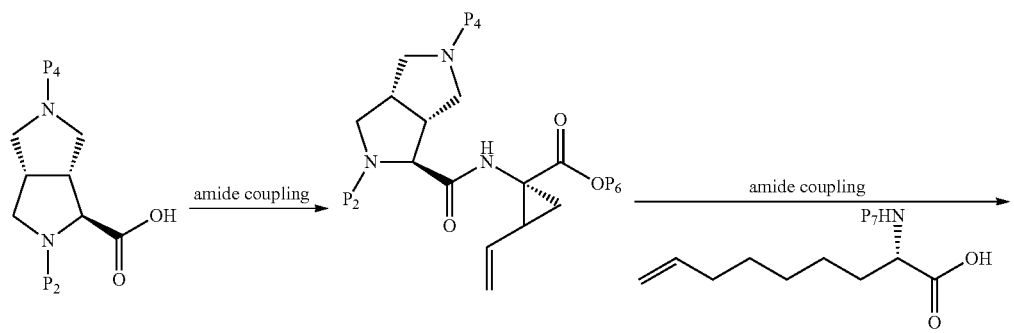

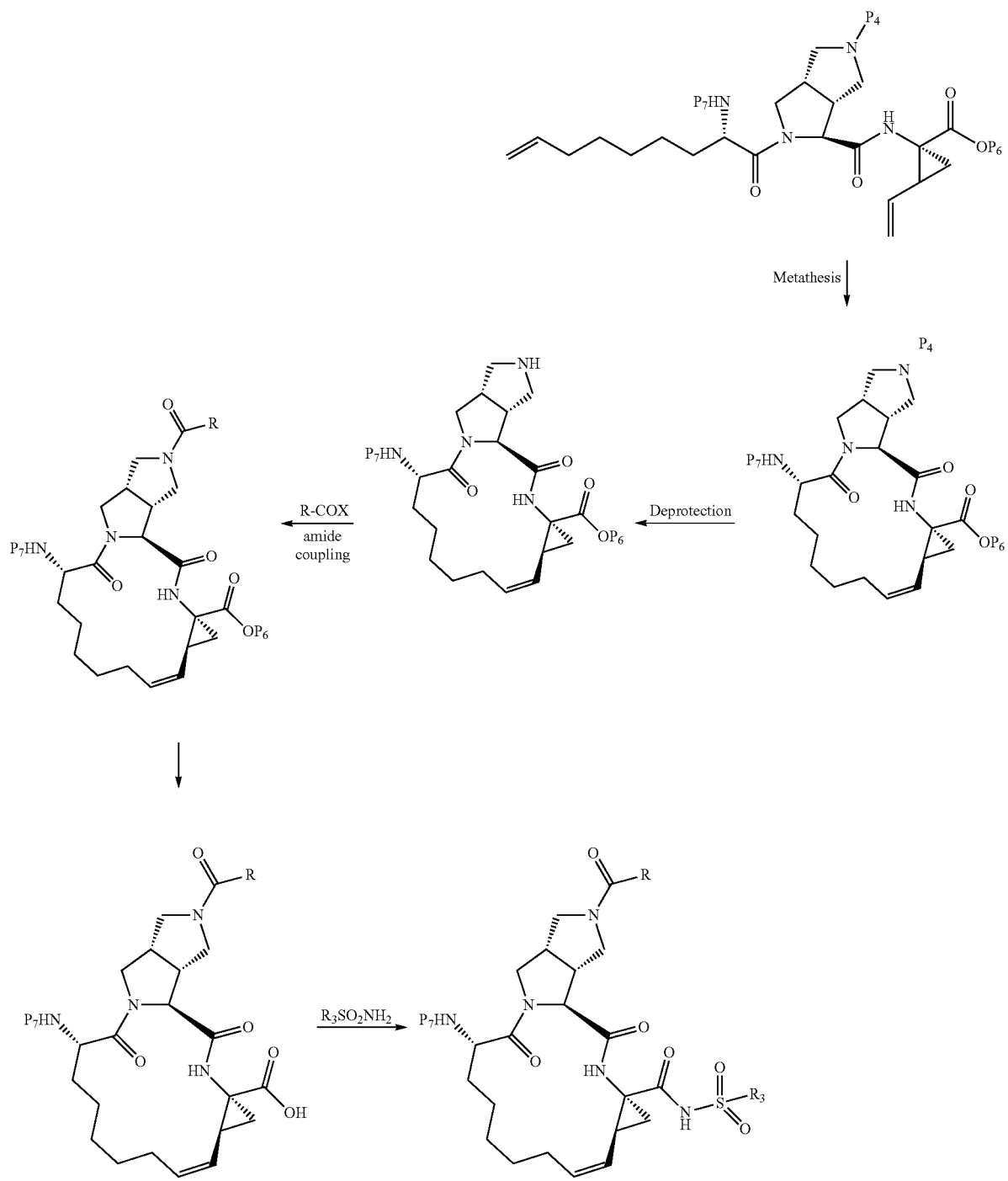

An amide coupling reaction allows extension of the carboxylic acid or derivative with a side chain containing a vinyl cyclopropyl ester moiety. Selective deprotection of one ring nitrogen atom followed by another amide coupling reaction provides a second side chain with a terminal alkene group as shown. A ring closing metathesis reaction can be employed to construct a macrocyclic ring. Protection, deprotection and other functional group transformations can provide the desired intermediates containing either the free carboxylic acid group or the corresponding sulfonamide derivatives as shown. In this scheme and the schemes below, P7 can be a protecting group, and/or can represent a moiety that is retained in the final compound. For example, P7 can be a Boc group that may be retained in the final compound, or the Boc group could be removed and the resulting amine group can be reacted to form, for example, an amide or a different urethane moiety. The skilled artisan will readily be familiar with selective deprotection and amine coupling schemes that can be used to achieve such results.

Scheme 3
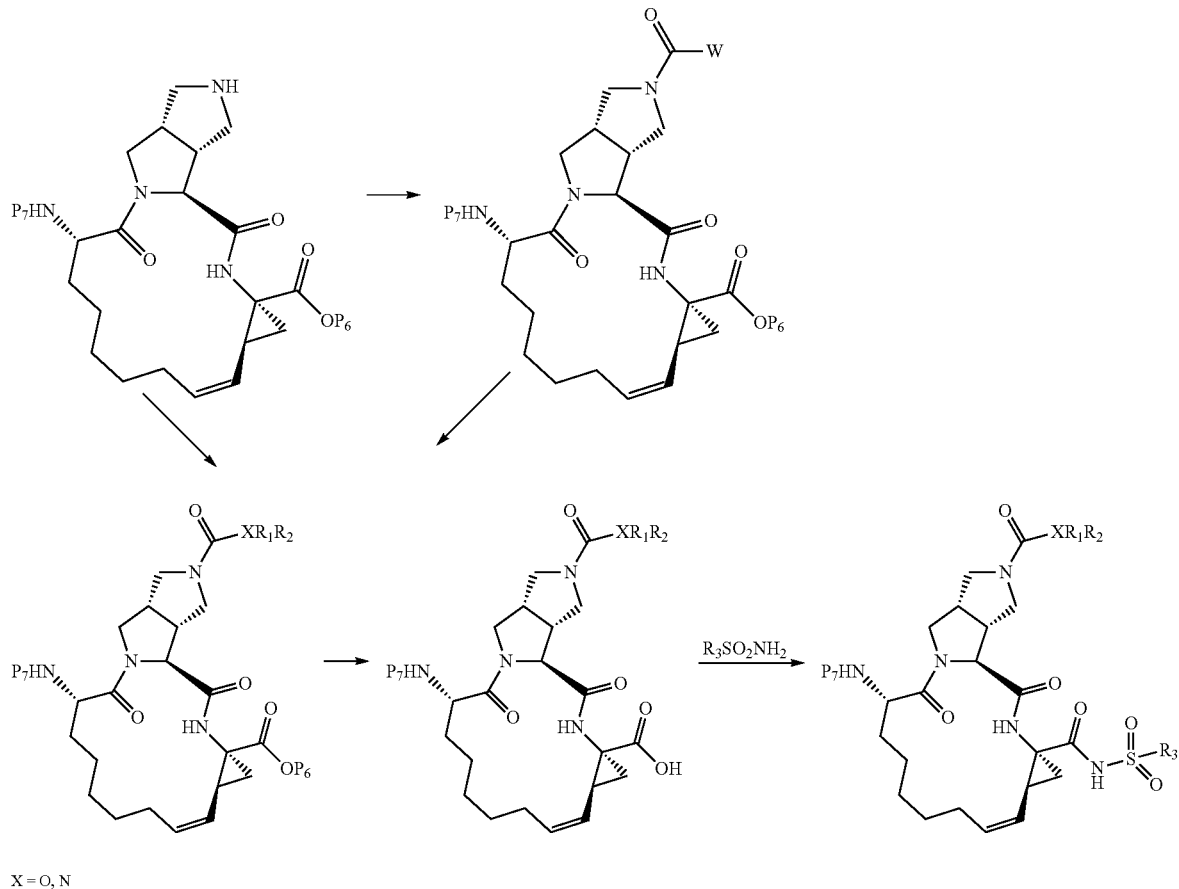
X = O, N
W represents an activating group such as chloro, imidazole and the like.
Schemes 3 and 4 show other possible protection, deprotection and functional group transformation steps to form other desired macrocyclic ring intermediates.
Scheme 4
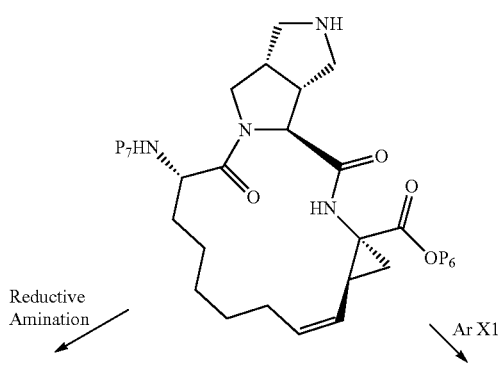

-continued

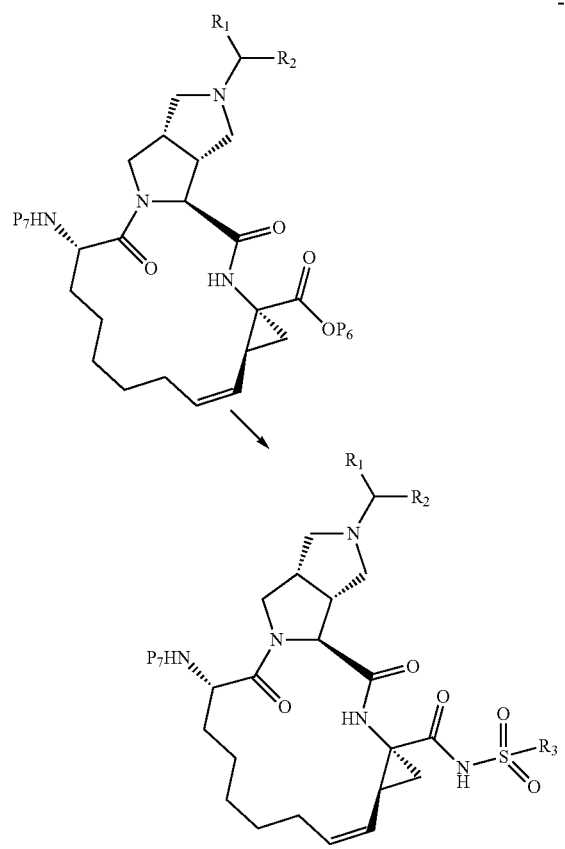
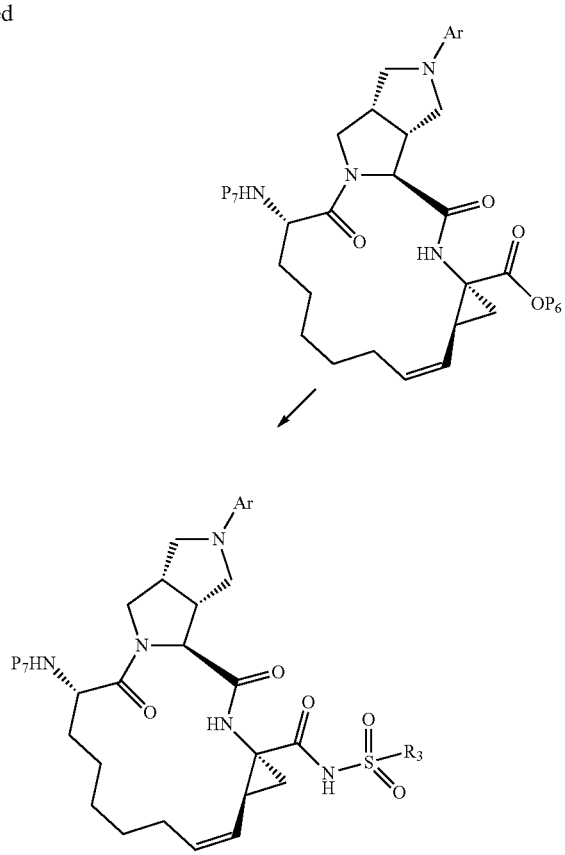

The synthesized compounds can be separated from a reaction mixture and further purified by methods such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired macrocyclic compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995).

Specific reaction schemes and conditions for carrying out the reactions are described in detail in the Examples shown below.

Definitions

The term "alkyl", alone or in combination with any other term, refers to a straight-chain or branch-chain saturated aliphatic hydrocarbon radical containing the specified number of carbon atoms, or where no number is specified, preferably from 1 to about 15 and more preferably from 1 to about 12 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like. When so designated, an alkyl group may be substituted with one or more groups independently selected from the group consisting of methyl, ethyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, dialkylsulfonamido, aryl, substituted aryl, heteroaryl, substituted heteroaryl, heterocycle, substituted heterocycle, cycloalkyl, substituted cycloalkyl, keto, and thioxo.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2-12 carbon atoms and more preferably, from 2-6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like. When so designated, an alkenyl group may be substituted with one or more groups as defined above for alkyl.

The term "alkynyl," alone or in combination with any other term, refers to a straight-chain or branched-chain hydrocarbon radical having one or more triple bonds containing the specified number of carbon atoms, or where no number is specified, preferably from 2 to about 12 carbon atoms. Examples of alkynyl radicals include, but are not limited to, ethynyl, propynyl, propargyl, butynyl, pentynyl and the like. When so designated, an alkynyl group may be substituted with one or more groups as defined above for alkyl.

The term "alkoxy" refers to an alkyl ether radical, where the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical, and can be unfused (such as phenyl) or fused (such as naphthyl). Advantageously, an aryl group contains from 6-15 carbon atoms, although the skilled artisan will recognize that aryl groups could be used that have more than 15 atoms and more preferably from 6-10 carbon atoms. Examples of aryl radicals include, but are not limited to phenyl, p-tolyl, 1-naphthyl, 2-naphthyl, indenyl, indanyl, azulenyl, fluorenyl, anthracenyl and the like. When so designated, an aryl group may be substituted with one or more groups independently selected from methyl, ethyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, and dialkylsulfonamido.

The term "aralkyl", alone or in combination, means an alkyl radical as defined above in which one hydrogen atom is replaced by a group such as phenyl, naphthyl and the like. When so designated, an aralkyl group may be substituted with one or more groups as defined above for alkyl and aryl.

The term "aryloxy", alone or in combination, means a radical of the formula aryl-O— in which the term "aryl" has the significance given above.

The term "carbocycle" or "carbocyclic" refers to a stable 3- to 8-membered carbon ring which may be saturated, mono-unsaturated or poly-unsaturated. The carbocycle may be attached at any endocyclic carbon atom which results in a stable structure. Preferred carbocycles have 5-7 carbons.

The term "cycloalkyl", alone or in combination, means an alkyl radical which advantageously contains from about 3 to about 8 carbon atoms and is cyclic. Examples of such cycloalkyl radicals include cyclopropyl, cyclobutyl, cyclopentyl, cyclohexyl and the like. When so designated, a cycloalkyl group may be substituted with one or more groups as defined above for alkyl.

The term "cycloalkylalkyl" means an alkyl radical as defined above which is substituted by a cycloalkyl radical containing from about 3 to about 8, preferably from about 3 to about 6, carbon atoms. When so designated, a cycloalkylalkyl group may be substituted with one or more groups as defined above for alkyl.

The term "cycloalkenyl" or "cycloalkene" alone or in combination with any other term, refers to a stable carbocyclic ring radical containing at least one endocyclic carbon-carbon double bond. The carbocycle may be attached at any cyclic carbon atom which results in a stable structure. A cycloalkenyl radical preferably has from 4-8 carbon atoms. Examples of cycloalkenyl radicals include, but are not limited to, cyclopentenyl, cyclohexenyl, cyclopentadienyl, indenyl and the like. When so designated, a cycloalkenyl group may be substituted with one or more groups as defined above for alkyl.

The term "heterocyclo," "heterocyclyl," or "heterocycle" refers to a stable 3-7 membered monocyclic heterocyclic ring or 8-11 membered bicyclic heterocyclic ring which is either saturated or partially unsaturated, and which may be optionally benzofused if monocyclic and which is optionally substituted on one or more carbon atoms and/or on a secondary nitrogen atom (i.e., —NH—) or on a tertiary nitrogen atom (i.e., +N—). Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5-7 membered monocyclic heterocycles and 8-10 membered bicyclic heterocycles. Examples of such groups are imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl. When so designated, a heterocyclo group may be substituted with one or more groups selected from alkyl, alkenyl, alkynyl, alkoxy, halo, haloalkyl, hydroxy, hydroxyalkyl, aryl, heteroaryl, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl and cyano.

The term heterocycloalkyl refers to an alkyl radical as defined above in which one or more hydrogen atoms are replaced by a heterocyclo or heterocyclic group as defined above.

The term heteroaryl refers to a stable 5-6 membered monocyclic or 8-11 membered bicyclic aromatic heterocycle where heterocycle is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiazolyl, thiadiazolyl, oxathiazolyl. When so designated, a heteroaryl group may be substituted with one or more groups selected from alkyl, alkenyl, alkynyl, alkoxy, trifluoromethoxy, halo, haloalkyl, hydroxy, hydroxyalkyl, carboxyalkyl, difluoromethyl, trifluoromethyl, nitro, cyano, carboxy, alkanoyl, alkoxycarbonyl, amido, alkylamido, dialkylamido, amino, alkylamino, dialkylamino, acylamino, sulfonylamino, alkylthio, trifluoromethylthio, alkylsulfinyl, alkylsulfonyl, sulfonamido, alkylsulfonamido, and dialkylsulfonamido.

The term "alkylene" as used herein refers to a divalent group derived from a straight or branched chain saturated hydrocarbon having from 1 to 12 carbon atoms by the removal of two hydrogen atoms. Examples of such groups include, but are not limited to methylene, 1,2-ethylene, 1,1-ethylene, 1,3-propylene, 2,2-dimethylpropylene, and the like. The term "halogen" means fluorine, chlorine, bromine or iodine.

The term haloalkyl means an alkyl with one or more of its hydrogens replaced by halogens. Haloalkyl also include perhaloalkyl groups or partially halogenated alkyl groups, including for example, halo-C1-C6 alkyl groups. Non-exclusive examples of haloalkyls include —CF3, —CF2CF3, —CH2CF3, and the like.

The term "substituted", and substitutions contained in formulas of this invention, refer to the replacement of one or more hydrogen radicals in a given structure with the radical of a specified substituent, provided that the replacement produces a stable compound. Examples of substituents include, but are not limited to, C1-C12 alkyl, C1-C12 alkylene, C2-C12 alkenyl, C2-C12 alkynyl, aryl, aralkyl, C3-C8 cycloalkyl, C4-C8 cycloalkenyl, heterocyclo, heteroaryl, bicycloalkyl, amino, amide, aldehyde, carboxyl, carbonyl, ester, halo, oxo, hydroxy, alkoxy, nitro, —C(S)—, —NRCONR—, —S—, —SO—, —SO2-, —SO2NR—, —NRSO2NR—, —CN, —OCF3, and the like. Also, each of the substituents may be further substituted by any one or more substituents.

When more than one position in a given structure may be substituted with more than one substituent, the substituents may be either the same or different at every position (for example, the moiety —N(R2)(R2)). Typically, when a structure may be optionally substituted, 0-3 substitutions are preferred, and 0-1 substitutions are more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Combinations of substituents and variables envisioned by this invention are those that result in the formation of stable compounds.

The term "stable", as used herein, refers to compounds which possess stability sufficient to allow manufacture and administration to a mammal by methods known in the art. Typically, such compounds are stable at a temperature of 40 degrees C. or less, in the absence of moisture or other chemically reactive conditions, for at least a week.

The term "protecting group" as used herein, refers to a labile chemical moiety which is known in the art to protect reactive groups including without limitation, hydroxyl, amino, carboxyl and thiol groups, against undesired reactions during synthetic procedures. Protecting groups are typically used selectively and/or orthogonally to protect one or more reactive sites during reactions at other reactive sites and can then be selectively removed under conditions of organic synthesis to leave the unprotected group as is or available for further reactions. Protecting groups as known in the art are described generally in Greene and Wuts, Protective Groups in Organic Synthesis, 3rd edition, John Wiley & Sons, New York (1999).

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

As used herein, the compounds of this invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The term "pharmaceutically effective amount" refers to an amount effective in treating a virus infection, for example an HCV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HCV infection, in a patient. As used herein, the term "patient" refers to a mammal, including a human.

As used herein, pharmaceutically acceptable derivatives of a compound include co-crystals, salts, esters, enol ethers, enol esters, acetals, ketals, orthoesters, hemiacetals, hemiketals, solvates, hydrates, tautomers or prodrugs thereof. Such derivatives may be readily prepared by those of skill in this art using known methods for such derivatization. The compounds produced may be administered to animals or humans without substantial toxic effects and are either pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable co-crystals are compositions that contain the active pharmaceutical ingredient (for example an HCV protease inhibitor as described herein, and at least one further molecule that can form hydrogen bonds with the active ingredient in such a manner as to form a stable crystal. Examples of co-crystals include, but are not limited to, maleates, oxalates, lactates, malates, tartrates, citrates, benzoates, salicylates, ascorbates, succinates, butyrates, valerates and fumarates. Methods of forming co-crystals are well known in the art. See, for example, *Molecular Pharmaceutics* 4, 301-309 (2007). Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable solvates and hydrates are complexes of a compound with one or more solvent or water molecules, or 1 to about 100, or 1 to about 10, or one to about 2, 3 or 4, solvent or water molecules.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorphs or polymorph mixtures are included in the present application.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is also to be understood that the compounds provided herein may exist in tautomeric forms. All such tautomeric forms are included within the scope of the instant disclosure.

Prodrugs

This invention also encompasses pharmaceutical compositions containing pharmaceutically acceptable prodrugs of compounds of the present invention. For example, compounds having free amino, amido, hydroxy or carboxylic groups can be converted into prodrugs. Prodrugs include compounds where an amino acid residue, or a polypeptide chain of two or more (e.g., two, three or four) amino acid residues is covalently joined through an amide or ester bond to a free amino, hydroxy or carboxylic acid group of the compounds. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers where the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including, but not limited to, ether, amine and carboxylic acid functionalities.

Pharmaceutical Compositions

The instant invention also provides pharmaceutical compositions which can be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

As a solid formulation for oral administration, the instant composition may be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

As used herein, "non-orally" includes subcutaneous injection, intravenous injection, intramuscular injections, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections may be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The instant pharmaceutical compositions may be formulated for nasal aerosol or inhalation and may be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, and which melts at body temperature to release the drug.

Examples of liquid preparations for oral administration include pharmaceutically acceptable emulsions, syrups, elixirs, suspensions and solutions, which may contain an inactive diluent, for example, water.

The pharmaceutical composition may be easily formulated for topical administration with a suitable ointment containing one or more of the instant compounds suspended or dissolved in a carrier, which includes, mineral oil, liquid petroleum, white petroleum, propylene glycol, polyoxyethylene polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and water.

Dosages of the instant compounds are dependent on age, body weight, general health conditions, sex, diet, dose interval, administration routes, excretion rate, combinations of drugs and conditions of the diseases treated, while taking these and other necessary factors into consideration. Generally, dosage levels of between about 10 μg per day to about 5000 mg per day, preferably between about 100 mg per day to about 1000 mg per day of the compound are useful in the prevention and treatment of viral infections, including HCV infection. Typically, the pharmaceutical compositions of this invention will be administered from about 1 to about 5 times per day or alternatively, as a continuous infusion. Such administration can be used as a chronic or acute therapy.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 0.05% to about 95% active compound (w/w). Preferably, such preparations contain from about 10% to about 80% active compound. The desired unit dose of the composition of this invention is administered once or multiple times daily.

In order to enhance the solubility and/or the stability of the compounds in pharmaceutical compositions, α-, β-, or γ-cyclodextrins or their derivatives may be employed. Also co-solvents such as alcohols may improve the solubility and/or the stability of the compounds in pharmaceutical compositions. In the preparation of aqueous compositions, addition salts of the subject compounds may be more suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with C1-C6alkyl, such as methyl, ethyl or isopropyl, e.g. randomly methylated β-CD; hydroxy C1-C6alkyl, particularly hydroxy-ethyl, hydroxypropyl or hydroxybutyl; carboxy C1-C6alkyl, particularly carboxymethyl or carboxyethyl; C1-C6alkyl-carbonyl, particularly acetyl; C1-C6 alkyloxycarbonyl-C1-C6alkyl or carboxy C1-C6 alkyloxy-C1-C6alkyl, particularly carboxymethoxypropyl or carboxyethoxypropyl; C1-C6alkylcarbonyloxyC1-C6alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxy-propyl-γ-CD and (2-carboxymethoxy)propyl-β-CD, and in particular 2-hydroxy-propyl-β-CD (2-HP-β-CD).

The term mixed ether denotes cyclodextrin derivatives where at least two cyclodextrin hydroxy groups are etherified with different groups such as, for example, hydroxy-propyl and hydroxyethyl.

The present compounds may be formulated in combination with a cyclodextrin or a derivative thereof as described in EP-A-721,331. Although the formulations described therein are with antifungal active ingredients, they are equally relevant for formulating compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations may also be rendered more palatable by adding pharmaceutically acceptable sweeteners and/or flavors.

Other convenient ways to enhance the solubility of the compounds of the present invention in pharmaceutical compositions are described in WO 94/05263, WO 98/42318, EP-A-499,299 and WO 97/44014, all incorporated herein by reference. For example, the present compounds may be formulated in a pharmaceutical composition comprising a therapeutically effective amount of particles consisting of a solid dispersion comprising a compound of formula I, and one or more pharmaceutically acceptable water-soluble polymers.

The term "a solid dispersion" defines a system in a solid state comprising at least two components, where one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

In some embodiments, the present compounds can be formulated in the form of nanoparticles which have a surface modifier adsorbed on the surface thereof in an amount sufficient to maintain an effective average particle size of less than 1000 nm.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The present compounds may also be incorporated into hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an HCV inhibitor agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration may depend on the condition of the subject, co-medication and the like.

In another embodiment the instant invention also contemplates compositions and formulations comprising one or more of the instant compounds in combination with one or more other HCV inhibitors.

Methods of Treating HCV Infection

The compounds of the present invention are useful in the treatment of individuals infected by HCV and for the prophylaxis of these individuals. The present invention may be useful in the treatment of mammals infected with viruses whose existence is mediated by, or depends upon, the HCV protease enzyme. The inhibitors are administered in a pharmaceutically effective amount.

The compounds of the invention may be administered to an uninfected or HCV-infected patient either as a single agent or in combination therapy with other anti-viral agents to increase the therapeutic effect of these compounds. Thus, the present invention also relates to compositions comprising a compound of the present invention, and one or more compounds as a combined preparation for simultaneous, separate or sequential use in treatment of HCV infections. The combination may in some cases provide a synergistic effect, whereby viral infectivity and its associated symptoms may be substantially reduced or eliminated completely.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothionate) cytokines (e.g. Th2), modulators of cytokines, chemokines or the receptors thereof (e.g. CCR5) or hormones (e.g. growth hormone) to ameliorate, combat, or eliminate HCV infection and its symptoms.

Treating or preventing refers to alleviating or hindering symptoms or effects of an HCV viral infection in an infected animal, such as a mammal, particularly a human. Treating includes prophylaxis as well as the treatment of viral infections or symptoms of viral infections. The instant methods comprise treating an animal with a therapeutically effective amount of a compound or composition according to the instant invention. According to a preferred embodiment, the viral infection is an HCV infection.

Such combination therapy in different formulations may be administered simultaneously, separately or sequentially. Alternatively, such combinations may be administered as a single formulation, whereby the active ingredients are released from the formulation simultaneously or separately.

Boosting

The compounds of the present invention may also be administered in combination with compounds that modulate the metabolic degradation of the HCV inhibitors following application of the drug to an individual. These modulators include compounds that interfere with metabolic degradation by cytochrome enzymes, such as cytochrome P450. Suitable modulators are described in, for example, WO 2008/02234, the contents of which are hereby incorporated by reference in their entirety, although the skilled artisan will recognize that other modulators can be used.

The modulators may be administered simultaneously, separately or sequentially with the HCV inhibitors. Alternatively, the protease inhibitor and modulator can be combined into a single formulation, whereby the active ingredients are released from the formulation simultaneously or separately. The modulator is used in an amount that is effective at inhibiting degradation of the HCV protease inhibitor to an extent that permits achieving and maintaining a therapeutically effective blood and/or liver concentration of the inhibitor. It may be administered at the same or different ratio as the compound of the present invention.

Preferably, the weight ratio of such modulator vs. a compound of the present invention (modulator:compound of the present invention) is 1:1 or lower, more preferably the ratio is 1:3 or lower, suitably the ratio is 1:10 or lower, more suitably the ratio is 1:30 or lower. The skilled artisan will recognize that the amount of the modulator that is to be used will vary with the nature of the modulator and of the HCV inhibitor, among other variables.

Testing of HCV Protease Inhibitory Activity and Antiviral Activity

The compounds of the invention may be tested in vitro for their ability to inhibit HCV protease and for their antiviral activity using methods that are well known in the art. For example, methods of testing the inhibition of HCV protease in vitro have been described, for example, by Taliani et al., *Anal. Biochem.* 240, 60-67 (1996). In these methods, apparent $IC_{50}$ values may be determined using a fluorogenic substrate. A suitable substrate is the peptide Ac-DE-D(Edans)-EE-Abu-ψ-[COO]-AS-K(Dabcyl)-NH2 (AnaSpec, San Jose, Calif., USA). This peptide contains two fluorophores in such proximity that their fluorescence is quenched. When the peptide is cleaved by HCV protease, the quenching is relieved, and an increase in fluorescence is observed.

Methods for testing the antiviral activity of the HCV protease inhibitors also are well known in the art. See, for example, U.S. Pat. No. 6,630,343. $IC_{50}$ values can be determined in a cell based assay using the HCV Con1 subgenomic replicon. Cell lines containing Huh-luc/neo-ET with the persistent replicon sequence $I_{389}$luc-ubi-neo/NS3-3'/ET can be obtained from ReBlikon GmbH [Schriesheim, Germany]. This construct expresses luciferase and the amount of luciferase protein is an accurate measure for RNA replication as determined by quantitative PCR (Taq-Man).

The following examples illustrate further the present invention but, of course, should not be construed in any way of limiting its scope.

EXAMPLES
Scheme 1
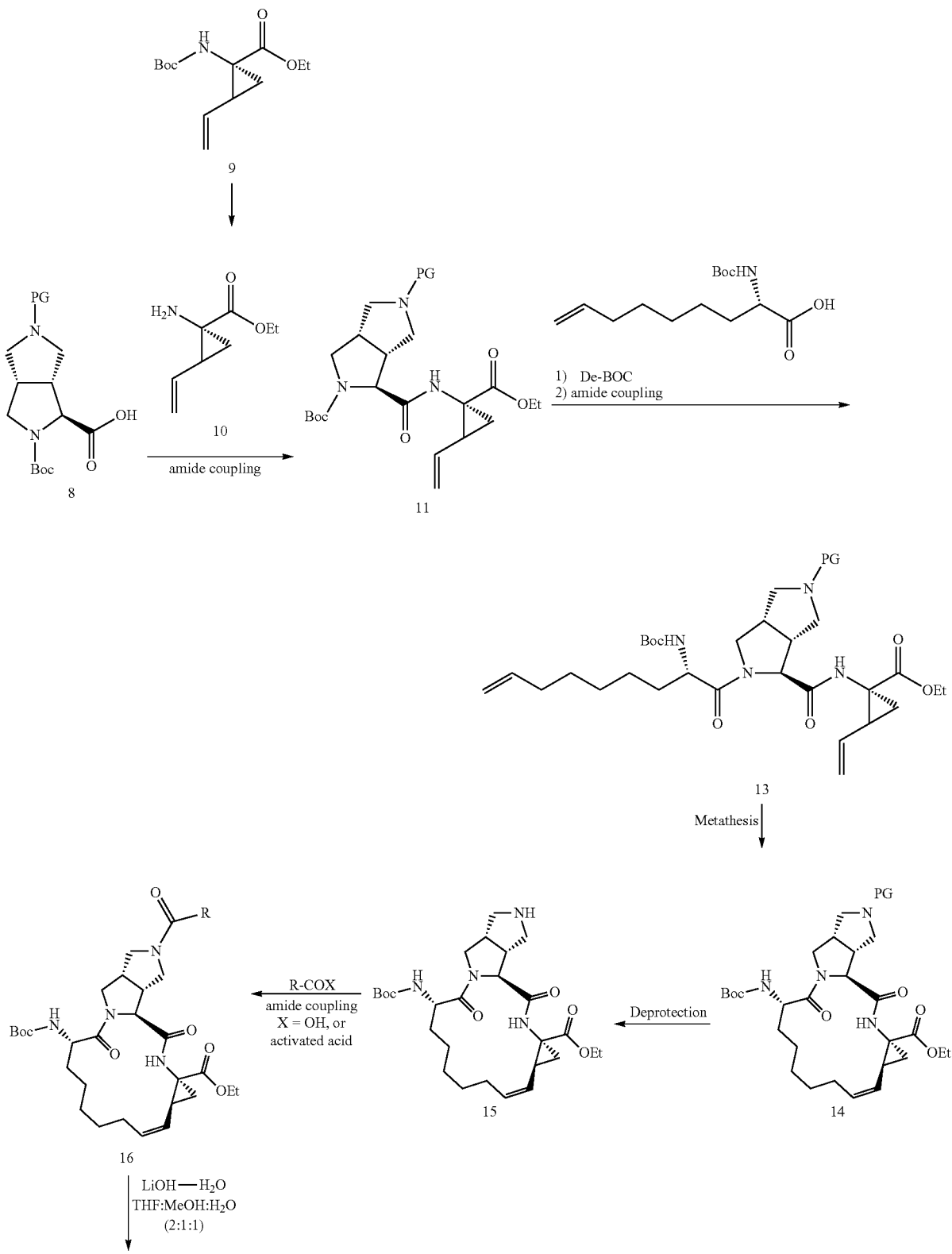

-continued

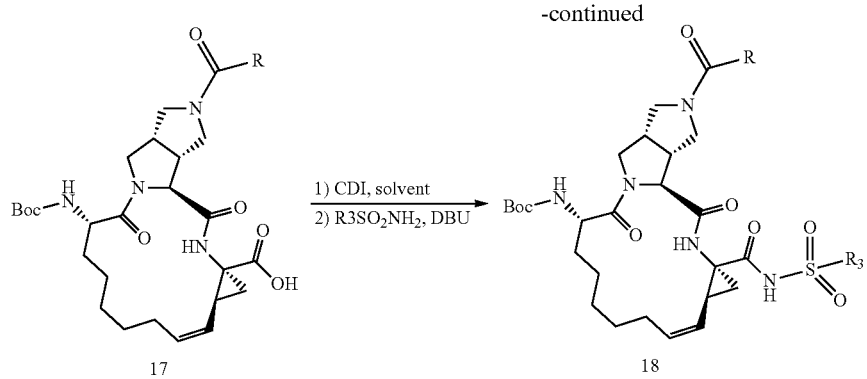

Scheme 1 outlines the synthesis of representative molecules (R is alkyl, aryl, heteroaryl, etc). Typically the acid 3,5-orthogonally protected hexahydropyrrolo[3,4-c]pyrrole-1-carboxylic acid 8 was coupled with the amine 10 using methods known in the art. The resulting compounds of formula II are treated with acid to removed the Boc, followed by typical amide coupling (1~10 hours) with protected amino acid 12. Preparation of macrocycle 14 can be accomplished using an olefin metathesis reaction. Macrocycle 14 is then deprotected and coupled with an acid or activated acid using methods described in the literature. The ester can be hydrolyzed with lithium hydroxide and then activated with CDI and coupled with the sulfonamide to provide the final products 18. (Greene, T. W., et al., *Protective Groups in Organic Synthesis*, John Wiley & Sons, 3$^{rd}$ edition 1999; Catalano eta al., WO03/062192; Trnka and Grubbs, *Acc. Chem. Res.* 2001, 34, 18; Drew, M. et al., Tetrahedron, 1999, 55, 1163; Shu, C., et al., *Org. Lett.;* 2008; 10, 1303; Tsantrizos Y., et al., WO 00/59929; Evans, et al., *J. Am. Chem. Soc.,* 1990, 112, 4011)

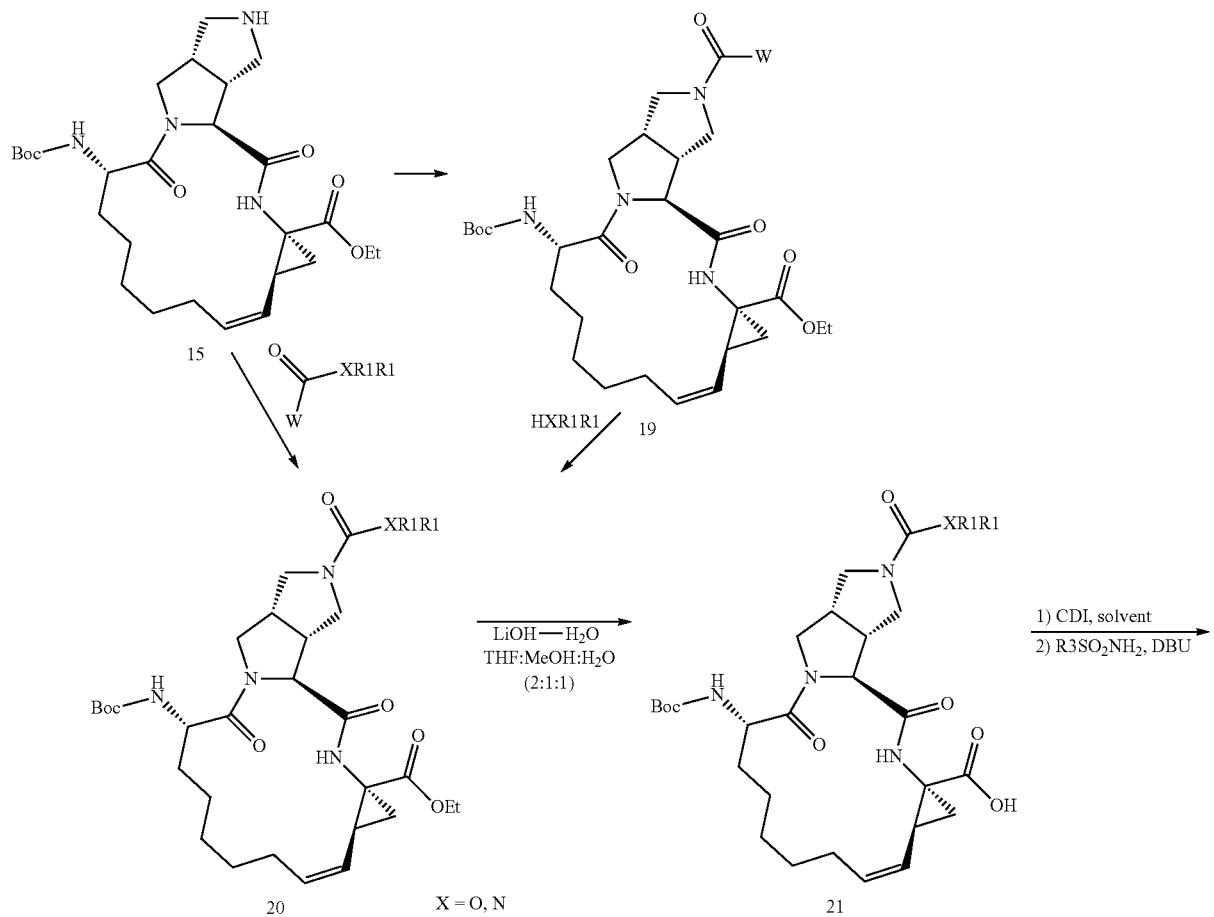

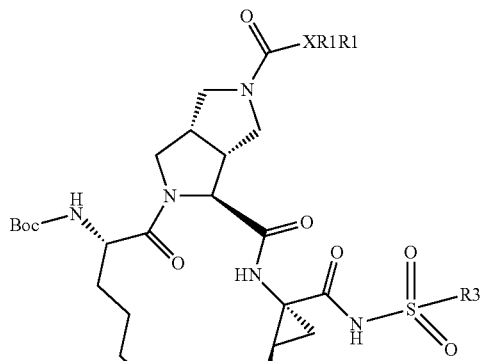

22

Scheme 2 (where W is chloro, imidazole etc., each R1 and R3 independently is alkyl, aryl, heteroaryl etc., X is O or N) describes the synthesis of representative urethane and urea analogs. Typically the amine 15 is treated with carbonyl diimidazole, phosgene, or triphosgene, followed by the amine or alcohol. Alternatively, the amine can be converted directly to 20 by reacting with an isocyanate, chloroformate, carbamoyl chloride etc.

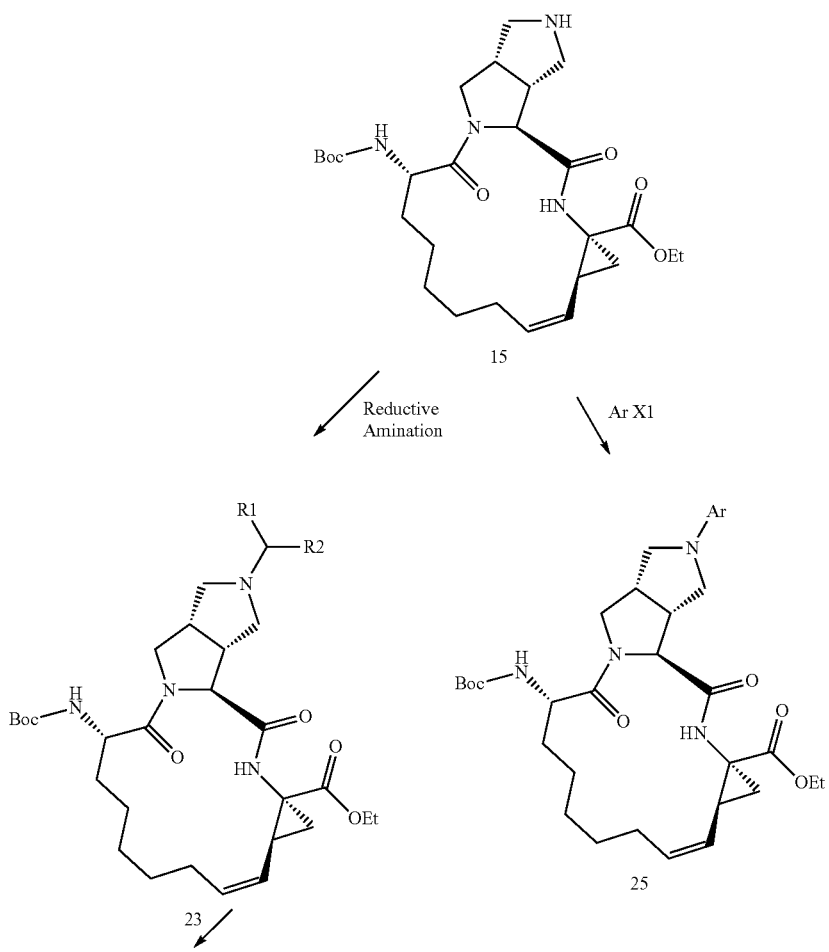

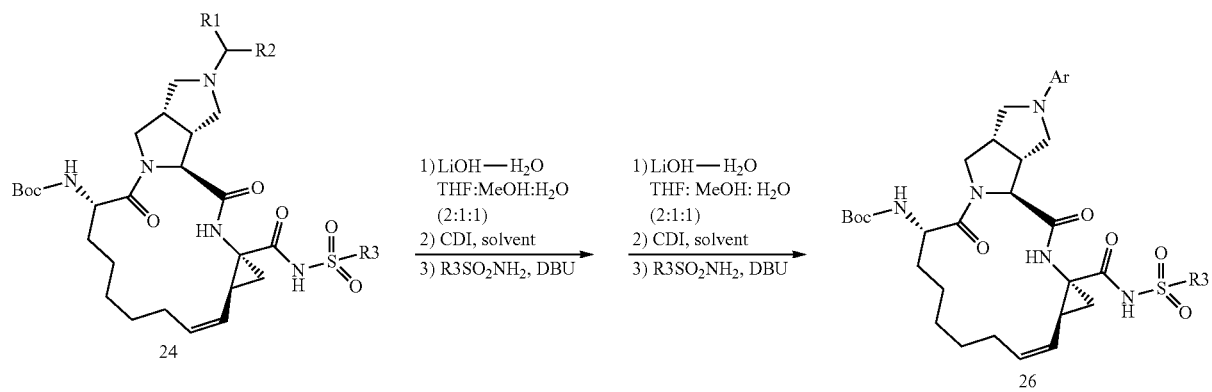

In Scheme 3, X1 is a leaving group, such as halide, that may be displaced to allow coupling of the amine to Ar. Amines 23 may be prepared according to scheme 3. Aldehydes or ketones can be reacted with amine 15 via reductive amination. Alternatively, 15 can be reacted with alkylating agent such as an alkyl halide or sulfonate. Analogs 25 can be prepared by reacting 15 with an aryl halide in the presence of a suitable catalyst such as copper(I) iodide and a base such us triethylamine, DIPEA, KOBu-t etc.

List Of Abbreviations
THF Tetrahydrofuran
TBTU O-benzotriazol-1-yl-N,N,N',N'-tetramethyluronium tetrafluoroborate
RT Room temperature
Pd/C Palladium on carbon
HCl Hydrochloric acid
MeOH Methanol
CH$_3$CN acetonitrile
DBU 1,4-Diazabicyclo[5.4.0]undec-7-ene
DCE Dichloroethane
DMF Dimethylformamide
Et$_3$N triethylamine
EtOAc Ethyl acetate
DCM Dichloromethane
DIPEA Diisopropylethylamine
Boc tert-Butoxycarbonyl
LHMDS Lithium Bis(trimethylsilyl)amide
TIPS Triisopropylsilyl
Fmoc-OSu 9-fluorenylmethoxycarbonyl N-hydroxysuccinimide ester
NaOH Sodium hydroxide
MgSO$_4$ Magnesium Sulfate
NaCNBH$_3$ Sodium cyanoborohydride
DMAP Dimethylaminopyridine
PG Protecting group
KOBu-t Potassium tert-butoxide Purification and Analytical Procedures Compounds requiring HPLC purification were purified on a system using a Gilson UV/VIS156 detector, Gilson 205 fraction collector, and Gilson 321 pump.
Mobile phases used were as follows,
A: 0.1% TFA in water; B: acetonitrile
Column used was Phenomenex 10 um C18, 300A, 250×21.2 mm
Analytical LC-MS LC-MS were analyzed on an Agilent 1100 MSD in positive and negative modes using an ESI (Electrospray Ionization) source. Scan range is 100-2000 amu. Mobile phase used was A: 1% acetic acid in water and B: 1% acetic acid in acetonitrile. UV detection at 220 or 254 was used. The column most commonly used was ZORBAX 3.5 um, SB-C18, 2.1×30 mm. Mass ("MS") calculations were made using the monoisotopic mass for the compound. Prep-TLC: partisil PK6F, silica gel 60A with fluorescent indicator 1000 or 500 um from Whatman Flash Chromatography silica gel type: Silica gel 60, particle size 0.0400~063 mm from EMD Scheme 4
Synthesis of intermediates hexahydro-pyrrolo[3,4-c]pyrrole-1-carboxylic acid (8) and ester (7),

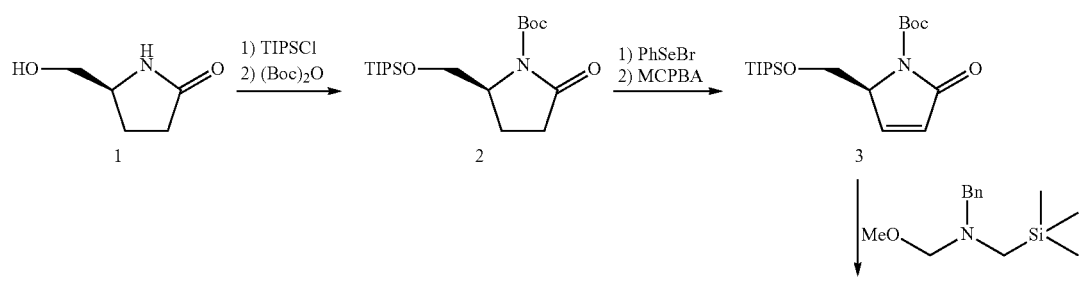

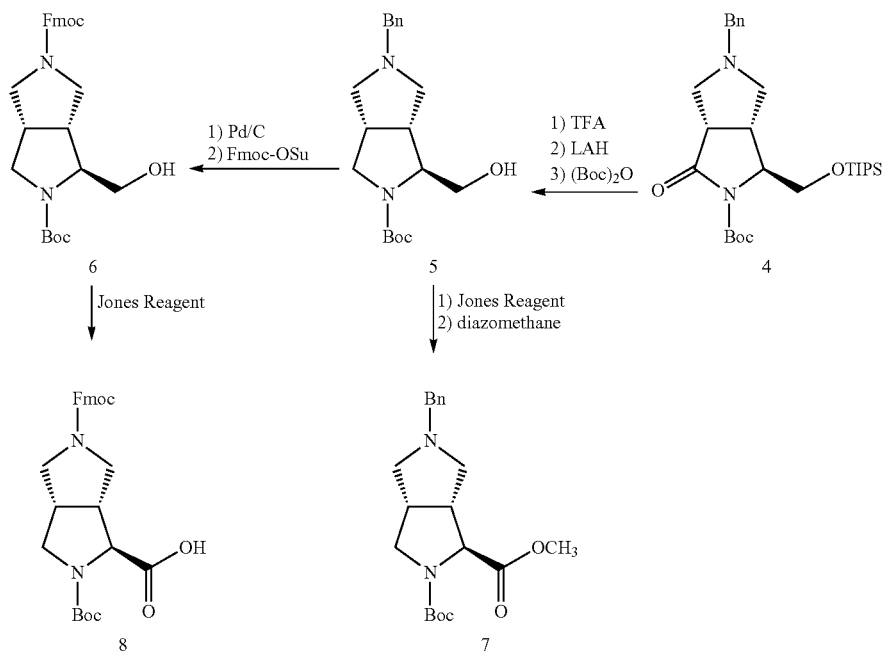

Synthesis of Compound 2

To a stirred solution of (S)-(+)-5-(hydroxymethyl)-pyrrolidin-2-one (5.0 g, 43 mmol) in 100 ml anhydrous dichloromethane at room temperature was slowly added imidazole (3.8 g, 56 mmol) and then TIPSCl (11 ml, 52 mmol). The mixture was stirred for 2 hours and the white solid was filtered off. The filtrate was concentrated, diluted with 300 ml ethyl acetate and then washed with 50 ml aqueous 0.5M citric acid. The organic phase was dried over $MgSO_4$ and concentrated to give the intermediate amide. This amide was dissolved in 150 ml acetonitrile, then cooled to 0° C. and treated with DMAP (1.05 g, 8.6 mmol) and then $(Boc)_2O$ (1.1 g, 52 mmol) (added in small portions). The mixture was stirred overnight at room temperature. After the completion of the reaction (TLC), the mixture was concentrated in vacuo, and then purified by column chromatography (5:1 hexane/ethyl acetate) to give compound 2 (15.1 g, 94%) as a yellow oil.

Synthesis of Compound 3

To a stirred solution of 2 (7.2 g, 19 mmol) in 70 ml anhydrous THF was added LHMDS [21 ml, 21 mmol, (1M in THF)] slowly at –78° C. The mixture was stirred for 15 minutes at –78° C. and then phenylselenyl bromide (5.0 g, 21 mmol) in anhydrous THF (20 ml) was slowly added. The cooling bath was removed and the reaction was stirred for 1 hour. The reaction mixture was concentrated in vacuo and the residue was dissolved in 150 ml ethyl acetate and washed with 3×50 ml saturated aq. $NH_4Cl$. The combined organic phase was dried over $MgSO_4$, concentrated in vacuo, and purified by column chromatography (6:1 hexanes/ethyl acetate) to give the intermediate selenyl compound. This intermediate was dissolved in 100 ml dichloromethane and cooled to –40° C. m-Chloroperbenzoic acid (5.0 g, 29 mmol) was added and the cooling bath was removed. Stirring was continued for 30 min (TLC check 3:1 hexanes/ethyl acetate) and the mixture was poured into 50 ml aqueous saturated $NaHCO_3$. The mixture was extracted with 2×100 ml dichloromethane. The combined organic phase was dried over $MgSO_4$ and concentrated in vacuo and then purified by column chromatography (4:1 hexanes/ethyl acetate) to give 3 (3.0 g, 43% for 2 steps).

$^1$H NMR: ($CDCl_3$) δ 7.30 (dd, J=2.1 and 6.1 Hz, 1H), 6.13 (dd, J=1.7 and 6.3 Hz, 1H), 4.63 (m, 1H), 4.26 (dd, J=3.8 and 9.3 Hz, 1H), 3.78 (dd, J=6.8 and 9.2 Hz, 1H), 1.55 (s, 9H), 1.04 (m, 21H).

Synthesis of Compound 4

To a stirred mixture of compound 3 (1.6 g, 4.3 mmol) and N-methoxymethyl-N-trimethylsilylmethyl-benzyl amine (1.7 ml, 6.5 mmol) in 40 ml dichloromethane was added trifluoroacetic acid (0.064 ml, 0.86 mmol) dropwise at room temperature. The mixture was stirred for 3 hours at room temperature. After the completion of the reaction (monitored by TLC, 15:1 DCM: ethyl acetate), the mixture was neutralized with $Et_3N$ (0.12 ml, 0.86 mmol), concentrated in vacuo and then purified by column chromatography (15:1 DCM: ethyl acetate) to give 4 (2.0 g, 91%) as a colorless oil.

MS: 503.7 ($MH^+$) and 1005.3 ($2M+H^+$).

$^1$H NMR: ($CDCl_3$) δ 7.27 (m, 5H), 4.00 (dd, J=3.5 and 10.0 Hz, 1H), 3.92 (m, 1H), 3.73 (dd, J=2.1 and 10.0 Hz, 1H), 3.65 (d, J=13.0 Hz, 1H), 3.50 (d, J=13.0 Hz, 1H), 3.12 (m, 1H), 3.01 (dd, J=2.8 and 9.4 Hz, 1H), 2.75-2.66 (m, 3H), 2.56 (dd, J=4.4 and 9.0 Hz, 1H), 1.53 (s, 9H), 1.02 (s, 21H).

Synthesis of Compound 5

To a stirred solution of compound 4 (7.2 g, 14.3 mmol) in 100 ml dichloromethane was added 25 ml trifluoroacetic acid slowly at room temperature. The mixture was stirred for 0.5 hour and was concentrated in vacuo to give crude intermediate cyclic amide. This amide dissolved in 30 ml dimethoxyethane was added slowly to a stirred suspension of lithium aluminum hydride (5.5 g, 144 mmol) in 200 ml dimethoxyethane at 0° C. After the completion of the addition the mixture was refluxed for 6 hours. After completion of the reaction (monitored by LC-MS), the mixture was cooled to 0° C. and was carefully quenched with 5 g ice in small portions, then 20 ml 5% NaOH followed by 20 ml H$_2$O. The mixture was stirred for 10 minutes at room temperature and then filtered. The filtrate was concentrated in vacuo. This intermediate amine was then dissolved in 50 ml dichloromethane and treated with (Boc)$_2$O at room temperature in small portions. The resulting mixture was stirred for 2 hours at room temperature. After the completion of the reaction (TLC), the mixture was concentrated in vacuo and then purified by column chromatography (ethyl acetate) to give compound 5 (3.3 g, 69%) as a colorless oil that crystallized on standing.

MS: 333.3 (MH$^+$).

Synthesis of Compound 6

To a stirred solution of compound 5 (2.9 g, 8.7 mmol) in 50 ml 4:1 methanol/dichloromethane was added 10% Pd/C (580 mg) carefully. Acetic acid (0.25 ml, 4.4 mmol) was added to the mixture and the mixture was hydrogenated overnight under an H$_2$ balloon at room temperature. The Pd/C was filtered-off and the filtrate was concentrated and then dissolved in 50 ml dichloromethane. NaHCO$_3$ (370 mg, 4.4 mmol) was added and then Fmoc-OSu (3.2 g, 9.6 mmol) was added in small portions at room temperature. The mixture was stirred for 2 hours at room temperature, concentrated in vacuo, and then purified by column chromatography (3:1 ethyl acetate/hexanes) to give compound 6 (3.5 g, 86%) as a colorless oil.

MS: 365.2 (MH$^+$-Boc) and 487.3 (M+Na$^+$).

Synthesis of Compound 7

Compound 5 (800 mg, 2.4 mmol) in 5 ml acetone was added slowly to a stirred solution of freshly prepared Jones reagent (8 ml) in 10 ml acetone at −2° C. (Brine+ice). The mixture was stirred for 30 minutes at this temperature and then poured into 150 ml ethyl acetate and the pH adjusted to ~7 with 40% NaOH and saturated aq. NaHCO$_3$. The mixture was then extracted with ethyl acetate (3×150 ml). The combined organic phase was dried over MgSO$_4$ and concentrated in vacuo. It was then dissolved in 10 ml dichloromethane. Freshly prepared diazomethane (~9.6 mmol) was added to the above solution with stirring. After stirring 20 minutes at room temperature, the mixture was concentrated in vacuo and then purified by column chromatography (1:2 ethyl acetate/hexanes) to give compound 7 (420 mg, 49% for 2 steps) as a colorless oil.

MS: 361.2 (MH$^+$).

Synthesis of Compound 8

To a stirred solution of freshly prepared Jones reagent (35 ml) in 30 ml CH$_3$CN was added compound 6 (3.5 g, 7.5 mmol) in 10 ml CH$_3$CN slowly at −2° C. (Brine+ice). The mixture was stirred for 30 minutes at this temperature. The mixture was quenched with 10 ml isopropyl alcohol dropwise and then diluted with 300 ml ethyl acetate. The ethyl acetate was decanted and then washed with 10 ml saturated aq. NaHCO$_3$. The combined aqueous phase was extracted with ethyl acetate (2×300 ml). The combined ethyl acetate phase was dried over MgSO$_4$, concentrated in vacuo and then purified by a short column chromatography (1:1 ethyl acetate/hexanes, then ethyl acetate followed by methyl alcohol) to give compound 8 (1.9 g, 52%) as a pale brown oil.

MS: 477.2 (M−H).

Synthesis of Intermediate 15

Step 1: Preparation of Compound 10

1(R)-t-Butoxycarbonylamino-2(S)-vinyl-cyclopropane carboxylic acid ethyl ester (compound 9, 2.0 g, 8.0 mmol) was treated with 20 ml 4 N HCl in dioxane at 0° C. The ice bath was removed and the stirring continued for 1 hour. After completion, the reaction was concentrated in vacuo and used without further purification.

MS: 156.0 (MH$^+$).

Step 2: Preparation of Compound 11

To a stirred solution of compound 8 (5.0 g, 10.5 mmol) in 30 ml DMF was added TBTU (5.0 g, 16 mmol) at room temperature. The mixture was stirred for 5 minutes and then a mixture of compound 10 (2.1 g, 11 mmol) and DIPEA (3.6 ml, 21 mmol) in 20 ml DMF was slowly added. The resulting mixture was stirred for 0.5 hour at rt. After the completion of the reaction (Monitored by LC-MS), the reaction was concentrated under high vacuum to 15 ml. This residue was dissolved in 500 ml ethyl acetate and washed with 20 ml 1N HCl and then 30 ml saturated aq. NaHCO$_3$. The organic phase was dried over MgSO$_4$ and concentrated in vacuo, and then purified by column chromatography (1:1 hexanes/ethyl acetate) to give compound 11 in quantitative yield as a yellow oil.

MS: 516.3 (MH$^+$-Boc).

Step 3: preparation of compound 13

70 ml 4N HCl in dioxane was added to compound 11 (6.2 g, 10.0 mmol) at 0° C. and was then stirred for 0.5 hour at room temperature. After the completion of the reaction (monitored by TLC, 1:3 hexanes/ethyl acetate), the mixture was concentrated in vacuo. To a stirred mixture of this intermediate amine, 2(S)-t-butoxycarbonylamino-non-8-enoic acid (compound 12, 3.0 g, 11 mmol), and DIPEA (1.7 ml, 10 mmol) in 80 ml DMF was added TBTU (4.8 g, 15 mmol) at room temperature. Additional DIPEA (3.4 ml, 20 mmol) was added dropwise at room temperature. The mixture was then stirred for 0.5 hour. After the completion of the reaction (LC-MS, TLC), DMF was removed with high vacuum leaving ~20 ml residue. The residue was dissolved in 500 ml ethyl acetate, washed with 20 ml 1N HCl, and then 30 ml saturated aq. NaHCO$_3$. The organic phase was dried over MgSO$_4$, concentrated in vacuo and then purified by column chromatography (1:1 hexanes/ethyl acetate) to give compound 13 (6.4 g, 83%) as a pale yellow oil.

MS: 669.2 (MH$^+$-Boc) and 769.2 (MH$^+$).

Step 4: Preparation of Compound 14

A stirred mixture of compound 13 (1.0 g, 1.3 mmol) and 2$^{nd}$ generation Grubbs catalyst (Benzylidene[1,3-bis(2,4,6-trimethylphenyl)-2-imidazolidinylidene]dichloro(tricyclohexylphosphine)ruthenium) (220 mg, 0.26 mmol) in 500 ml anhydrous DCM, was heated at reflux for 18 hours. The mixture was cooled to room temperature and then carefully concentrated in vacuo and then purified by column chromatography (1:3 hexanes/ethyl acetate) to give compound 14 (0.9 g, 93%) as a brown oil.

MS: 641.3 (MH$^+$-Boc).

Step 5: Preparation of Compound 15

To a stirred solution of compound 14 (4.5 g, 6.1 mmol) in 60 ml CH$_3$CN at room temperature was slowly added 40 ml piperidine. The mixture was stirred for 0.5 hour and, after the completion of the reaction (TLC), concentrated in vacuo and then purified by short column chromatography (10:1 DCM/MeOH) to give compound 15 (3.1 g, 99%).

MS: 519.2 (MH$^+$).

Procedure for the Coupling Between Compound 15 and Carboxylic Acids; Synthesis of Compound 20

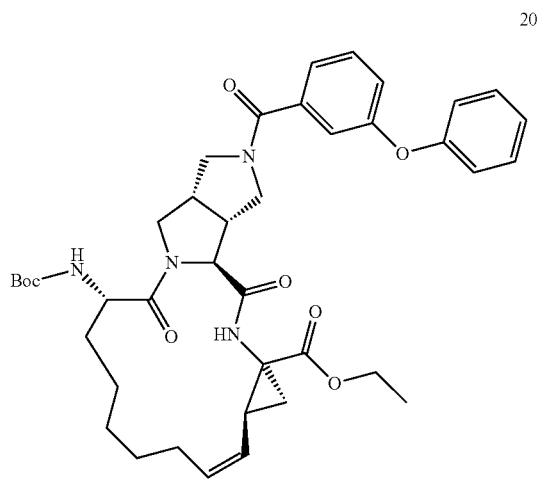

20

To a stirred solution of compound 15 (0.06 mmol) and 3-phenoxybenzoic acid (51 mg, 0.24 mmol) in 1.5 ml DMF was added TBTU (77 mg, 0.24 mmol) at room temperature. The mixture was stirred at room temperature overnight. After the completion of the reaction (LC-MS), DMF was removed using high vacuum. The residue was dissolved in 3 ml DCM and then purified by preparative TLC (1:3 hexanes/ethyl acetate) to give compound 20 (36 mg, 83%) as a white semi-solid.

MS: 713.0 (M−H).

Procedure for the Coupling Between Compound 15 and Aldehydes; Synthesis of Compound 21).

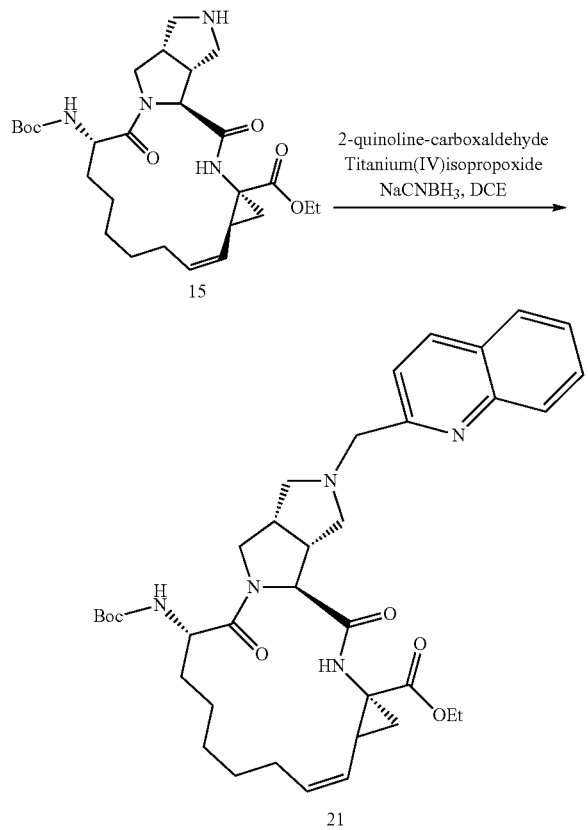

To a stirred mixture of compound 15 (0.04 mmol) and 2-quinoline-carboxaldehyde (19 mg, 0.12 mmol) in 1.5 ml DCE was added titanium(IV) isopropoxide (24 μL, 0.08 mmol) at room temperature. The mixture was then stirred at room temperature for 1 hour. NaCNBH$_3$ (5 mg, 0.08 mmol) was then added and the whole mixture stirred overnight at room temperature. After the completion of the reaction (LC-MS), the mixture was directly loaded onto a preparative TLC plate (ethyl acetate) to give 21 (26 mg, ~100%) as a yellow oil.

MS: 660.3 (MH$^+$).

Procedure for the Coupling Between Compound 15 and Acyl or Sulfonyl Chlorides; Synthesis of Compound 22.

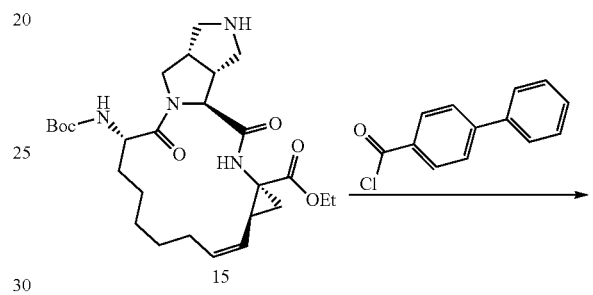

15

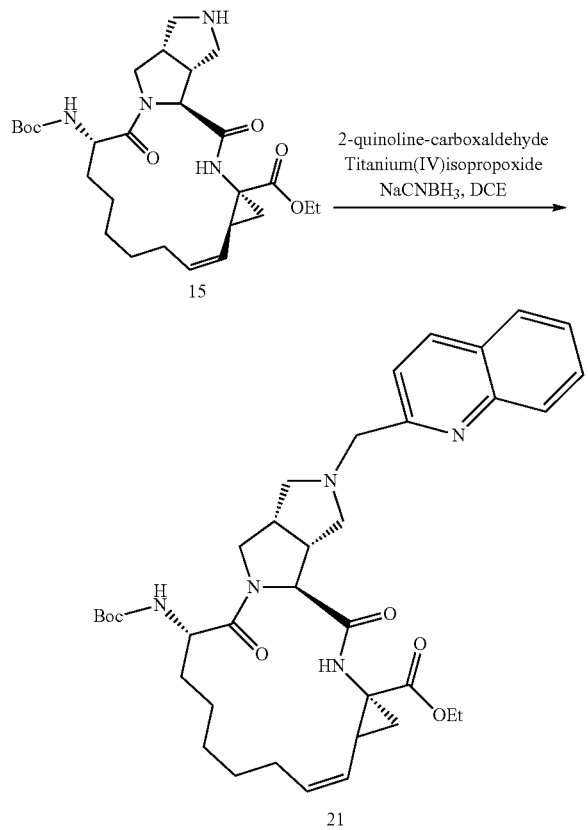

22

To a stirred mixture of compound 15 (0.04 mmol) and Et$_3$N (33 μL, 0.24 mmol) in 1.5 ml DCM at room temperature was added 4-biphenylcarbonyl chloride (26 mg, 0.12 mmol). The mixture was stirred for 0.5 hour at this temperature. After the completion of the reaction (monitored by LC-MS), the mixture was directly purified by preparative TLC (Ethyl acetate) to give compound 22 (27 mg, 96%) as a colorless oil.

MS: 697.2 (M−H).

Procedure for the Coupling Between Compound 15 and Carbamoyl Chlorides and Chloroformates; Synthesis of Compound 23.

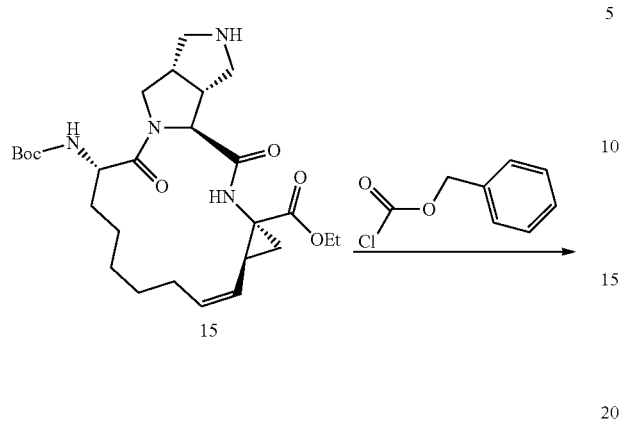

15

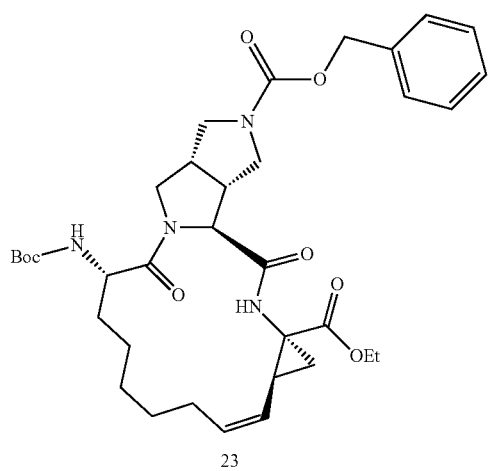

23

To stirred solution of 15 (0.06 mmol) and Et₃N (50 µL, 0.36 mmol) in 1.5 ml DCM was added dropwise at 0° C. benzyl chloroformate (34 µL, 0.24 mmol) diluted in 0.5 ml DCM. The mixture was stirred for 0.5 hour at room temperature and after the completion of the reaction (LC-MS), the mixture was directly loaded onto a preparative TLC plate (1;3 hexanes/ethyl acetate) to give compound 23 (25 mg, 65%) as a yellow oil.

MS: 651.2 (M−H).

Procedure for Urea Synthesis; Synthesis of Compound 24.

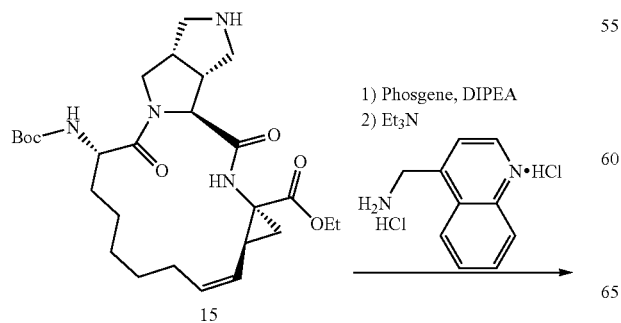

15

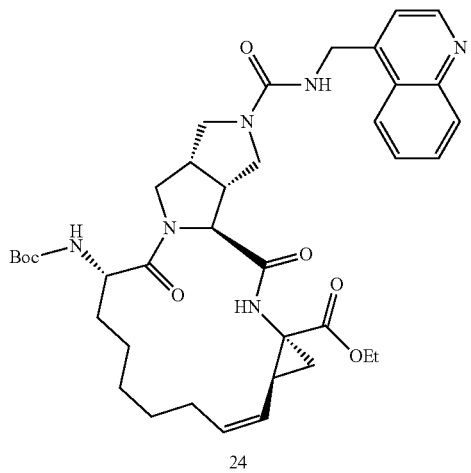

24

To a stirred solution of 9 ml phosgene (20% in toluene) at 0° C. was added a mixture of compound 15 (0.08 mmol) and DIPEA (84 µL, 0.48 mmol) in 2 ml DCM dropwise. The ice bath was removed and the stirring continued for 10 minutes. The reaction mixture was concentrated in vacuo. The residue was dissolved in 3 ml DCM and a mixture of (quinoline-4-yl-methyl)amine (55 mg, 0.24 mmol) and DIPEA (84 µL, 0.48 mmol) in 3 ml DCM was added at 0° C. The mixture was stirred for 1 hour at room temperature and then directly purified by Prep TLC (20:1 ethyl acetate/MeOH) to give compound 24 (50 mg, 89%) as a colorless semi-solid.

MS: 703.3 (MH⁺).

Procedure for Alkylation; Synthesis of Compound 25.

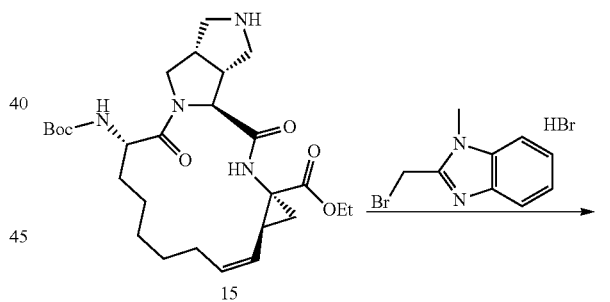

15

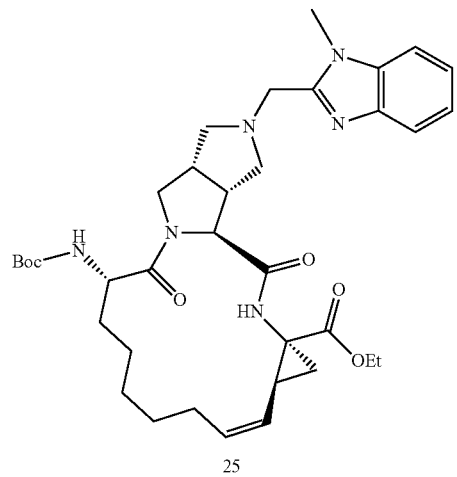

25

To a stirred solution of compound 15 (0.054 mmol) in 2 ml CH₃CN at room temperature was added KI (36 mg, 0.22 mmol), K₂CO₃ (37 mg, 0.27 mmol) and then 2-(bromomethyl)-1-methyl-1H-benzimidazole hydrobromide (66 mg, 0.22 mmol). The mixture was stirred for 1 hour at 50° C. and then overnight at room temperature. After the completion of the reaction (LC-MS) the mixture was directly purified by Prep TLC (1:3 hexanes/ethyl acetate) to give compound 25 (26 mg, 74%) as a yellow oil.

MS: 663.3 (MH⁺).

Procedure for Hydrolysis of the Ester; Synthesis of Compound 26.

To a stirred solution of compound 21 (26 mg, 0.04 mmol) in THF/MeOH/H₂O (0.5 ml/0.5 ml/0.7 ml) at room temperature was added LiOH·H₂O (25 mg, 0.6 mmol). The mixture was then stirred overnight at room temperature. After the completion of the reaction (LC-MS), the mixture was neutralized with 0.6 ml 1N HCl and then directly purified by HPLC to give compound 26 (8 mg, 32%) as a white solid.

MS: 632.2 (MH⁺).

Procedure for the Synthesis of Sulfonamides; Synthesis of Compound 27.

To a stirred solution of compound 26 (6 mg, 0.0095 mmol) in 1.0 ml anhydrous THF was added CDI (15 mg, 0.095 mmol) at room temperature. The mixture was heated to 50° C. for 1 hour and then cooled to room temperature. Cyclopropanesulfonamide (12 mg, 0.095 mmol) was added and then DBU (14 μL, 0.095 mmol). The mixture was stirred overnight at room temperature and was directly purified by HPLC to give compound 27 (5 mg, 71%) as a white solid after being lyophilized.

MS: 735.3 (MH⁺).

General Procedure for the Conversion from Boc to Cyclopentyloxycarbonyl; Synthesis of Compound 29.

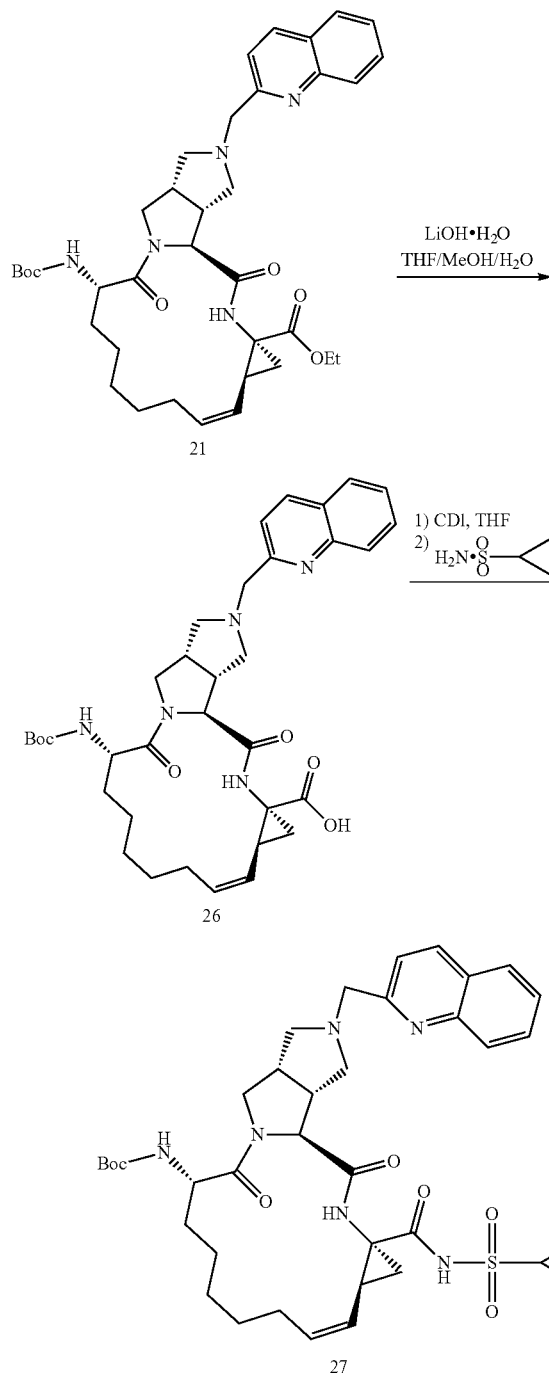

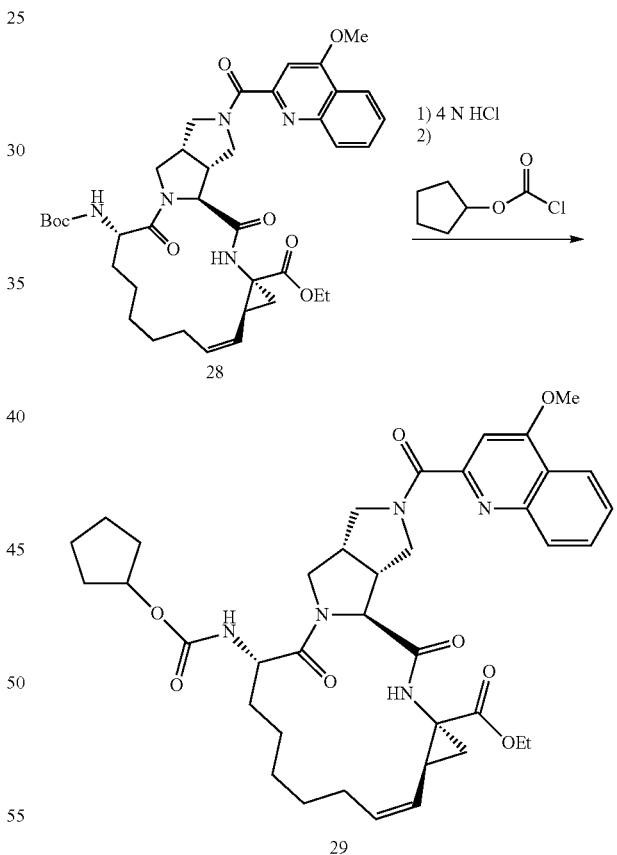

2 ml 4N HCl in dioxane was added to compound 28 (0.05 mmol) at 0° C. The ice bath was removed and the reaction mixture stirred for 0.5 hour at room temperature. After the completion of the reaction (monitored by TLC; 30:1 ethyl acetate/MeOH), the mixture was completely dried in vacuo. The residue was dissolved in 2 ml DCM and then treated with Et₃N (33 μL, 0.24 mmol) at 0° C. Cyclopentyl chloroformate (89 mg, 0.6 mmol) in 0.5 ml DCM was added to the above mixture at 0° C. The ice bath was removed and the stirring continued for 20 minutes. After the completion of the reaction (LC-MS), the mixture was directly purified by Prep TLC (40:1 ethyl acetate/MeOH) to give the compound 29 (40 mg, 93%) as a colorless oil.

MS: 716.2 (MH$^+$).

Testing of HCV Protease Inhibition
NS3/NS4A Inhibition Assay.

Apparent IC50 values were determined using the fluorogenic substrate Ac-DE-D(Edans)-EE-Abu-ψ-[COO]-AS-K (Dabcyl)-NH2 (AnaSpec, San Jose, Calif., USA) in the assay buffer: 50 mM HEPES, pH 7.5, containing 20% Glycerol and 10 mM DTT (added fresh before use from 100× stock solution in water). The enzyme solution was prepared as follows: for 10 mL of solution 0.1 mL of 10 mM solution of truncated modified NS4A peptide KGSVVIVGRIILSGKK (AnaSpec, San Jose, Calif., USA) was added to 10 mL of pre-warmed assay buffer followed by the addition of 3 uL of 10 uM stock solution of NS3 protease. The enzyme concentration was determined from the absorbance at 280 nm ($A_{280}$ for 1 mg/mL solution=0.934). The substrate/inhibitor solution was prepared as follows: 98 uL of pre-warmed assay buffer was dispensed onto each well of a pre-warmed 96-well plate and 2 uL of 100× stock solution of inhibitor at a specified concentration was added to each well. In the control sample 2 uL of DMSO without inhibitor was added. Seven inhibitor concentrations were generally used to obtain the IC50 curve using 3-fold dilutions starting from 10, 1 and 0.1 uM, depending on the potency of the inhibitor. The reaction was initiated by the addition of 100 uL of freshly prepared enzyme mix solution prepared as described above to an equal volume of substrate/inhibitor solution on the pre-warmed (30° C.) 96-well black plate. Final concentrations were: NS3; 1.5 nM (based on estimated protein concentration), NS4A; 50 uM, DMSO; 2%. Increase in fluorescence intensity at the emission maximum of 520 nm (excitation wavelength was 340 nm, cut off filter 495 nm) was monitored as a function of time using a SpectraMAX Gemini fluorescence plate reader (Molecular Devices, CA., USA). The initial rate of hydrolysis was calculated by first-degree polynomial fit using SoftMAX operating software. IC50 values were estimated by fitting data to the equation:

% inhibition=$(A+((B-A)/(1+(((B-E)\cdot(IC50/I)^S))/(E-A)))))$ with the program XLfit, version 4.2.2, where A=0, B=100, E=50, I is inhibitor concentration, and s is a slope factor.

$IC_{50}$ Determination of Protease Inhibitors in the HCV Replicon Cell

The $IC_{50}$ values of the antiviral agents were determined in a cell based assay with the HCV Con1 subgenomic replicon. Cell lines Huh-luc/neo-ET with persistent replicon sequence I$_{389}$luc-ubi-neo/NS3-3'/ET were obtained from ReBlikon GmbH (Schriesheim, Germany). I$_{389}$luc-ubi-neo/NS3-3'/ET contained a bicistronic construct composed of following elements: HCV IRES (nucleotides 1-389) directing firefly luciferase-ubiquitin-neomycin phosphotransferase fusion protein and ECMV IRES driven NS3-NS5B HCV polyprotein that harbors the cell culture adaptive mutations (E1202G, T12801, K1846T). It has been shown that that amount of luciferase protein is an accurate measure for RNA replication as determined by quantitative PCR (Taq-Man). The inhibitory activity of IFN-alpha was used as a reference. HCV replicon cells (10,000/well) were plated in a 96-well plate in Dulbecco's modified Eagle's medium plus 10% fetal bovine serum. The next day, the medium was removed, and antiviral agents serially diluted in the same media were added. Each dilution was added to 4 wells. Medium with freshly diluted compounds was replaced every 24 h. The replicon cells were incubated with the antiviral agents for 72 h. The luciferase activity was measured by Steady-Glo Luciferase assay system (Promega) according to the protocol. Luciferase signal was measured in Optima (BMG LABTECH Inc.) plate reader. Data were fit by Excel Fit to calculate $IC_{50}$.

What is claimed is:
1. A compound represented by the formula:

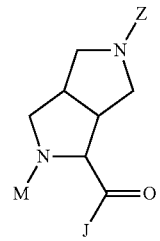

wherein,

Z is hydrogen, a protecting group that can be selectively removed under the conditions of organic synthesis, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted heterocycloalkyl, optionally substituted $C_3$-$C_8$ cycloalkyl, optionally substituted $C_4$-$C_8$ cycloalkenyl, optionally substituted heterocyclo, optionally substituted heteroaryl, CONRR, COOR, COR3, SO$_2$R3, SOR3, SO$_2$NRR, —PO(NRR)R3, or PO(OR)R3;

M is H, a protecting group that can be selectively removed under the conditions of organic synthesis, or a moiety selected from the group consisting of:

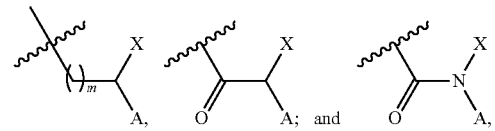

wherein m=1-3;

X is -NRR2, —OR, —NRP$^1$ wherein P$^1$ is a protecting group that can be selectively removed under the conditions of organic synthesis, optionally substituted $C_1$-$C_{12}$ alkyl, optionally substituted $C_3$-$C_7$ cycloalkyl, optionally substituted $C_2$-$C_{12}$ alkenyl, optionally substituted $C_4$-$C_7$ cycloalkenyl or X is a moiety selected from the group consisting of

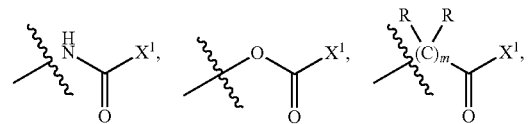

and —NSO$_2$-X$^1$;

wherein X$^1$ is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, OR, or —NRR;

A is -D-R1, wherein D is a bond or optionally substituted $C_1$-$C_{12}$ alkylene, wherein up to three alkylene units of D are optionally and independently replaced by alkyl, alkenyl, alkynyl, aryl, $C_3$-$C_7$ cycloalkyl, $C_4$-$C_7$ cycloalkenyl, heterocyclo, heteroaryl, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—, wherein up to 3 carbon atoms of D are optionally and independently substituted by R1;

J is a OH, OP$^2$, wherein P$^2$ is a protecting group that can be selectively removed under the conditions of organic synthesis, —NR—, or

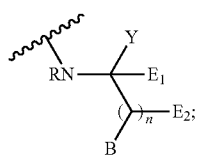

wherein when J is —NR— or

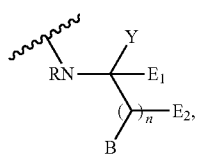

and D is optionally substituted $C_1$-$C_{12}$ alkylene, then one carbon atom of D is optionally covalently linked to —NR— or B to form a macrocylic ring;

n=0 or 1, wherein when n =0 then E$_2$ is absent and B is linked directly to the carbon atom bearing Y and E$_1$;

B is —CH═CH2, R, or B is a bond to D when B and D form a macrocyclic ring,

E$_1$ and E$_2$ are H, R, or E$_1$ and E$_2$ together form a 3 to 6-membered optionally substituted saturated or unsaturated carbocylic ring;

Y is COOH, COOR, CONHR, —COCONHR, CONHSO$_2$R, CONH(SO$_2$)NRR, CONHP(O)(OR)$_2$, or CONHP(O)(OR)(NRR);

each R independently is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, or optionally substituted heteroaryl, or R and R together form a 5-7-membered carbocyclic ring, optionally fused to an aryl or heteroaryl ring, wherein said aryl or heteroaryl ring optionally is substituted by up to 3 R3 moieties, R1 is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, amido, carboxyl, sulfonamido, halo, —OR, —CN, —NO$_2$, —NRR, or —OCF$_3$, R2 is H, —COOR, CONRR, COR, SO$_2$R, SOR, or SO$_2$NRR; and R3 independently is selected from the group consisting of $C_1$-$C_{12}$ alkyl, $C_2$-$C_{12}$ alkenyl, $C_2$-$C_{12}$ alkynyl, $C_3$-$C_8$ cycloalkyl, $C_4$-$C_8$ cycloalkenyl, aryl, heteroaryl, and heterocyclo, each optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —NO$_2$, —NRR, —OCF$_3$, —COOR, CONRR, COR, SO$_2$R, and SOR.

2. The compound of claim 1 wherein Z is a protecting group, M is a protecting group, and J is OP$^2$.

3. The compound according to claim 1 wherein, J is

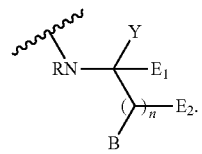

4. The compound according to claim 1 wherein, M is

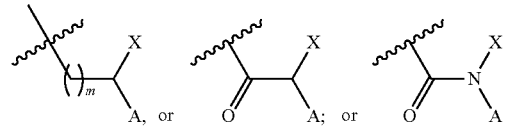

and J is

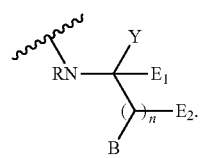

5. The compound according to claim 1 wherein X is —NRR2, Y is CO$_2$R or CONHSO$_2$R, and E$_1$ and E$_2$ together form a 3 to 6 membered optionally substituted saturated carbocylic ring.

6. The compound according to claim 1 represented by the formula:

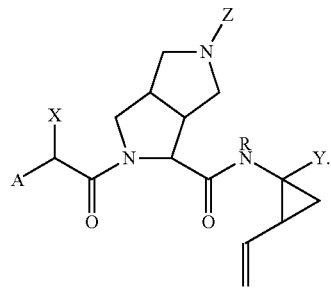

7. The compound according to claim 1 represented by the formula:

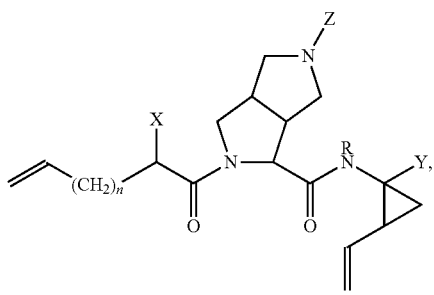

wherein n is 0-10.

8. The compound according claim 1 represented by the formula:

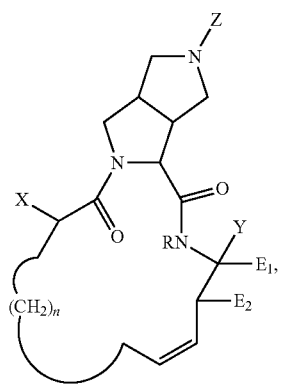

wherein n is 0-8.

9. The compound according to claim 1 represented by the formula:

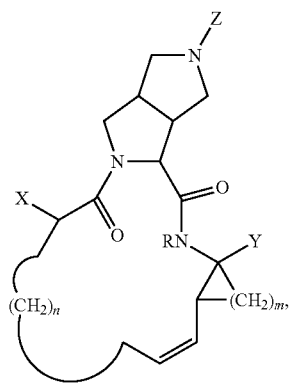

wherein m is 0-3.

10. The compound according to claim 1 represented by the formula:

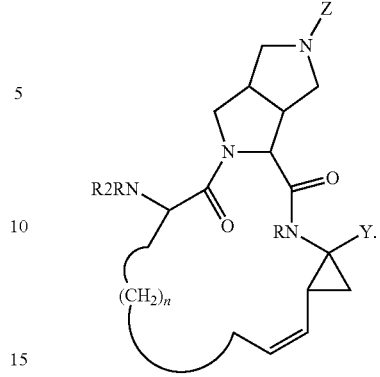

11. The compound according to claim 10 wherein n is 3.

12. The compound according to claim 10, wherein R2 is COOR.

13. The compound according to claim 1, wherein Y is $CO_2H$ or $CONHSO_2R$.

14. The compound according to claim 1 wherein Z is COR3.

15. The compound according to claim 14, wherein R3 is aryl or heteroaryl, wherein R3 is optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —$NO_2$, —NRR,—$OCF_3$, —COOR, CONRR, COR, $SO_2R$, and SOR.

16. The compound according to claim 15, wherein R3 is aryl substituted with at least one aryl or heteroaryl group, and wherein said at least one aryl or heteroaryl group optionally is substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, halo, —OR, —CN, —$NO_2$, —NRR,—$OCF_3$, —COOR, CONRR, COR, $SO_2R$, and SOR.

17. The compound according to claim 15, wherein R3 is heteroaryl substituted with at least one aryl or heteroaryl group, and wherein said at least one aryl or heteroaryl group optionally is substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, halo, —OR, —CN, —$NO_2$, —NRR,—$OCF_3$, —COOR, CONRR, COR, $SO_2R$, and SOR.

18. The compound according to claim 15, wherein R3 is selected from the group consisting of

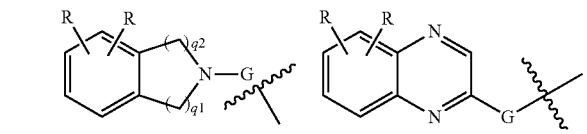

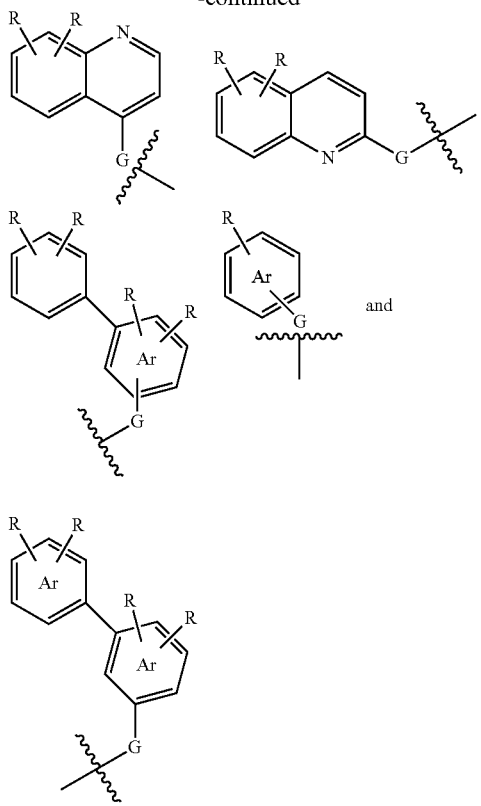

where G is selected from the group consisting of a bond, CH$_2$—, CHR—, CHRCHR—, CO—, COCHR—, SO$_2$,—PO(OR)—, PO(NRR)—, NRCO—, and —(CHR)$_{1-3}$—C(O)N —;

wherein

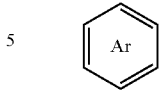

is aryl or heteroaryl, and
wherein q1 and q2 are independently 1 or 2.

19. The compound according to claim 18, wherein R3 is selected from the group consisting of 4-aryl-2-thiazolyl, 6-aryl-2-pyridyl, 3-aryl-phenyl, 5-aryl-3-pyridyl, 4-aryl-2-pyridyl, 3-thiazolyl-aryl, 4-aryl-3-thienyl, 3-thienylaryl, 2-aryl-4-quinolinyl, 2-aryl-4-thiazolyl, 3-pyridylphenyl, 2-phenyl-3-indolyl, 3-pyrazolylphenyl, and 3-phenyl-2-indolyl.

20. A method of inhibiting hepatitis C virus comprising administering to a patient a compound according to claim 8.

21. A pharmaceutical composition comprising a therapeutically effective amount of a compound according to claim 8 and a pharmaceutically acceptable diluent, adjuvant or excipient.

22. A method of treating hepatitis C infection in a subject comprising administering to a patient a composition according to claim 21.

23. The method according to claim 20, further comprising administering to said subject an additional anti-hepatitis C agent.

24. The method according to claim 23, wherein said additional agent is selected from the group consisting of interferon, interferon, ribivarin, adamantine.

25. The method according to claim 23, wherein said additional agent is an inhibitor of HCV metalloprotease, IRES, HCV viral polymerase, HCV entry, HCV replicase, HCV helicase, or HCV NS51, or said agent is ribavarin, pegylated, interferon, or. an RNAi molecule targeting viral gene expression.

26. The compound according to claim 1, selected from the group consisting of of :

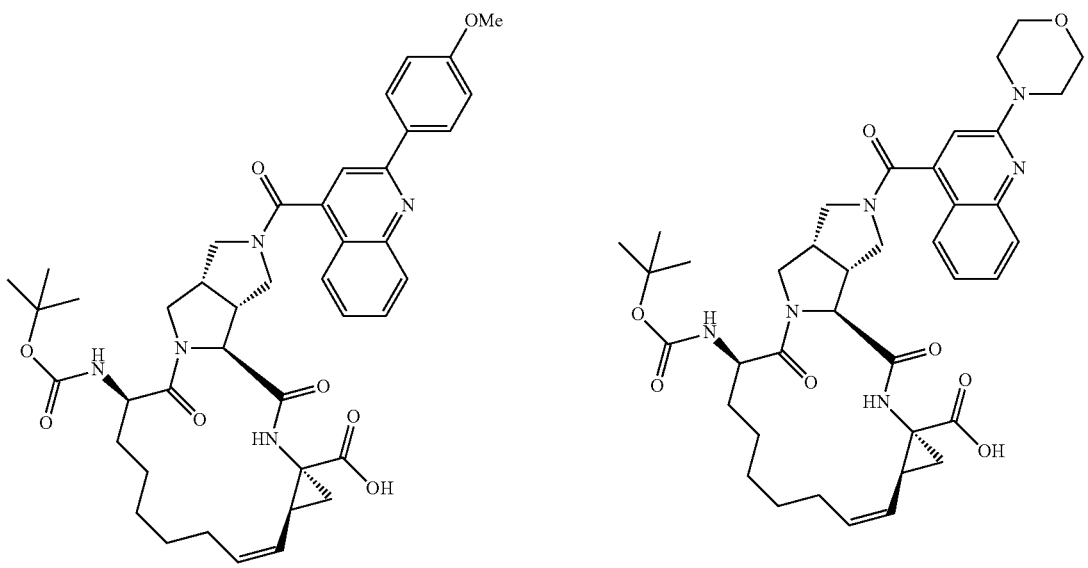

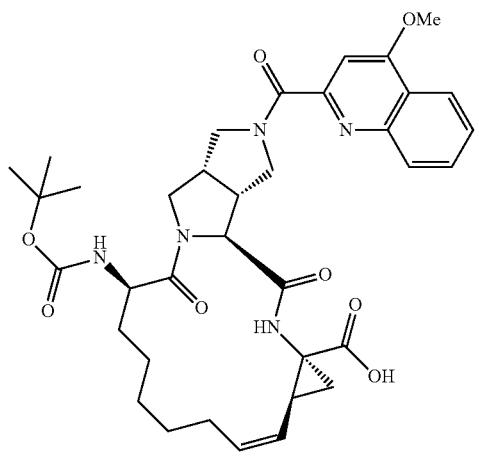
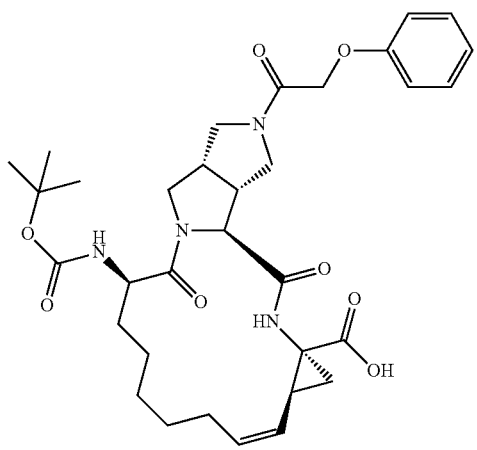
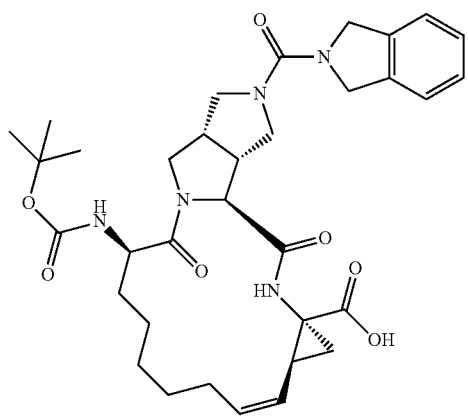
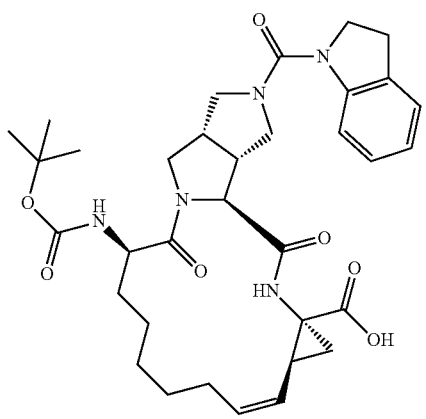
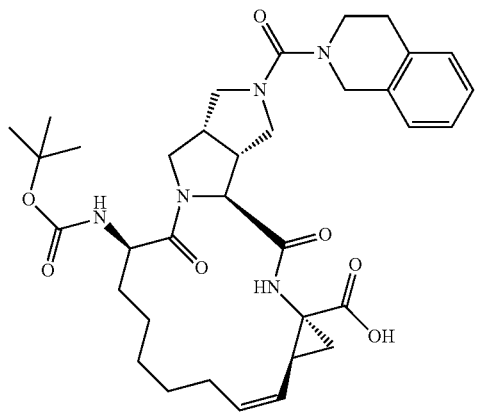
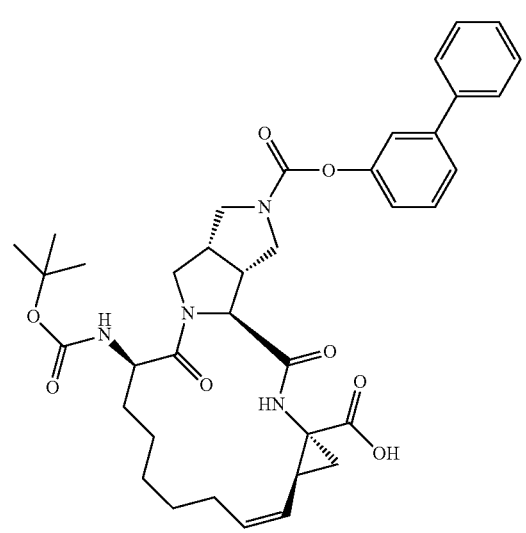

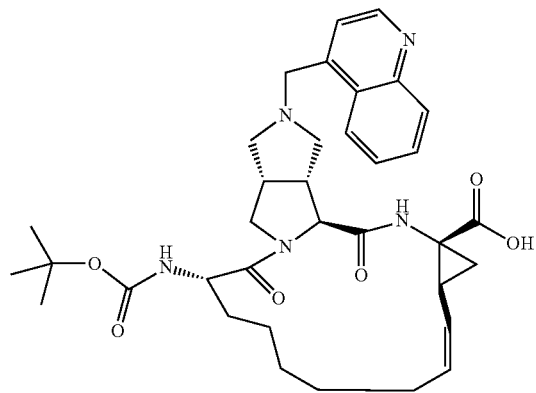
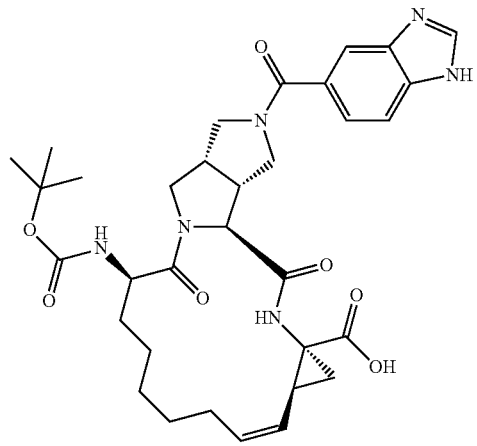
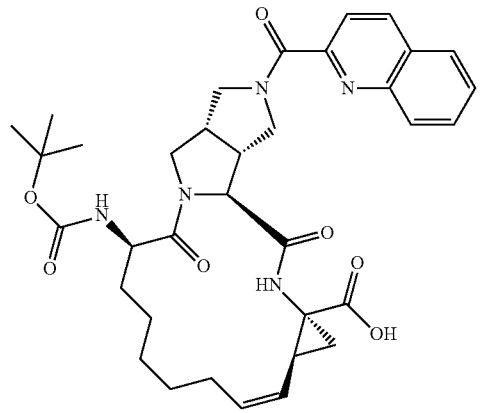
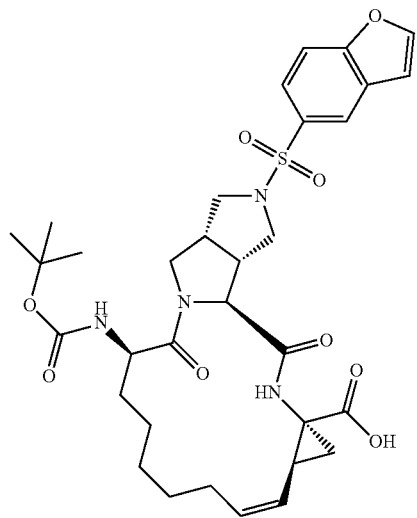
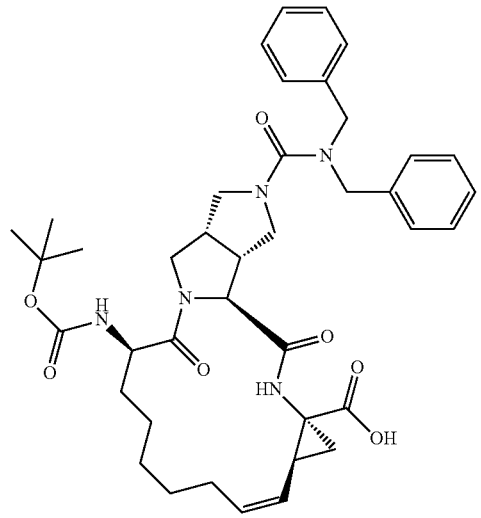
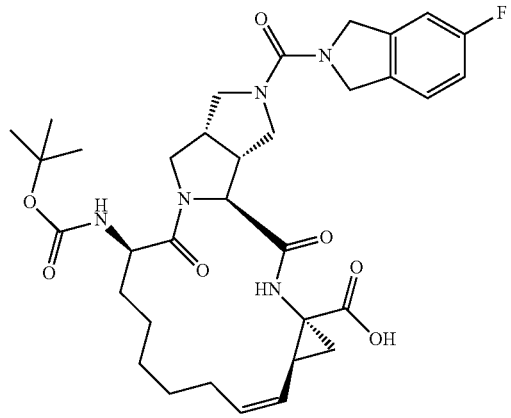

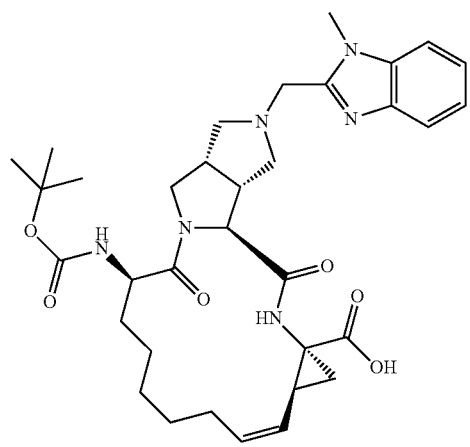
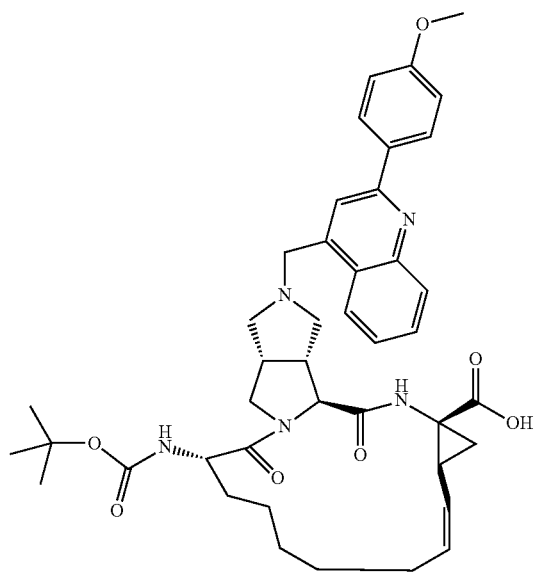
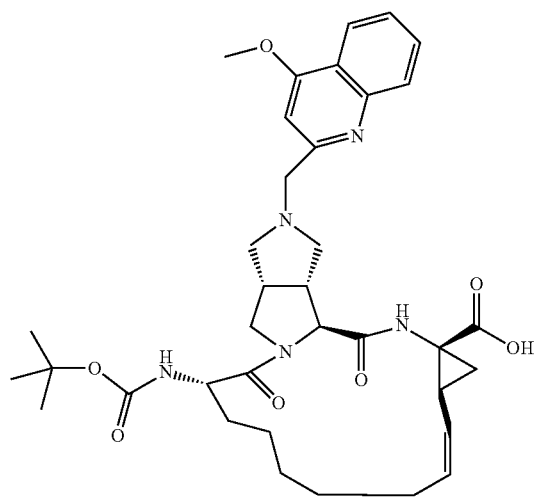
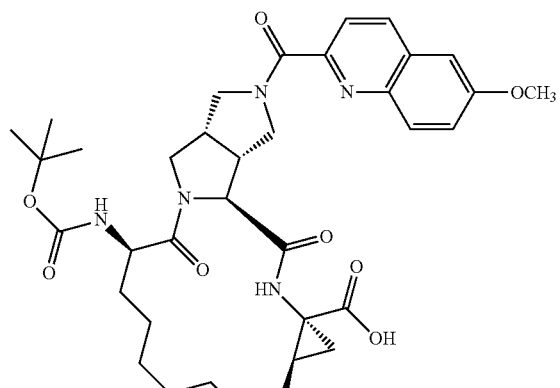
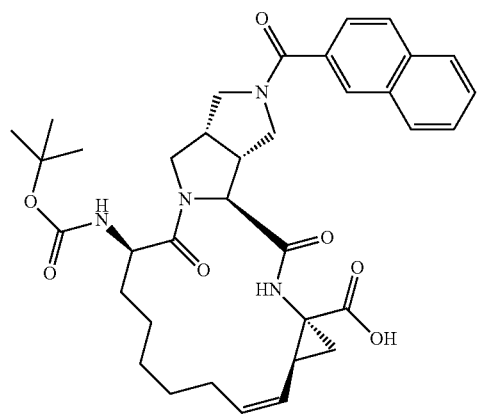
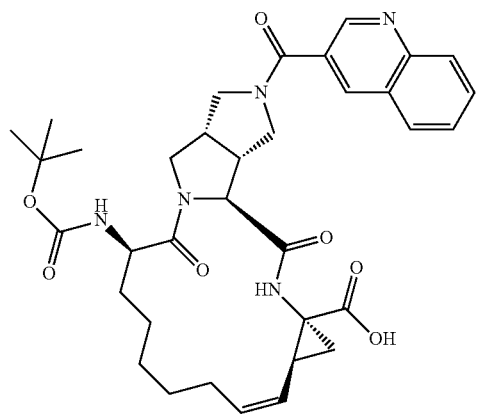

67
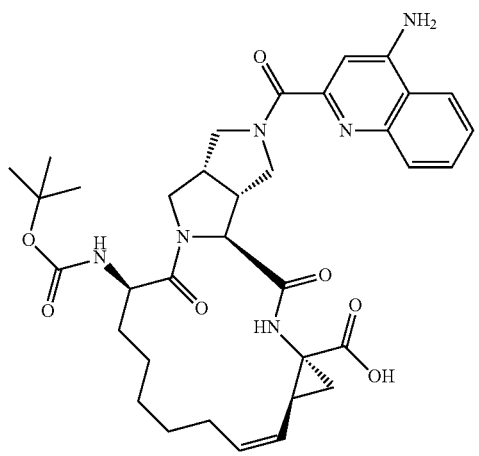
68
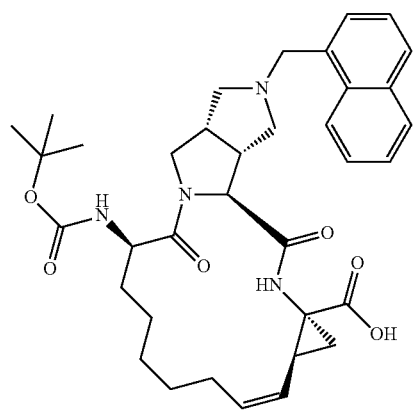
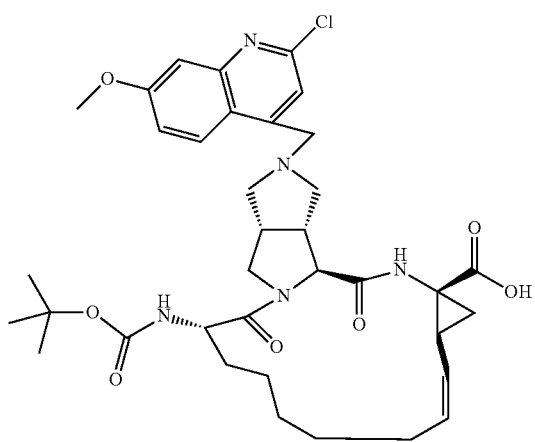
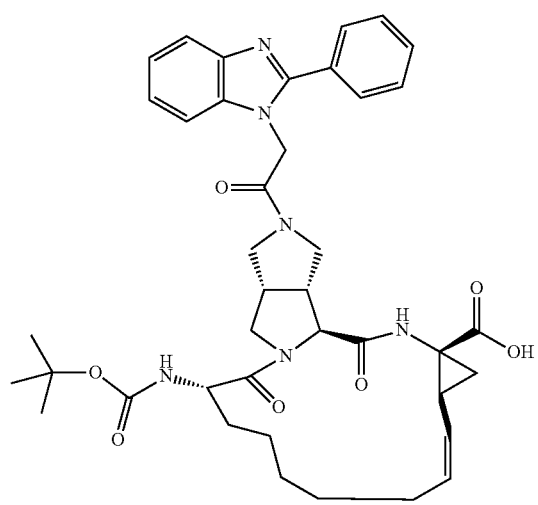
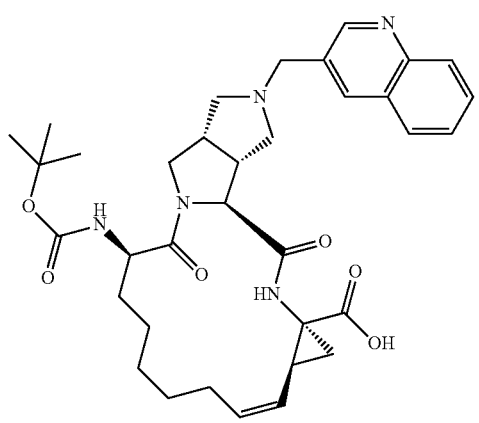
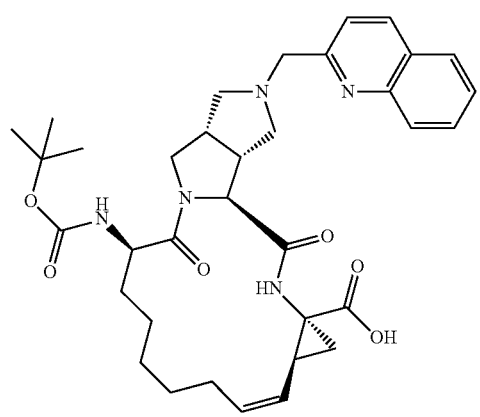

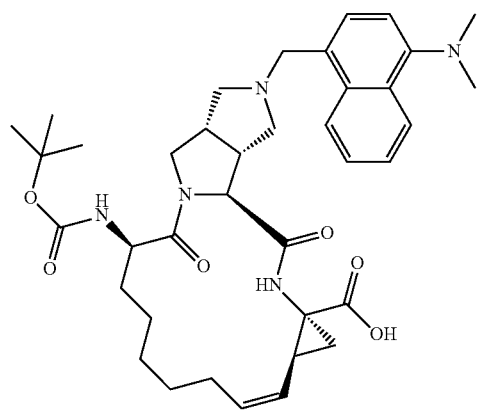
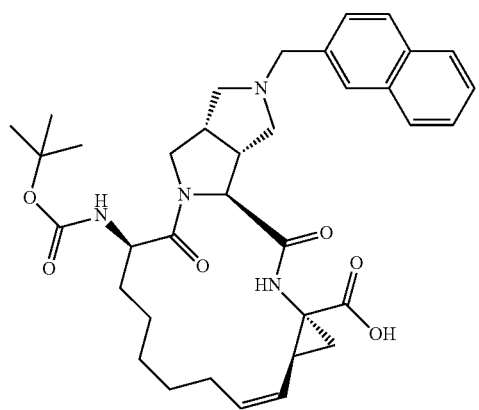
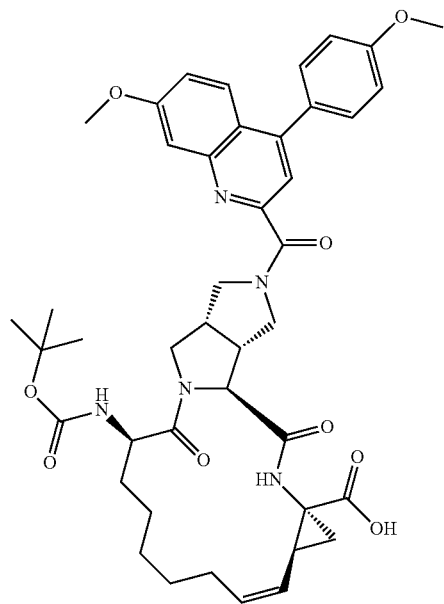
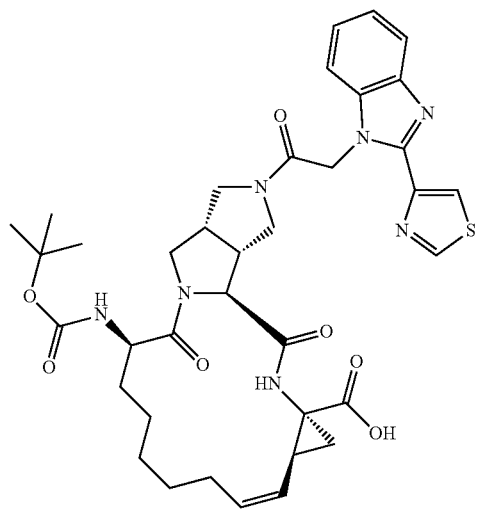
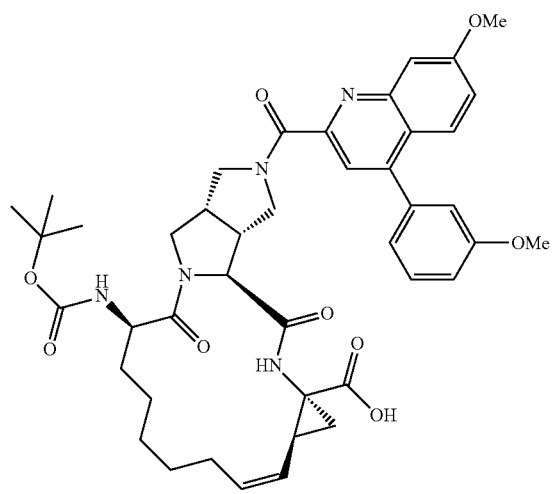
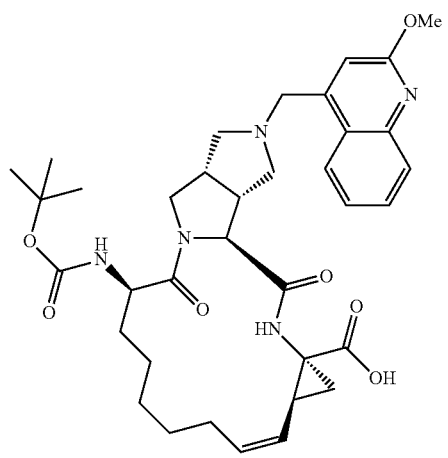

-continued
71
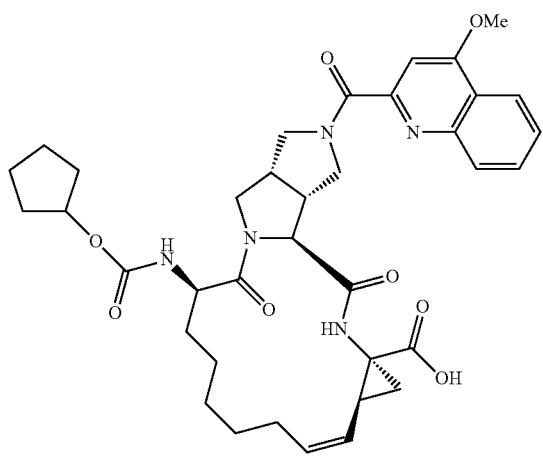
72
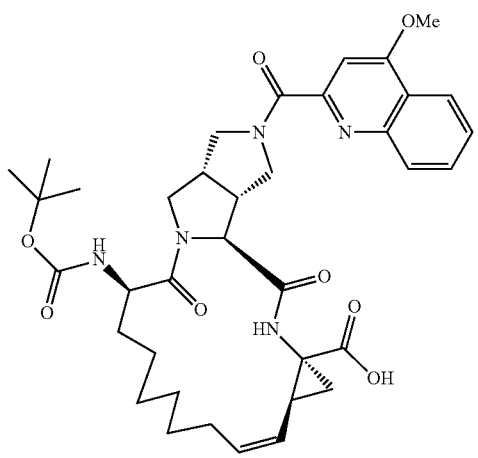
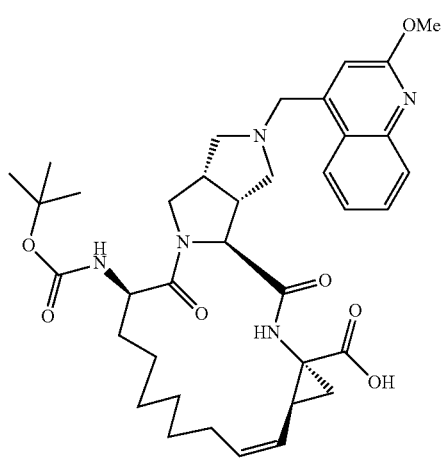
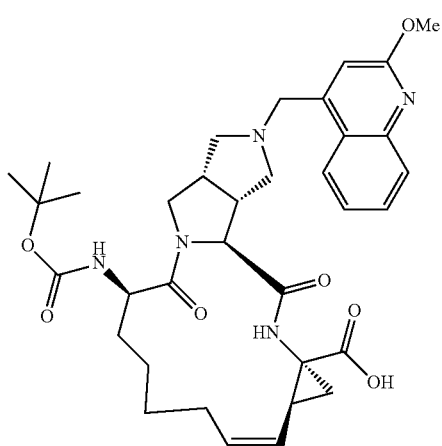
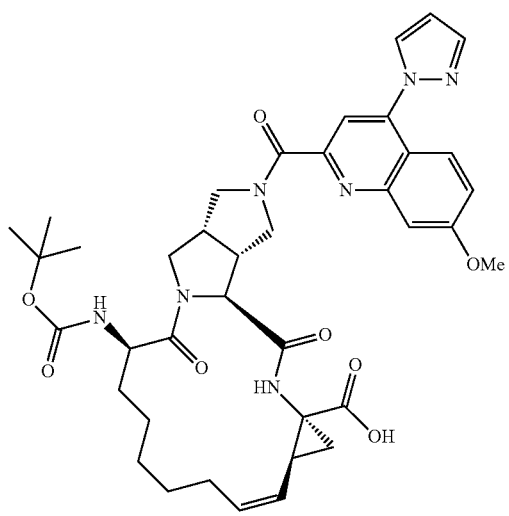
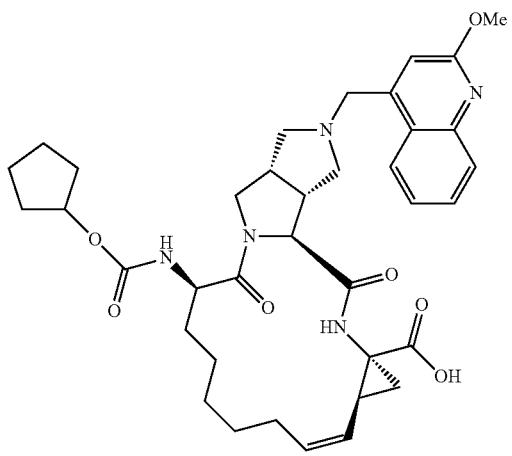

73
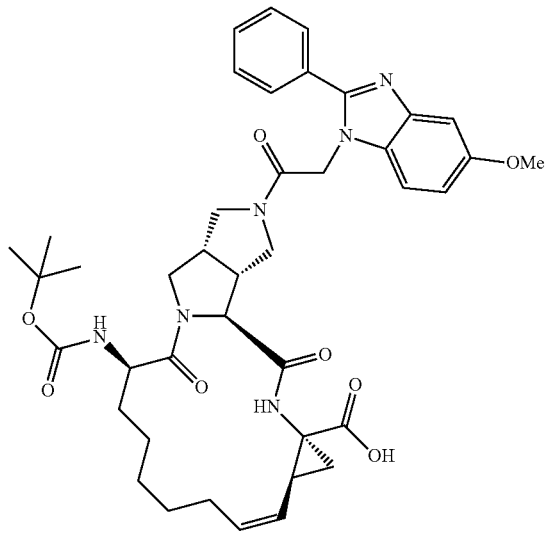
74
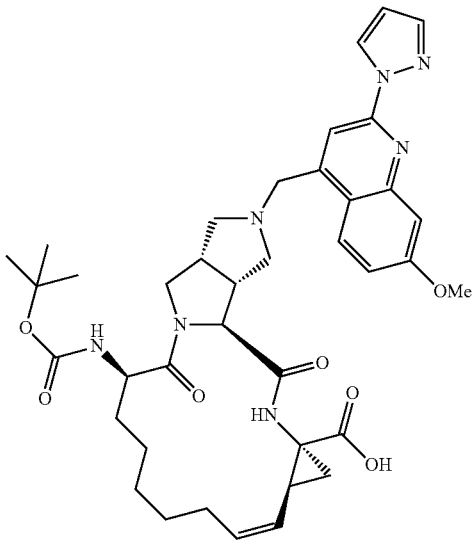
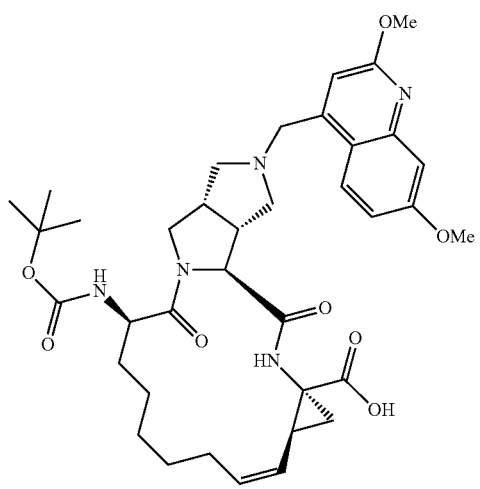
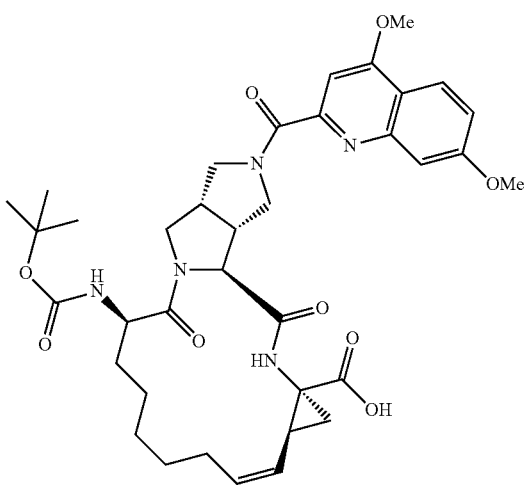
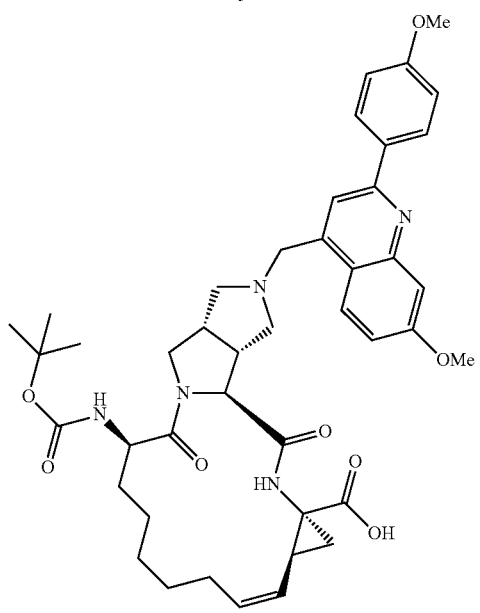
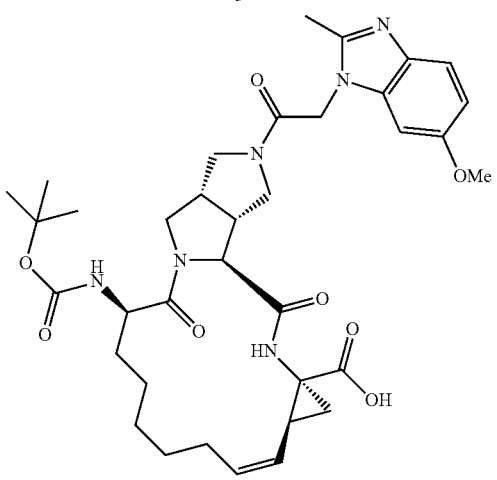

75 76
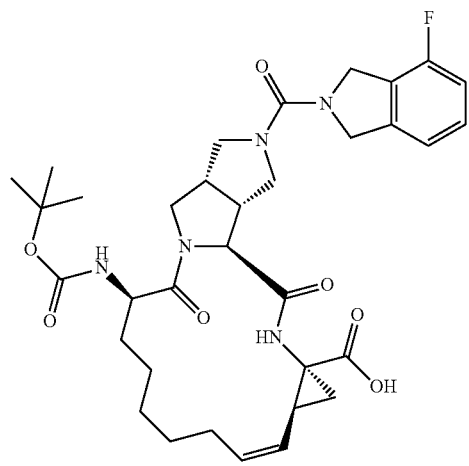
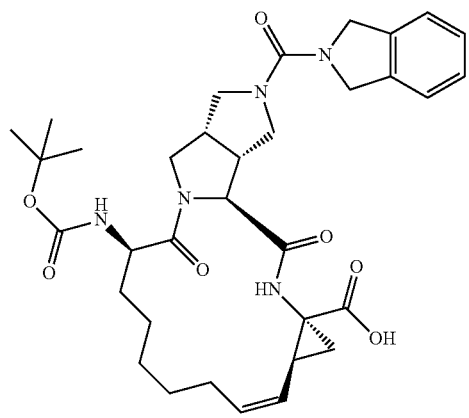
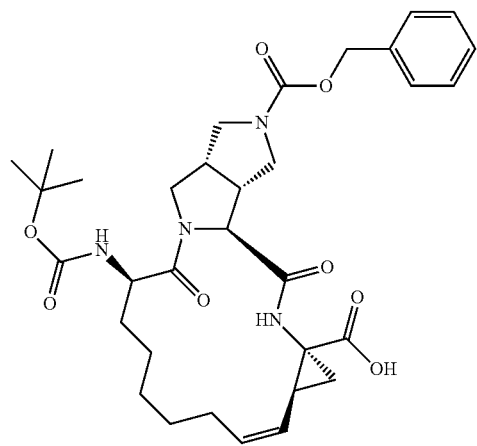
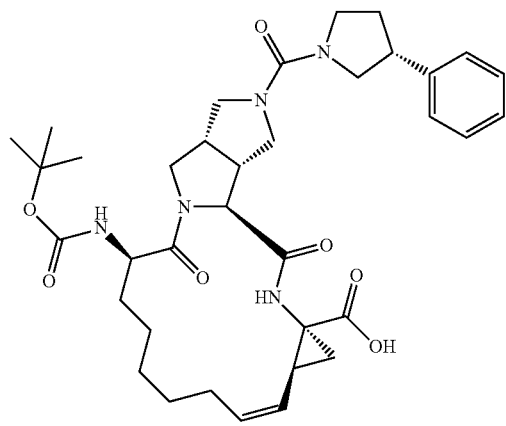
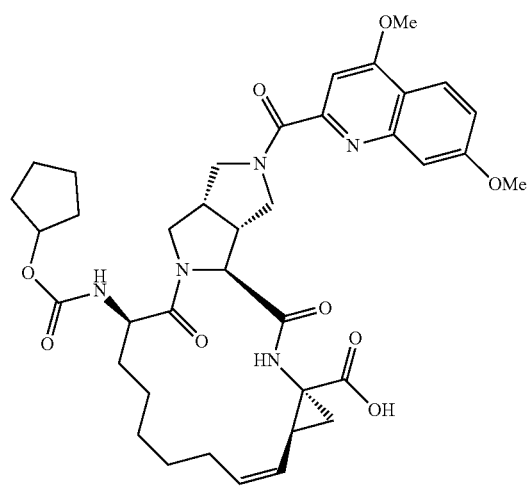
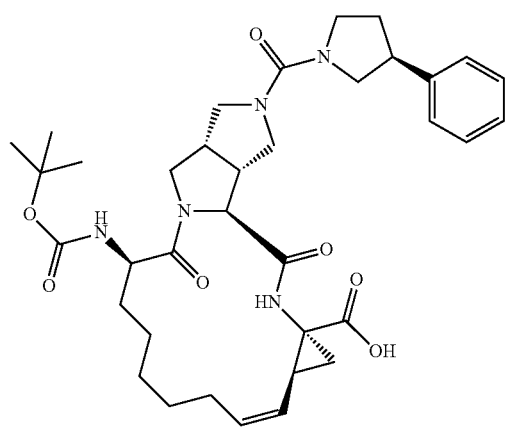

-continued
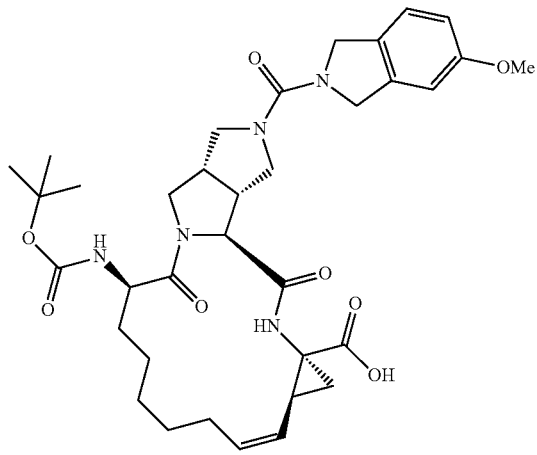
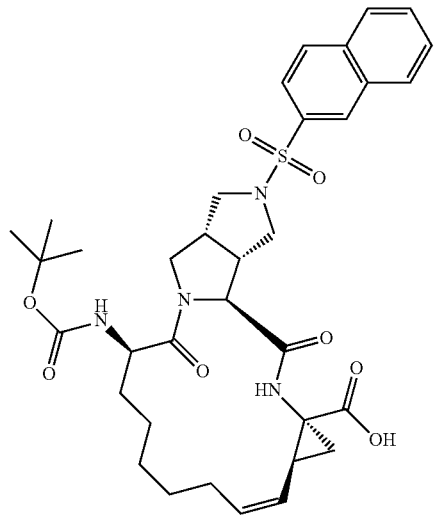
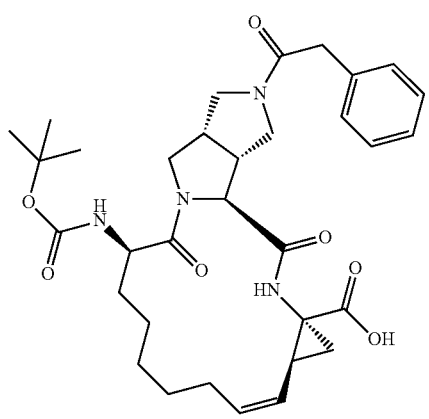
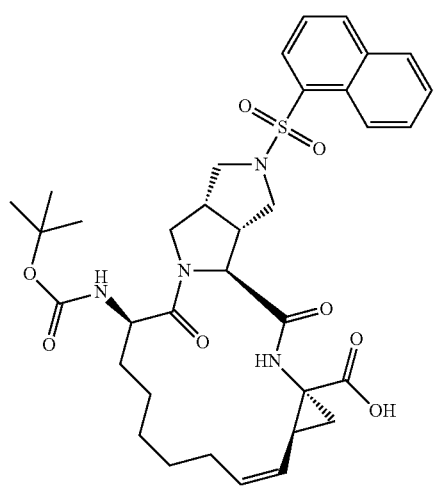
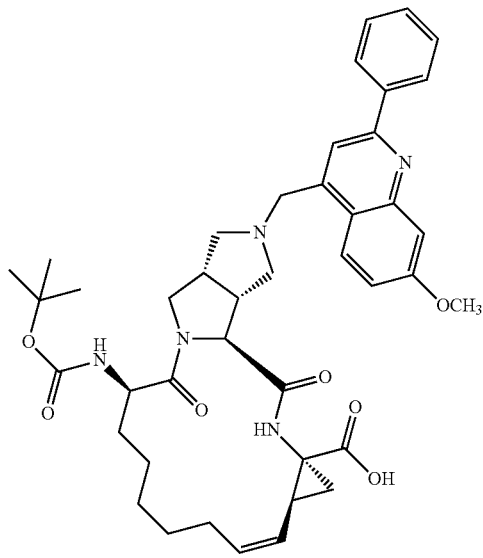

-continued
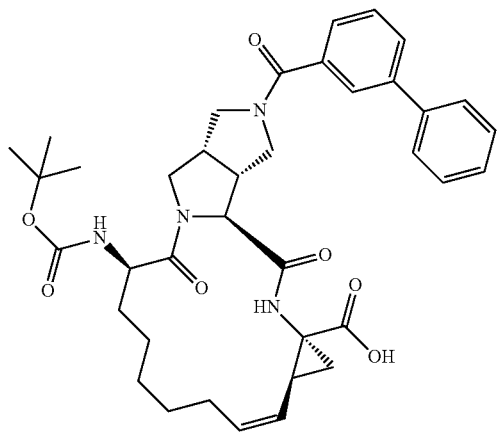
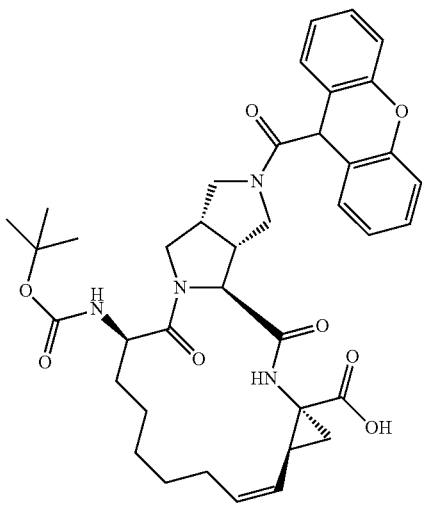
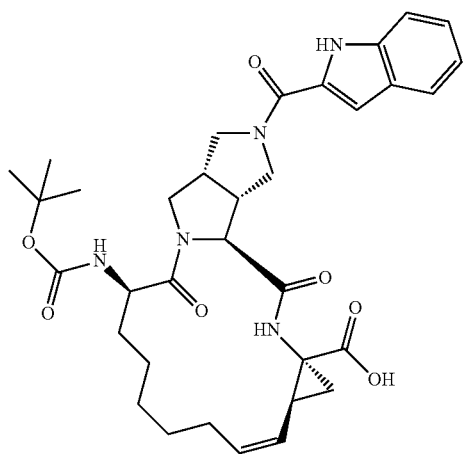
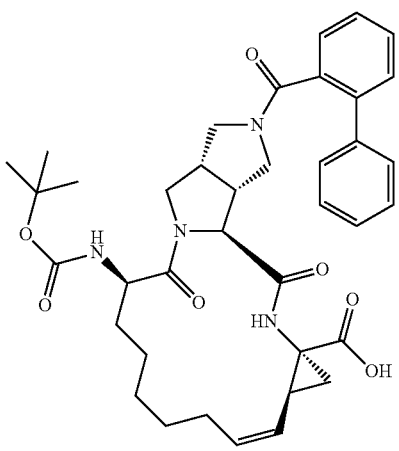
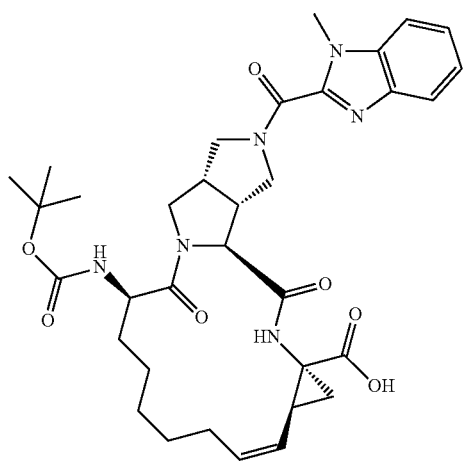
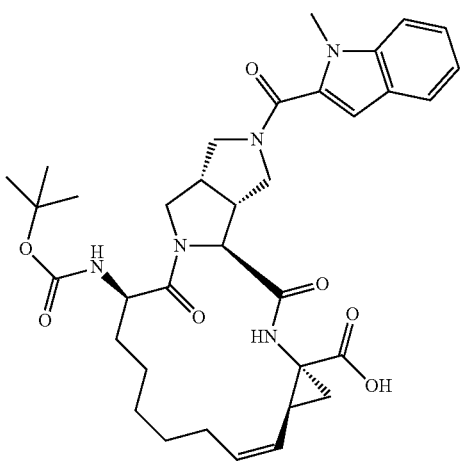

81
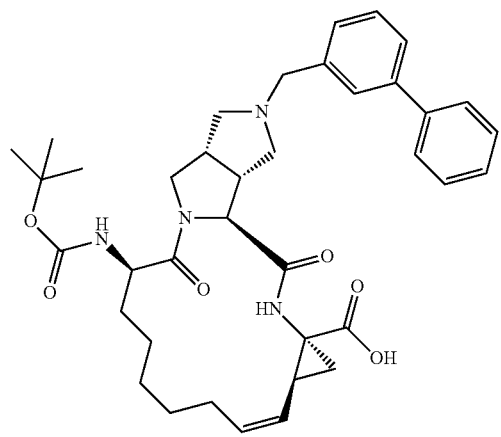
82
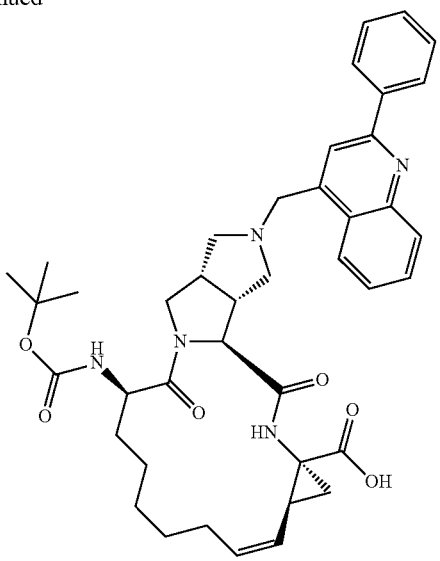
-continued
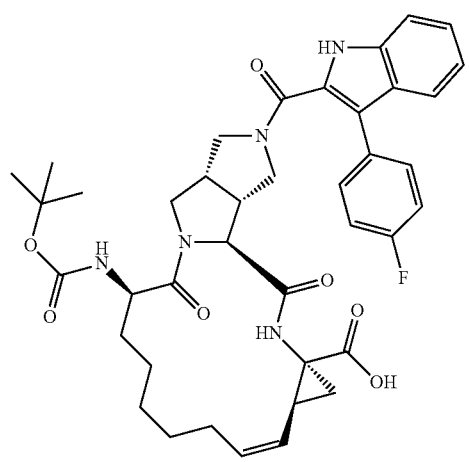
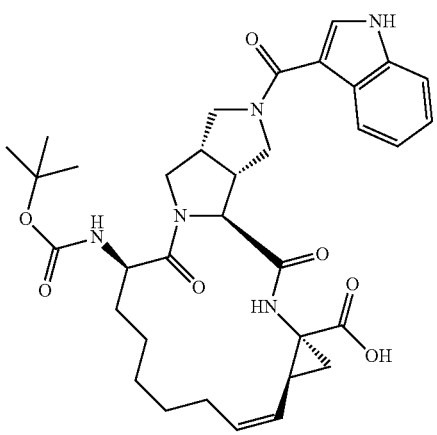
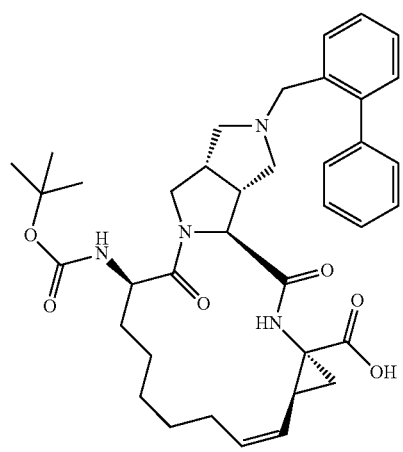
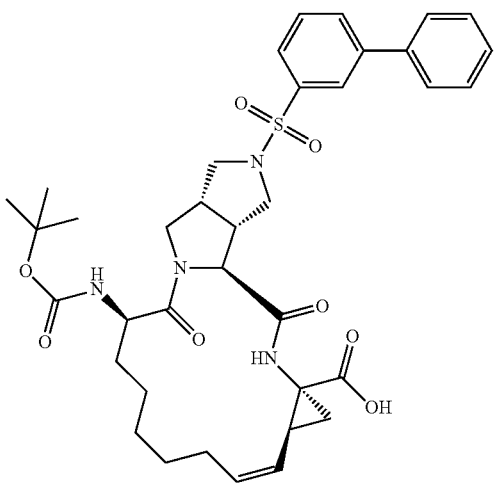

| 83 | 84 |
|---|---|
| 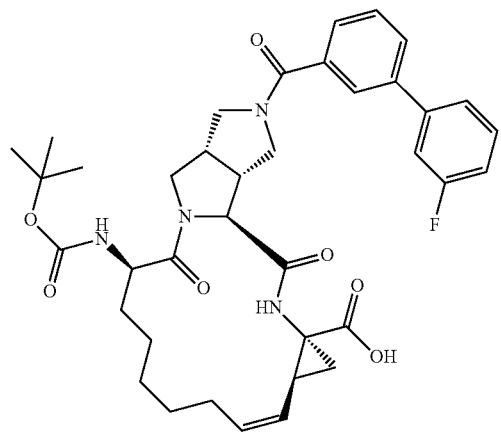 | 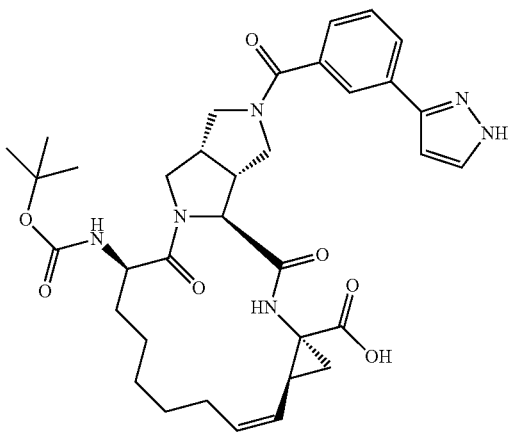 |
| 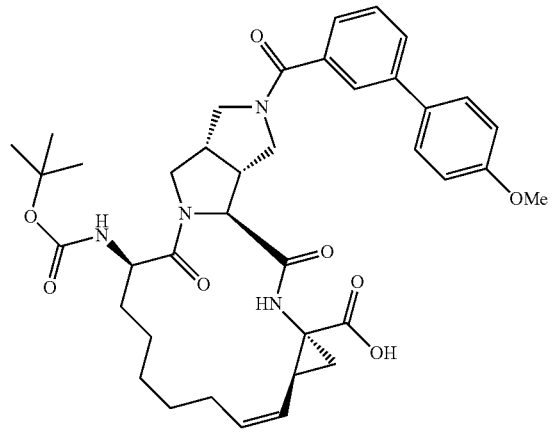 | 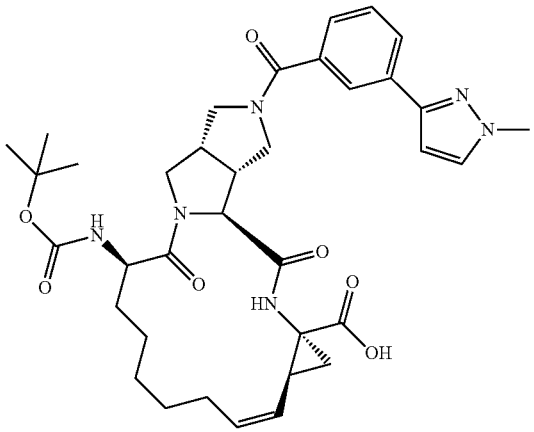 |
| 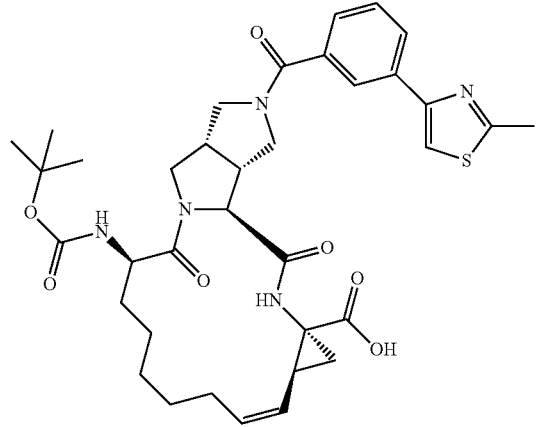 | 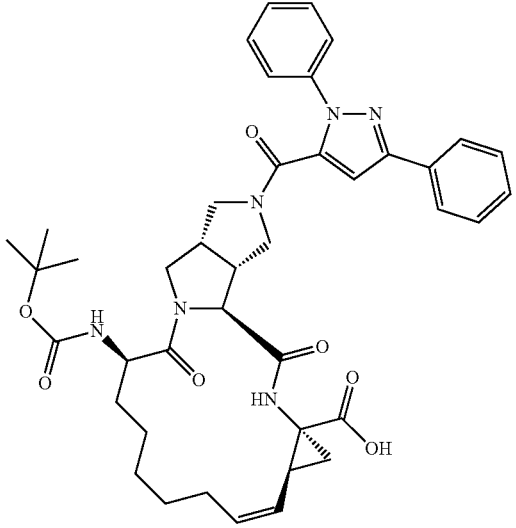 |

85
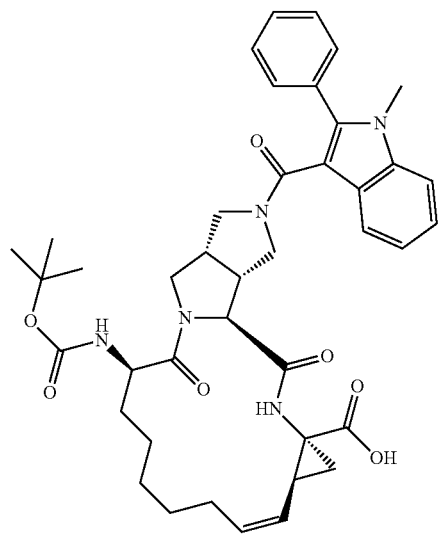
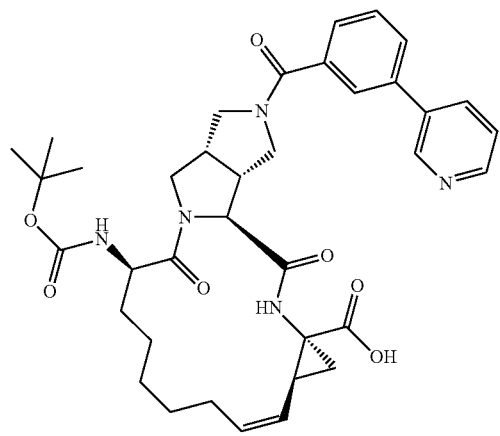
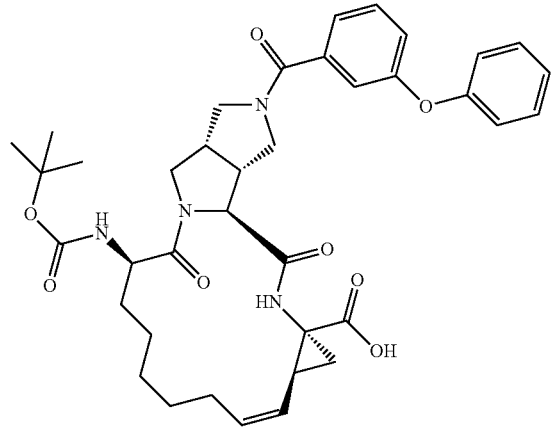
86
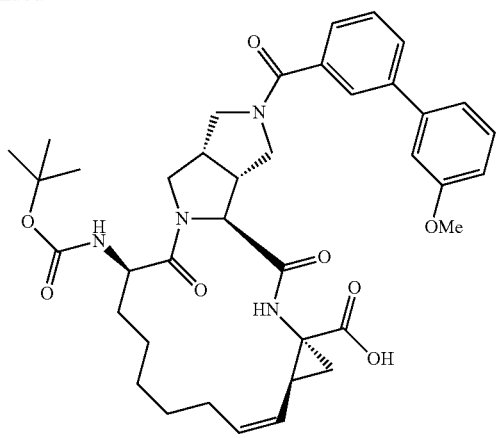
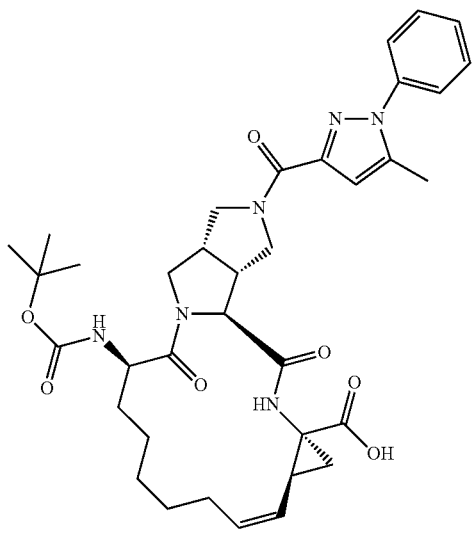
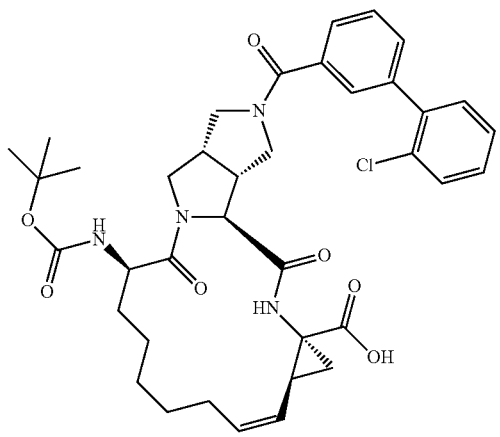

87
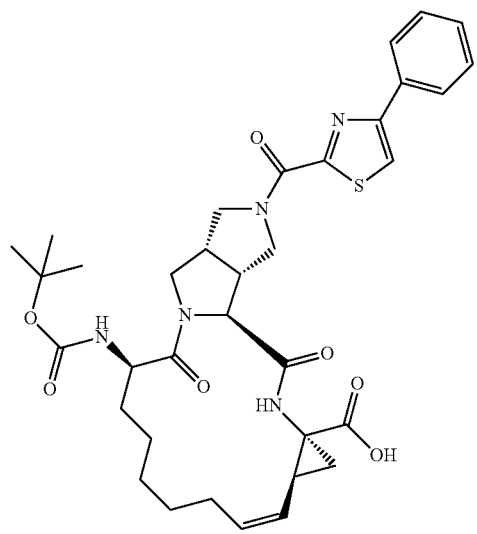
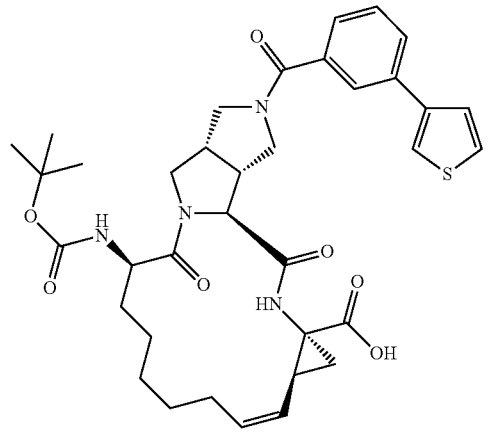
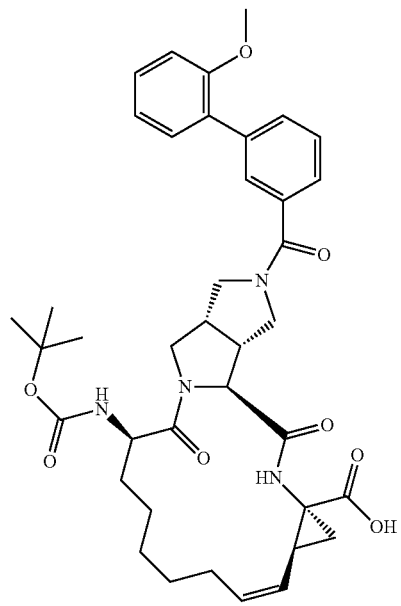
88
-continued
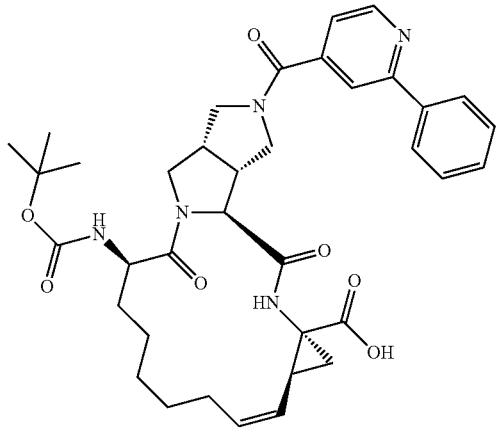
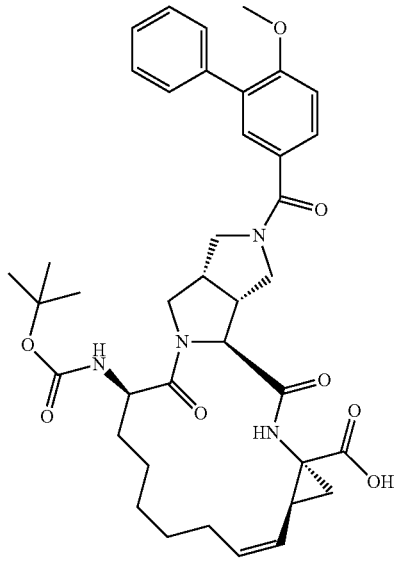
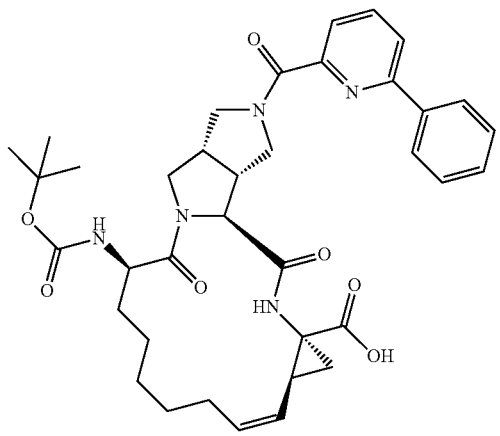

89
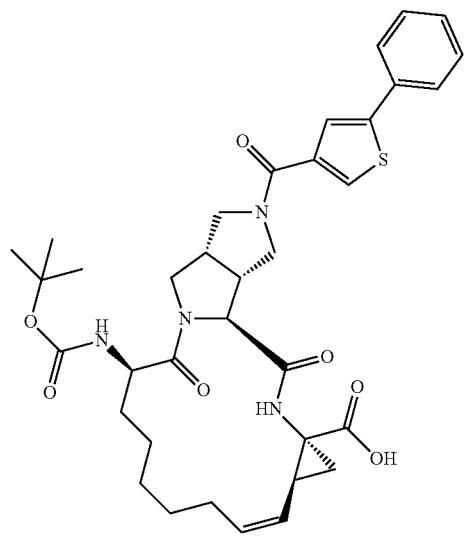
90
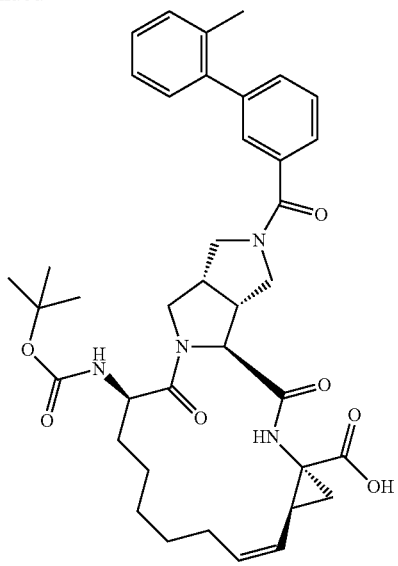
-continued
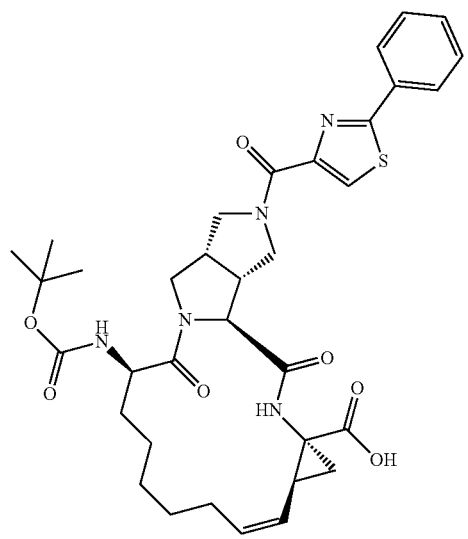
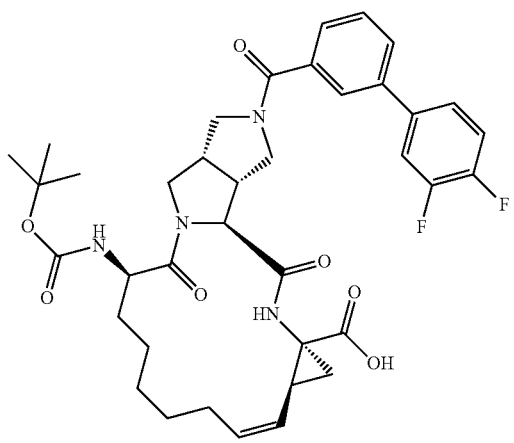
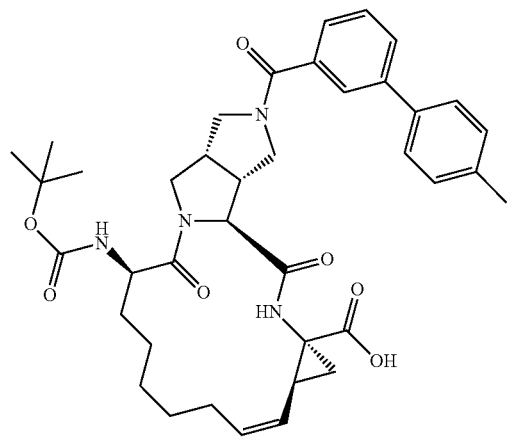
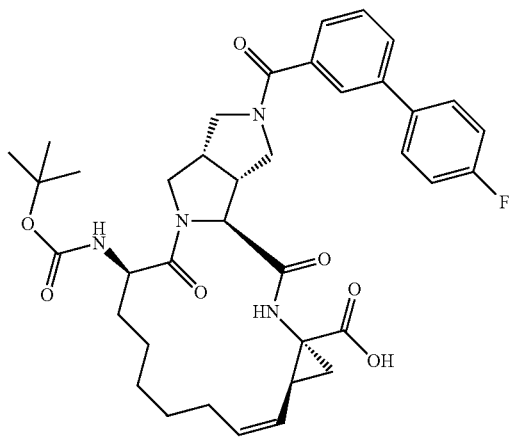

91
92
-continued
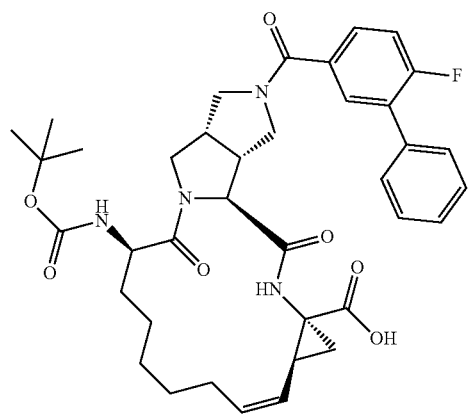
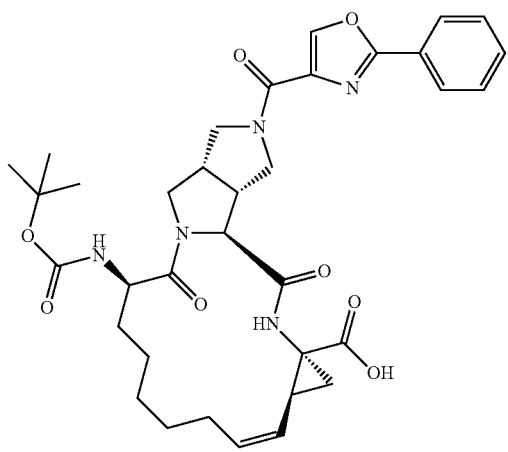
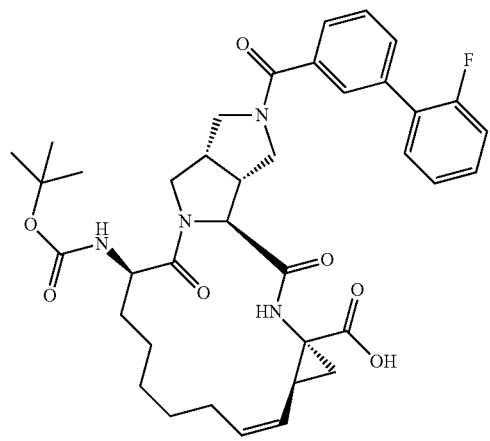
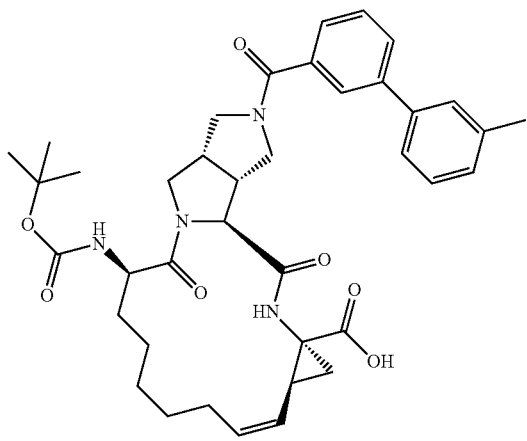
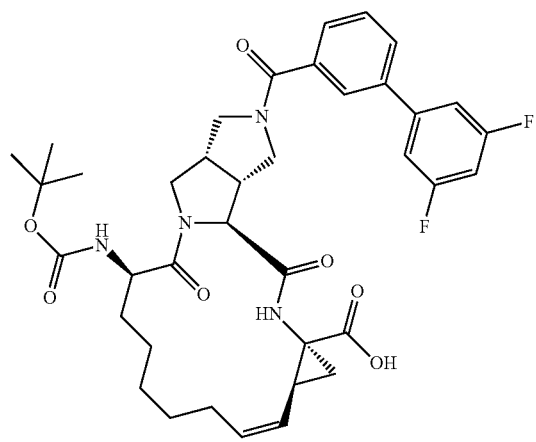
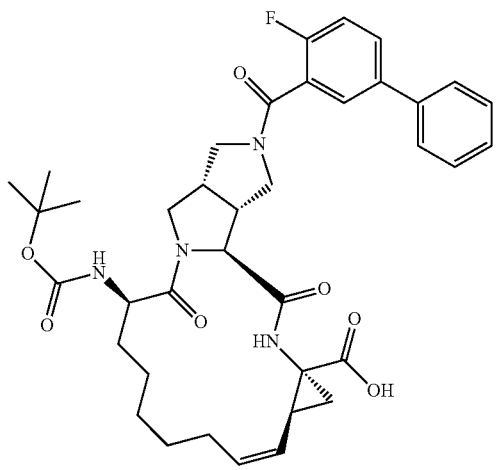

93
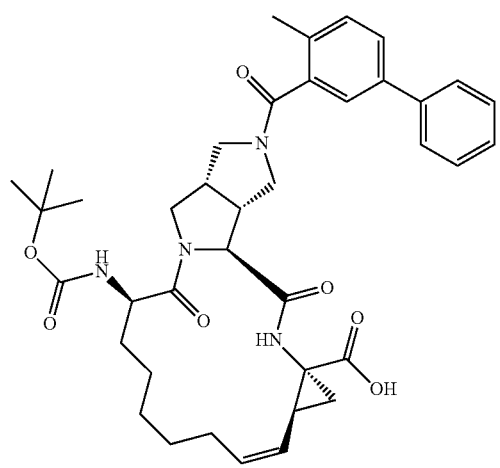
94
-continued
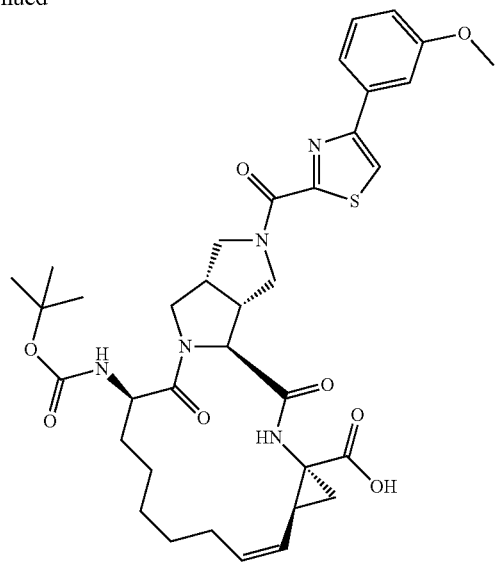
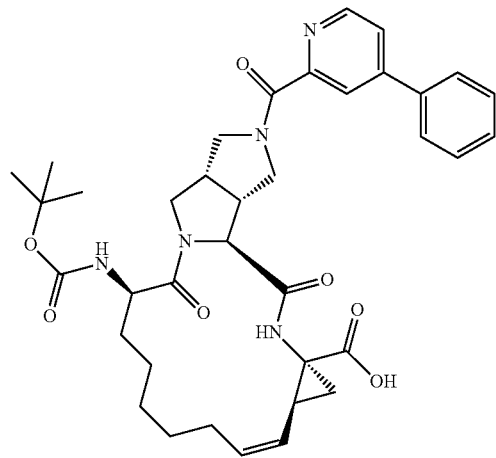
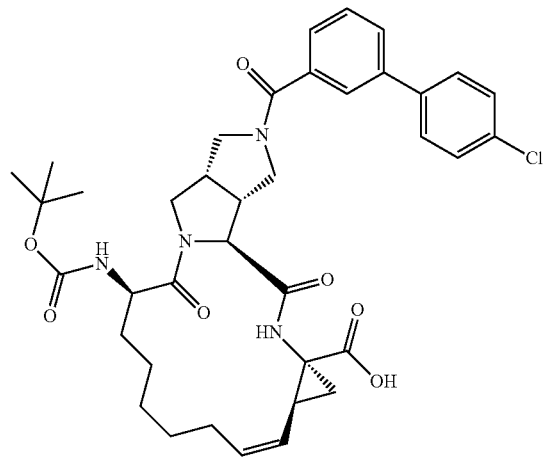
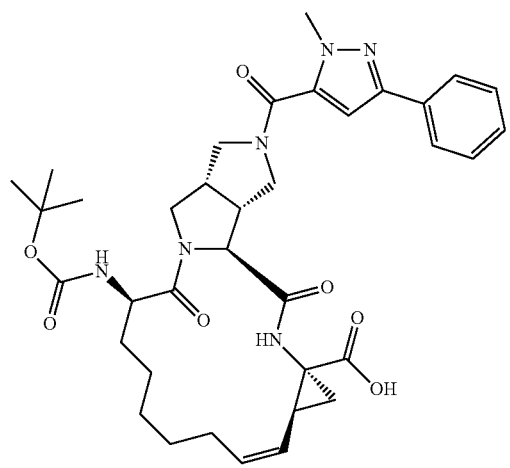
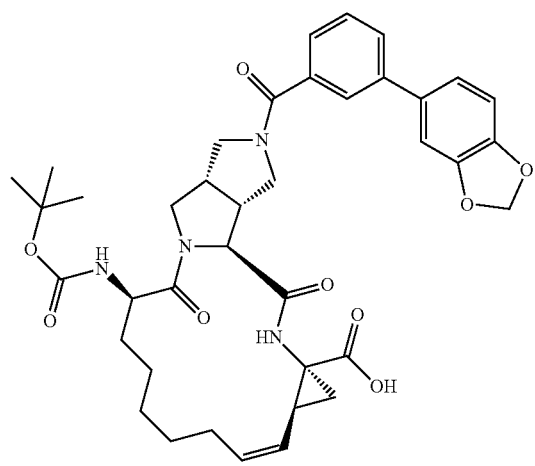

95 96
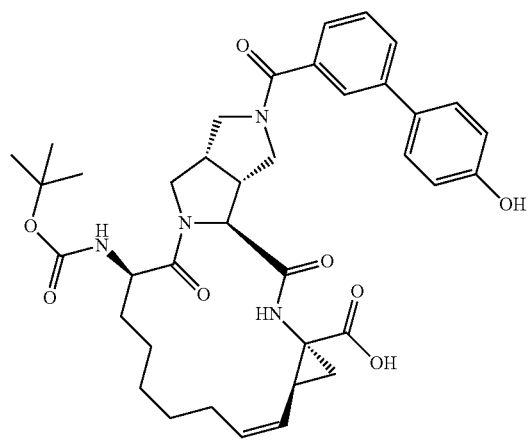
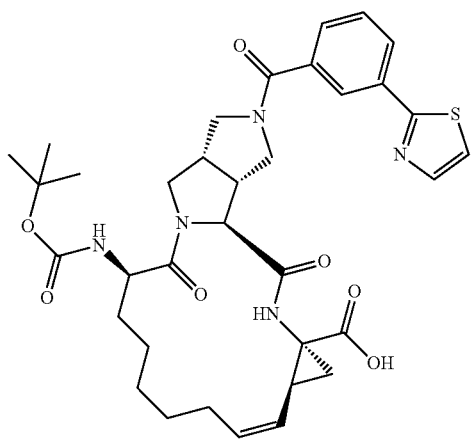
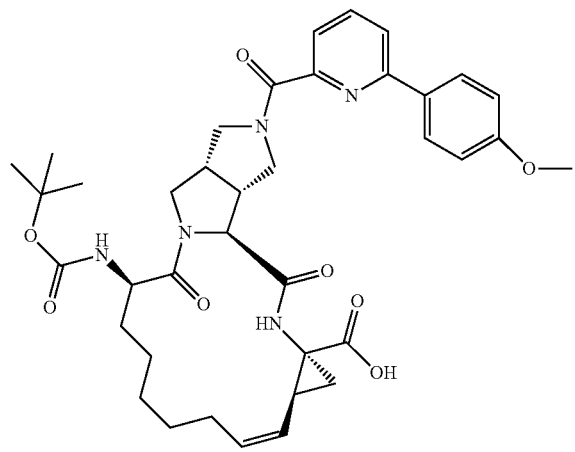
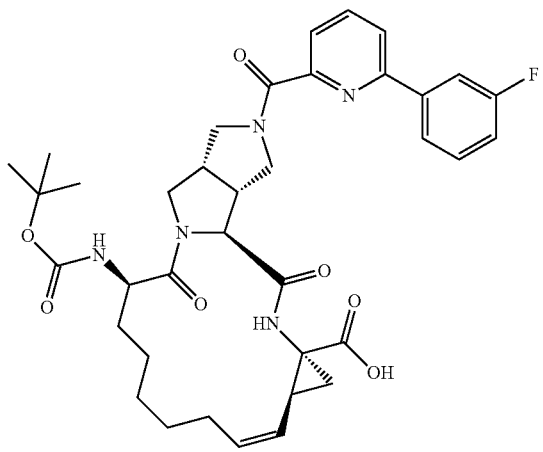
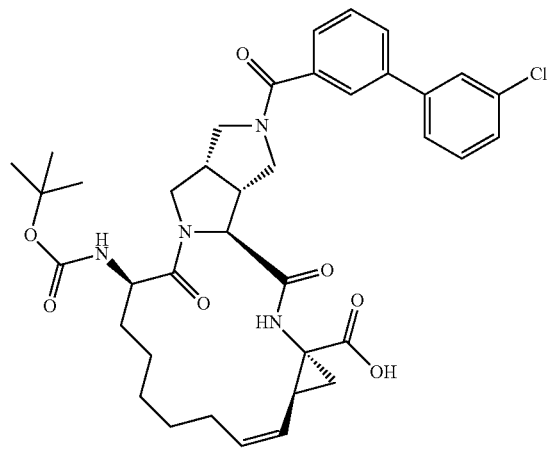
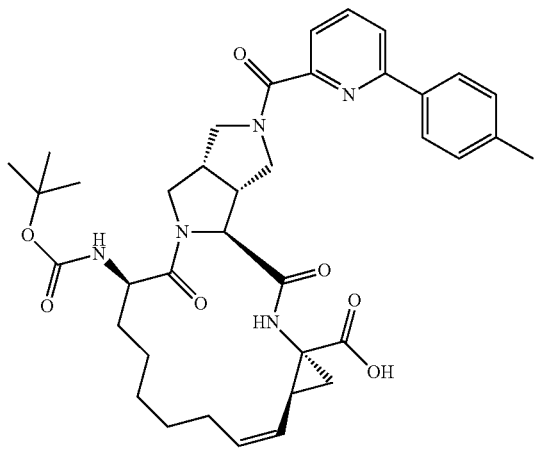

-continued
97
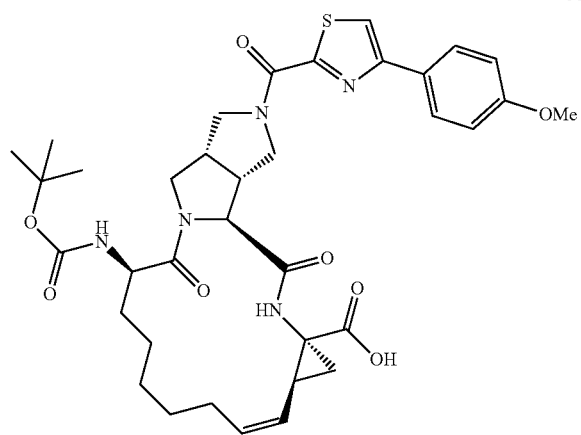
98
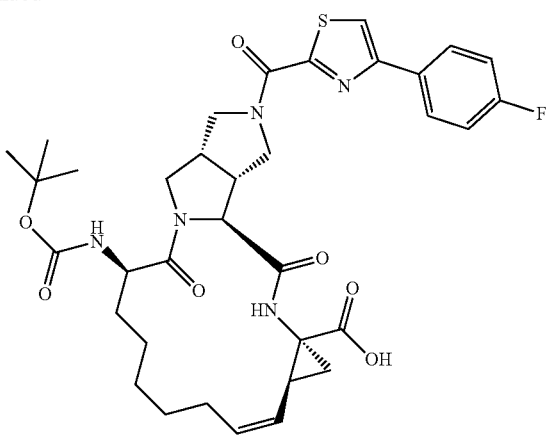
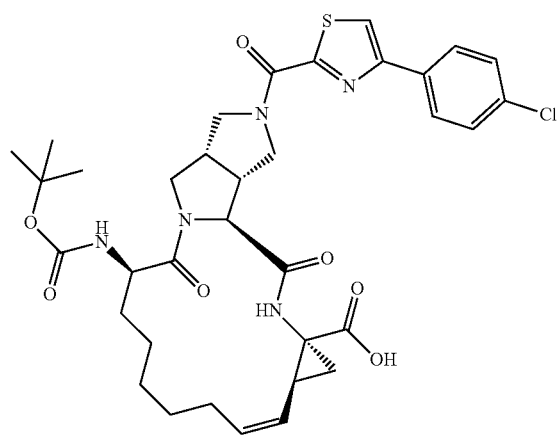
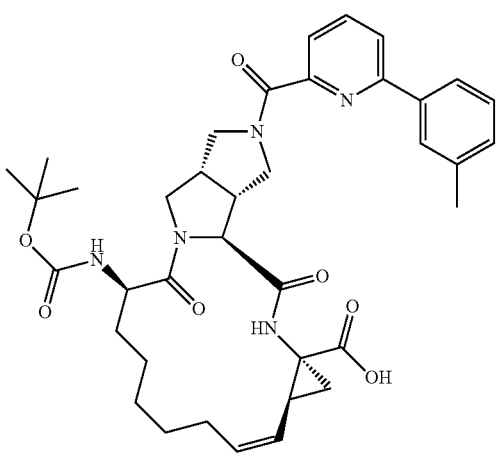
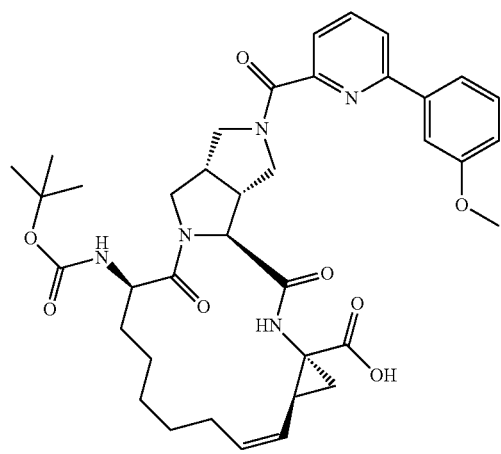
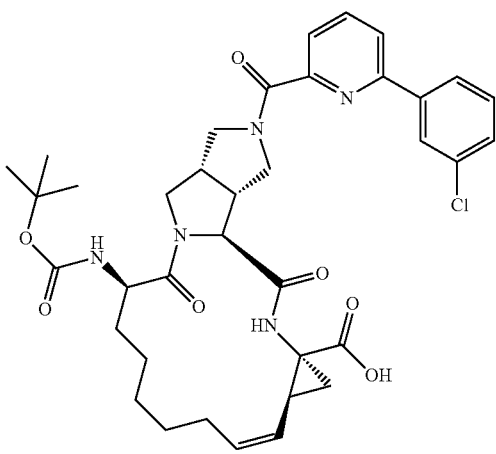

99 100
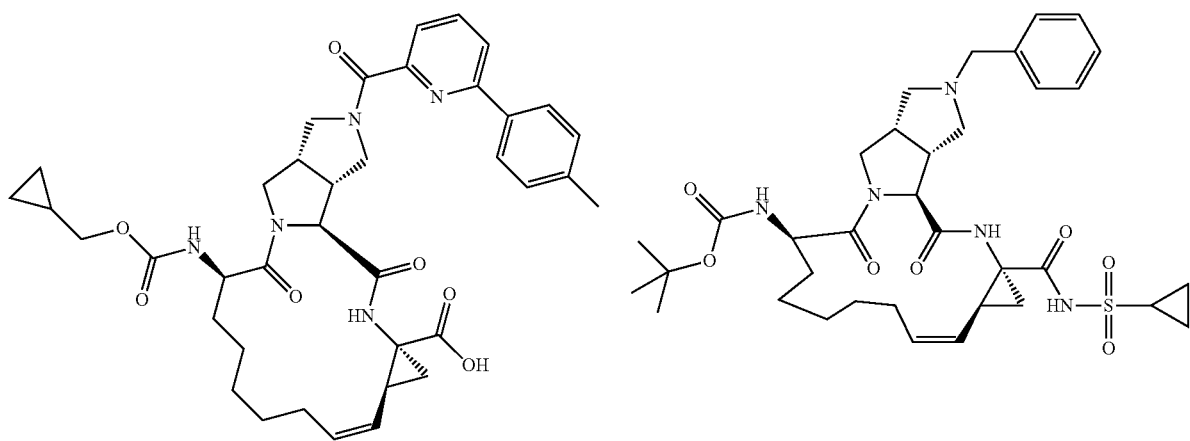
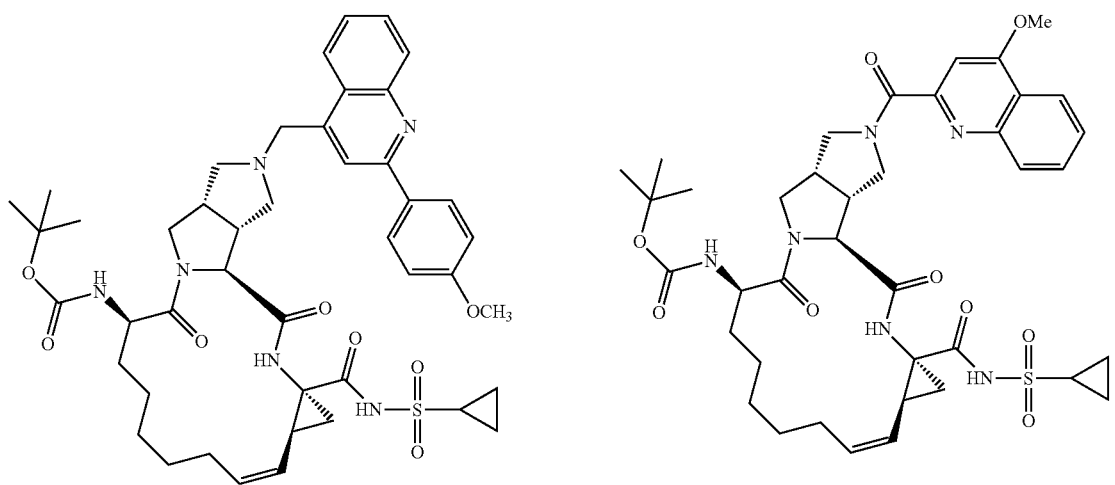
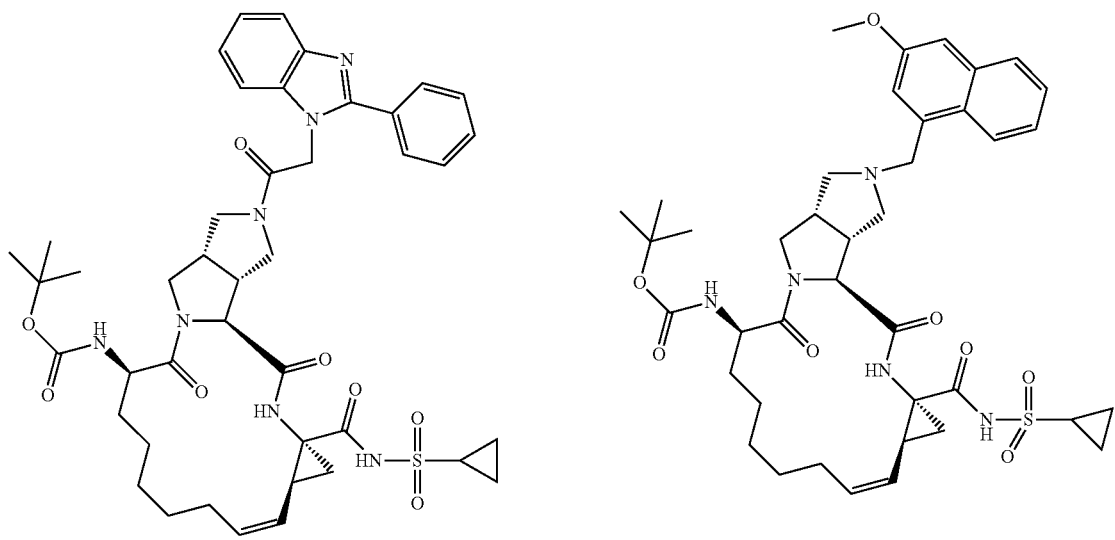

-continued
101
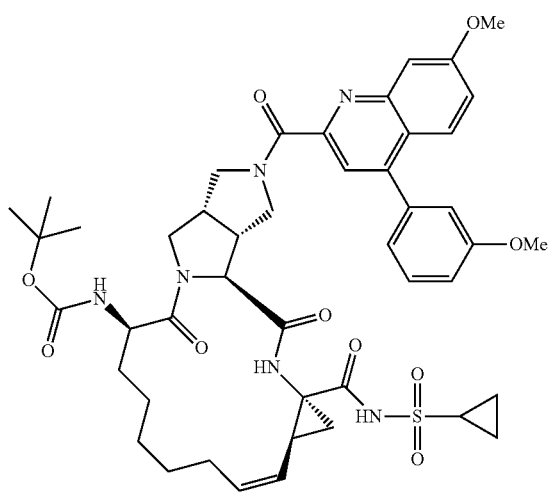
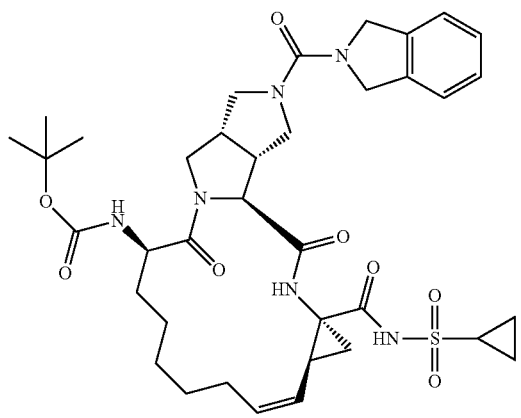
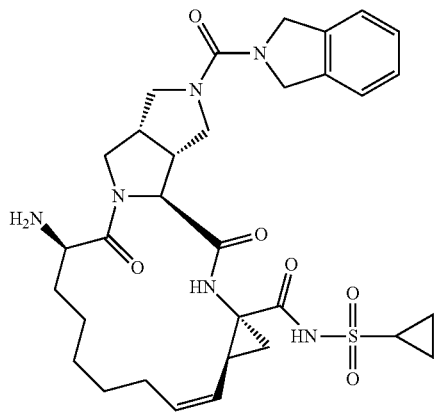
102
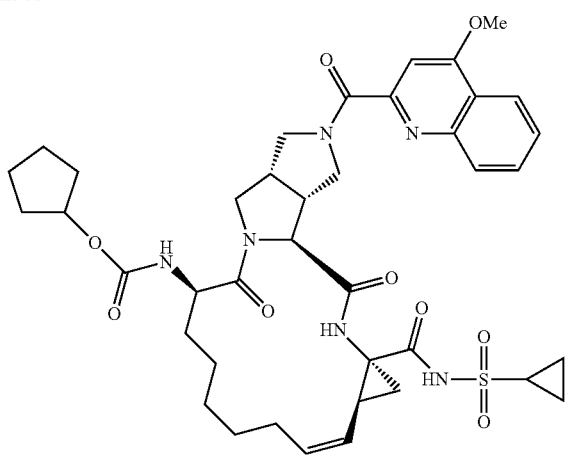
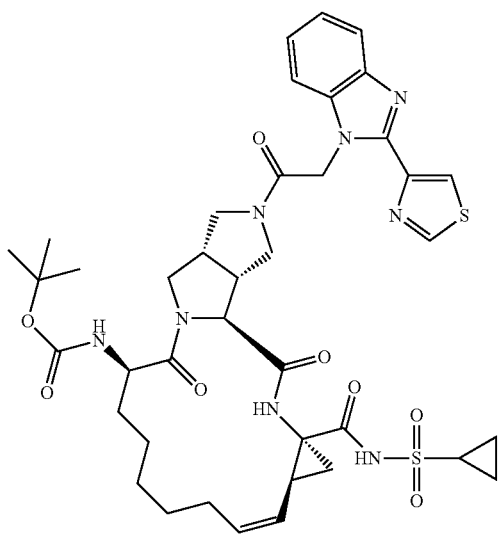
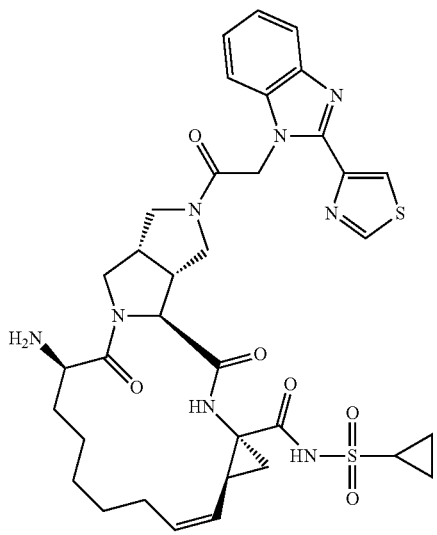

103
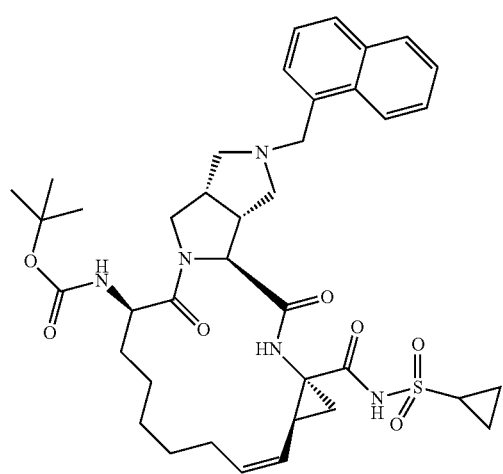
104
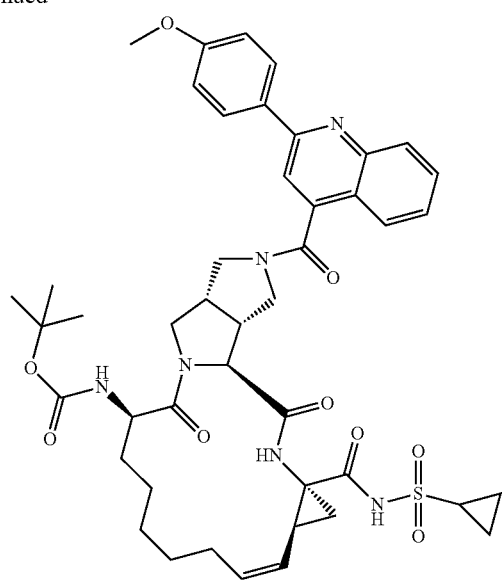
-continued
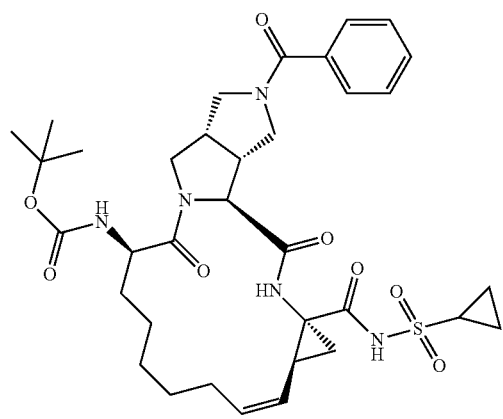
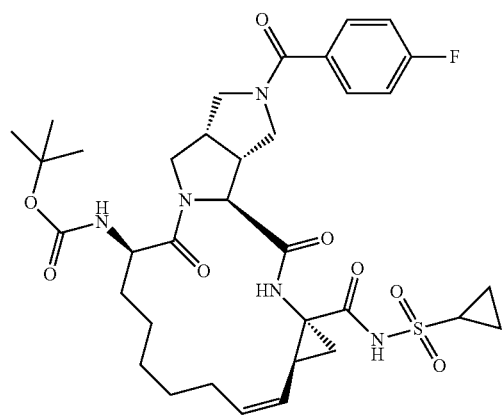
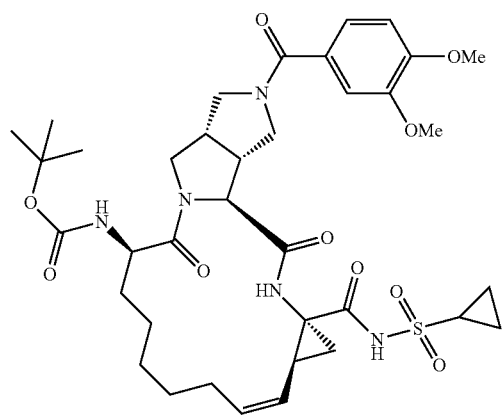
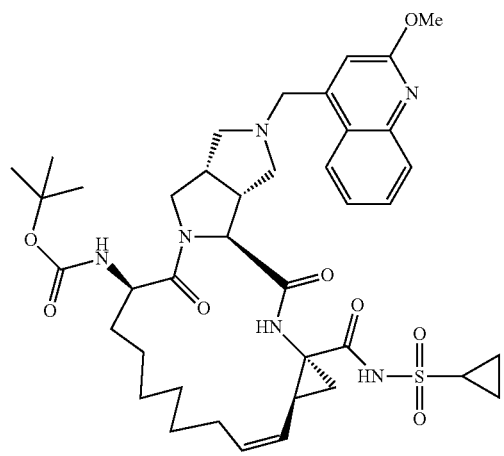

-continued
105
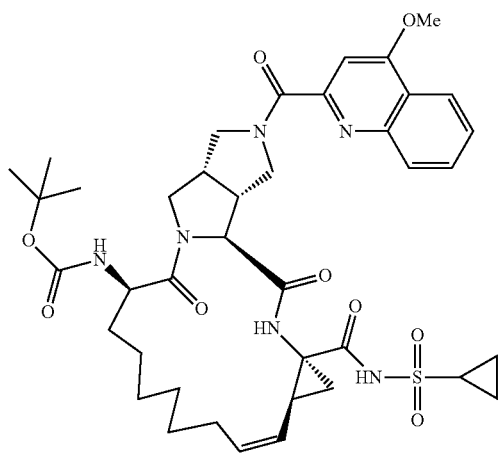
106
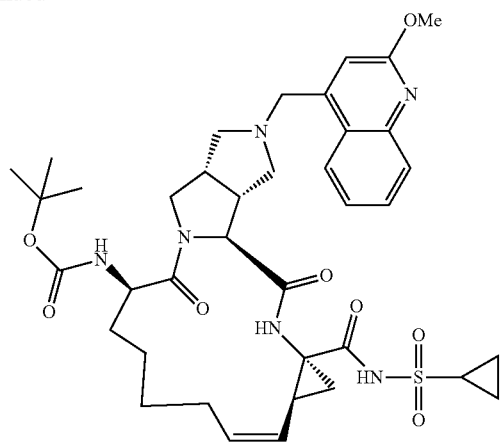
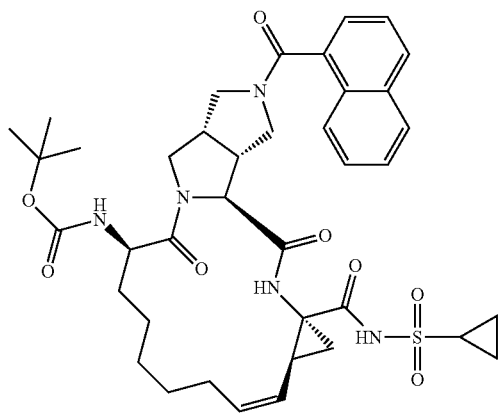
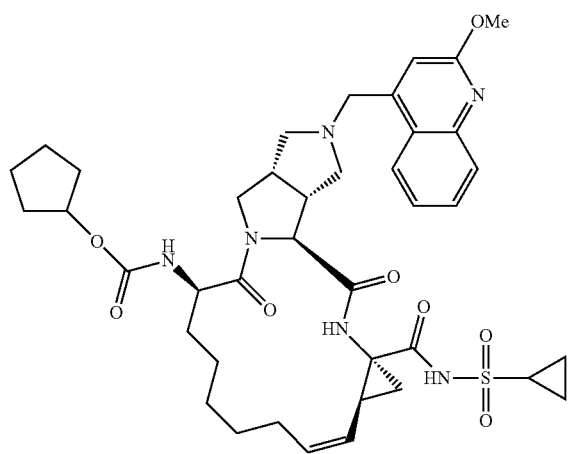
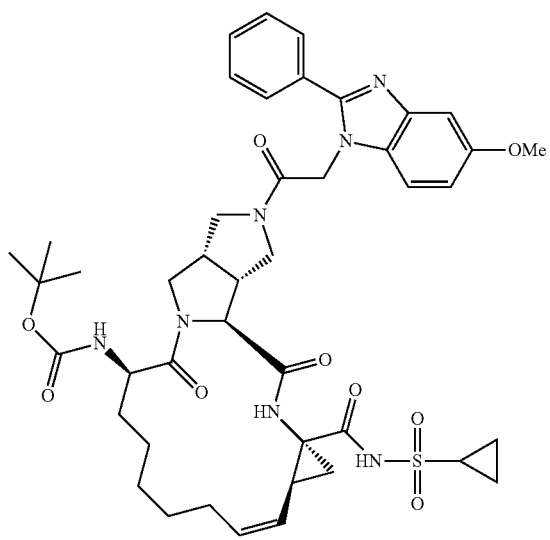
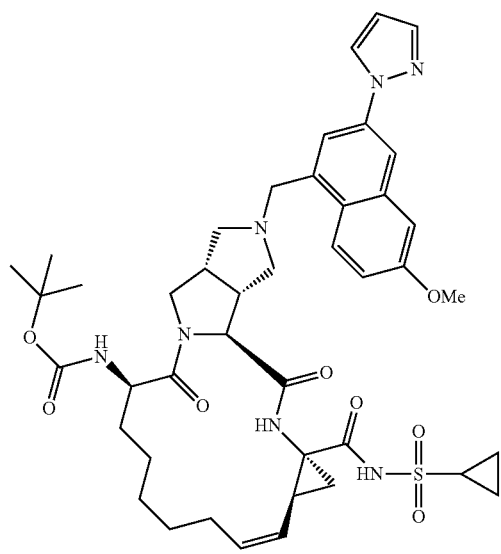

107 108
-continued
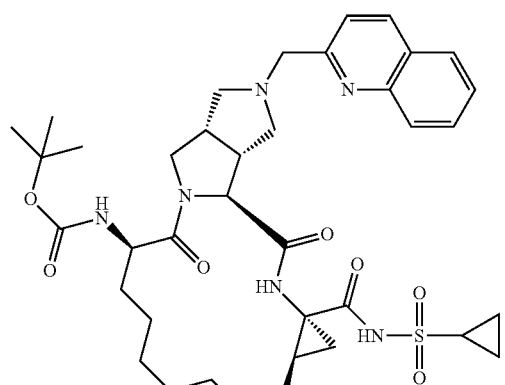
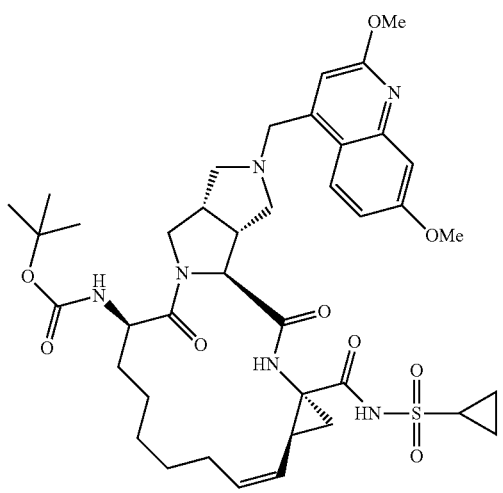
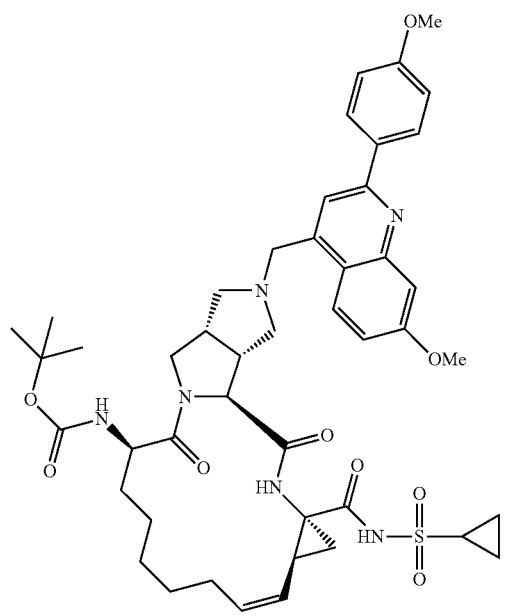
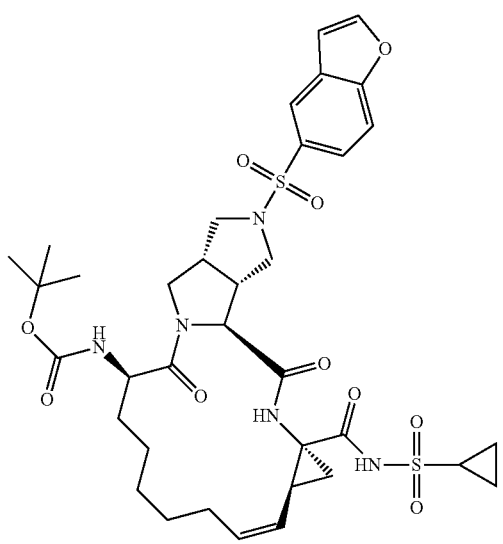
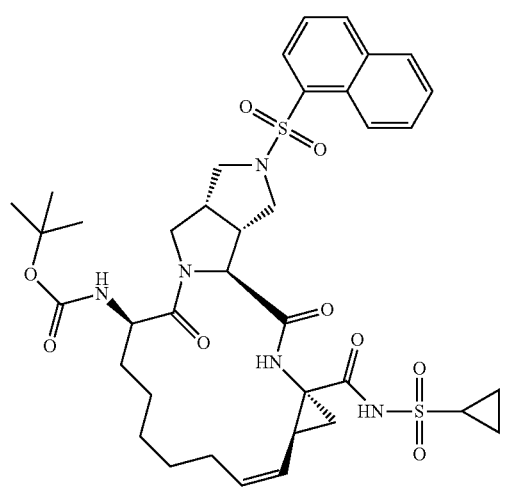
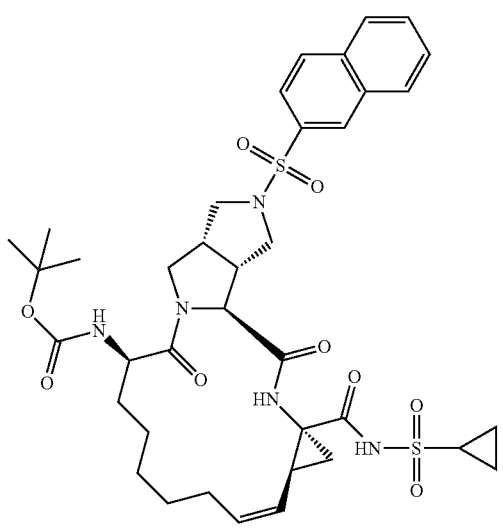

-continued
109
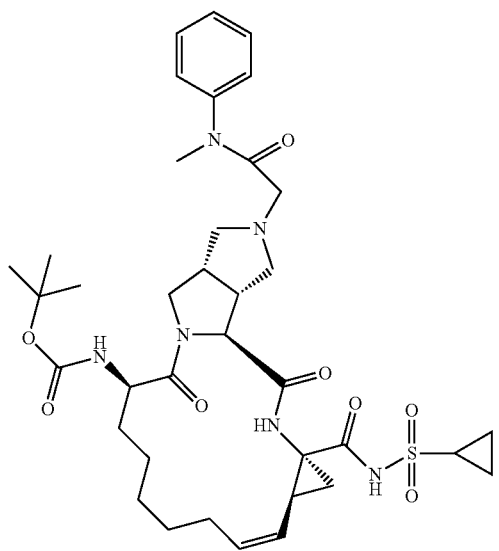
110
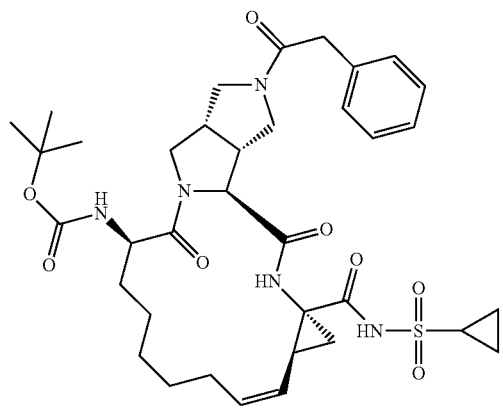
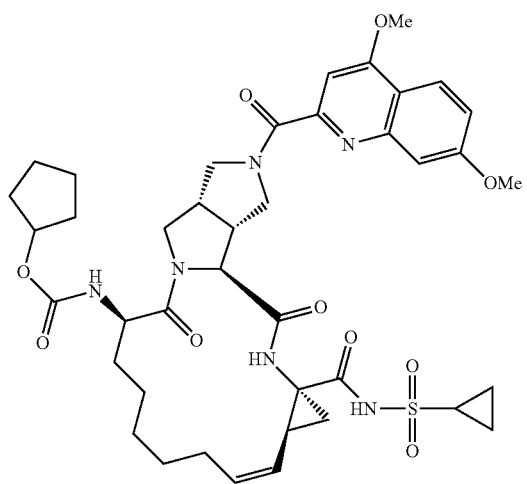
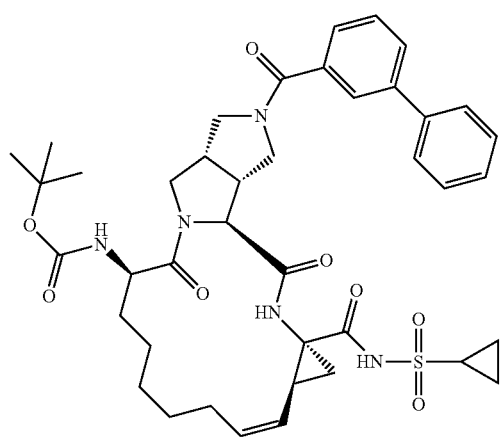
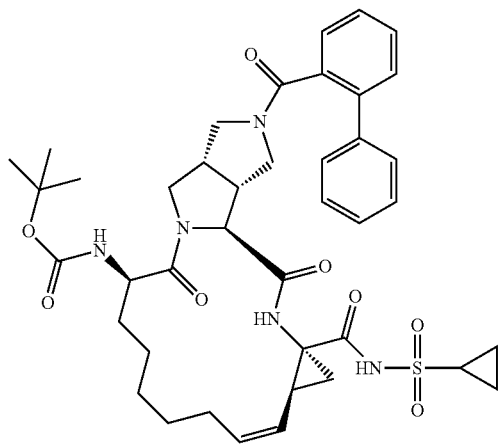
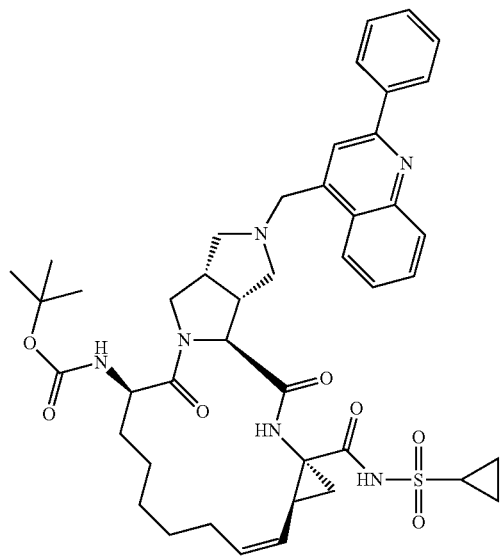

111 112
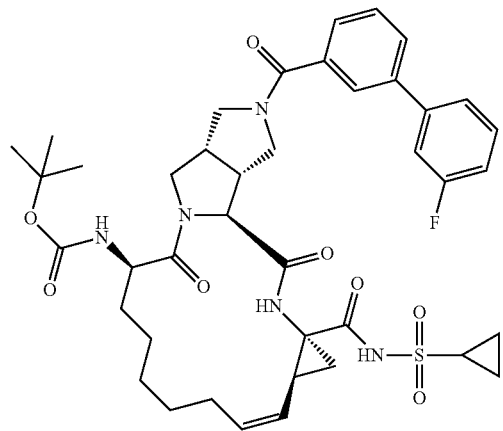 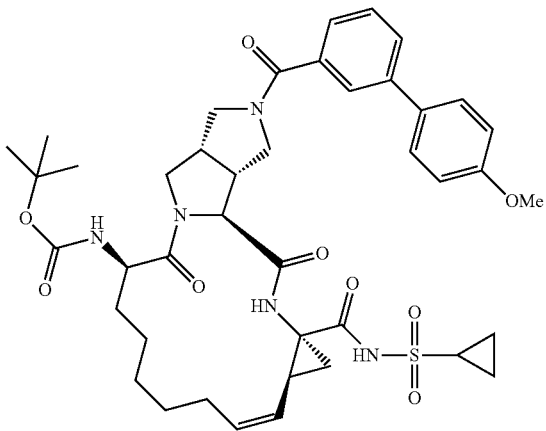
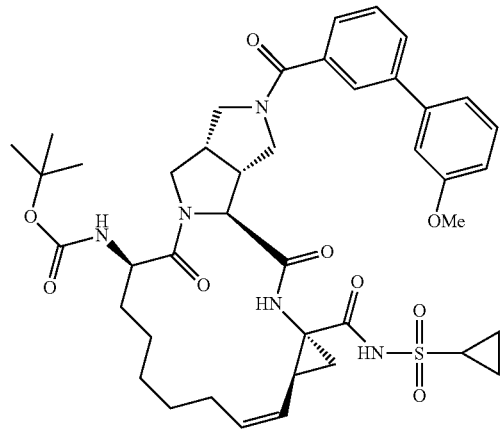 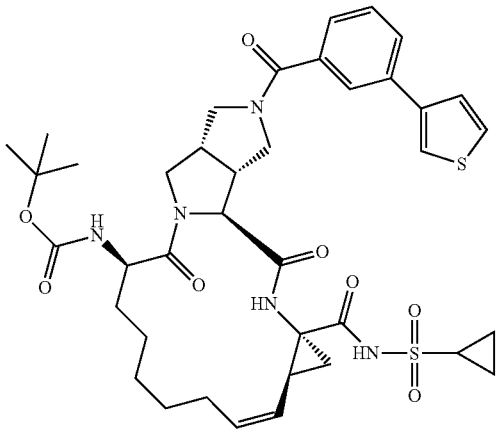
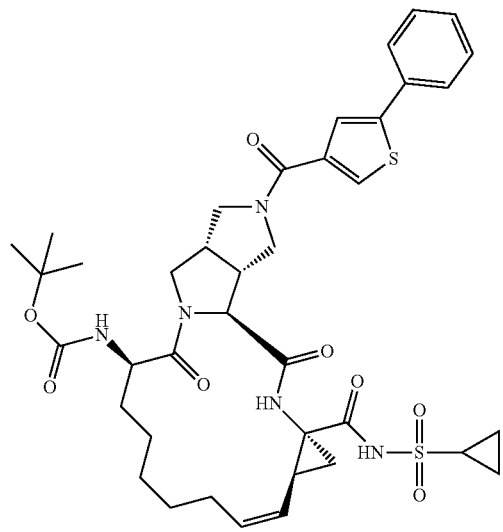 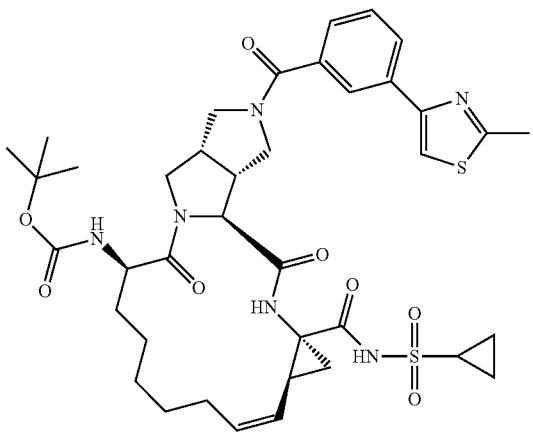

-continued
| 113 | 114 |
|---|---|
| 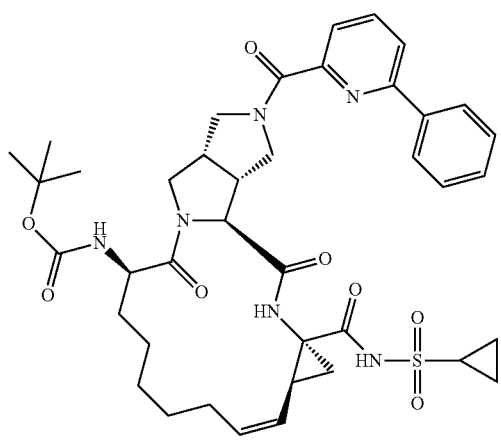 | 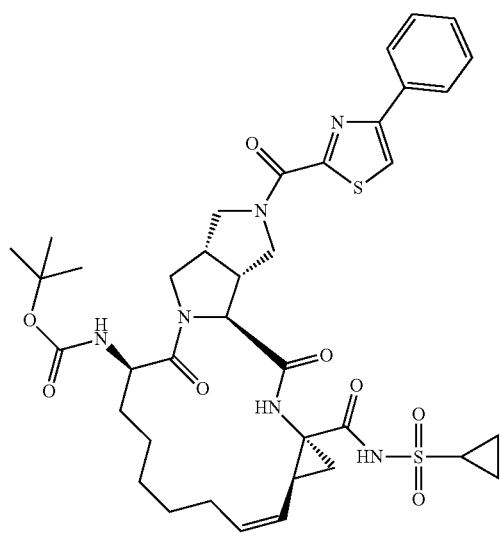 |
| 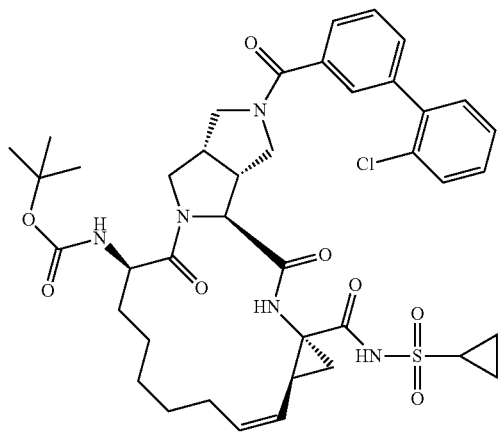 | 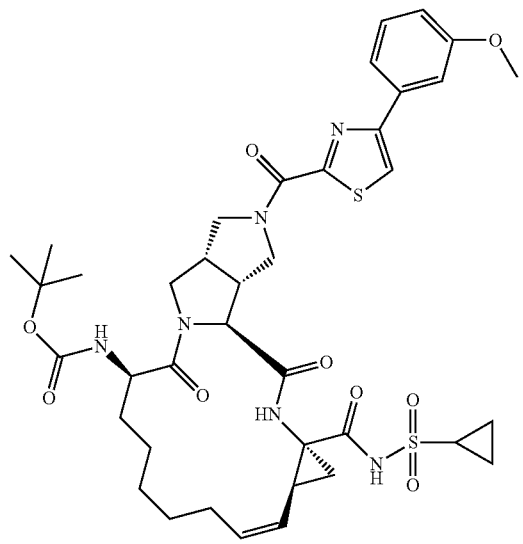 |
| 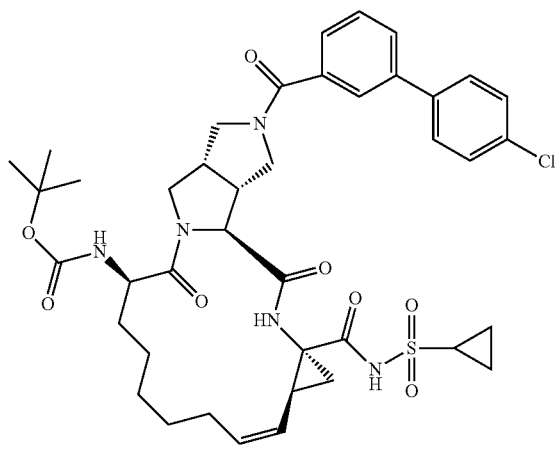 | 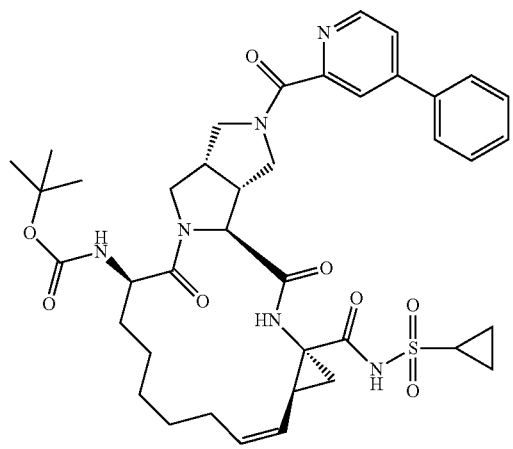 |

115 116
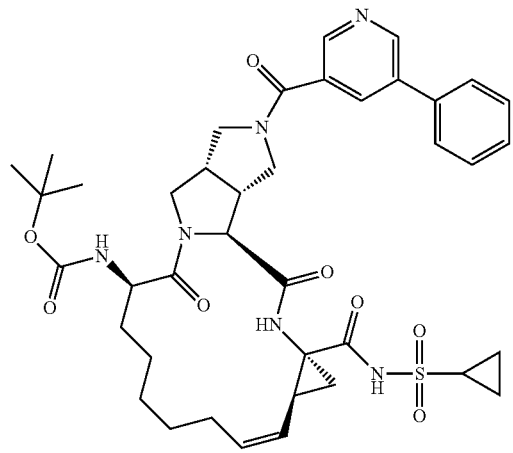
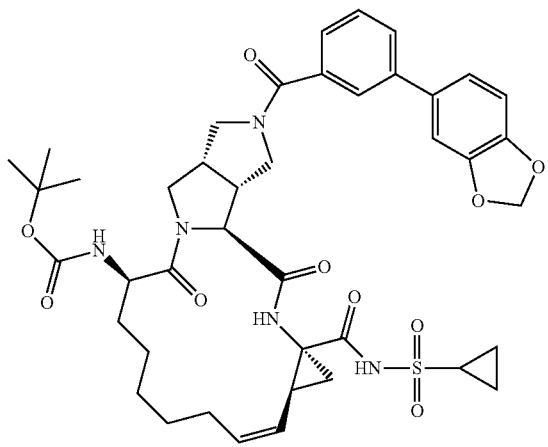
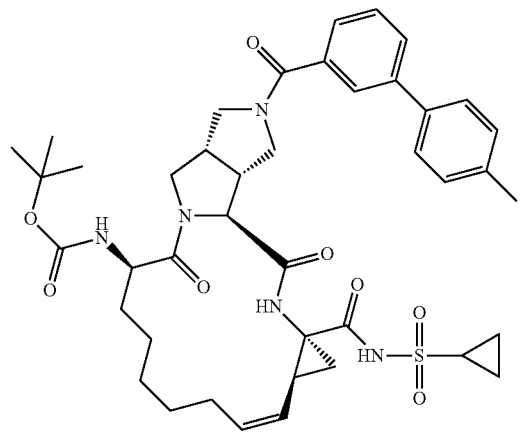
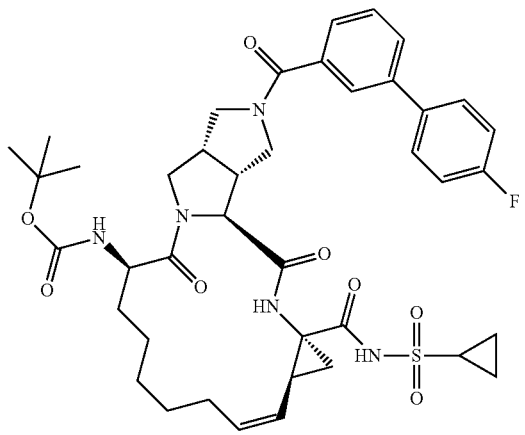
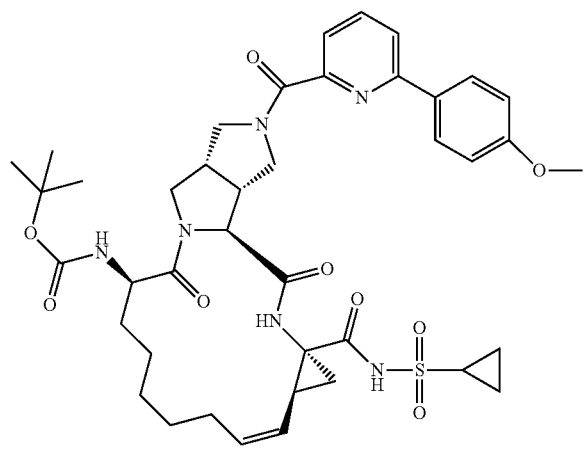
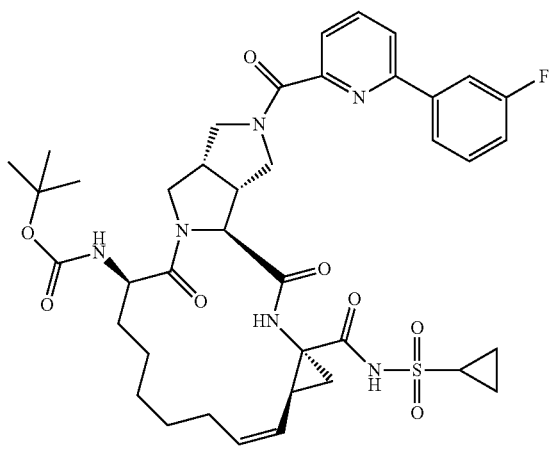

117
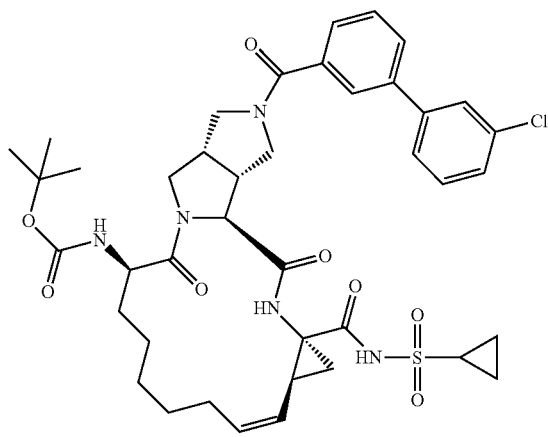
118
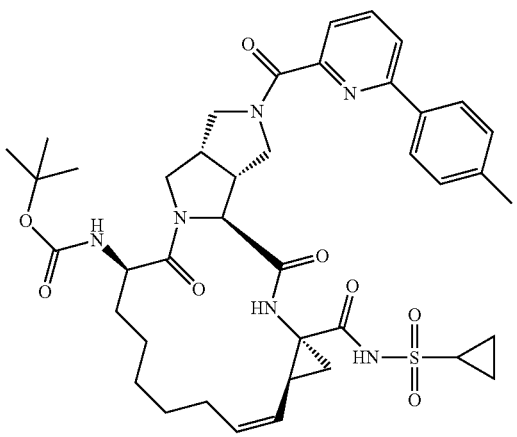
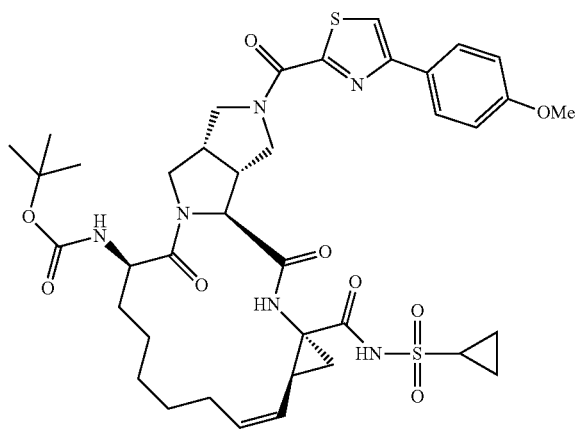
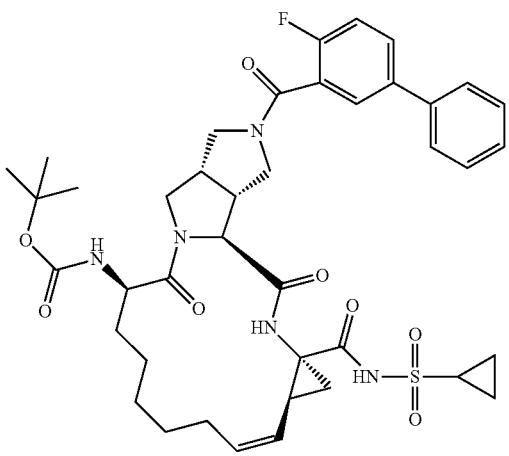
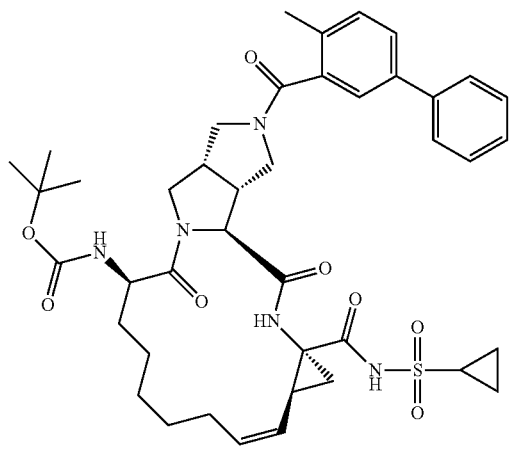
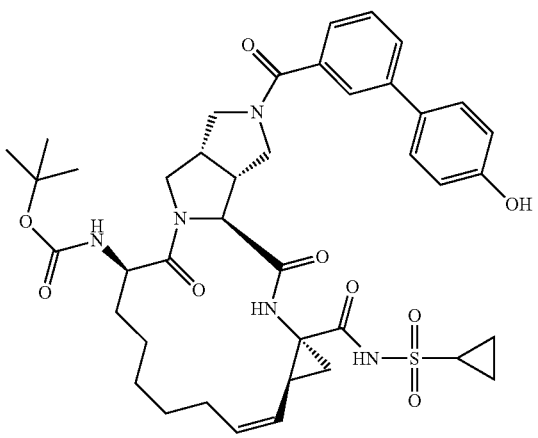

119
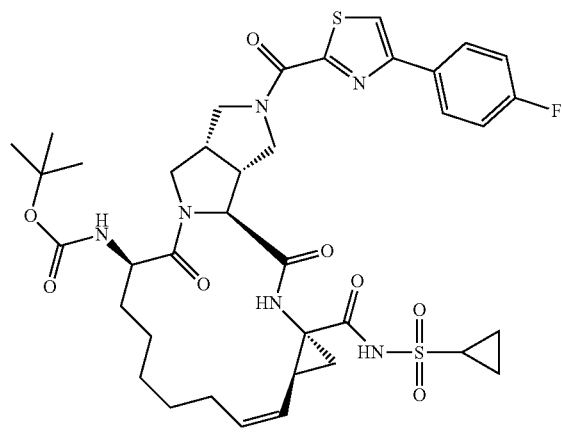
120
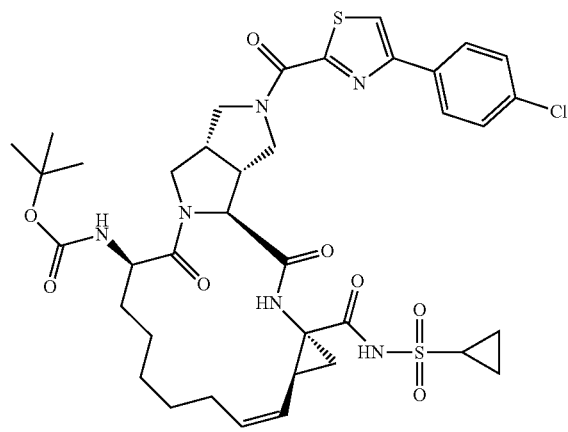
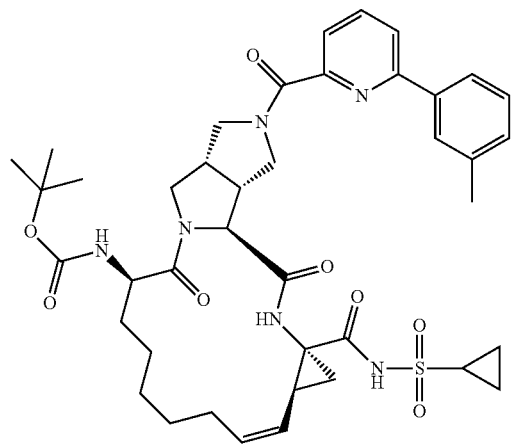
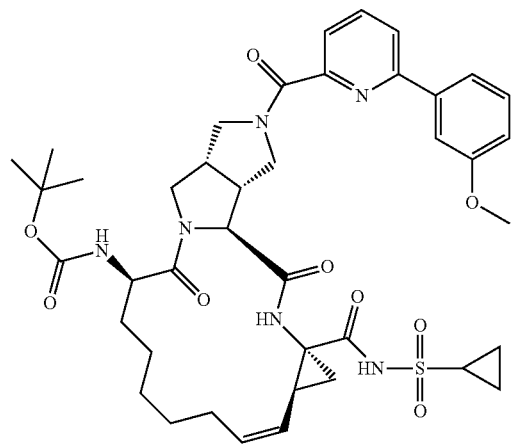
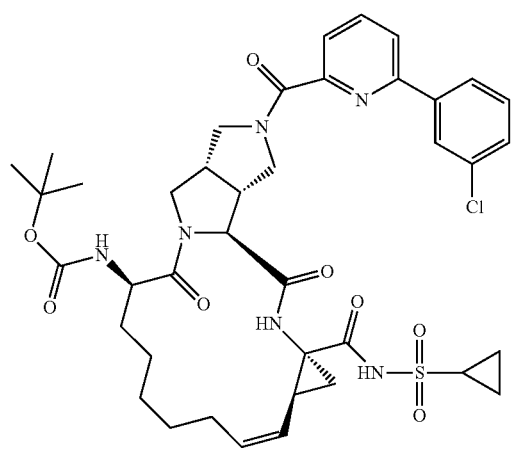
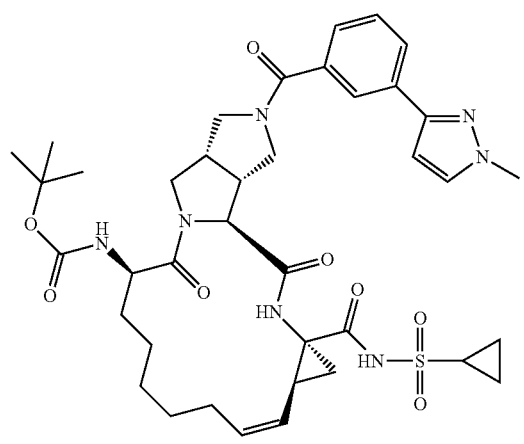

121 122
-continued
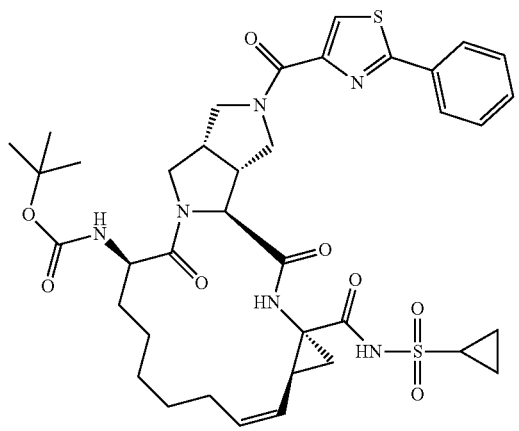
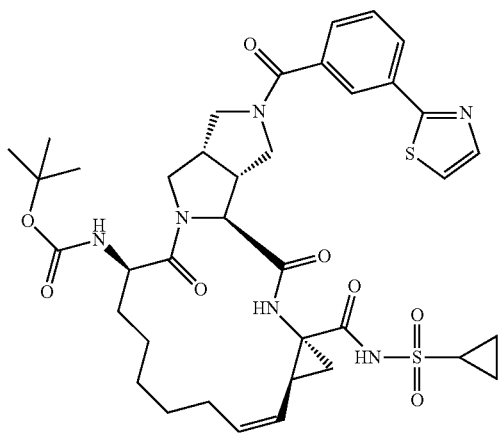
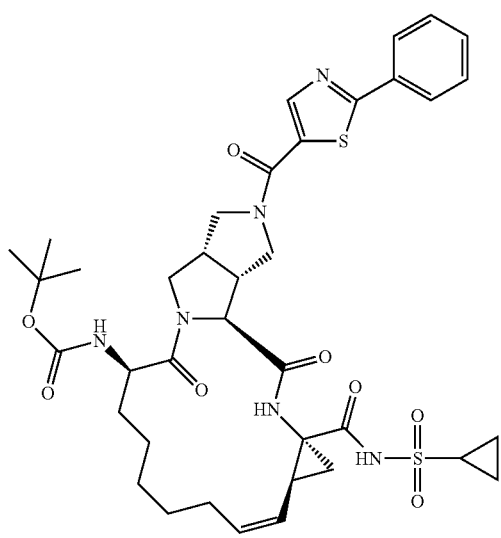
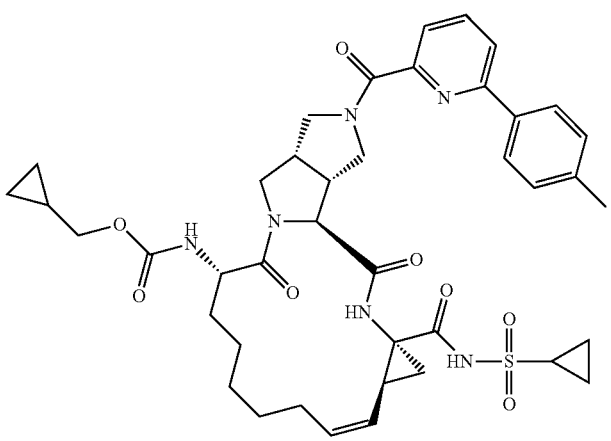
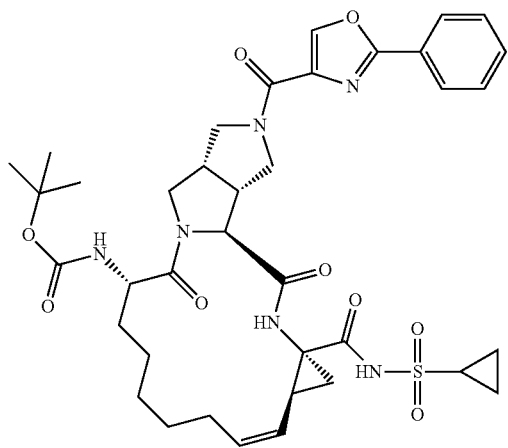
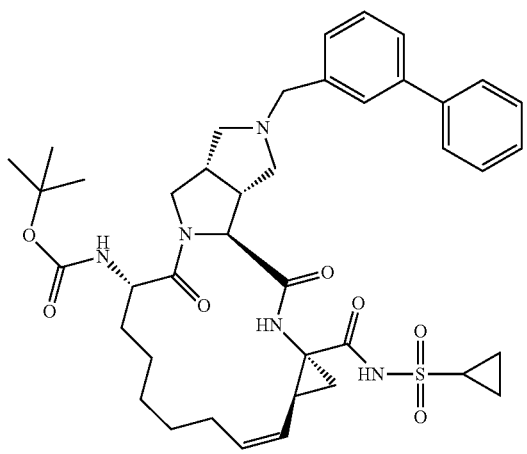

123
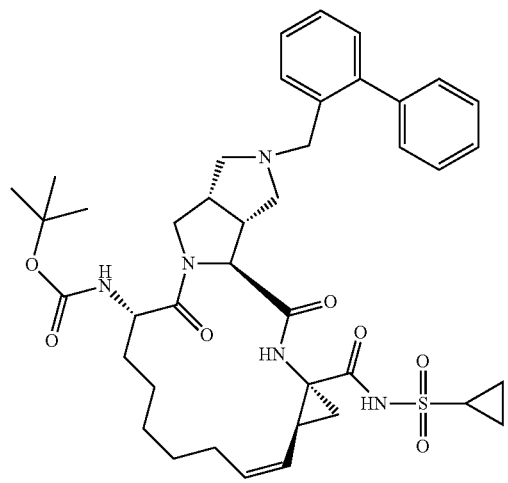
124
-continued
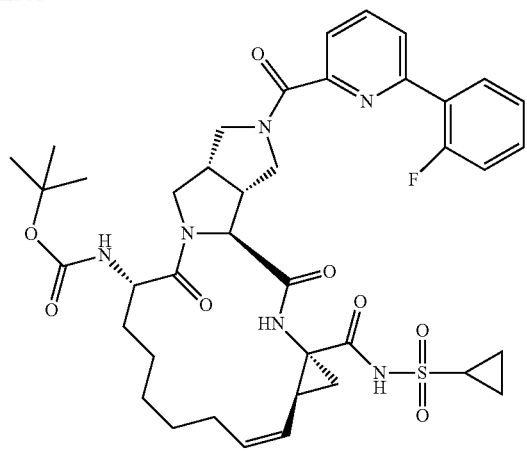
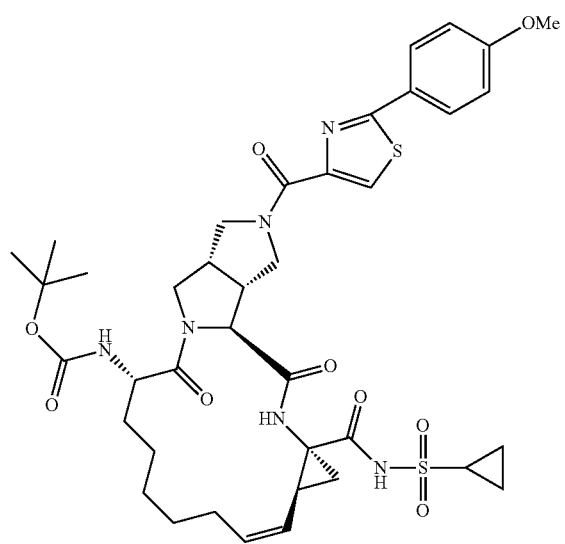
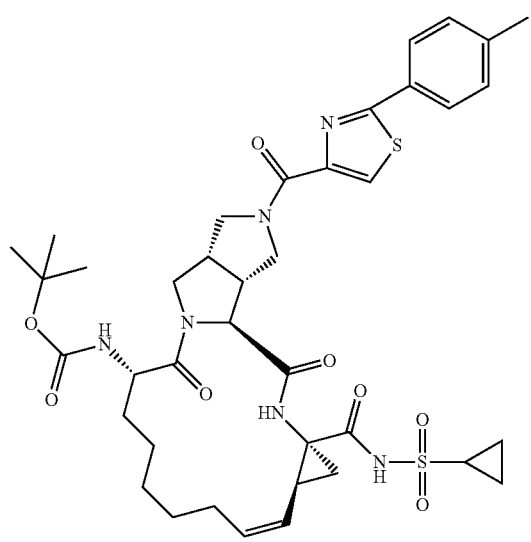
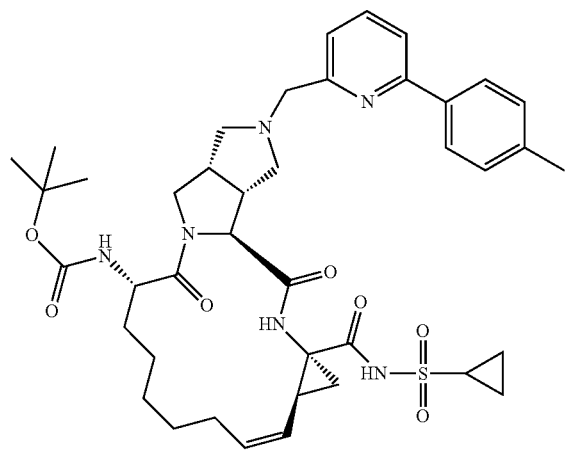
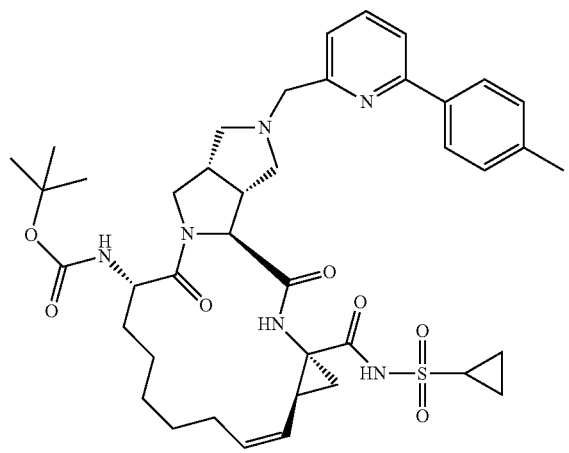

-continued
125
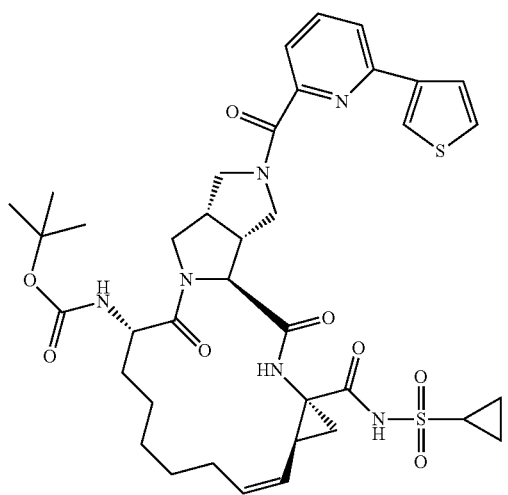
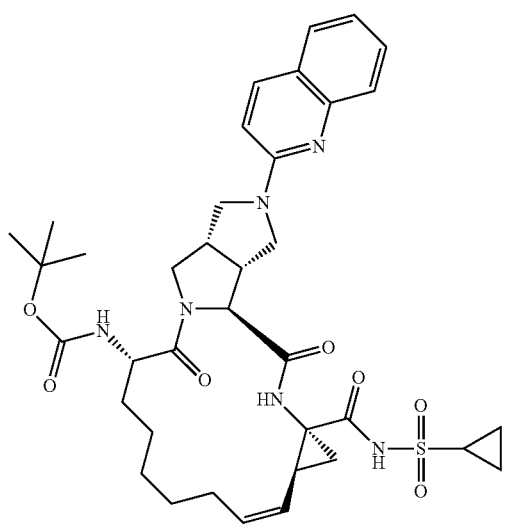
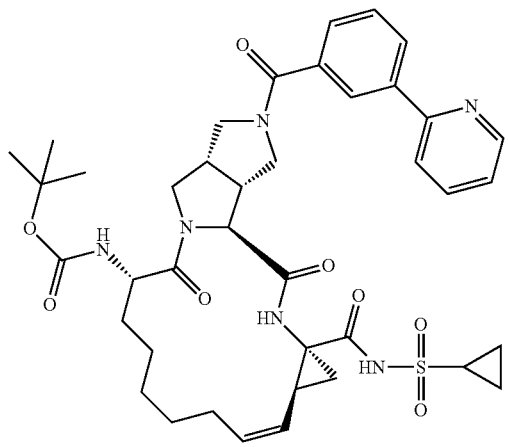
126
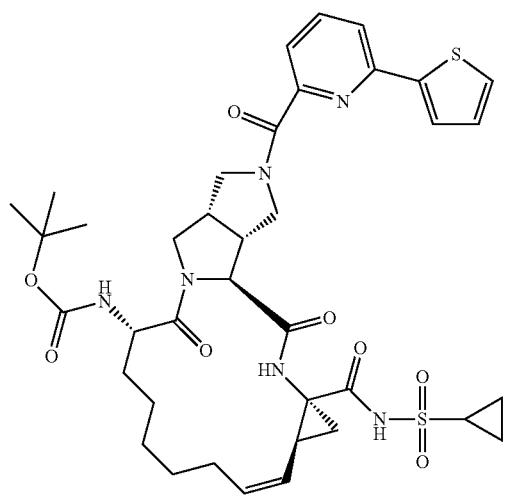
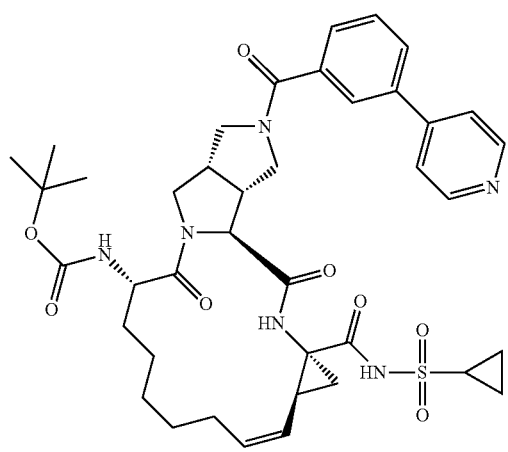
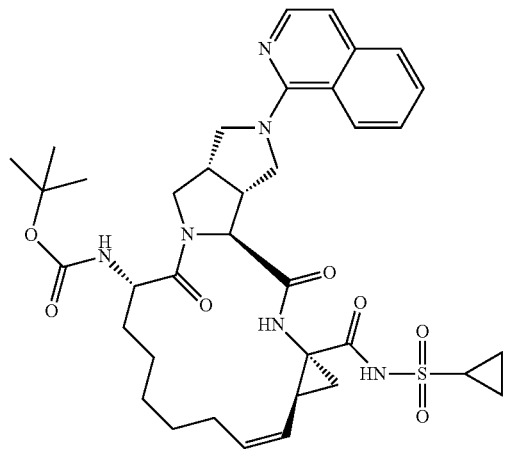

127 | 128
-continued
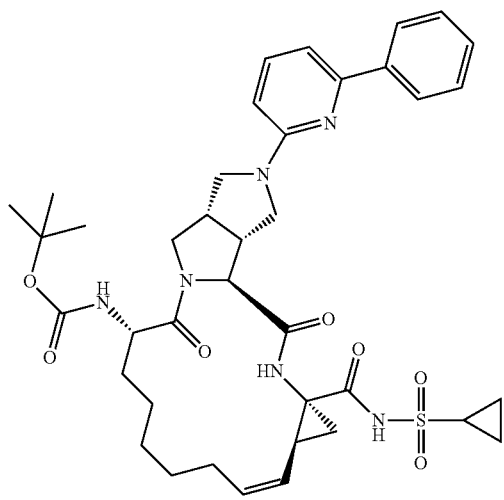
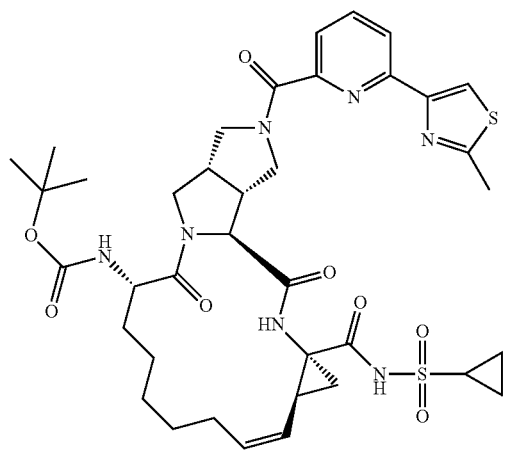
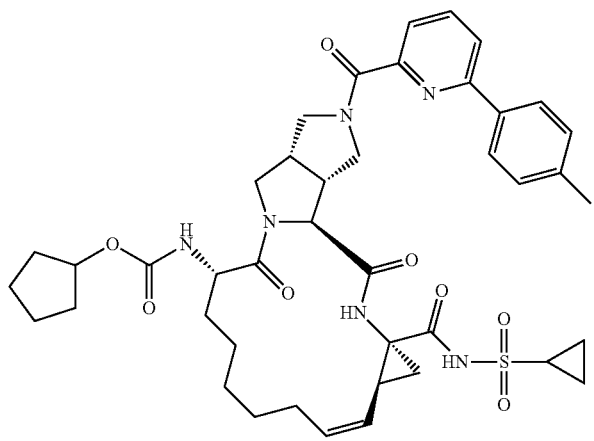
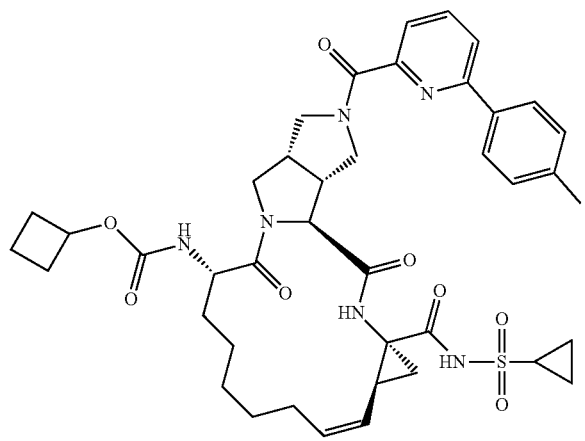
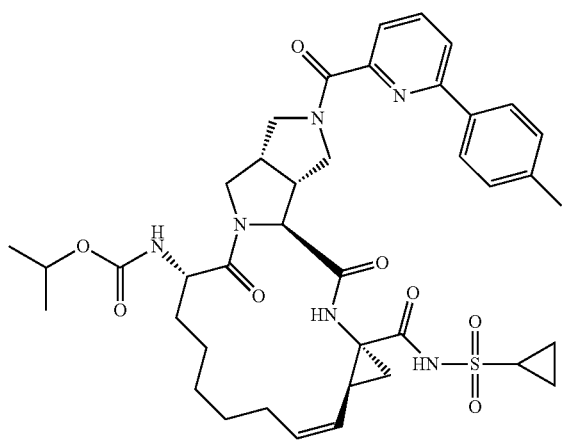
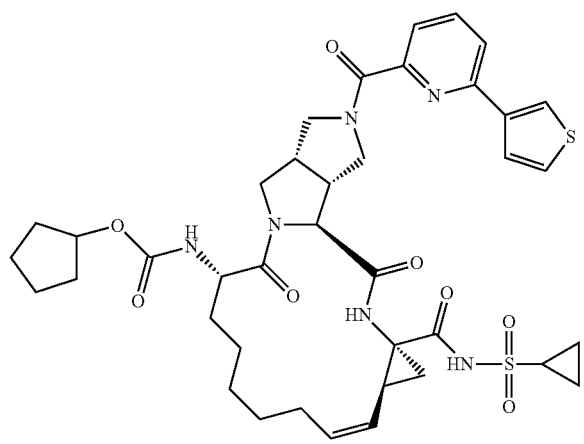

-continued
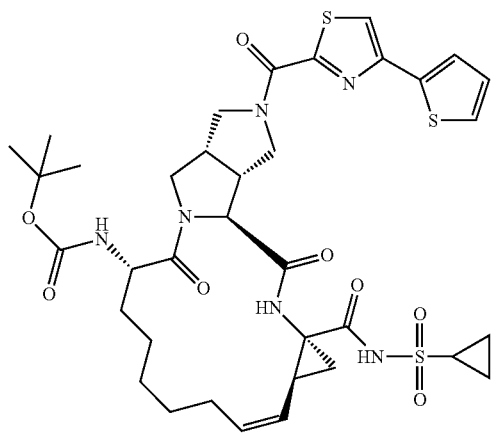
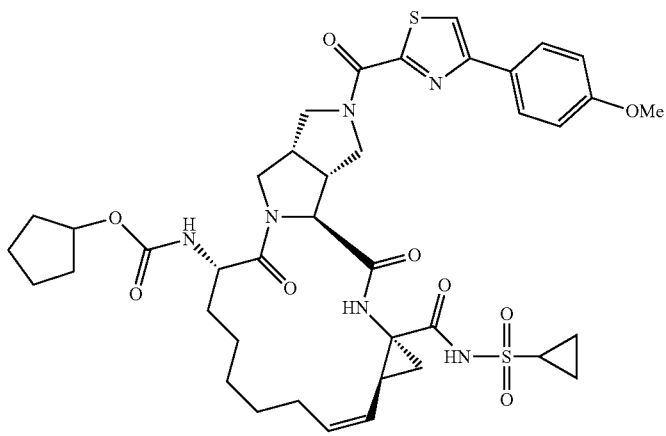
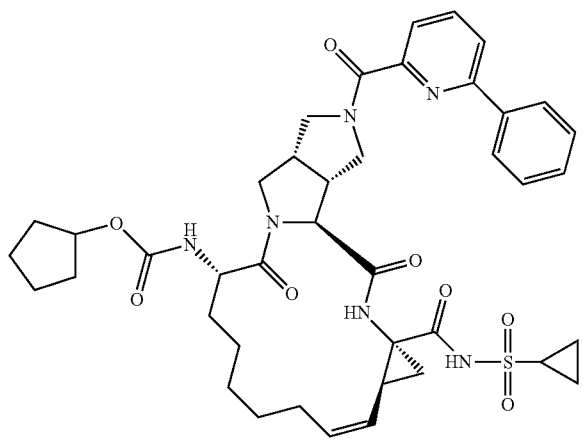
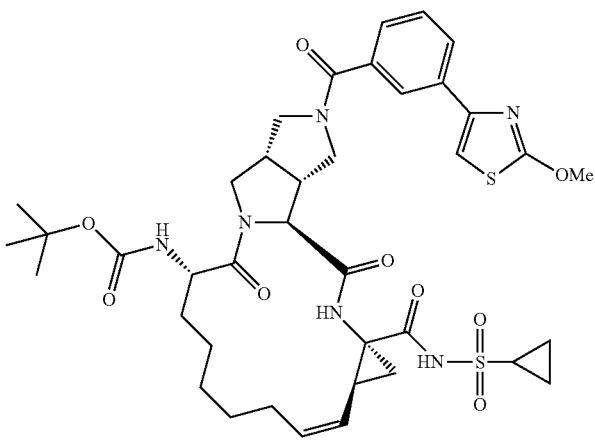
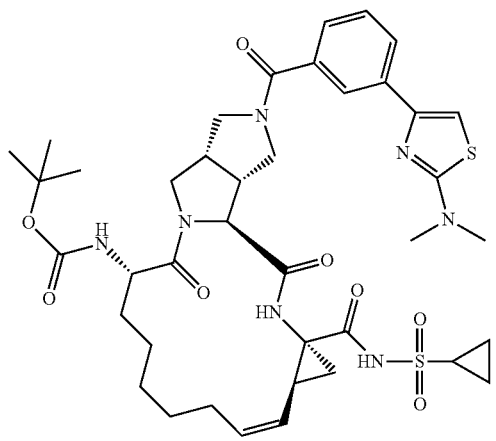
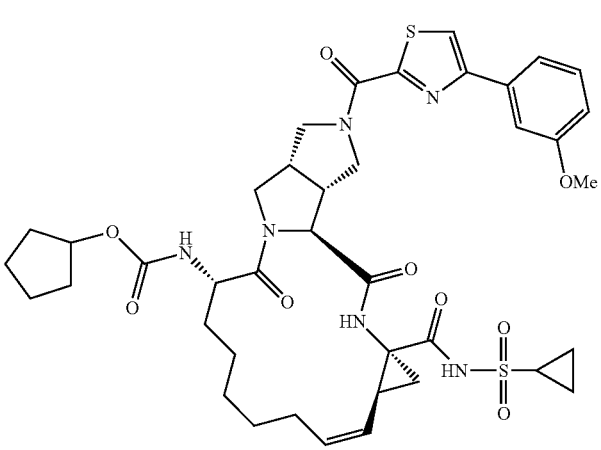

131
132
-continued
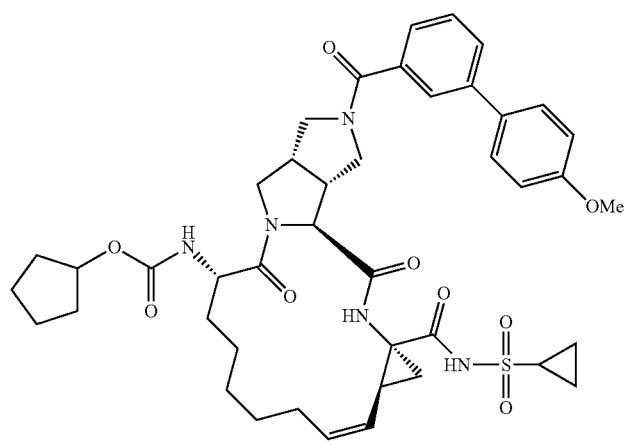
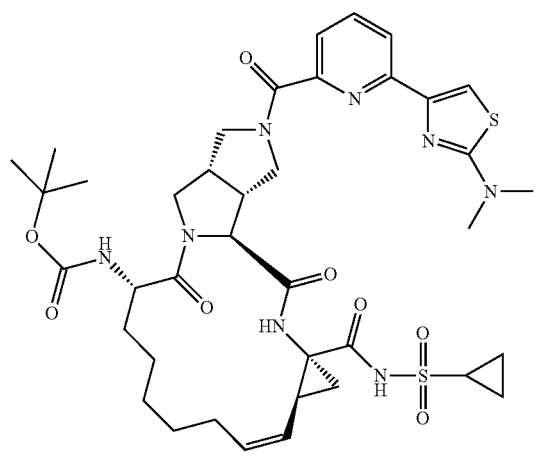
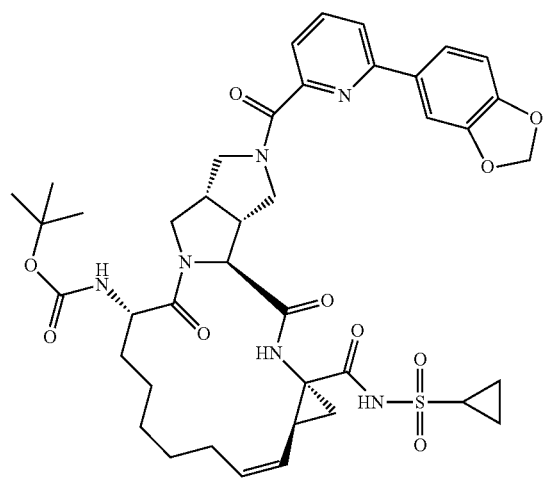
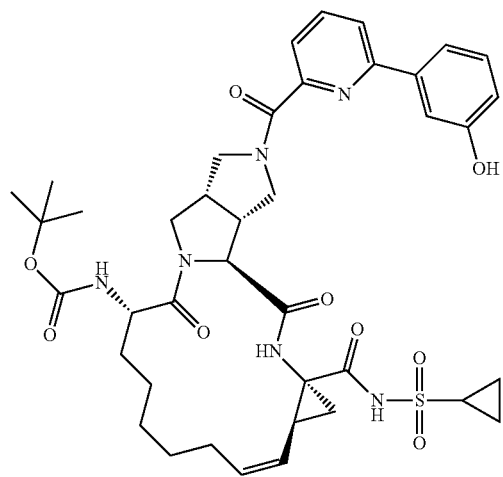
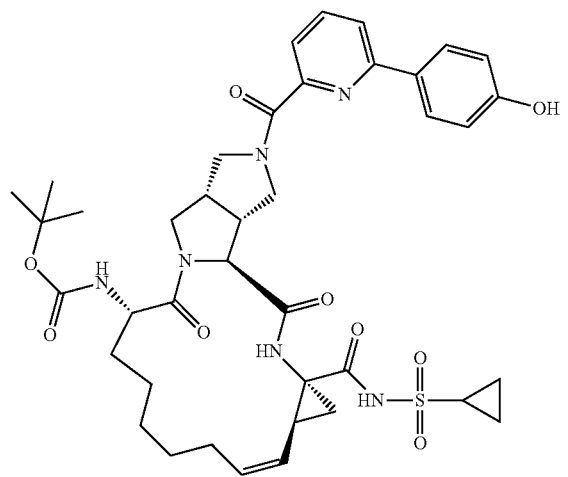

-continued
133
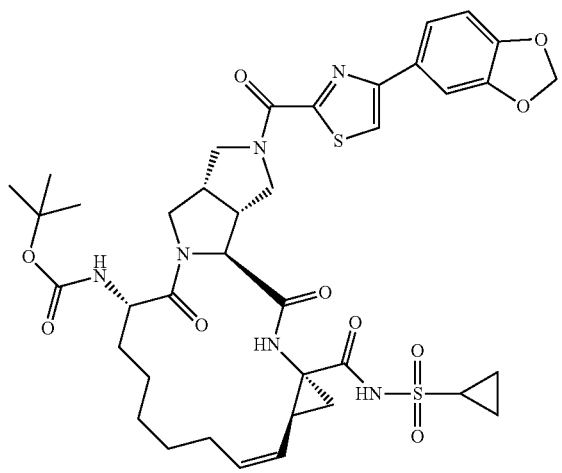
134
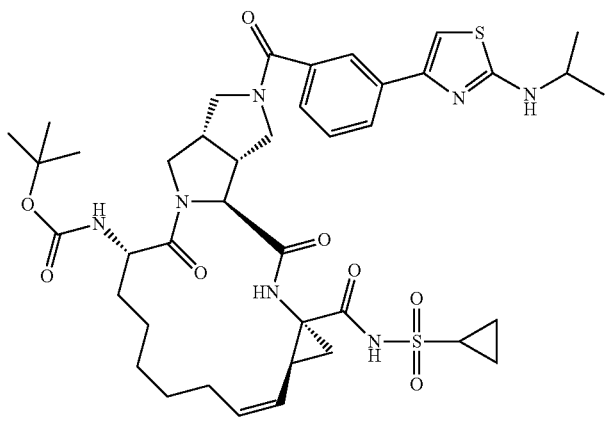
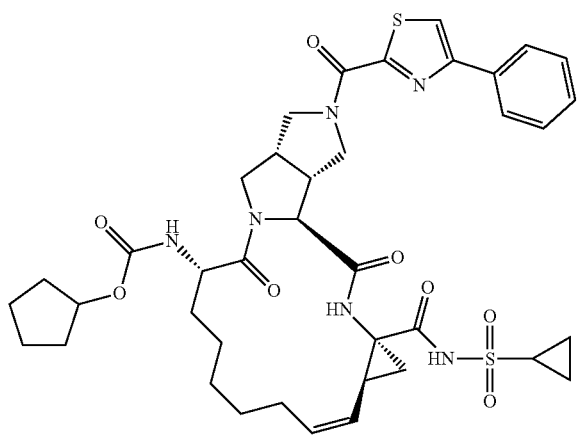
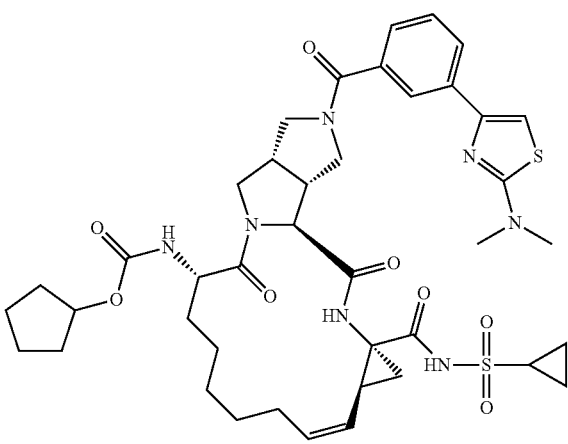
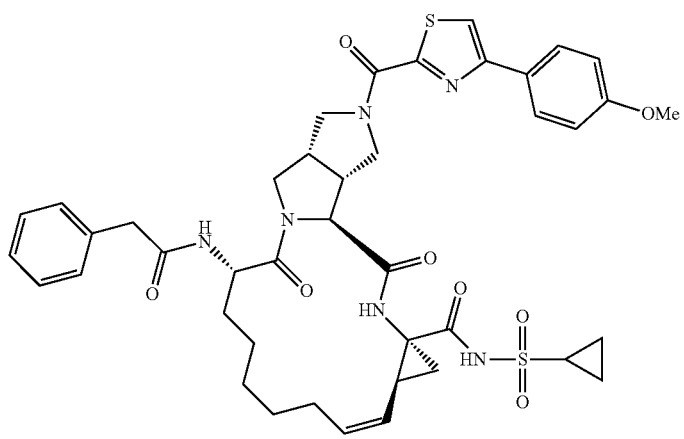

-continued
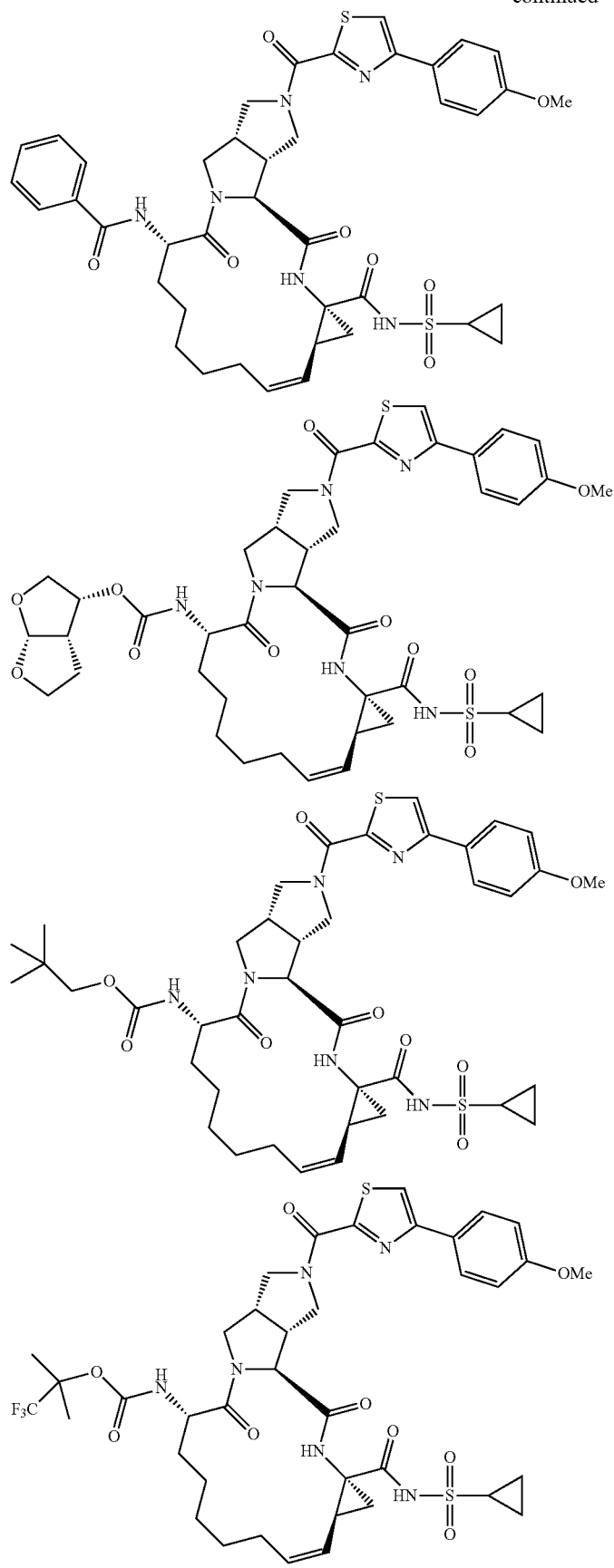

-continued
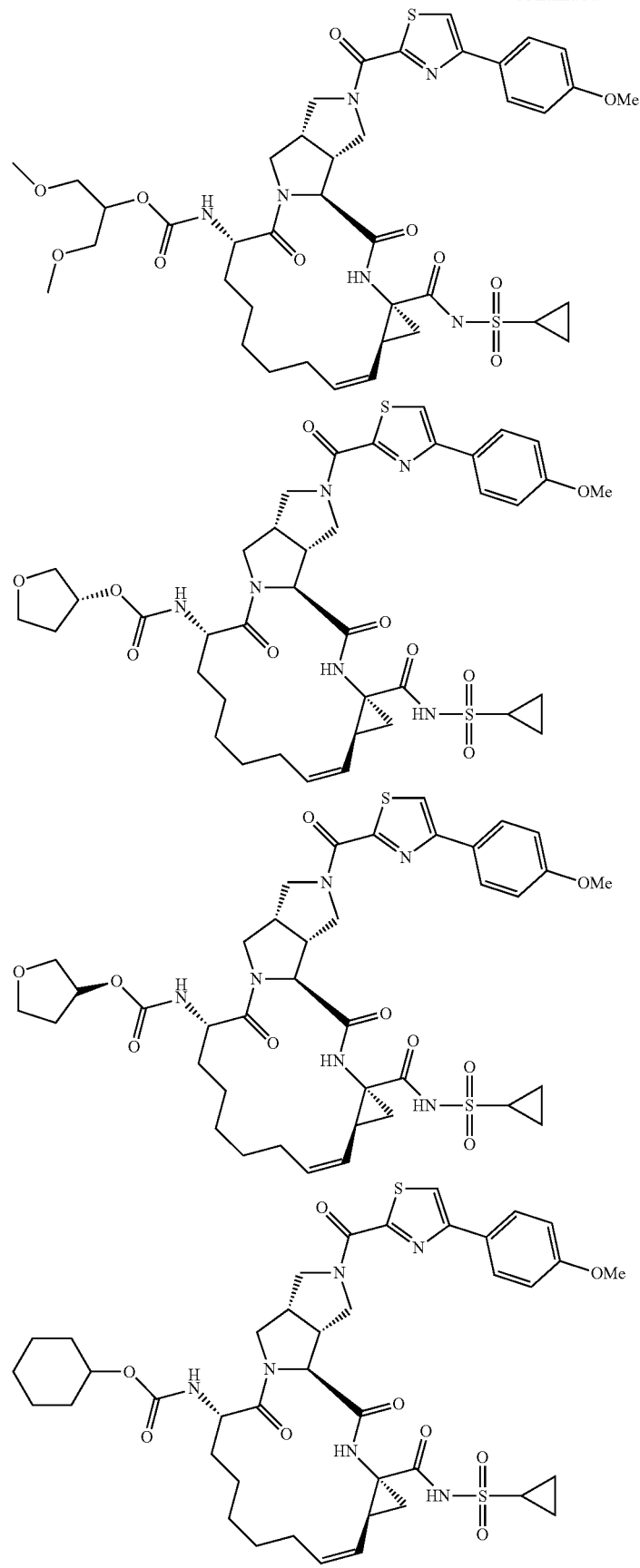

-continued
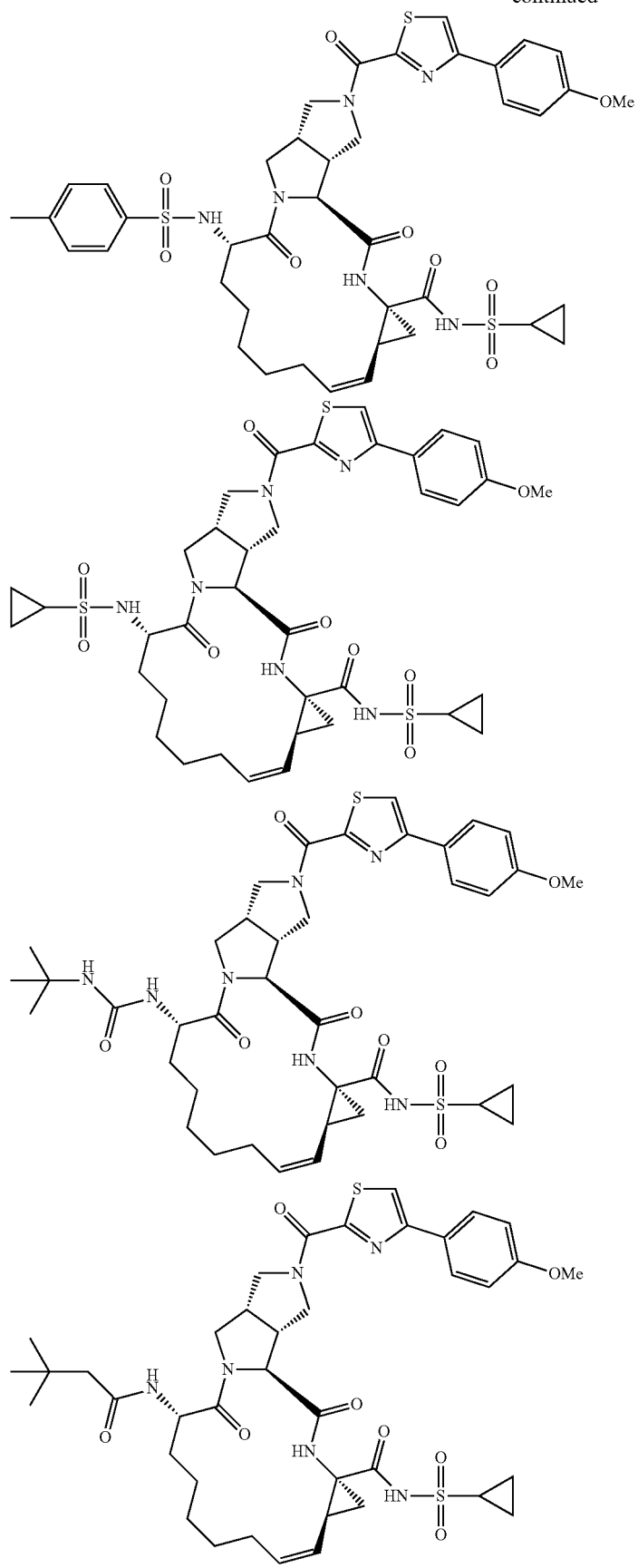

-continued
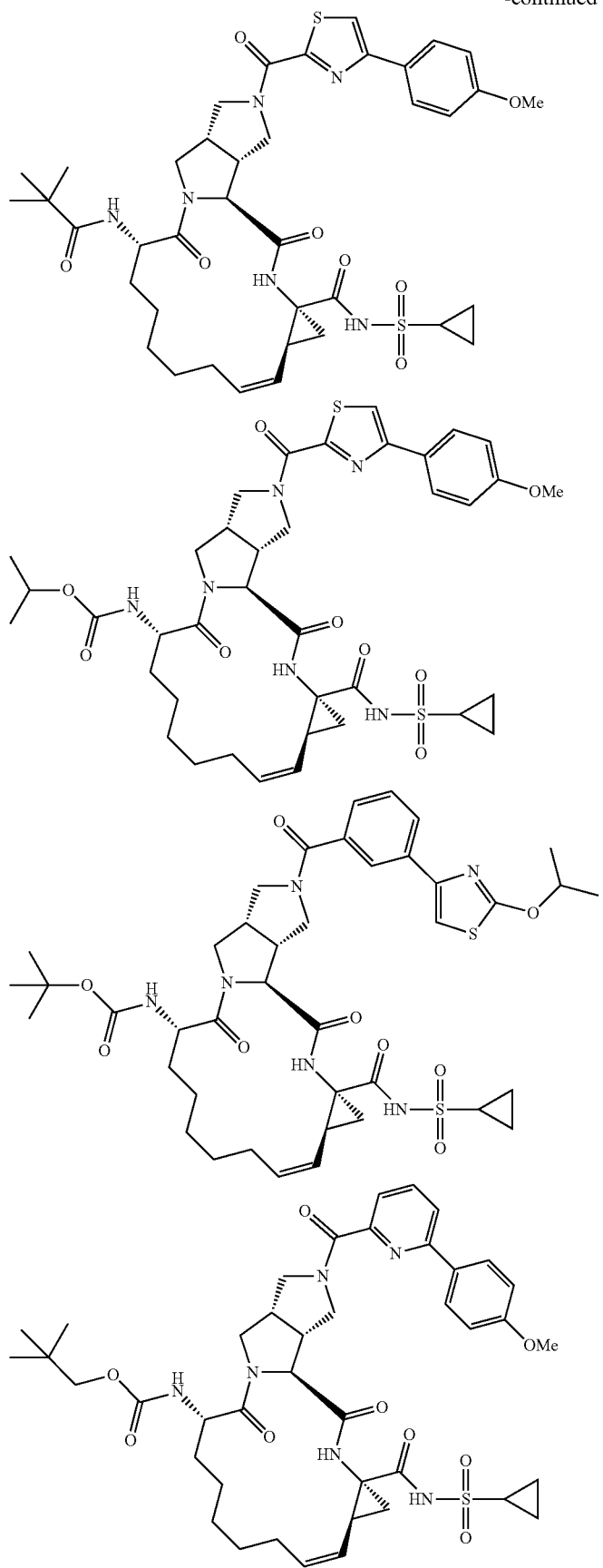

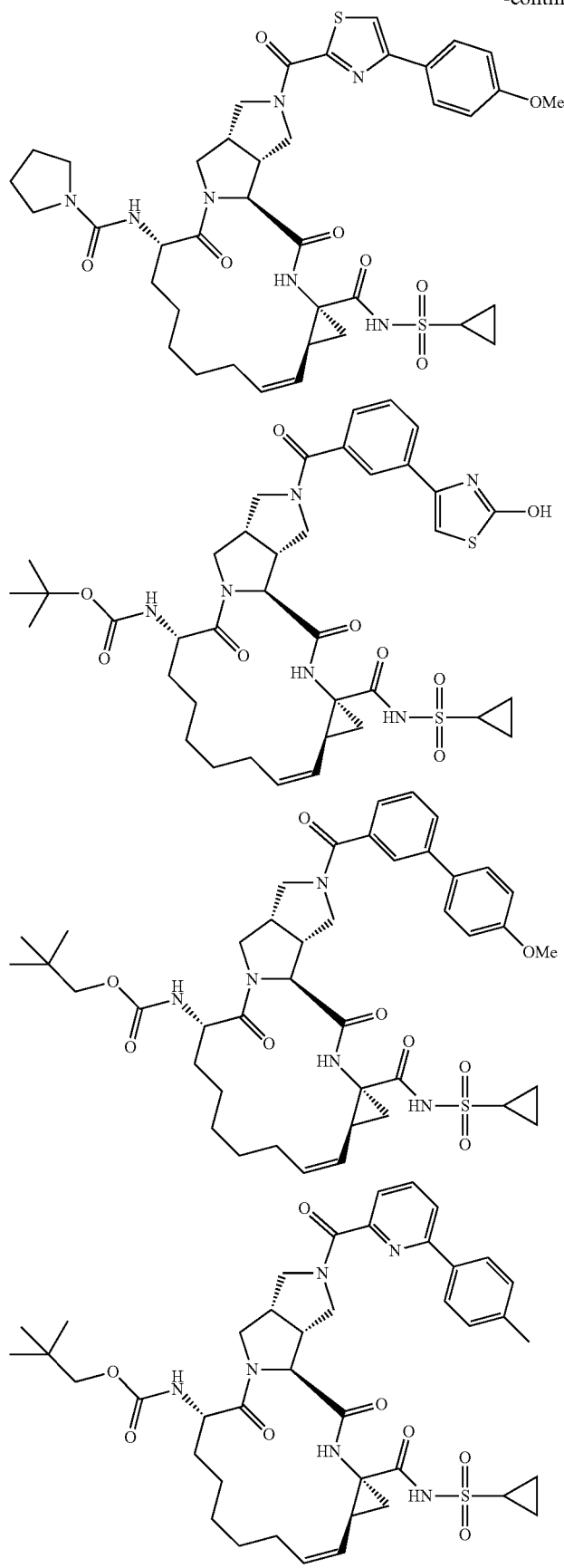

145
-continued
146
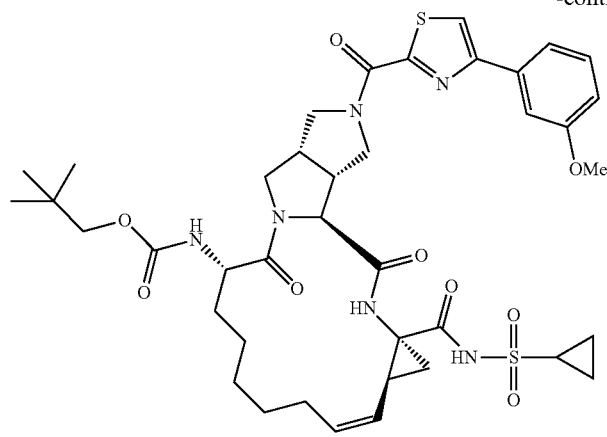
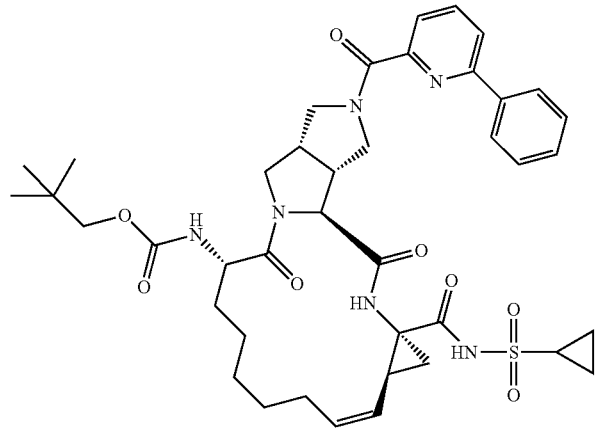
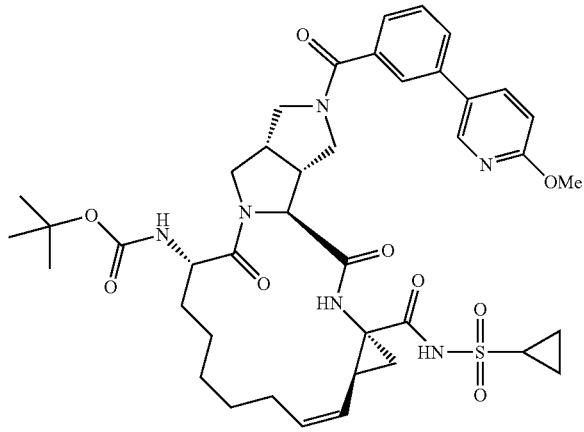
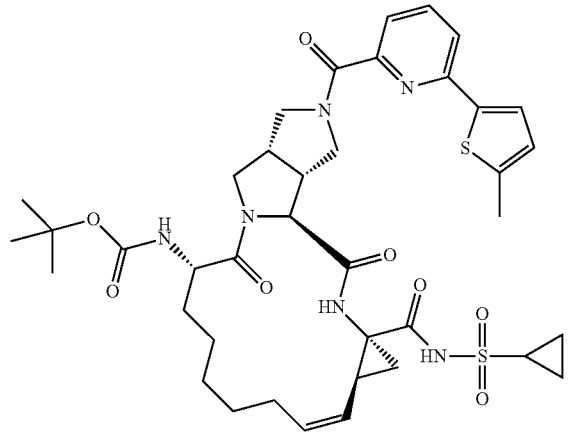
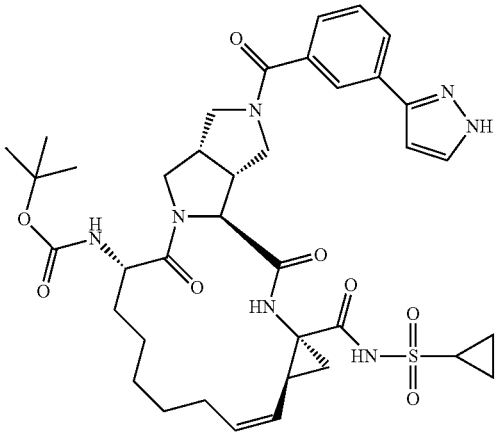
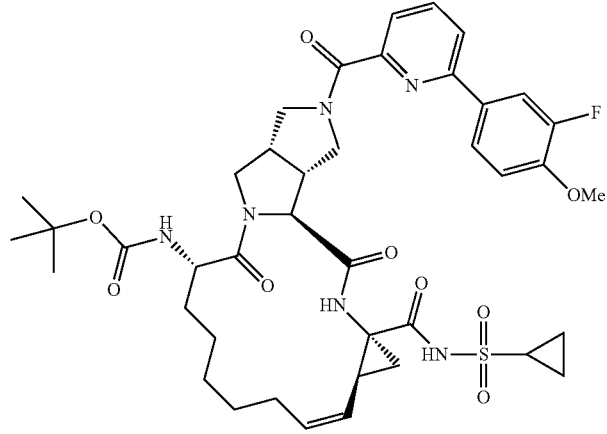

147
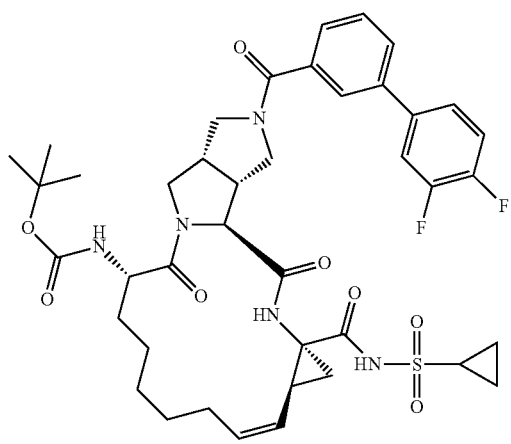
148
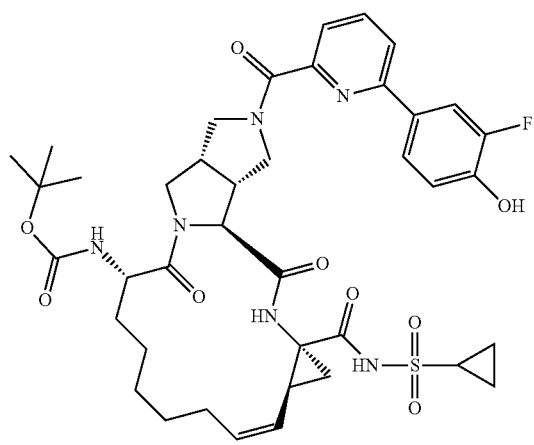
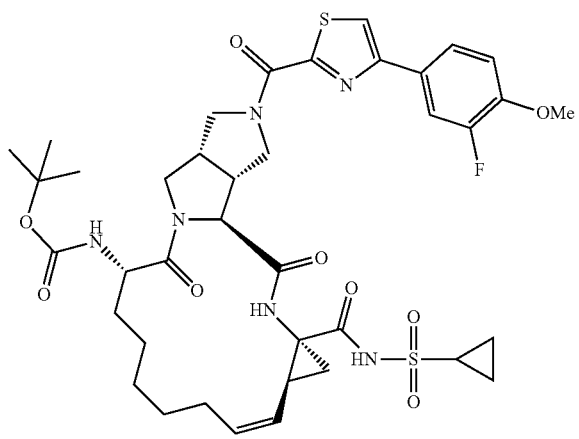
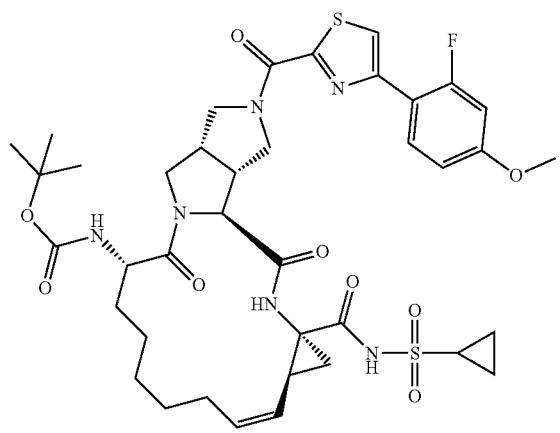
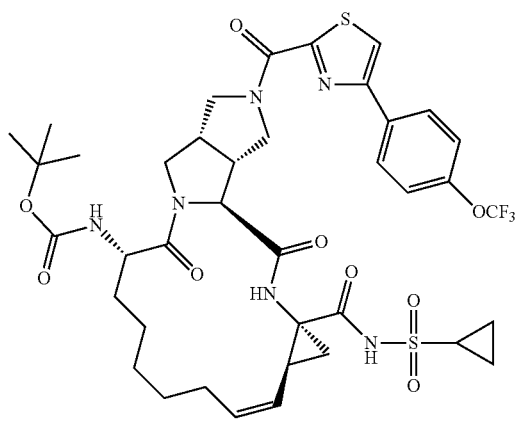
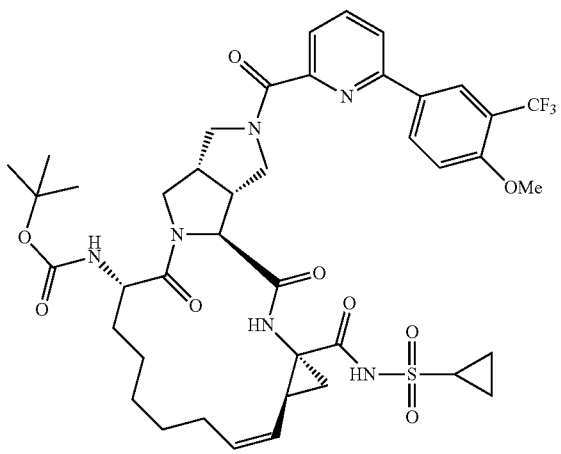

-continued
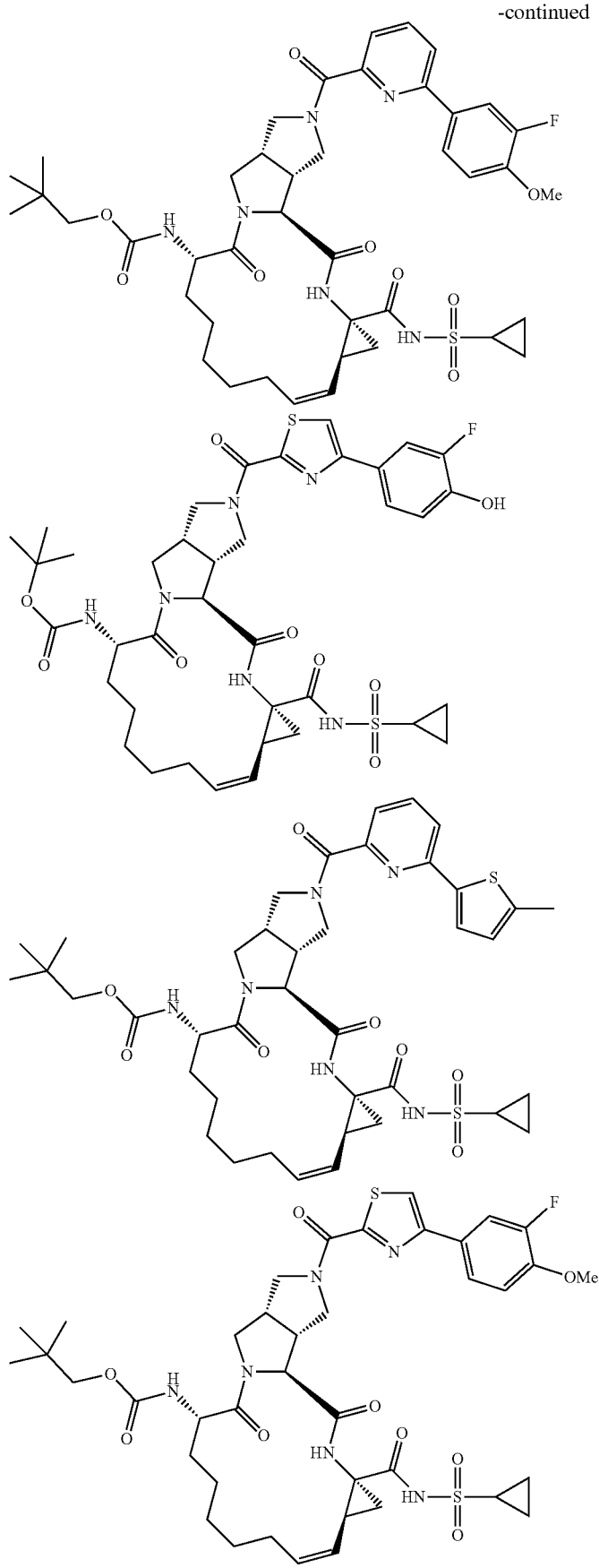

151
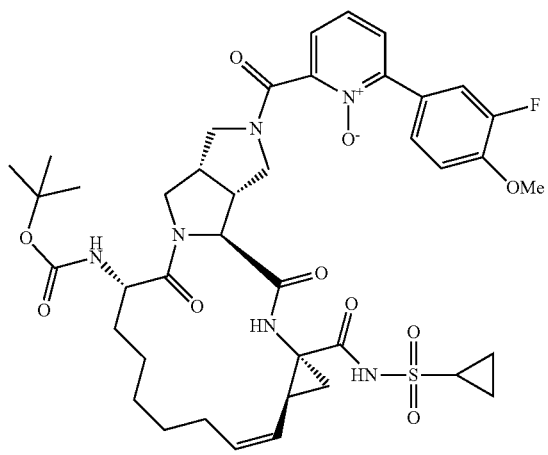
152
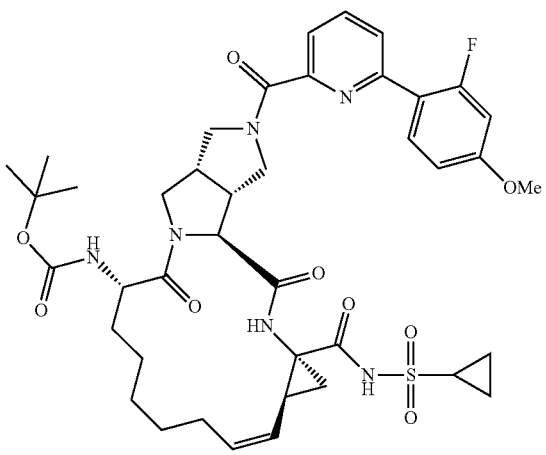
-continued
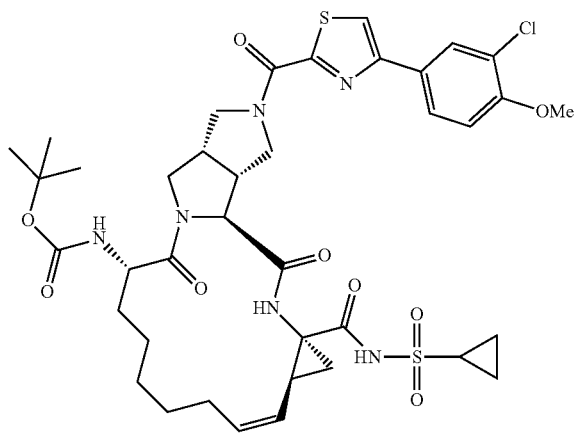
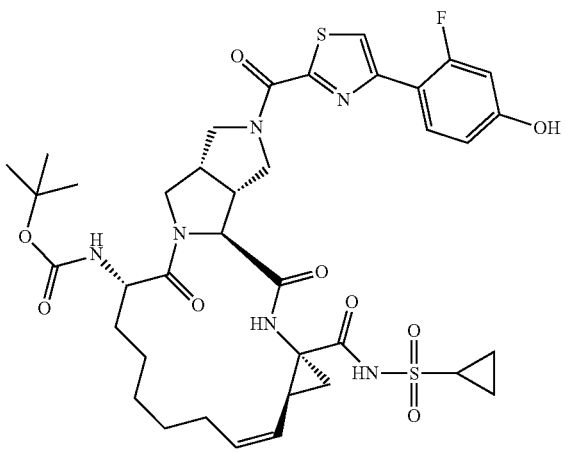
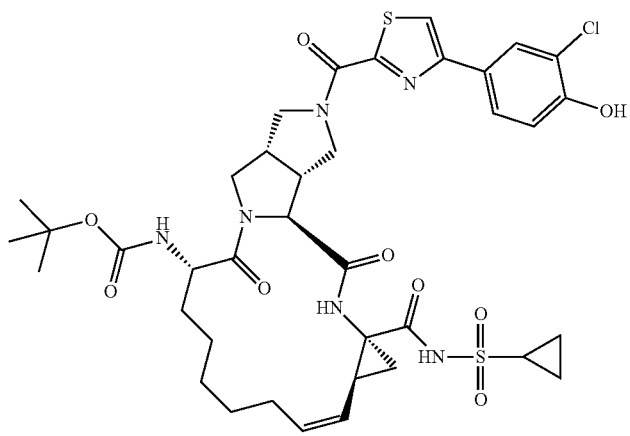

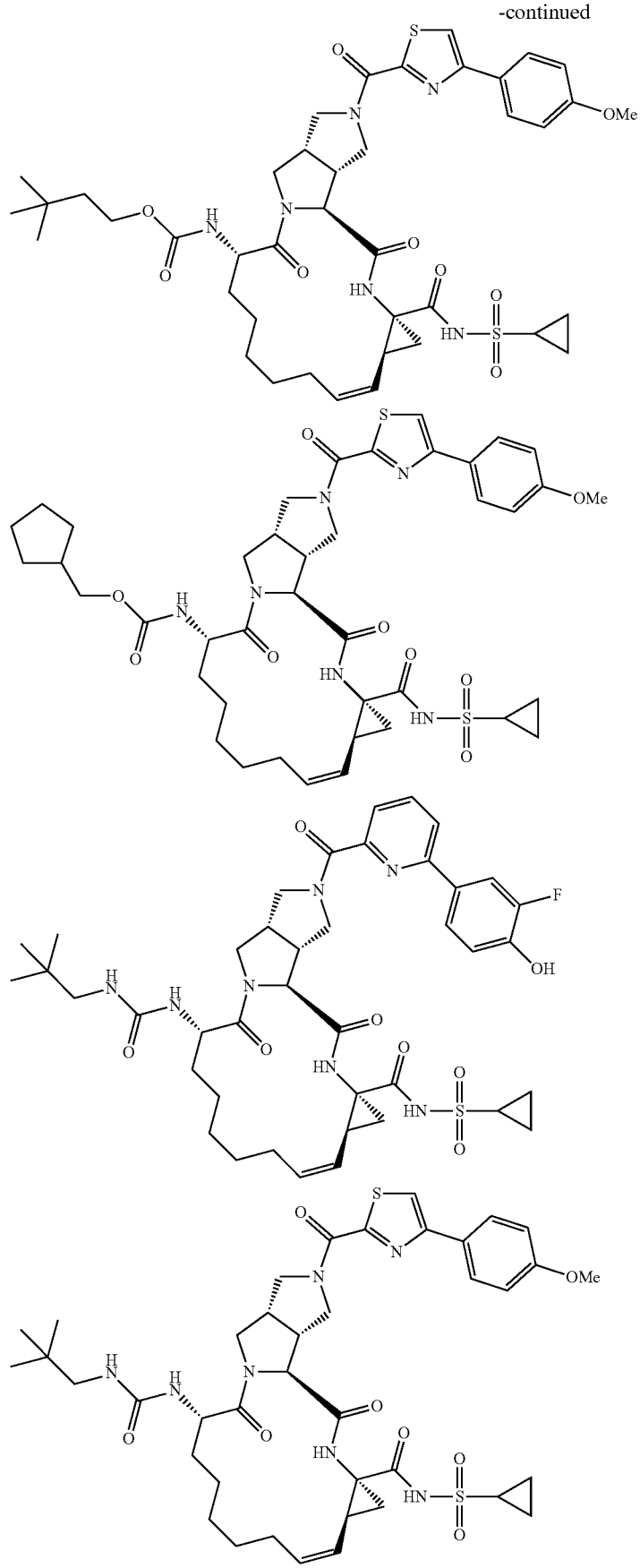

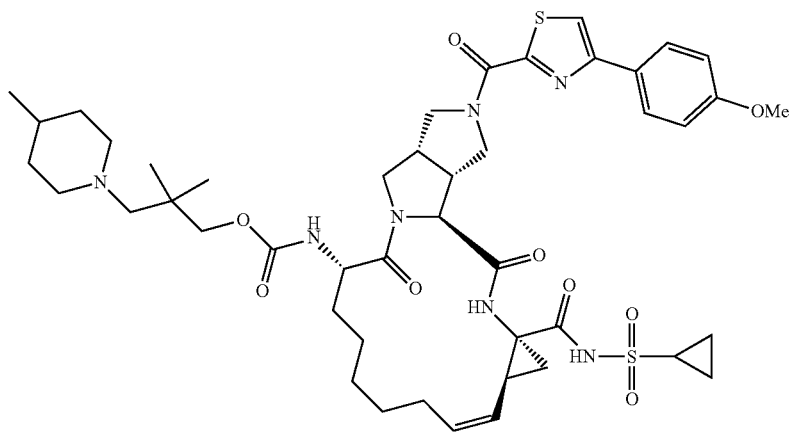
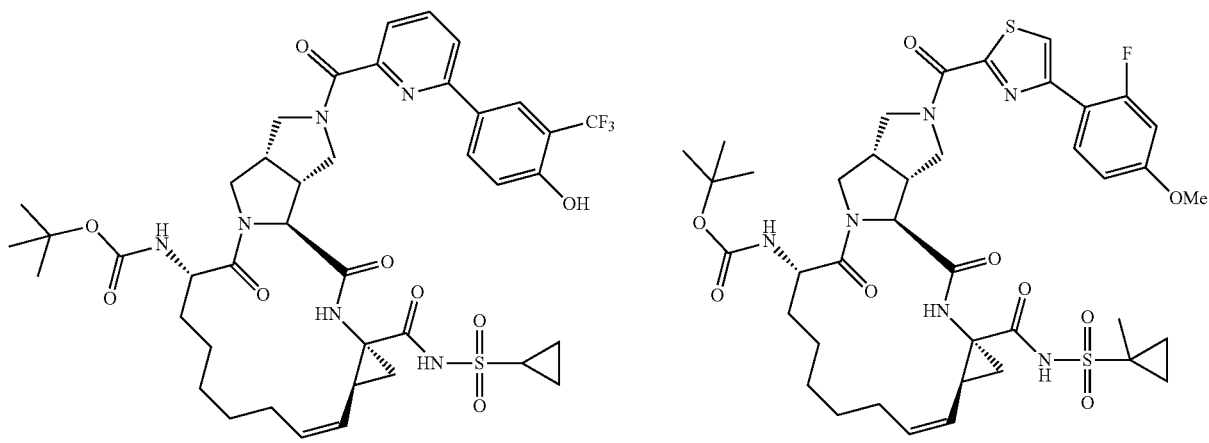
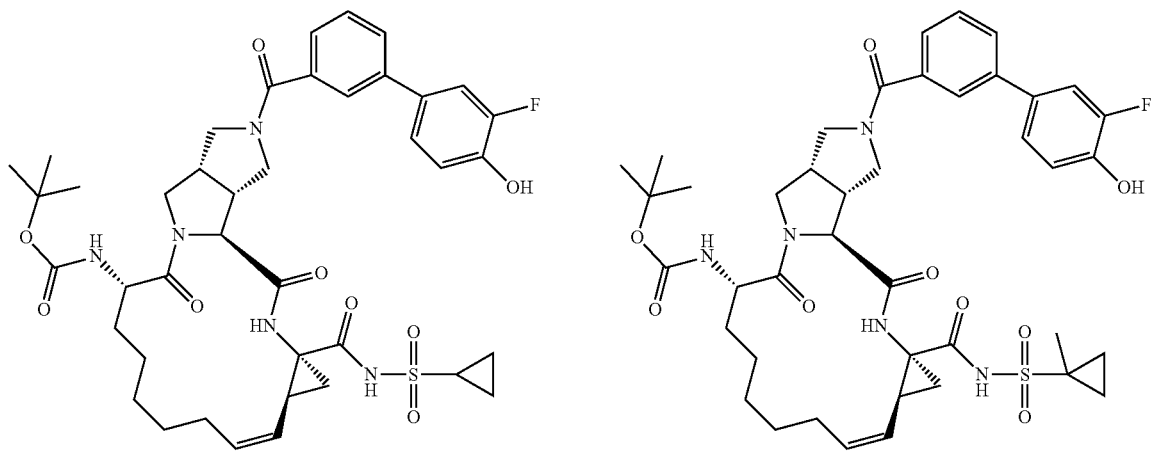

-continued
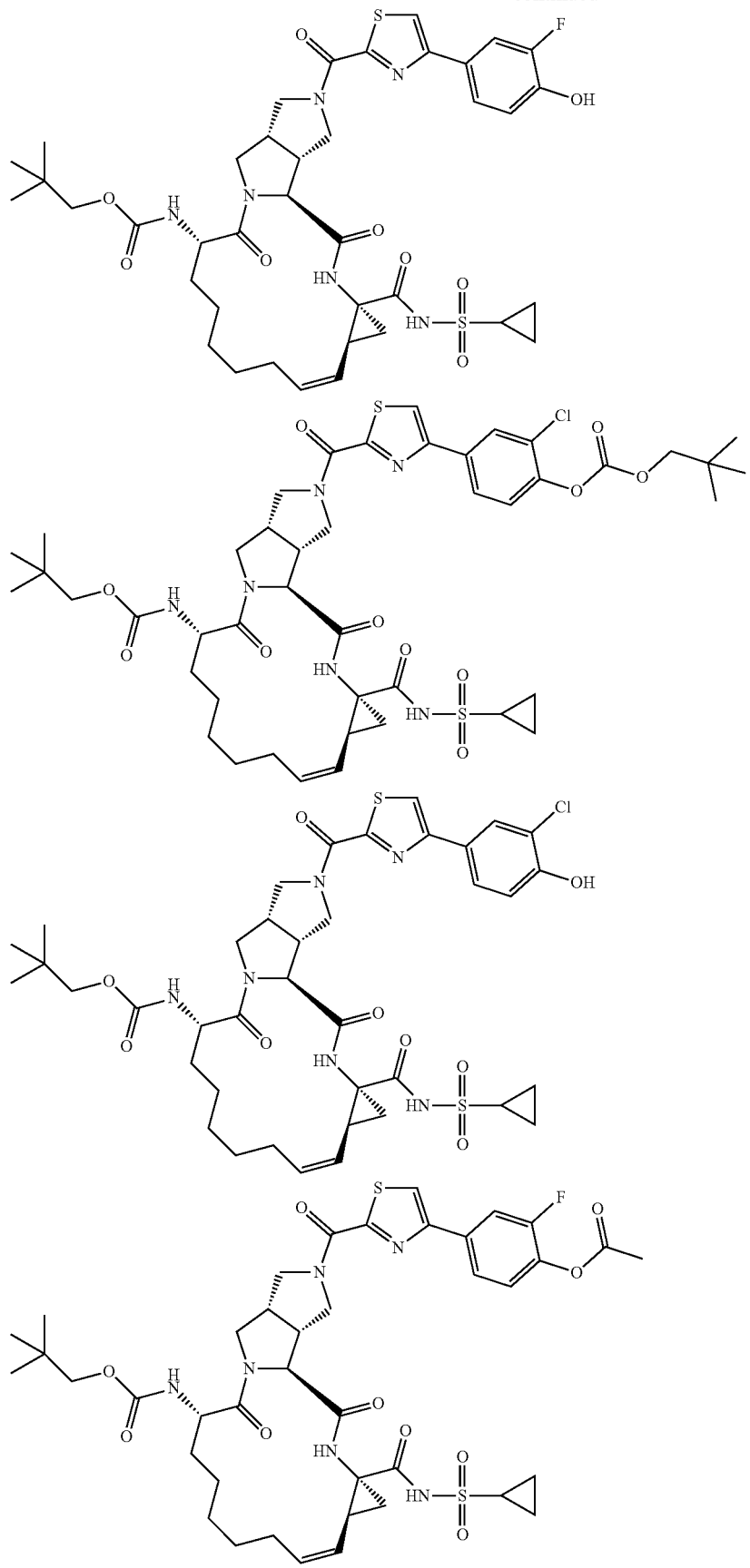

-continued
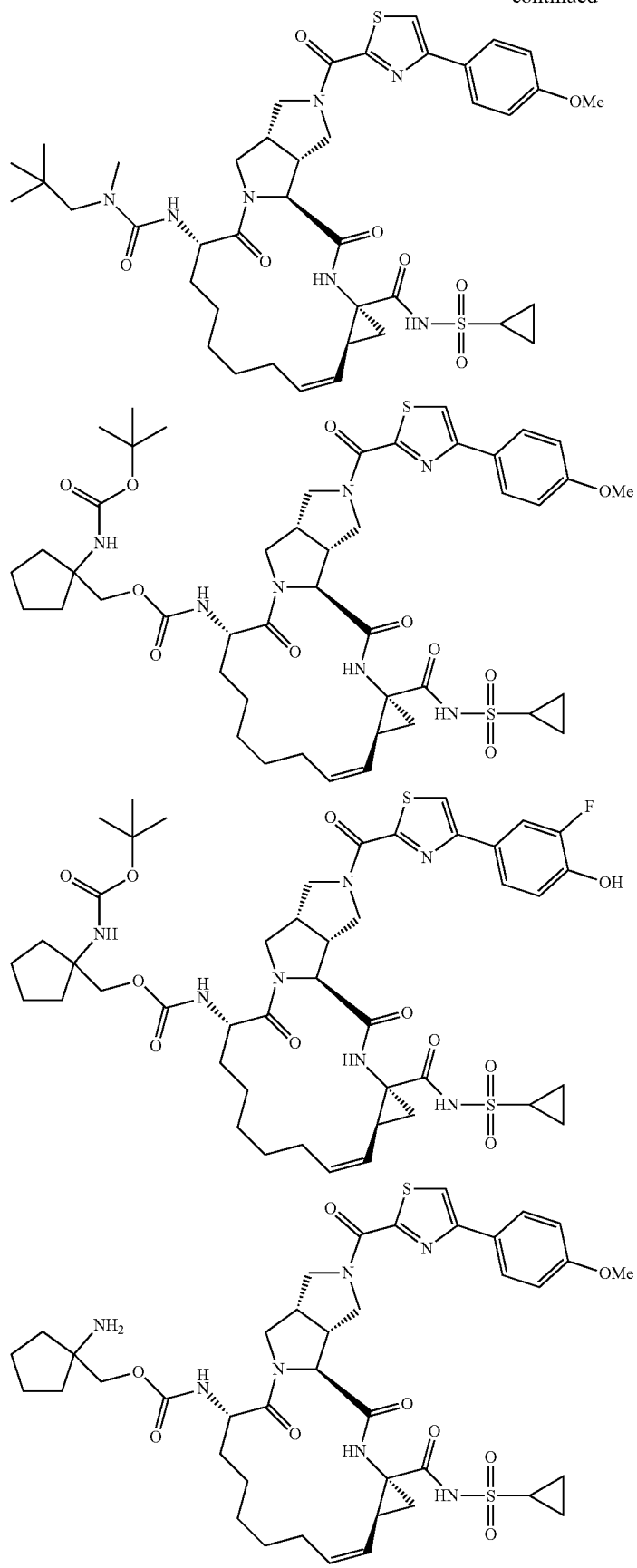

-continued
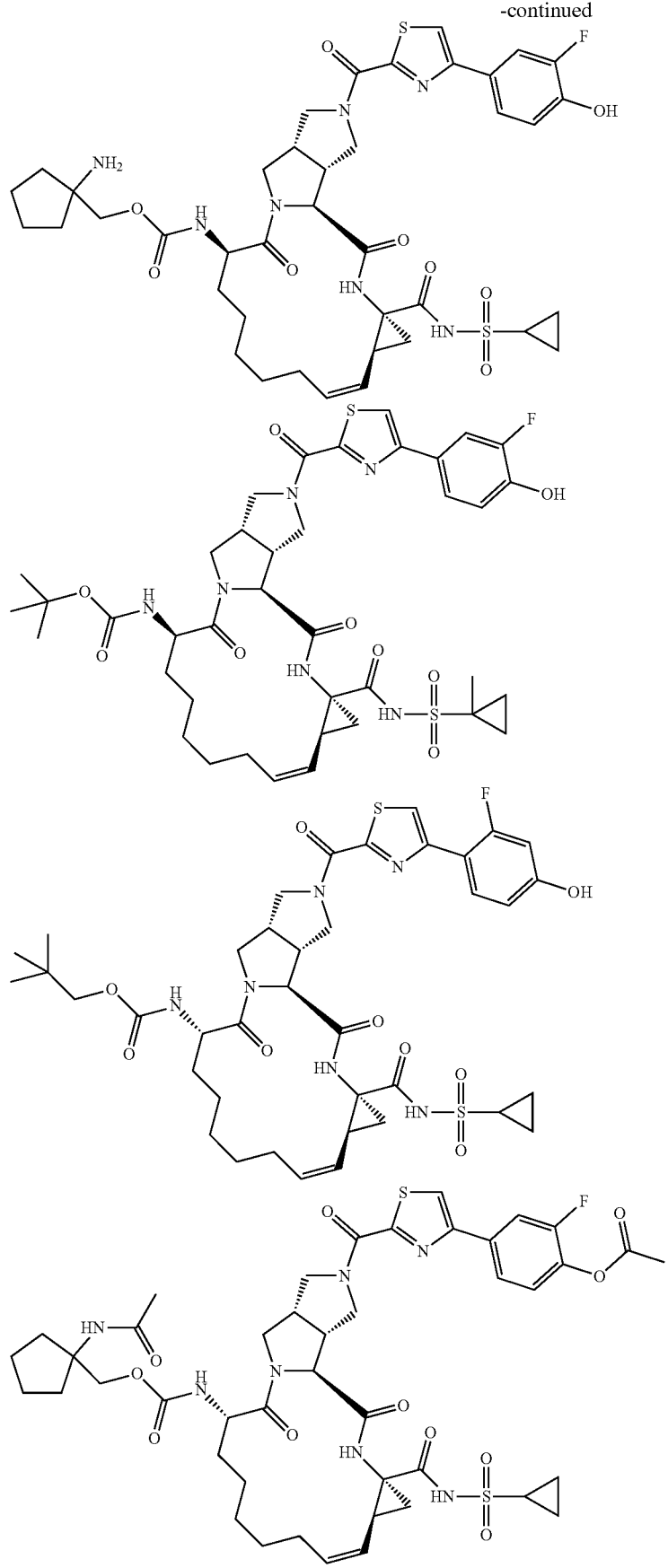

163
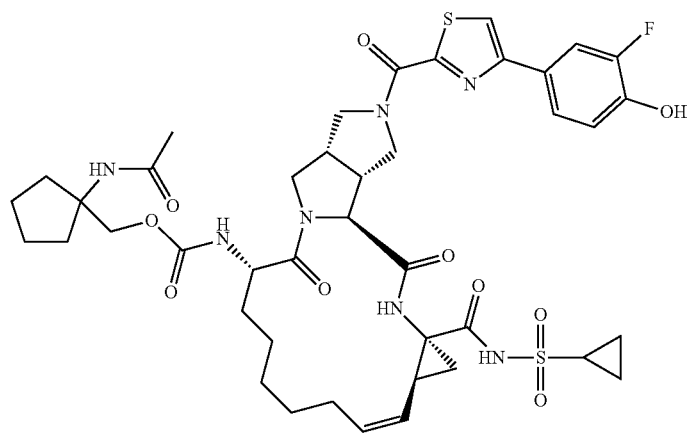
164
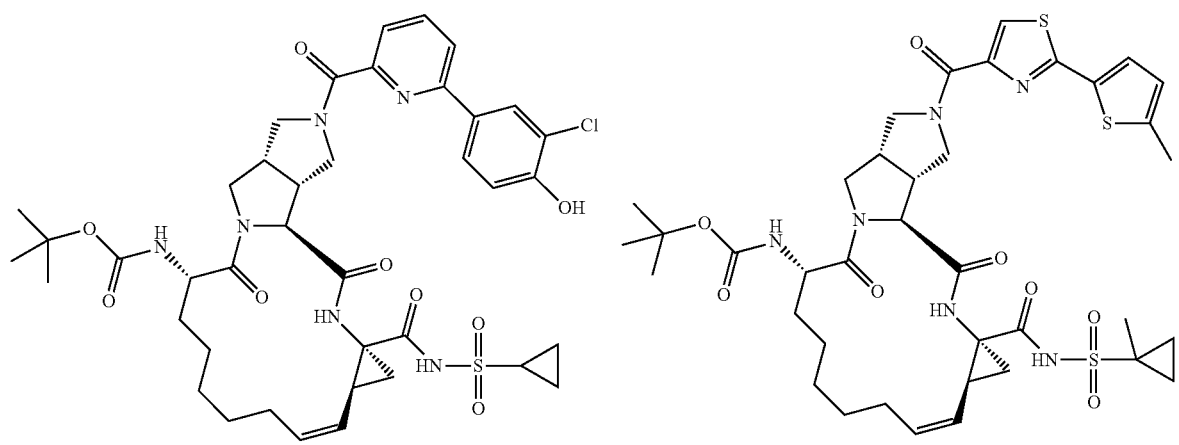
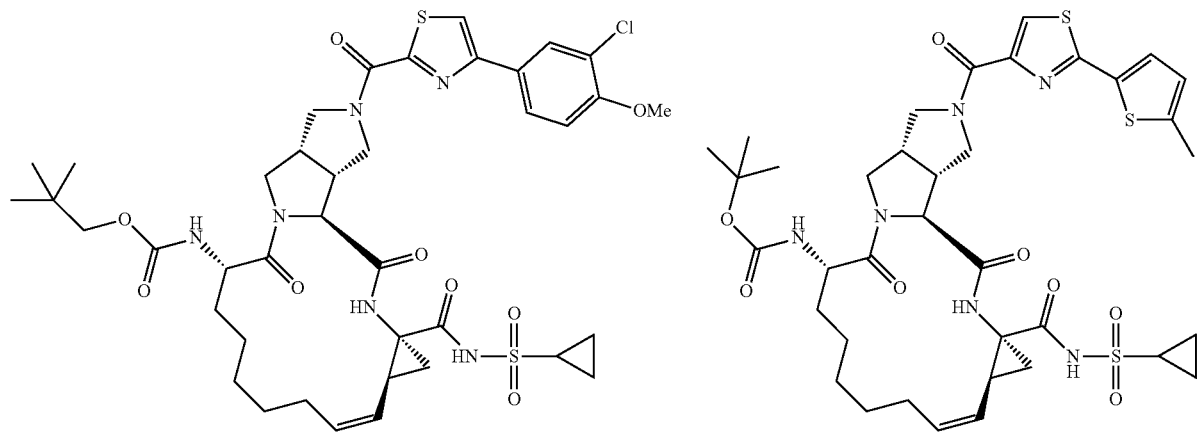

-continued
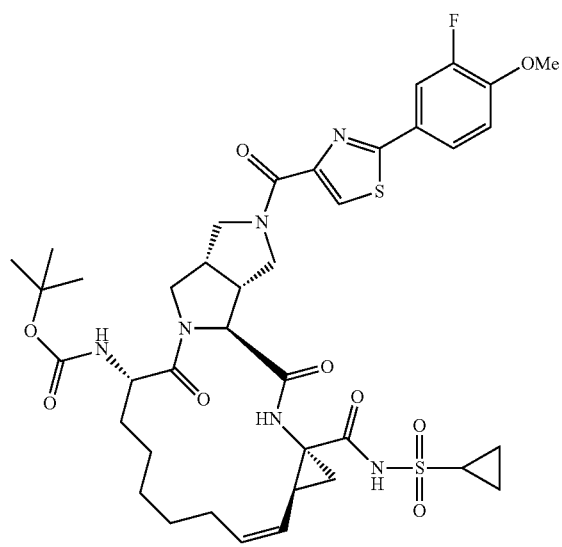
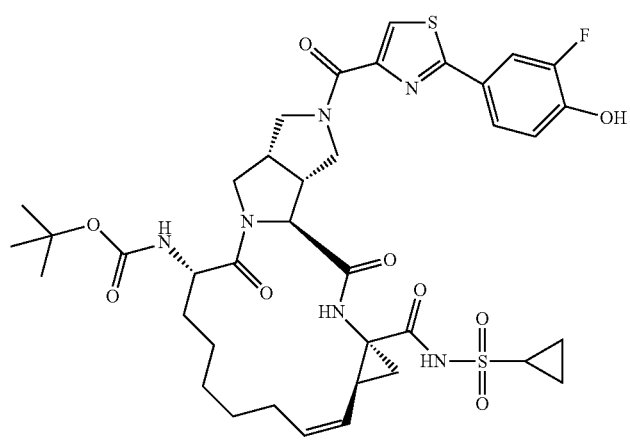
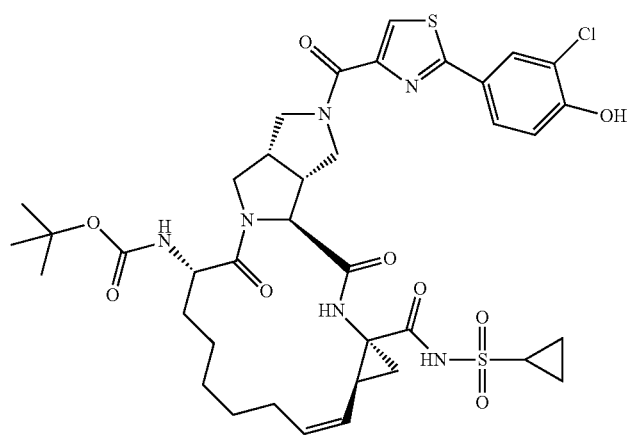

167
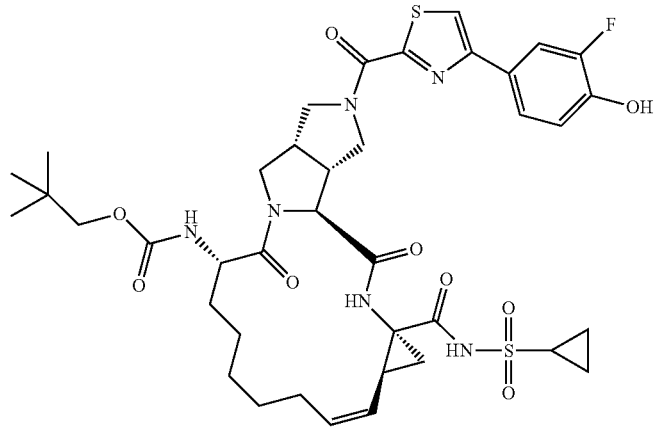
-continued
168
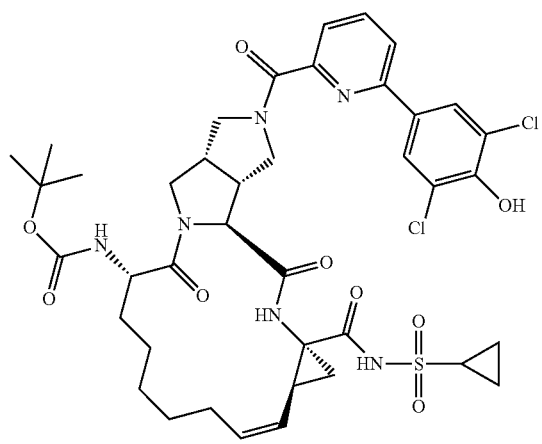
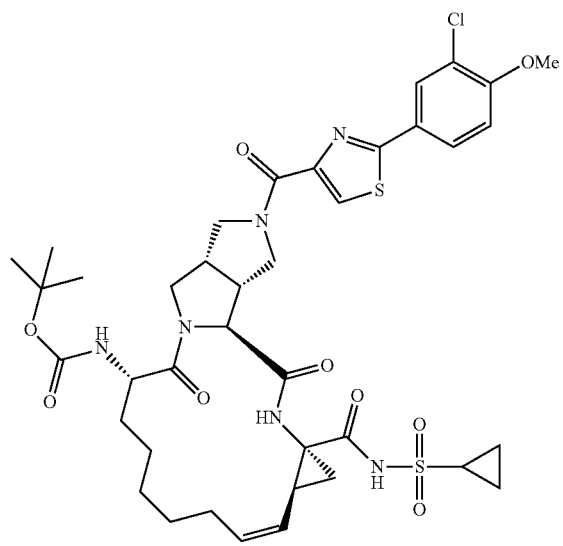
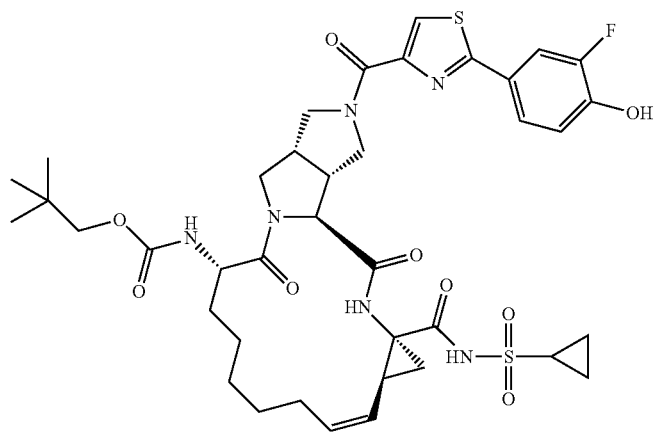

169
-continued
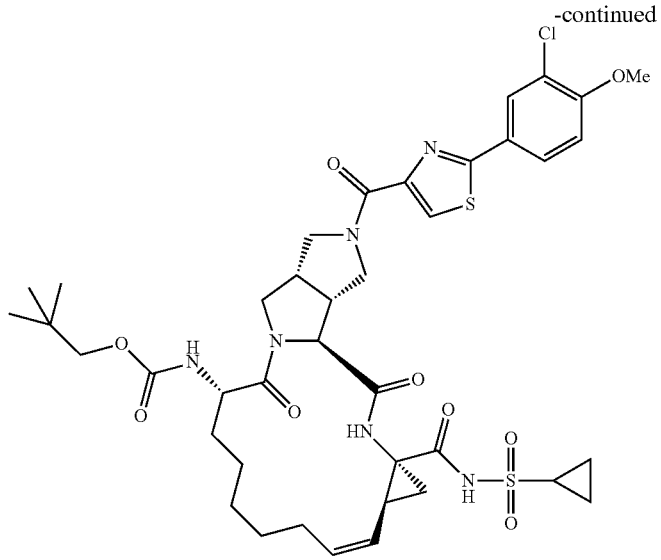
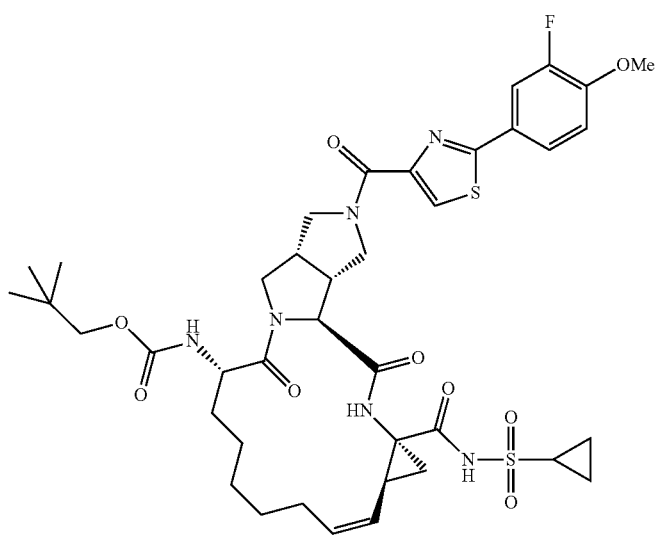
170
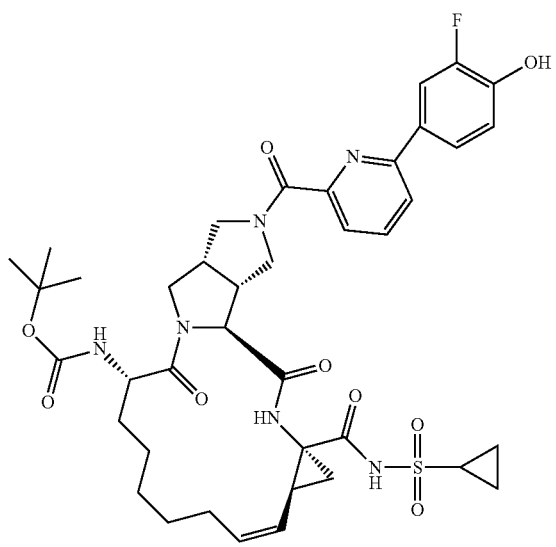
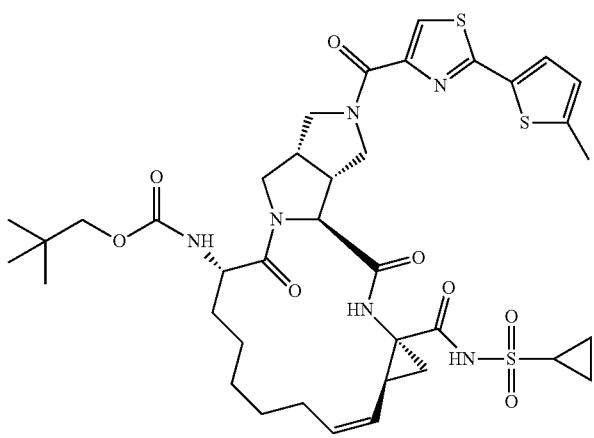

-continued
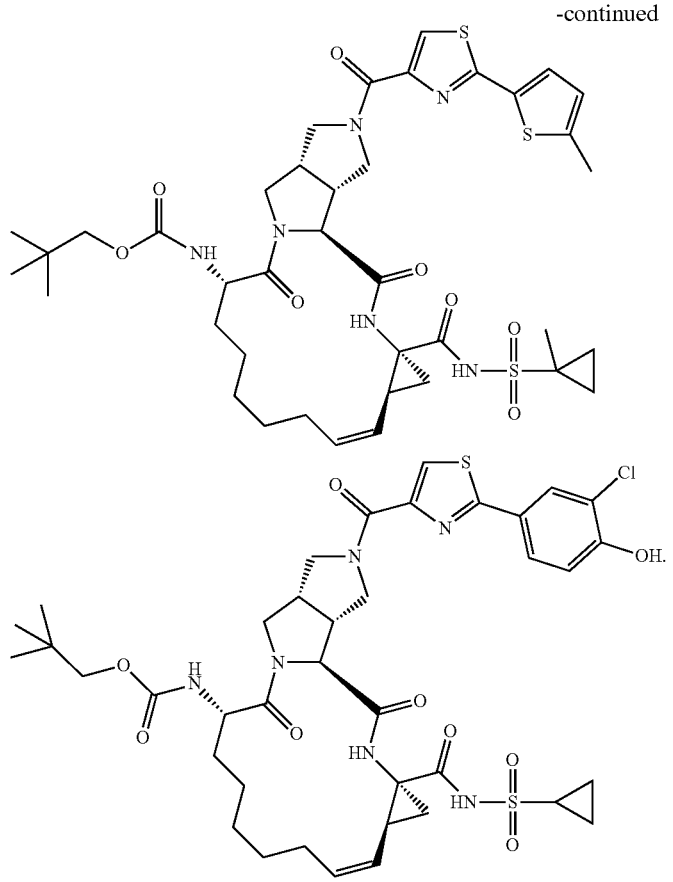
* * * * *